(12) United States Patent
Koike et al.

(10) Patent No.: US 9,770,388 B2
(45) Date of Patent: Sep. 26, 2017

(54) CO-INFUSION APPARATUS AND CO-INFUSION METHOD

(71) Applicant: Yuyama Mfg. Co., Ltd., Toyonaka-shi, Osaka (JP)

(72) Inventors: Naoki Koike, Toyonaka (JP); Akitomi Kohama, Toyonaka (JP); Masatoshi Warashina, Toyonaka (JP); Fumitaka Hino, Toyonaka (JP); Takuya Tsugui, Toyonaka (JP); Kazuki Kawauchi, Toyonaka (JP); Sho Oya, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 13 days.

(21) Appl. No.: 14/898,673

(22) PCT Filed: Sep. 8, 2014

(86) PCT No.: PCT/JP2014/073699
§ 371 (c)(1),
(2) Date: Dec. 15, 2015

(87) PCT Pub. No.: WO2015/041092
PCT Pub. Date: Mar. 26, 2015

(65) Prior Publication Data
US 2016/0136052 A1 May 19, 2016

(30) Foreign Application Priority Data

Sep. 19, 2013 (JP) .................................. 2013-194548
Feb. 28, 2014 (JP) .................................. 2014-039249
Mar. 26, 2014 (JP) .................................. 2014-064597

(51) Int. Cl.
*A61J 1/14* (2006.01)
*A61J 1/20* (2006.01)
(Continued)

(52) U.S. Cl.
CPC ............... *A61J 1/2096* (2013.01); *A61J 1/16* (2013.01); *A61J 1/18* (2013.01); *A61J 1/22* (2013.01);
(Continued)

(58) Field of Classification Search
CPC .... A61J 1/2096; A61J 1/16; A61J 1/18; A61J 1/22; A61J 3/002; A61J 2200/74; G05D 9/00; B65B 39/12; B65B 3/003
(Continued)

(56) References Cited

U.S. PATENT DOCUMENTS 7,610,115 B2 * 10/2009 Rob ........................... A61J 1/20
318/568.11
7,783,383 B2 * 8/2010 Eliuk ........................ A61J 1/20
141/1
(Continued)

FOREIGN PATENT DOCUMENTS

JP 2009-504199 A 2/2009
JP 2012-250016 A 12/2012
(Continued)

OTHER PUBLICATIONS

WIPO, Japanese International Search Authority, International Search Report and Written Opinion mailed Dec. 16, 2014 in International Patent Application No. PCT/JP2014/073699, 8 pages.

*Primary Examiner* — Nicolas A Arnett
(74) *Attorney, Agent, or Firm* — Masuvalley & Partners

(57) ABSTRACT

The present application provides a co-infusion apparatus and a co-infusion method which can photograph an image suitable for inspecting whether or not a co-infusion process in the co-infusion apparatus is properly carried out.

19 Claims, 54 Drawing Sheets

(51) Int. Cl.
*B65B 3/00* (2006.01)
*A61J 3/00* (2006.01)
*B65B 39/12* (2006.01)
*A61M 5/178* (2006.01)
*A61J 1/16* (2006.01)
*A61J 1/18* (2006.01)
*A61J 1/22* (2006.01)
*G05D 9/00* (2006.01)

(52) U.S. Cl.
CPC ............ *A61J 3/002* (2013.01); *A61M 5/1782* (2013.01); *B65B 3/003* (2013.01); *B65B 39/12* (2013.01); *G05D 9/00* (2013.01); *A61J 2200/74* (2013.01)

(58) Field of Classification Search
USPC ................ 141/18, 21, 83, 94, 104, 192, 198
See application file for complete search history.

(56) References Cited

U.S. PATENT DOCUMENTS

| | | | | |
|---|---|---|---|---|
| 8,857,476 | B2* | 10/2014 | Koike | A61J 3/002 141/114 |
| 9,474,691 | B2* | 10/2016 | Yuyama | A61J 1/20 |
| 9,561,156 | B2* | 2/2017 | Koike | A61J 3/002 |
| 2014/0020790 | A1* | 1/2014 | Yuyama | A61J 1/20 141/27 |
| 2014/0174600 | A1* | 6/2014 | Koike | A61J 3/002 141/89 |
| 2014/0373975 | A1* | 12/2014 | Koike | A61J 3/002 141/114 |
| 2015/0335531 | A1* | 11/2015 | Yuyama | A61J 1/20 141/18 |

FOREIGN PATENT DOCUMENTS

| WO | WO2012/133052 | * | 10/2012 | ................ A61J 3/00 |
|---|---|---|---|---|
| WO | WO2012/133052 A1 | | 10/2012 | |

\* cited by examiner

FIG. 23
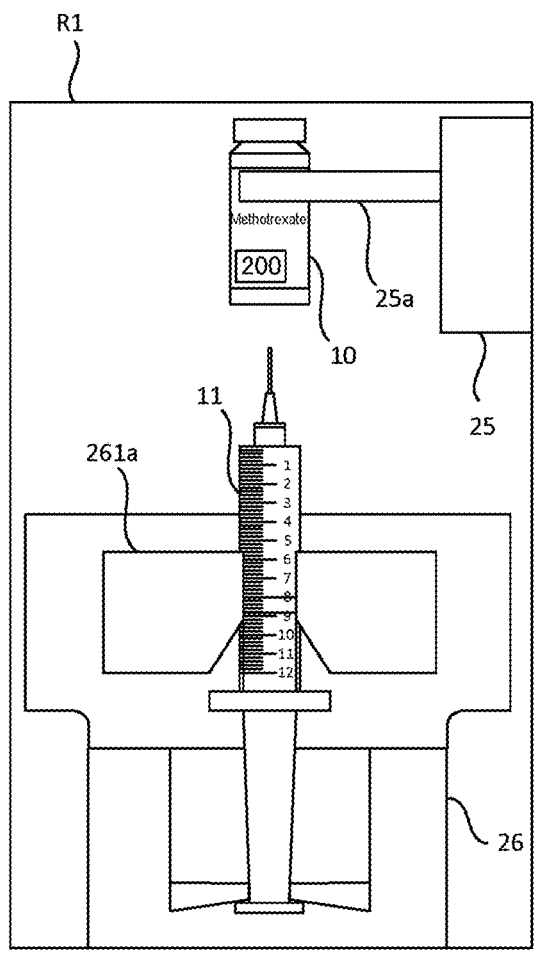
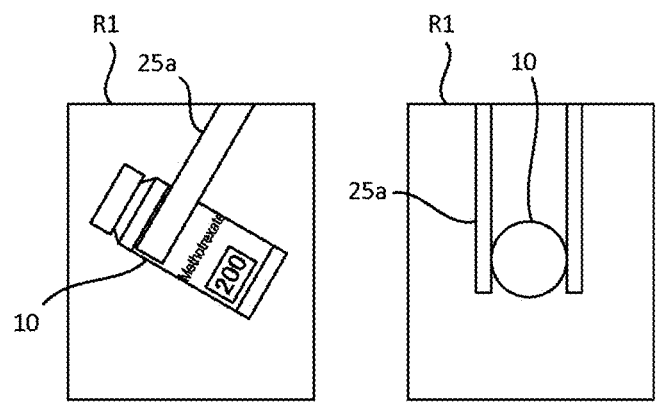
FIG. 24(A)    FIG. 24(B)

FIG. 27

| Standard volume | Usable range | Acceptable range | | Provision of the Heath, Labor and Welfare Ministry | |
|---|---|---|---|---|---|
| Equal to or more than 2.5 ml and less than 5ml | 0.5ml~ | ±4% | ±0.1ml | ±5% | ±0.125ml |
| Equal to or more than 5ml and less than 10 ml | 1ml~ | ±3% | ±0.15ml | ±4% | ±0.2ml |
| Equal to or more than 10 ml and less than 20 ml | 2ml~ | ±3% | ±0.3ml | ±4% | ±0.4ml |
| Equal to or more than 20 ml and less than 30 ml | 4ml~ | ±2% | ±0.4ml | ±4% | ±0.8ml |
| Equal to or more than 30 ml and less than 50 ml | 6ml~ | ±2% | ±0.6ml | ±4% | ±1.2ml |
| Equal to or more than 50 ml | 10ml~ | ±2% | ±1ml | ±4% | ±2.0ml |

FIG. 34

| Type | Volume [mL] | Formation | Full amount [mL] | Injectable amount without releasing air [mL] | Injectable amount with releasing air [mL] |
|---|---|---|---|---|---|
| Saline A | 100 | Plastic bottle | 157 | 0 | 57 |
| Saline B | 250 | Soft bag | 425 | 117.6 | 175 |
| SalineC | 500 | Soft bag | 700 | 129.2 | 200 |
| 5% Glucose | 250 | Plastic bottle | 415 | 7 | 165 |
| ... | ... | ... | ... | ... | ... |

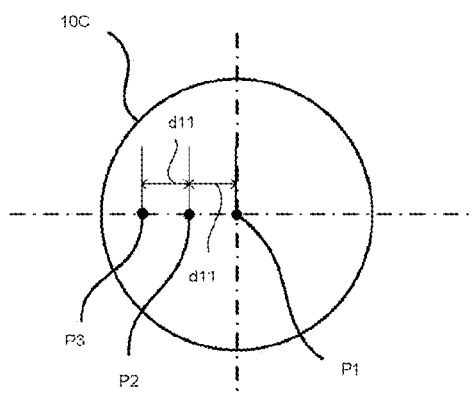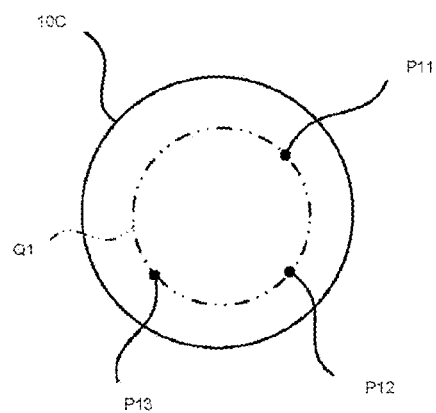
FIG. 49(A)          FIG. 49(B)

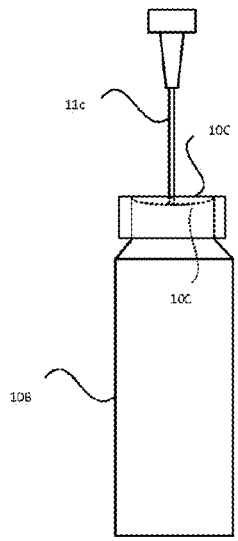 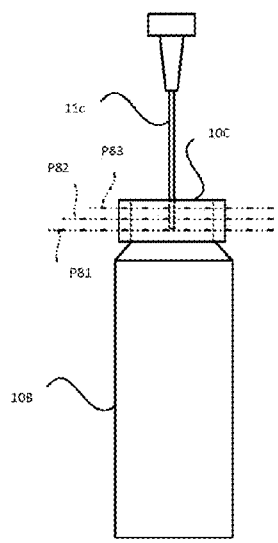
FIG. 59(A)  FIG. 59(B)
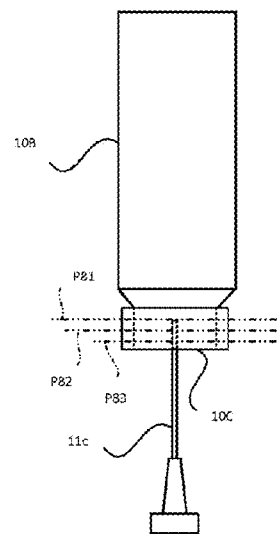 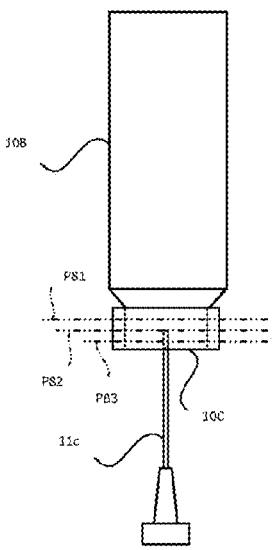 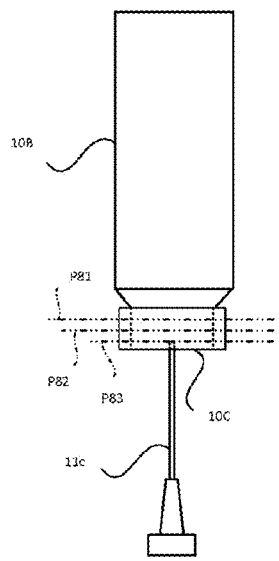
FIG. 59(C)  FIG. 59(D)  FIG. 59(E)

CO-INFUSION APPARATUS AND CO-INFUSION METHOD

RELATED APPLICATIONS

This application is the U.S. National Phase of and claims priority to International Patent Application No. PCT/JP2014/073699, International Filing Date Sep. 8, 2014, entitled Coinjection Device And Coinjection Method; which claims benefit of Japanese Application No. JP2013-194548 filed Sep. 19, 2013; Japanese Application No. JP2014-039249 filed Feb. 28, 2014; and Japanese Application No. JP2014-064597 filed Mar. 26, 2014; all of which are incorporated herein by reference in their entireties.

TECHNICAL FIELD

The present invention relates to a co-infusion apparatus and a co-infusion method for carrying out a co-infusion process for injecting a medicine such as an anticancer medicine contained in a medicine container into a transfusion container.

BACKGROUND ART

There is known a co-infusion apparatus for carrying out a co-infusion process for suctioning a medicine such as an anticancer medicine contained in a medicine container such as an ampule and a vial bottle with an injector and injecting the medicine into a transfusion container in which transfusion is contained.

In this kind of co-infusion apparatus, there are cases where the injector after the medicine has been suctioned from the medicine container in practice is photographed in order to record steps in the co-infusion process (for example, see patent document 1). For example, in a co-infusion apparatus disclosed in the patent document 1, a plurality of portions of an injector are photographed with one or more of cameras and then an image of the injector is produced by connecting these photographed images for the plurality of portions of the injector. At this time, the produced image also contains a side image of a medicine container.

RELATED ART

Patent Document

Patent document 1: JP 2012-250016A

SUMMARY OF THE INVENTION

Problem to be Solved by the Invention

However, from a point of view of inspecting whether or not the co-infusion process is properly carried out according to preparation data by utilizing an image, it is not preferable to utilize the image produced by connecting the photographed images for the plurality of portions of the injector with an image processing as described above because such a produced image is low reliable.

It is an object of the present invention to provide a co-infusion apparatus and a co-infusion method which can photograph an image being suitable for inspecting whether or not a co-infusion process is properly carried out by the co-infusion apparatus.

Means for Solving Problem

A co-infusion apparatus according to the present invention suctions a medicine from a medicine container with an injector based on preparation data and injects the medicine from the injector into a transfusion container. The co-infusion apparatus includes a first driving means, a second driving means, a suctioning control means, a transfer control means and a suctioning timing photographing means. The first driving means is capable of transferring one or both of the medicine container and the injector to an arbitrary position. The second driving means is capable of handling the injector. The suctioning control means controls the first driving means and the second driving means to suction the medicine from the medicine container with the injector. The transfer control means controls the first driving means to transfer, into a photographing range, the medicine container after the medicine is suctioned by the suctioning control means and the injector in which the medicine has been suctioned. The suctioning timing photographing means photographs, at one time, the medicine container and the injector transferred in the photographing range by the transfer control means at one time.

A co-infusion method according to the present invention is carried out by a co-infusion apparatus for suctioning a medicine from a medicine container with an injector based on preparation data and injecting the medicine from the injector into a transfusion container. The co-infusion method includes controlling a first driving means being capable of transferring one or both of the medicine container and the injector to an arbitrary position and a second driving means being capable of handling the injector to suction the medicine from the medicine container with the injector, controlling the first driving means to transfer, into a photographing range, the medicine container after the medicine is suctioned and the injector in which the medicine has been suctioned and photographing, at one time, the medicine container and the injector transferred in the photographing range.

According to the present invention, by utilizing a highly reliable image obtained by photographing the medicine container and the injector at one time, it becomes possible to inspect whether or not steps in the co-infusion process by the co-infusion apparatus are properly carried out.

Specifically, it may be considered that the first driving means includes a first robot arm and a second robot arm each having a multiple joint structure. With this configuration, it is possible to allow the medicine container and the injector to be set an arbitrary posture and photograph them with photographing means.

Further, it may be considered that the transfer control means allows the medicine container and the injector to be arranged in the photographing range so that characters of a medicine name on the medicine container and characters of a scale of the injector are directed the same. With this configuration, it is possible to make the characters of the medicine name on the medicine container and the characters of the scale of the injector more visible for a user, thereby improving usability.

Further, it may be considered that the transfer control means allows the medicine container and the injector to be arranged in the photographing range so that vertical directions of the characters of the medicine name on the medicine container and the characters of the scale of the injector and a vertical direction in the photographing range are the same. With this configuration, it is possible to make the characters of the medicine name on the medicine container and the characters of the scale of the injector even more visible for the user, thereby more improving the usability.

Further, it may be considered that the transfer control means allows the medicine container and the injector to be arranged in the photographing range so that the medicine container and the injector are aligned in a direction perpendicular to a longitudinal direction of the injector. With this configuration, it is possible to prevent the photographing range from being lengthened.

In this regard, it may be considered that the transfer control means allows the first driving means to keep holding states of the medicine container and the injector until the medicine container and the injector are photographed by the suctioning timing photographing means after the medicine is suctioned from the medicine container with the injector. With this configuration, it is possible to improve reliability for ensuring that the medicine in the injector in a photographed image photographed by the suctioning timing photographing means is the same as the medicine in the medicine container.

Further, it may be considered that the co-infusion apparatus further includes an inspection image display means for displaying an image photographed by the suctioning timing photographing means as an inspection image. With this configuration, the user can inspect the co-infusion process from the inspection image with using the co-infusion apparatus.

Here, it may be considered that the inspection image display means allows a medicine name and a medicine volume contained in the preparation data to be displayed together with the inspection image. With this configuration, the user can confirm the medicine name and the medicine volume contained in the preparation data together with the inspection image from one screen.

Particularly, it may be considered that the co-infusion apparatus further includes a medicine weight capturing means for capturing a weight of the medicine injected from the medicine container into the transfusion container with the injector and the inspection image display means allows the weight of the medicine captured by the medicine weight capturing means and a predetermined acceptable range for the weight of the medicine to be displayed together with the inspection image. With this configuration, the user can easily carry out inspection with using a weight by referring a display screen due to the inspection image display means.

At this time, it may be considered that the medicine weight capturing means calculates, as the weight of the medicine, a difference between a weight of the injector after the medicine is suctioned from the medicine container and a weight of the injector after the medicine is injected from the injector into the transfusion container. With this configuration, it is possible to eliminate influence caused by an individual difference of the injector or the like and inspect the co-infusion process with using the weight of the medicine injected into the transfusion container in practice.

Further, it may be considered that the co-infusion apparatus further includes a weight inspecting means for determining whether or not a difference between the weight of the medicine captured by the medicine weight capturing means and a weight of the medicine corresponding to the medicine volume contained in the preparation data is in a predetermined acceptable rang and the inspection image display means allows a determination result from the weight inspecting means to be displayed together with the inspection image. With this configuration, the user can recognize an inspection result for the co-infusion process with using the weight at one view by referring an indication of the determination result.

Here, it may be considered that the predetermined acceptable range is a range that is set in advance for a standard volume of each injector. With this configuration, it is possible to inspect the co-infusion process based on the acceptable range being suitable for the standard volume of each injector.

Further, it may be considered that the co-infusion apparatus further includes a whole amount obtaining timing photographing means for photographing a bottom surface or a side surface of the medicine container in a state that an opening portion of the medicine container is directed toward a vertical upper direction or in a state that the opening portion of the medicine container is inclined at a predetermined angle with respect to the vertical upper direction when a whole amount obtaining process for suctioning a whole amount of the medicine contained in the medicine container with the injector based on the preparation data is carried out by the suctioning control means. With this configuration, it is possible to easily determine whether or not the medicine remains in the medicine container based on a photographed image photographed by the whole amount obtaining timing photographing means.

Further, it may be considered that the co-infusion apparatus further includes a container position adjusting means for adjusting a circumferential position of the medicine container held by the first driving means so that characters of a medicine name on the medicine container are located in the photographing range. For example, it may be considered that the co-infusion apparatus further includes a rotation driving means for rotating the medicine container in a circumferential direction and a container reading means for reading medicine information from the medicine container rotated by the rotation driving means. In addition, the container position adjusting means allows the rotation driving means to rotate the medicine container by a rotation amount predetermined for each medicine container and then stop the rotation of the medicine container after the medicine information is read by the container reading means. With this configuration, it is possible to reliably recognize the characters of the medicine name on the medicine container in the photographed image photographed by the suctioning timing photographing means.

Further, it may be considered that the co-infusion apparatus further includes an injector position adjusting means for adjusting a circumferential position of the injector held by the first driving means so that characters of a scale of the injector are located in the photographing range. For example, it may be considered that the injector position adjusting means includes a direction detecting means for detecting a circumferential direction of the injector placed at a predetermined placing position and an injector rotating means for allowing the first driving means to rotate the injector based on a detection result from the direction detecting means so that the characters of the scale of the injector are located in the photographing range when the injector is transferred into the photographing range by the first driving means. With this configuration, it is possible to reliably recognize the characters of the scale of the injector in the photographed image photographed by the suctioning timing photographing means.

Further, it may be considered that the co-infusion apparatus further includes a tray reading means, a collating means and a discharge control means. The tray reading means reads identification information from a storage medium included in a tray on which at least one of the medicine container, a syringe of the injector, an injection needle of the injector, and the transfusion container is placed when the at least one of the medicine container, the syringe of the injector, the injection needle of the injector and the transfusion container is loaded into the co-infusion apparatus. The collating means collates a content of the preparation data preliminarily associated with the identification information read by the tray reading means with a content of at least one of the medicine container, the syringe of the injector, the injection needle of the injector and the transfusion container loaded in the co-infusion apparatus. The discharge control means allows the medicine container, the syringe of the injector, the injection needle of the injector, or the transfusion container, whose collation result is not matched by the collating means, to be removed together with the tray from a predetermined discharge port. With this configuration, the use can remove the tray from the co-infusion apparatus to appropriately place the medicine container, the injector and the transfusion container on the tray and then re-load the tray into the co-infusion apparatus.

Particularly, it may be considered that the co-infusion apparatus further includes an informing means for informing a message indicating that identification information read by the tray reading means from a subsequent tray subsequently loaded in the co-infusion apparatus after the tray is allowed to be removed by the discharge control means is not matched with the identification information read by the tray reading means from the tray allowed to be removed by the discharge control means if both of the identification information are not matched with each other. With this configuration, it is possible to determine whether or not the tray is replaced with another tray at the time of re-loading the tray, thereby preventing an inappropriate tray from being loaded into the co-infusion apparatus at the time of re-loading the tray. As a result, for example, it is possible to prevent the medicine on the tray loaded in the co-infusion apparatus from being treated as a medicine corresponding to another patient.

Further, it may be considered that the co-infusion apparatus further includes a placing timing photographing means, an interference determining means and a separating means. The placing timing photographing means photographs objects including the medicine container and the injector placed on a predetermined object placing member from an upper side of the object placing member. The interference determining means determines whether or not an object whose only one side interferes with another exists among the objects placed on the object placing member based on a photographing result from the placing timing photographing means. The separating means inserts a gripping member of the first driving means used for gripping the object between the two objects interfering with each other in a state that the gripping member is closed if the interference determining means determines that the object whose only one side interferes with the other exists. With this configuration, it becomes possible to solve the interference between the objects even if the objects interfere with each other on the object placing member and then take one of the objects from the object placing member.

Further, it may be considered that the co-infusion apparatus further includes a taking control means for taking the object on both sides, of which predetermined gaps are formed in the photographing result from the placing timing photographing means more preferentially than the object on one side or both sides, of which the gap is not formed in the photographing result from the placing timing photographing means. With this configuration, by utilizing a space formed by preferentially taking the one of the objects before the other object, it is possible to solve the interference of the other object.

Further, it may be considered that the taking control means stops taking of the object from the object placing member if all of the objects placed on the object placing member fall under the category of an object whose one side or both sides interfere with a constituent element of the object placing member or the category of an object whose both sides interfere with another object. With this configuration, it is possible to stop the taking of the object without solving the interference between the objects by the gripping member, thereby preventing breakage of the object due to the gripping member or the like.

In this regard, it may be considered that when an ampule is used as the medicine container, the suctioning control means allows the injector to suction the medicine from the ampule with an injection needle of the injector being directed toward a lower side, and then the suctioning control means allows the needle tip of the injector to be directed toward an upper side, and the injection needle is replaced with an injection needle having a syringe filter to push out air in the injector in a predetermined amount. With this configuration, it is possible to suction the medicine with preventing the air from remaining in the injector, thereby preventing breakage of the injector, which is caused by the fact that the syringe filter does not allow air to pass through the syringe filter after water penetrates into the syringe filter, or the like.

Here, it may be considered that the suctioning control means allows the injector to additionally suction a predetermined extra amount of the medicine, and the needle tip of the injector to be directed toward the lower side to discharge an extra amount of the medicine after the air in the injector is pushed out in the predetermined amount. With this configuration, it is possible to eliminate influence caused by an individual volume difference of the injection needle or the syringe filter of the injection or the like, thereby suppressing an accidental error of an amount of the medicine to be injected from the medicine into the transfusion container with the injector.

In this regard, it may be considered that the co-infusion apparatus further includes an injection control means for releasing air from the transfusion container if an injection amount of the medicine to be injected from the injector into the transfusion container is larger than an injectable amount predetermined so as to correspond to the transfusion container. Specifically, it may be considered that the injection control means carries out a process for releasing the air in the transfusion container with the injector before the medicine is suctioned with the injector. Furthermore, it may be considered that the injection control means subsequently carries out a process for releasing the air in the transfusion container with the injector after the medicine is suctioned with the injector and then the medicine is injected from the injector into the transfusion container. With this configuration, it is possible to prevent pressure inside the transfusion container from being positive pressure.

Further, a co-infusion apparatus according to the present invention is capable of suctioning transfusion from a transfusion container with an injector and injecting the transfusion into a medicine container. The co-infusion apparatus includes a first robot arm, a second robot arm, a weighing device, a first control means, a second control means, a third control means and a transfusion weight capturing means. The first robot arm is capable of holding and transferring the medicine container. The second robot arm is capable of holding and transferring the injector and handling the injector. The weighing device is provided in a movable range of the first robot arm or on the first robot arm. The first control means concurrently carries out a first weighing process for controlling the first robot arm to weigh the medicine container with the weighing device and a first transfusion suctioning process for controlling the second robot arm to suction the transfusion from the transfusion container with the injector. The second control means carries out an injection process for controlling the first robot arm and the second robot arm to inject the transfusion in the injector into the medicine container after the first weighing process and the first transfusion suctioning process complete. The third control means carries out the second weighing process and a stirring process for controlling the first robot arm to weigh the medicine container with the weighing device after the injection process completes in parallel with the second transfusion suctioning process. The transfusion weight capturing means captures a difference between a weighing result from the first weighing process and a weighing result from the second weighing process as a weight of the transfusion injected into the medicine container.

According to the co-infusion configured as described above, it becomes possible to shorten a required time for the co-infusion process and measure the weight of the transfusion injected into the medicine. Particularly, according to the co-infusion apparatus, it is possible to weigh the object such as the medicine container and the injector, which is a weighing object, in a state that the object is held by the first robot arm. Thus, it is possible to omit, for example, a working process for setting the object on the weighing device, a working process for again holding the object set on the weighing device after the object is weighed or the like, thereby significantly shortening the required time for the co-infusion process.

Here, it may be considered that the third control means concurrently carries out the second weighing process carried out for one medicine container and a second transfusion suctioning process for controlling the second robot arm to suction the transfusion to be injected from the transfusion container into another medicine container with the injector. With this configuration, it is possible to more shorten the required time for the co-infusion process in the case where a plurality of medicine containers are used in the co-infusion process.

Further, it may be considered that the first control means carries out the second weighing process for the one medicine container and the first weighing process for the other medicine container in parallel with the second transfusion suctioning process. With this configuration, it is possible to more shorten the required time for the co-infusion process in the case where the plurality of medicine containers are used in the co-infusion process.

Further, in a configuration in which the co-infusion apparatus further includes a stirring device being capable of stirring the medicine container, it may be considered that the third control means carries out a stirring process for controlling the first robot arm to allow the stirring device to stir the medicine container after the second weighing process completes in parallel with the second transfusion suctioning process. With this configuration, it is possible to more shorten the required time for the co-infusion process in the case where the plurality of medicine containers are used in the co-infusion process.

In the case where the stirring device is capable of simultaneously stirring a plurality of predetermined medicine containers, it may be considered that the second control means starts the injection process on condition that the stirring device is available. With this configuration, it is possible to suppress poor dissolution or the like caused by coagulation of the medicine in the medicine container generated when the medicine is left in a long term as it is after the transfusion is injected into the medicine container.

Further, it may be considered that the co-infusion apparatus further includes a suctioning amount setting means for setting an amount of medicinal solution to be suctioned from the medicine container with the injector based on the weight of the transfusion captured by the transfusion weight capturing means. With this configuration, it is possible to set the amount of the medicinal solution based on the weight of the transfusion injected into the medicine container in practice. As a result, it becomes unnecessary to extra suction the medicinal solution with the injector.

Further, it may be considered that the co-infusion apparatus further includes a fourth control means for changing an insertion position of an injection needle of the injector with respect to a rubber plug of the medicine container for every time if the injection needle of the injector is inserted into the rubber plug of the medicine container multiple times. With this configuration, it is possible to suppress occurrence of a core ring compared with the case where the injection needle of the injector is inserted into the rubber plug of the medicine container at one position or in the vicinity of the one position multiple times, thereby suppressing liquid leakage from the medicine container.

Further, it may be considered that the insertion position contains a plurality of insertion positions separated from each other in a radial direction on the rubber plug. With this configuration, it is possible to set the insertion position of the injection needle with respect to the rubber plug to be an insertion position differing each time regardless of a rotational position of the medicine container in a circumferential direction thereof.

On the other hand, it may be considered that the co-infusion apparatus further includes a rotation driving means, a container reading means and a container position adjusting means. The rotation driving means is capable of rotating the medicine container in a circumferential direction. The container reading means is capable of reading medicine information from the medicine container rotated by the rotation driving means. The container position adjusting means is capable of allowing the rotation driving means to stop the rotation of the medicine container at the time when the medicine information is read by the container reading means or for allowing the rotation driving means to rotate the medicine container by a rotation amount predetermined for each medicine container and then stopping the rotation of the medicine container after the medicine information is read by the container reading means. In this case, it may be considered that the fourth control means sets the inserting position differing each time that the injection needle is inserted into the rubber plug based on a rotation stop position of the medicine container at the time when the rotation is stopped by the container position adjusting means. With this configuration, it is possible to set the insertion position of the injection needle with respect to the rubber plug to be the insertion position differing each time regardless of the rotational position of the medicine container in the circumferential direction thereof.

Further, the following configuration may be considered as another example of the configuration in which the co-infusion apparatus further includes a rotation driving means, a container reading means and a container position adjusting means. Specifically, the rotation driving means is capable of rotating the medicine container in a circumferential direction. The container reading means is capable of reading medicine information from the medicine container rotated by the rotation driving means. The container position adjusting means is capable of allowing the rotation driving means to stop the rotation of the medicine container at the time when the medicine information is read by the container reading means or allowing the rotation driving means to rotate the medicine container by a rotation amount predetermined for each medicine container and then stop the rotation of the medicine container after the medicine information is read by the container reading means. Furthermore, it may be considered that the fourth control means allows the container position adjusting means to change a rotation stop position of the medicine container for every time that the injection needle is inserted into the rubber plug. In this case, it is also possible to the insertion position of the injection needle with respect to the rubber plug to be the insertion position differing each time regardless of the rotational position of the medicine container in the circumferential direction thereof.

Further, the present invention relates to a co-infusion method being capable of suctioning transfusion from a transfusion container with an injector and injecting the transfusion into a medicine container. The co-infusion method may be considered as a co-infusion method including (1) concurrently carrying out a first weighing process for controlling a first robot arm being capable of holding and transferring the medicine container to weigh the medicine container with a weighing device provided in a movable range of the first robot arm or on the first robot arm and a first transfusion suctioning process for controlling a second robot arm being capable of holding and transferring the injector and handling the injector to suction the transfusion from the transfusion container with the injector, (2) carrying out an injection process for controlling the first robot arm and the second robot arm to inject the transfusion in the injector into the medicine container after the first weighing process and the first transfusion suctioning process complete, (3) carrying out a second weighing process for controlling the first robot arm to weigh the medicine container with the weighing device after the injection process completes and (4) capturing a difference between a weighing result from the first weighing process and a weighing result from the second weighing process as a weight of the transfusion injected into the medicine container.

Further, the present invention relates to a co-infusion apparatus being capable of suctioning transfusion from a transfusion container with an injector and injecting the transfusion into a medicine container. The co-infusion apparatus includes a first robot arm, a second robot arm, a fifth control means and a photographing control means. The first robot arm is capable of holding and transferring the medicine container. The second robot arm is capable of holding and transferring the injector and handling the injector. The fifth control means carries out an injection process for controlling the first robot arm and the second robot arm to inject the transfusion into the medicine container with the injector and a suctioning process for suctioning the transfusion from the medicine container with the injector. The photographing control means is capable of photographing a scale of the injector in a state that an injection needle of the injector is inserted into the medicine container after the transfusion is suctioned from the medicine container in the suctioning process. With this configuration, it becomes unnecessary to carry out a process for discharge extra air from the injector and a process for again suctioning extra air with the injector, thereby suppressing delay of the co-infusion process caused by a process for photographing the scale of the injector.

Specifically, it may be considered that the suctioning process includes suctioning the transfusion from the medicine container with the injector in a state that a rubber plug of the medicine container is directed toward a lower side and the injection needle of the injector is directed toward an upper side, inverting vertical positions of the injector and the medicine container in a state that the injection needle of the injector is inserted into the medicine container and pulling the injection needle of the injector from the medicine container after the injector suctions air in a predetermined amount. Further, it may be considered that the photographing control means allows the scale of the injector to be photographed before the injector suctions the air in the predetermined amount after the vertical positions of the injector and the medicine container are inverted in a state that the injection needle of the injector is inserted into the medicine container.

Further, the present invention relates to a co-infusion method being capable of suctioning transfusion from a transfusion container with an injector and injecting the transfusion into a medicine container. The co-infusion method may be considered as a method including carrying out an injection process for controlling a first robot arm being capable of holding and transferring the medicine container and a second robot arm being capable of holding and transferring the injector and handling the injector to inject the transfusion into the medicine container with the injector and a suctioning process for suctioning the transfusion from the medicine container with the injector and photographing a scale of the injector in a state before an injection needle of the injector is pulled from the medicine container after the transfusion is suctioned from the medicine container in the suctioning process.

Further, the present invention relates to a co-infusion apparatus including a second driving means, a gripping member, a sixth control means and a seventh control means. The second driving means is capable of handling a plunger of an injector. The gripping member grips a syringe of the injector in a direction perpendicular to a handling direction of the plunger. The sixth control means controls the second driving means in a state that an aperture of a medicine container is directed toward an upper side and a tip end of the injector is directed toward a lower side to alternately carry out a first replacement process for allowing the injector to suction air from the medicine container and a second replacement process for injecting the transfusion in the injector into the medicine container. The seventh control means changes at least one of a pulling speed of the second driving means for pulling the plunger, an acceleration at the time of staring to pull the plunger and a pulling amount of the plunger in the first replacement process according to the number of executions of the first replacement process. With this configuration, it is possible to enable the co-infusion apparatus to adjust the pulling speed for pulling the plunger, the acceleration at the time of staring to pull the plunger or the pulling amount of the plunger in the first replacement process so that, for example, force for pulling the plunger does not exceed gripping force of the gripping member for the syringe.

More specifically, it may be considered that the seventh control means increases the acceleration at the time of staring to pull the plunger in a step-by-step manner along with an increase of the number of executions of the first replacement process. With this configuration, it is possible to prevent a position gap of the syringe and shorten a required time for the injection process, thereby shortening a required time for a co-infusion action.

Further, it may be considered that the seventh control means increases the pulling amount of the plunger in a step-by-step manner along with an increase of the number of executions of the first replacement process. With this configuration, it is possible to prevent the position gap of the syringe and increase a suctioning amount at one time in the first replacement process, thereby reducing a repeat count of the first replacement process. As a result, it is possible to shorten the required time for the injection process and the required time for the co-infusion action.

Further, it may be considered that the seventh control means increases the pulling speed for pulling the plunger in a step-by-step manner along with an increase of the number of executions of the first replacement process. In this case, it is also possible to prevent the position gap of the syringe and shorten the required time of the injection process, thereby shortening the required time of the co-infusion action.

Further, the present invention may be considered as a co-infusion method. The co-infusion method includes controlling second driving means being capable of handling a plunger of an injector in a state that an aperture of a medicine container is directed toward an upper side, a tip end of the injector is directed toward a lower side and a syringe of the injector is gripped by a gripping member for gripping the syringe of the injector in a direction perpendicular to a handling direction of the plunger of the injector to alternately carry out a first replacement process for allowing the injector to suction air from the medicine container and a second replacement process for injecting the transfusion in the injector into the medicine container and changing at least one of a pulling speed of the second driving means for pulling the plunger, an acceleration at the time of staring to pull the plunger and a pulling amount of the plunger in the first replacement process according to the number of executions of the first replacement process.

Further, the present invention relates to a co-infusion apparatus including a second driving means, a gripping member, a sixth control means and an eighth control means. The second driving means is capable of handling a plunger of an injector. The gripping member grips a syringe of the injector in a direction perpendicular to a handling direction of the plunger. The sixth control means controls the second driving means in a state that an aperture of a medicine container is directed toward an upper side and a tip end of the injector is directed toward a lower side to alternately carry out a first replacement process for allowing the injector to suction air from the medicine container and a second replacement process for injecting the transfusion in the injector into the medicine container. The eighth control means changes at least one of a pulling speed of the second driving means for pulling the plunger, an acceleration at the time of staring to pull the plunger and a pulling amount of the plunger in the first replacement process according to an expansion rate of air in the syringe at the time of pulling the plunger. With the co-infusion apparatus having such a configuration, it is also possible to adjust the pulling speed for pulling the plunger, the acceleration at the time of staring to pull the plunger or the pulling amount of the plunger in the first replacement process so that, for example, force for pulling the plunger does not exceed gripping force of the gripping member for the syringe.

Further, the present invention may be considered as a co-infusion method. The co-infusion method includes controlling second driving means being capable of handling a plunger of an injector in a state that an aperture of a medicine container is directed toward an upper side, a tip end of the injector is directed toward a lower side and a syringe of the injector is gripped by a gripping member for gripping the syringe of the injector in a direction perpendicular to a handling direction of the plunger of the injector to alternately carry out a first replacement process for allowing the injector to suction air from the medicine container and a second replacement process for injecting the transfusion in the injector into the medicine container and changing at least one of a pulling speed of the second driving means for pulling the plunger, an acceleration at the time of staring to pull the plunger and a pulling amount of the plunger in the first replacement process according to an expansion rate of air in the syringe at the time of pulling the plunger. With this configuration, it is possible to enable the co-infusion apparatus to adjust the pulling speed for pulling the plunger, the acceleration at the time of staring to pull the plunger or the pulling amount of the plunger in the first replacement process so that, for example, force for pulling the plunger does not exceed gripping force of the gripping member for the syringe.

Further, the present invention relates to a co-infusion apparatus including a cap attaching and detaching means, a second driving means, a third driving means, a sixth control means and a ninth control means. The cap attaching and detaching means is used for detaching a cap of an injection needle of an injector and capable of holding the cap detached from the injector. The second driving means is capable of handling the injector. The third driving means is capable of transferring one or both of the injector and the cap attaching and detaching means to an arbitrary position. The sixth control means controls the second driving means in a state that an aperture of a medicine container is directed toward an upper side and a tip end of the injector is directed toward a lower side to alternately carry out a first replacement process for allowing the injector to suction air from the medicine container and a second replacement process for injecting the transfusion in the injector into the medicine container. The ninth control means for controlling the third driving means to insert an injection needle of the injector into the cap held by the cap attaching and detaching means and controlling the second driving means to discharge air existing in the injector after the transfusion in the injector is injected into the medicine container by the sixth control means. With this configuration, it is possible to carry out the discharge of the air in a state that the injection needle is inserted into the cap, thereby limiting scatter of the medicinal solution within the cap even if the medicinal solution scatters from the injection needle.

Further, the present invention may be considered as a co-infusion method to be carried out by a co-infusion apparatus including a cap attaching and detaching means used for detaching a cap of an injection needle of an injector and being capable of holding the cap detached from the injector, a second driving means being capable of handling the injector and a third driving means being capable of transferring one or both of the injector and the cap attaching and detaching means to an arbitrary position. The co-infusion apparatus includes controlling the second driving means in a state that an aperture of a medicine container is directed toward an upper side and a tip end of the injector is directed toward a lower side to alternately carry out a first replacement process for allowing the injector to suction air from the medicine container and a second replacement process for injecting the transfusion in the injector into the medicine container and controlling the third driving means to insert an injection needle of the injector into the cap held by the cap attaching and detaching means and controlling the second driving means to discharge air existing in the injector after the transfusion in the injector is injected into the medicine container by the above process. With this configuration, it is possible to carry out the discharge of the air in a state that the injection needle is inserted into the cap, thereby limiting scatter of the medicinal solution within the cap even if the medicinal solution scatters from the injection needle.

Further, the present invention relates to a co-infusion apparatus including a first driving means, a second driving means, a tenth control means and an eleventh control means. The first driving means is capable of transferring one or both of an injector and a medicine container to an arbitrary position. The second driving means is capable of handling the injector. The tenth control means controls the second driving means in a state that an aperture of the medicine container is directed toward a lower side and a tip end of the injector is directed toward an upper side to carry out a suctioning process for suctioning transfusion from the medicine container with the injector. The eleventh control means controls the first driving means to decrease an insertion amount of an injection needle of the injector with respect to the medicine container in a step-by-step manner in the suctioning process along with a decrease of an amount of the transfusion in the medicine container. With this configuration, it is possible to reliably allow the injection needle to penetrate into the medicine container and suction the medicinal solution in the medicine container with preventing the medicinal solution from remaining in the medicine container.

Further, the present invention may be considered as a co-infusion method carried out by a co-infusion apparatus including a first driving means being capable of transferring one or both of an injector and a medicine container to an arbitrary position and a second driving means being capable of handling the injector. The co-infusion method includes controlling the second driving means in a state that an aperture of the medicine container is directed toward a lower side and a tip end of the injector is directed toward an upper side to carry out a suctioning process for suctioning transfusion from the medicine container with the injector and controlling the first driving means to decrease an insertion amount of an injection needle of the injector with respect to the medicine container in a step-by-step manner in the suctioning process along with a decrease of an amount of the transfusion in the medicine container. With this configuration, it is possible to reliably allow the injection needle to penetrate into the medicine container and suction the medicinal solution in the medicine container with preventing the medicinal solution from remaining in the medicine container.

Effects of the Invention

According to the present invention, it is possible to achieve a co-infusion apparatus and a co-infusion method which can photograph an image being suitable for inspecting whether or not a co-infusion process is properly carried out by the co-infusion apparatus.

BRIEF DESCRIPTION OF THE DRAWINGS

FIG. 23 is another view showing one example of the positional relationship between the medicine container and the injector.

FIG. 24 is a view showing one example of a photographing result in the inspection control process carried out by the co-infusion apparatus according to the embodiment of the present invention.

FIG. 27 is a view showing one example of correspondence information defining a relationship between a standard volume and an acceptable range of the injector to be used in the co-infusion apparatus according to the embodiment of the present invention.

FIG. 34 is a view showing one example of transfusion information used in the co-infusion apparatus according to the embodiment of the present invention.

FIG. 49 is a view showing one example of an insertion position with respect to a rubber plug of the medicine container in the co-infusion apparatus according to the other embodiment of the present invention.

FIG. 59 is a view for explaining a suctioning process in the co-infusion apparatus according to the other embodiment of the present invention.

MODE FOR CARRYING OUT THE INVENTION

Hereinafter, description will be given to embodiments of the present invention with reference to the accompanying drawings for the purpose of understanding the present invention. It is to be noted that each of the following embodiments is described as one example embodying the present invention and is not intended for use in determining or limiting the technical scope of the present invention.

[First Embodiment]

First, description will be given to a first embodiment of the present invention with reference to FIGS. 1 to 38.

[Co-Infusion Apparatus 1]

Figure 1:
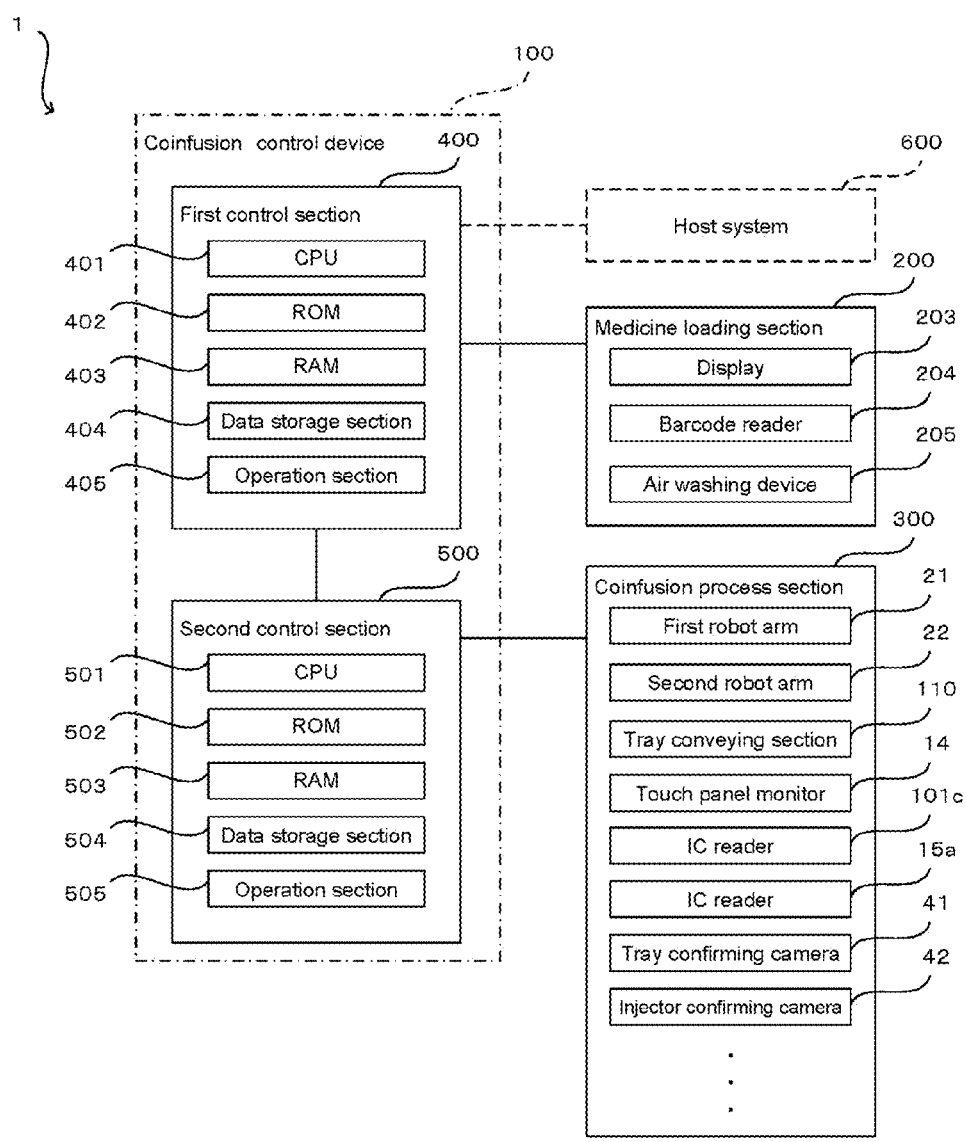
FIG. 1 is a block diagram showing a system configuration of a co-infusion apparatus according to an embodiment of the present invention.
Figure 2:
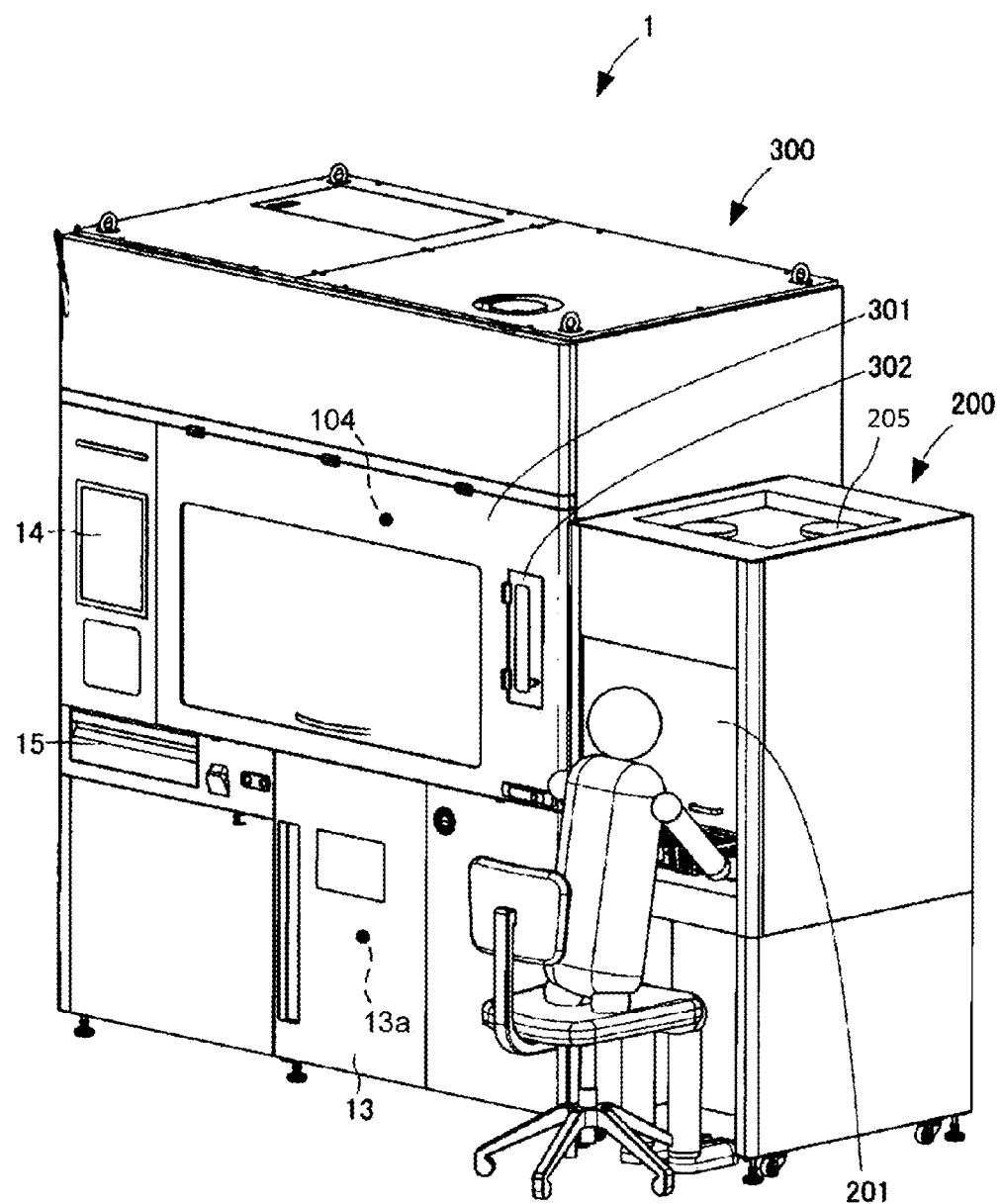
FIG. 2 is a perspective view showing an exterior view of the co-infusion apparatus according to the embodiment of the present invention.

As shown in FIGS. 1 and 2, a co-infusion apparatus 1 according to this embodiment includes a co-infusion control device 100, a medicine loading section 200 and a co-infusion process section 300. In the co-infusion apparatus 1, the co-infusion control device 100 controls an action of the co-infusion process section 300 to carry out a co-infusion process for injecting a medicine such as an anticancer medicine indicated in preparation data from one or more of medicine containers in which a predetermined amount of the medicine has been contained into a transfusion container.

[Co-infusion Control Device 100]

First, description will be given to a schematic configuration of the co-infusion control device 100 with reference to FIG. 1. The co-infusion control device 100 includes a first control section 400 and a second control section 500 which are communicatively connected with each other. The first control section 400 is provided on the side of the medicine loading section 200. The second control section 500 is provided on the side of the co-infusion process section 300.

It is to be noted that division of processes between the first control section 400 and the second control section 500 described in this embodiment is merely one example. Each step of the co-infusion process may be carried out by one of the first control section 400 and the second control section 500. Further, another configuration in which the co-infusion control device 100 includes one control section or three or more of control sections may be considered as another embodiment. Furthermore, a part or all of processes carried out by the first control section 400 and the second control section 500 may be carried out by an electronic circuit such as an ASIC and a DSP.

The first control section 400 can communicate with a host system 600 such as an electronic health record system and a preparation administration system for inputting the preparation data into the co-infusion apparatus 1. The preparation data is data for preparation produced based on prescription data or the prescription data itself. For example, the prescription data contains a date of issue of prescription, a patient ID, a patient name, a date of birth of patient, medicine information (such as a medicine code, a medicine name and a dosage of medicine), a dosage form (such as internal use and external use), usage information (such as three times a day after each meal), a type of medical care (such as an outpatient and a hospital admission), a diagnosis and treatment department, a hospital ward, a hospital room and the like. Further, the preparation data contains patient information, doctor information, medicine information, a prescription amount of medicine, a type of medicine container (such as an ampule containing medicinal solution, a vial bottle containing medicinal solution and a vial bottle containing a powdered medicine), preparation content information (such as types and the numbers of a medicine container, an injector and an injection needle used for the co-infusion process), preparation step information (such as a working content, a dissolving medicine, a solvent, a dissolving medicine amount, a solvent amount and a suctioning amount), a date of preparation, a category of prescription, a date of medication, a diagnosis and treatment department, a hospital ward, time of preparation and the like.

The first control section 400 is a personal computer including a CPU 401, a ROM 402, a RAM 403, a data storage section 404, an operation section 405 and the like. A variety of electronic components such as a display 203, a barcode reader 204 and an air washing device 205 described below and provided in the medicine loading section 200 are connected to the first control section 400.

The CPU 401 is a processor for executing processes according to a variety of control programs. The ROM 402 is a non-volatile memory in which programs such as a BIOS executed by the CPU 401 is preliminarily stored. The RAM 403 is a volatile memory or a non-volatile memory used for expansions of the variety of control programs by the CPU 401 and a temporary storage of data.

The data storage section 404 is a hard disk or the like for storing a variety of application programs executed by the CPU 401 and a variety of data. Specifically, the preparation data inputted from the host system 600 is stored in the data storage section 404.

The first control section 400 stores identification information for an after-mentioned tray 101 corresponding to each preparation data together with the preparation data inputted from the host system 600. For example, an association between the preparation data and the tray 101 is carried out by the first control section 400. Further, it may be considered that information for indicating a correspondence relationship between the preparation data and the tray 101 is inputted into the co-infusion apparatus 1 together with the preparation data.

Further, the data storage section 404 stores a variety of databases such as a medicine master, a patient master, a doctor master, a prescription category master, a diagnosis and treatment department master and a hospital ward master. For example, the medicine master contains information such as a medicine code, a medicine name, a JAN code (or an RSS), a medicine bottle code, a category (such as a dosage form: a powdered medicine, a medicinal tablet, medicinal water, a medicine for external use or the like), a specific weight, a type of medicine (such as a common medicine, an anticancer medicine, a poisonous medicine, a narcotic drug, a drastic medicine, an antipsychotic medicine and a curative medicine), a change upon mixing, an excipient medicine, a precaution statement, a type of medicine container (such as an ampule and a vial bottle), a contained amount (predetermined amount) of medicine per medicine container unit and a weight of medicine container.

Further, the data storage section 404 preliminarily stores a co-infusion control program for allowing the CPU 401 to execute a variety of processes. The co-infusion control program may be read by a reading device (not shown in the drawings) contained in the first control section 400 from a storage medium such as a CD, a DVD, a BD and a flash memory and installed into the data storage section 404.

The operation section 405 contains a variety of operation means such as a key board, a mouse and a touch panel for receiving a variety of user operations with respect to the first control section 400.

The second control section 500 is a personal computer including a CPU 501, a ROM 502, a RAM 503, a data storage section 504, an operation section 505 and the like. A variety of electronic components such as a first robot arm 21, a second robot arm 22, a tray conveying section 110, a touch panel monitor 14, an IC reader 101c, an IC reader 15a, a tray confirming camera 41 and an injector confirming camera 42 described below and provided in the co-infusion process section 300 are connected to the second control section 500.

The CPU 501 is a processor for executing processes according to a variety of control programs. The ROM 502 is a non-volatile memory in which programs such as a BIOS executed by the CPU 501 are preliminarily stored. The RAM 503 is a volatile memory or a non-volatile memory used for expansions of the variety of control programs by the CPU 501 and a temporary storage of data.

The data storage section 504 is a hard disk or the like for storing a variety of application programs executed by the CPU 501 and a variety of data. Specifically, the data storage section 504 preliminarily stores a co-infusion control program for allowing the CPU 501 to execute the co-infusion process described below or the like. The co-infusion control program may be read by a reading device (not shown in the drawings) contained in the second control section 500 from a storage medium such as a CD, a DVD, a BD and a flash memory and installed into the data storage section 504.

The present invention may be considered as an invention of a computer readable storage medium storing the co-infusion control program or the co-infusion control program for allowing the CPU 401 and the CPU 501 to execute the variety of processes in the co-infusion control device 100. Further, the present invention may be considered as an invention of a co-infusion method for carrying out each step of the co-infusion process in the co-infusion apparatus 1.

The operation section 505 contains a variety of operation means such as a key board, a mouse and a touch panel for receiving a variety of user operations with respect to the second control section 500.

[Medicine Loading Section 200]

Next, description will be given to a schematic configuration of the medicine loading section 200 with reference to FIGS. 2 and 3.

Figure 3:
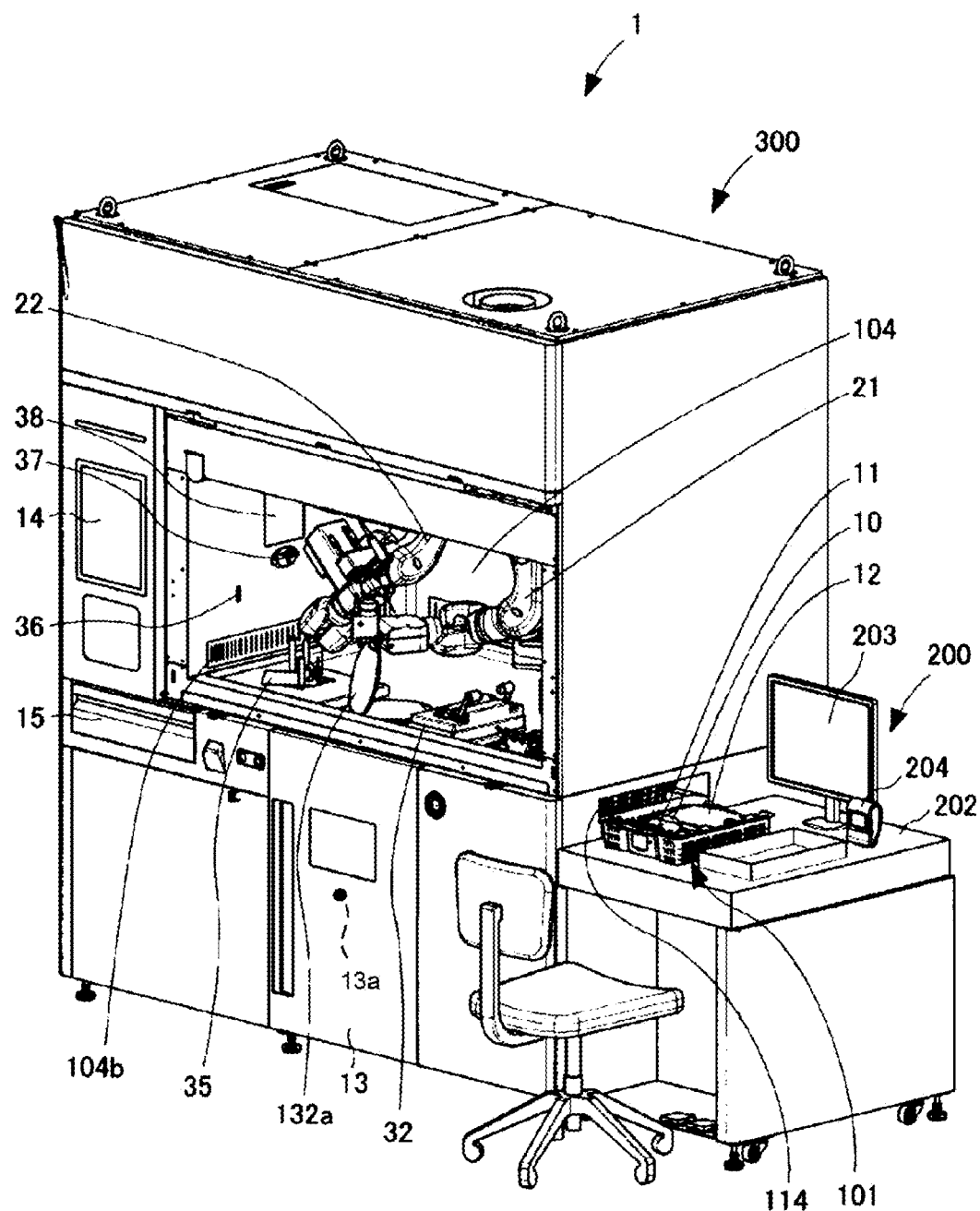
FIG. 3 is a perspective view showing a state that a main door of the co-infusion apparatus according to the embodiment of the present invention is opened.

As shown in FIGS. 2 and 3, the medicine loading section 200 is a clean bench including a door 201, a work table 202, a display 203, a barcode reader 204 and an air washing device 205. As shown in FIG. 3, the medicine loading section 200 is communicated with the co-infusion process section 300 through a tray insertion port 114 provided on a side surface of the co-infusion process section 300.

The display 203 is a display means such as a liquid crystal display and an organic EL display for displaying a variety of information according to a control instruction from the first control section 400. Specifically, the preparation data for a prospective objection of the co-infusion process in the co-infusion apparatus 1 or the like is displayed on the display 203. The barcode reader 204 reads a barcode written on a prescription, a preparation instruction paper or the like to input a content of the barcode into the first control section 400. The air washing device 205 supplies air into the medicine loading section 200 through a predetermined filter.

Figure 5:
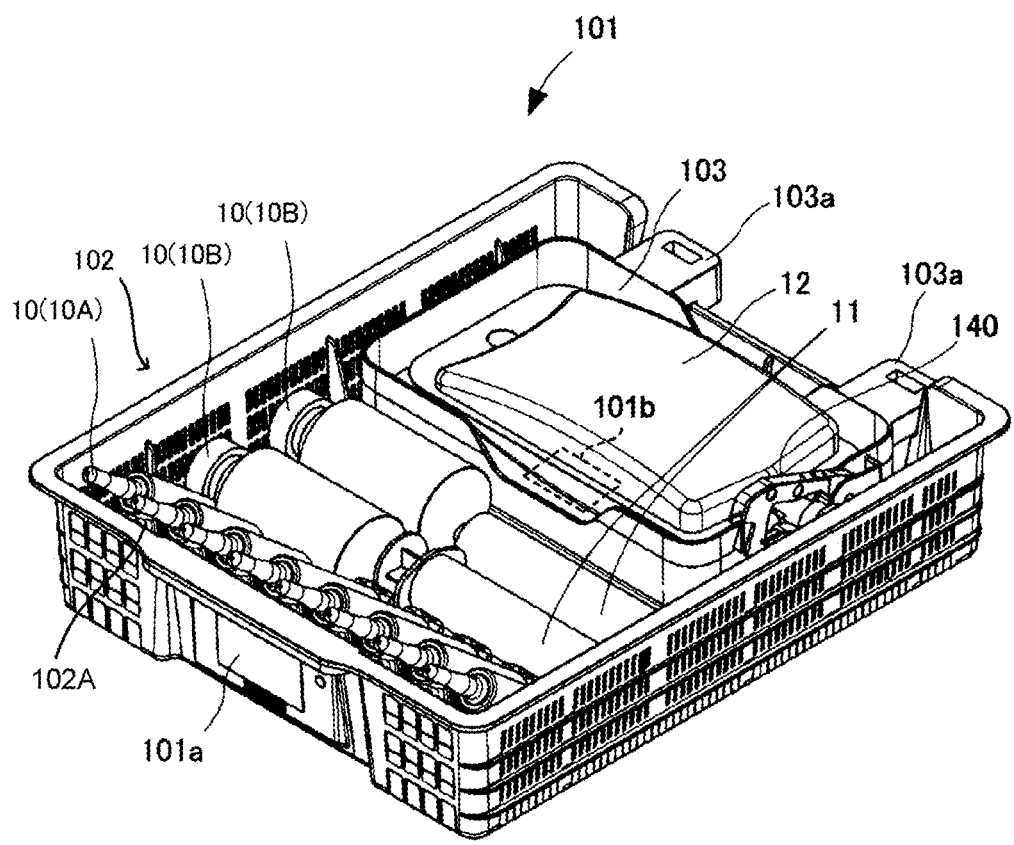
FIG. 5 is a perspective view showing a tray to be used in the co-infusion apparatus according to the embodiment of the present invention.

The door 201 is provided on a front surface of the medicine loading section 200 and can be opened and closed in a vertical direction. A user carries out a preliminary work for the co-infusion process carried out by the co-infusion apparatus 1 in a state that the user puts hands (or a hand) thereof in the medicine loading section 200 through the door 201 slightly opened as shown in FIG. 2. Specifically, a medicine container 10, an injector 11, a transfusion bag 12 (one example of a transfusion container) and the like used in the co-infusion process carried out by the co-infusion apparatus 1 are contained in the tray 101 placed on the word table 202 as shown in FIG. 5. The preliminary work contains, for example, a loading work for placing the medicine container 10, the injector 11 and the transfusion bag 12 at arbitrary positions in the tray 101 to load the tray 101 into the co-infusion process section 300. Hereinafter, the medicine container 10 is referred to as "ampule 10A" when an ampule is used as the medicine container 10. Alternatively, the medicine container 10 is referred to as "vial bottle 10B" when a vial bottle is used as the medicine container.

As shown in FIG. 5, the tray 101 includes an electronic paper 101a on which characters such as a patient name and an application method are displayed and an IC tag 101b (one example of a storage medium) such as an RFID (Radio Frequency Identification) tag to/from which a variety of information can be written and read. The IC tag 101b stores identification information for identifying the tray 101.

Further, the tray 101 includes an object placing member 102 (see FIG. 9) on which the medicine container 10 and the injector 11 (including a syringe 11a and an injection needle 11c) are placed and a transfusion bag holding member 103 (see FIG. 5) for holding the transfusion bag 12. The object placing member 102 and the transfusion bag holding member 103 can be separately attached and detached to/from the tray 101.

As shown in FIG. 5, a supporting member 102A for supporting the ampule 10A in a state that the ampule 10A is inclined is provided on the object placing member 102. The ampule 10A is set on the supporting member 102A so that the ampule 10A is obliquely inclined. With this configuration, it is possible to prevent a medicine in the ampule 10A from remaining at a neck portion of the ampule 10A. Further, in addition to the ampule 10A, the injection needle 11c of the injector 11 or the like may be also set on the supporting member 102A so that the injection needle 11c is obliquely inclined.

The injection needle 11c contains an injection needle having a syringe filter. Specifically, the injection needle having the syringe filter is used in the case of using the ampule 10A in order to prevent pieces generated at the time of breaking the neck portion of the ampule 10A from being injected into the transfusion bag 12 from the injector 11 or prevent the pieces from flowing into the injector 11. The syringe filter is a filter generally referred to as "top-shaped filter" and has a function of preventing foreign substances other than the medicine from passing through the filter. For example, a syringe filter made by Nihon Pall Ltd. is generally known.

Figure 9:
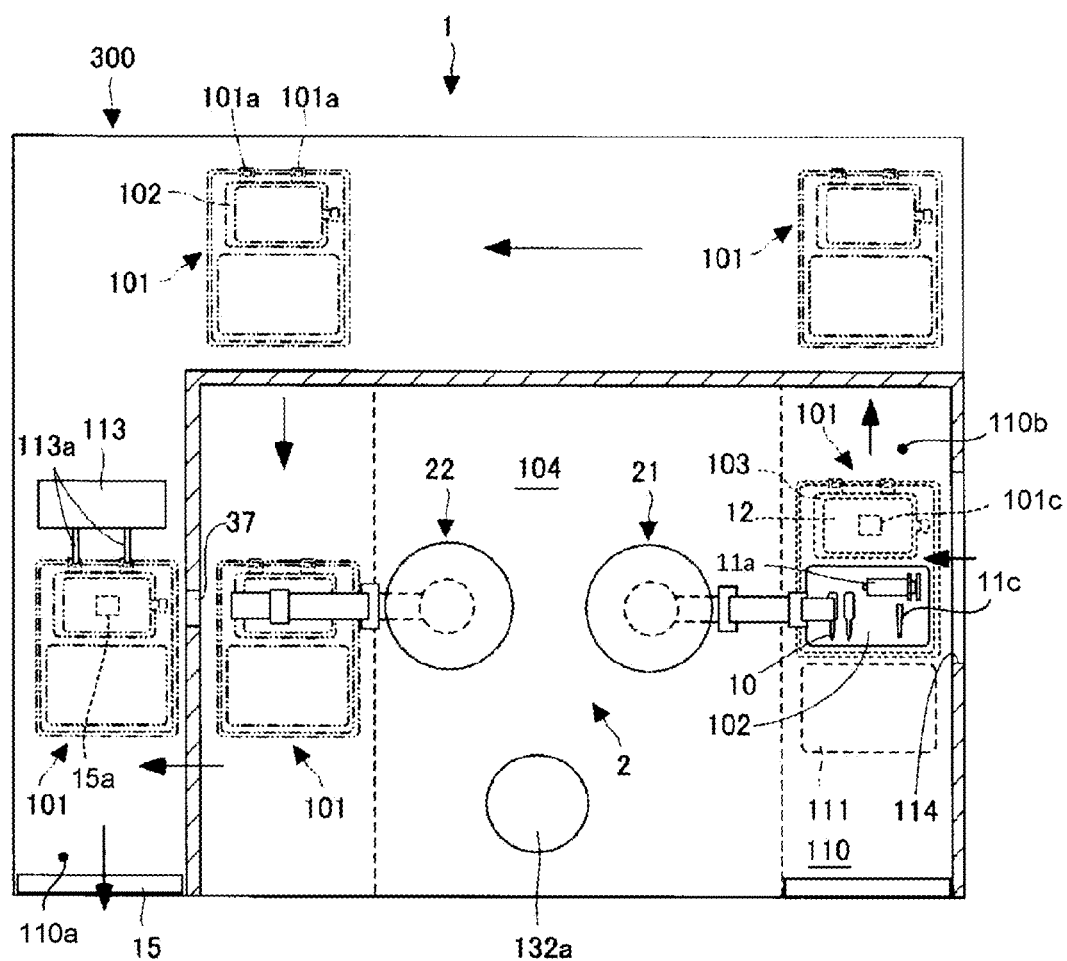
FIG. 9 is a planar schematic view showing a tray conveying section of the co-infusion apparatus according to the embodiment of the present invention.

On the other hand, the vial bottle 10B and the injector 11 are set on the object placing member 102 so that the vial bottle 10B and the injector 11 are laid down on the object placing member 102 as shown in FIGS. 5 and 9. At this time, the injector 11 is in a separated state that the syringe 11a and the injection needle 11c are separated from each other. Of course, this arrangement configuration in the object placing member 102 described here is merely one example, thus the arrangement configuration of the present invention is not limited thereto.

Further, as shown in FIG. 5, a chuck member 140 for fixing a co-infusion port (neck portion) of the transfusion bag 12 is provided in the transfusion bag holding member 103. In the preliminary work, the user sets the transfusion bag 12 on the transfusion bag holding member 103 in a state that the transfusion bag 12 is held by the chuck member 140. Furthermore, an engagement hole portion 103a used for moving up and down the transfusion bag holding member 103 is provided in the transfusion bag holding member 103.

The tray 101 is fed into the co-infusion process section 300 through the tray insertion port 114 after the user sets the medicine container 10, the injector 11 and the transfusion bag 12 on the tray 101. Further, it may be considered that the medicine loading section 200 includes a conveying mechanism such as a conveyor belt for automatically conveying the tray 101 into the co-infusion process section 300.

[Co-infusion Process Section 300]

Next, description will be given to a schematic configuration of the co-infusion process section 300.

Figure 4:
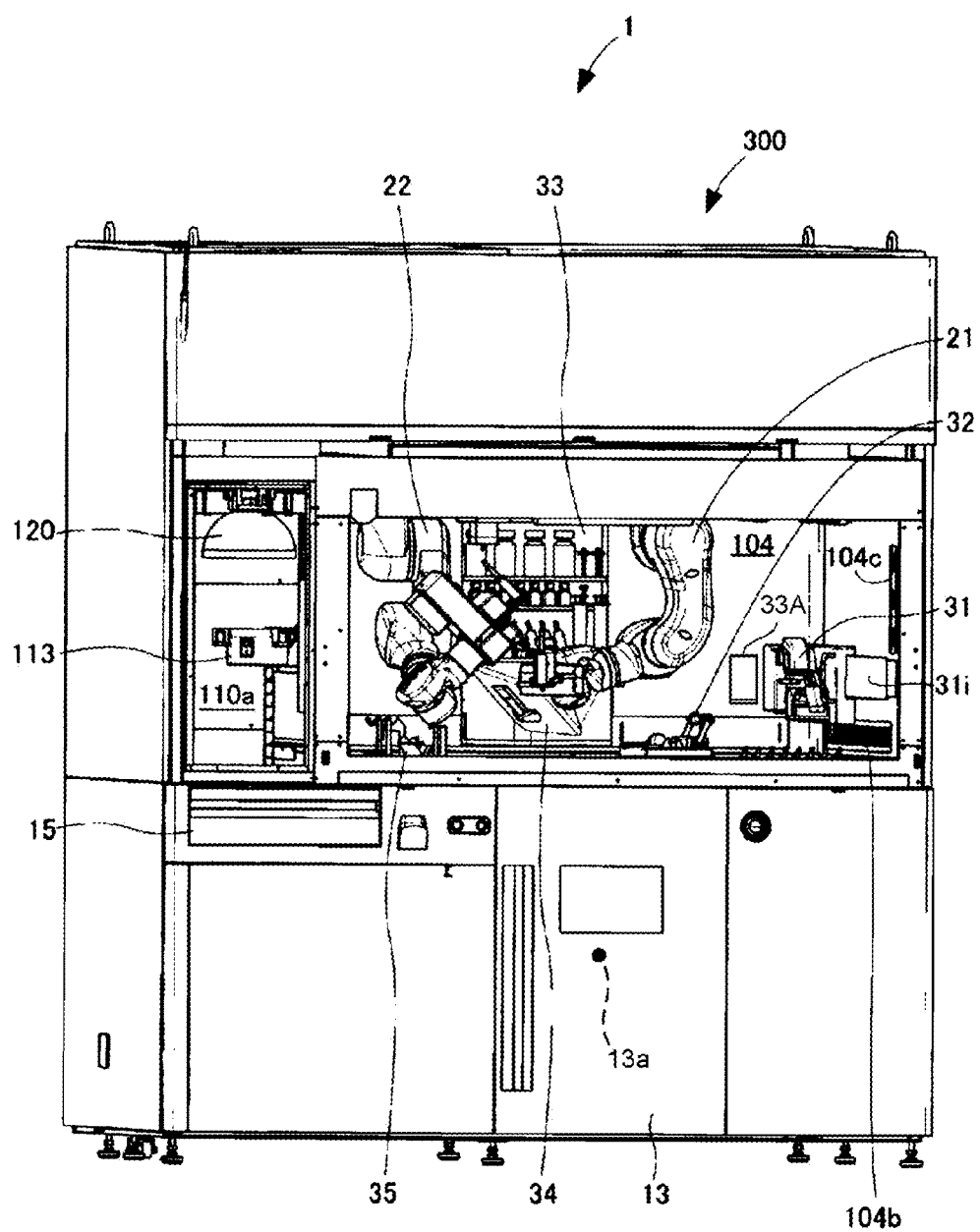
FIG. 4 is a front view showing a state that the main door and a part of a front wall of the co-infusion apparatus according to the embodiment of the present invention are removed.

As shown in FIGS. 2 to 4, a main door 301, an injector removing door 302, a waste containing chamber door 13, a touch panel monitor 14, a tray discharge port 15 and the like are provided on a front surface of the co-infusion process section 300.

For example, the main door 301 is opened and closed to access into a co-infusion process chamber 104 provided in the co-infusion process section 300 at the time of cleaning an inside of the co-infusion process chamber 104 or the like. Further, the co-infusion apparatus 1 can dispense the injector 11 filled with the medicine as well as the transfusion bag 12 in which the medicine has been injected. The injector removing door 302 is opened and closed at the time of removing the injector 11 from the co-infusion process chamber 104.

The waste containing chamber door 13 is opened and closed to remove a waste such as the medicine container and the injector 11 after used in the co-infusion process in the co-infusion process chamber 104 from a waste containing chamber 13a in which the waste is contained. Further, the tray discharge port 15 is opened and closed to remove the tray 101 on which the transfusion bag 12 is placed after the medicine has been coinfused into the transfusion bag 12 in the co-infusion process in the co-infusion process chamber 104.

The touch panel monitor 14 is a display means such as a liquid crystal display and an organic EL display for displaying a variety of information according to a control instruction from the second control section 500. The touch panel monitor 14 can display an image or a movie photographed by, for example, a variety of cameras described below.

[Co-infusion Chamber 104]

As shown in FIGS. 3 and 4, the first robot arm 21, the second robot arm 22, an ampule cutter 31, a stirring device 32, a placing shelf 33, a placing member for rotation 33A, a medicine reading section 34, a weighing scale 35, a needle bending detecting section 36, a co-infusion communication port 37, a needle insertion confirming transparent window 38, a waste cover 132a and the like are provided in the co-infusion process chamber 104. Further, as shown in FIG. 6, a tray confirming camera 41, an injector confirming camera 42, an injection needle attaching and detaching device 43, a needle insertion confirming camera 44, sterilizing lamps 45 and the like are provided on the side of a ceiling of the co-infusion process chamber 104.

[First Robot Arm 21 and Second Robot Arm 22]

Each of the first robot arm 21 and the second robot arm 22 is a driving section having a multiple joint structure. Each of the first robot arm 21 and the second robot arm 22 is provided in the co-infusion process chamber 104 in a suspended state that a proximal portion of each of the first robot arm 21 and the second robot arm 22 is fixed on the side of the ceiling of the co-infusion process chamber 104. The number of joints of each of the first robot arm 21 and the second robot arm 22 is in the range of about 5 to 8. Further, in the co-infusion apparatus 1, each working process in the co-infusion process is carried out by a double arm constituted of the first robot arm 21 and the second robot arm 22. Specifically, the second control section 500 individually drives a driving motor provided in each joint of the first robot arm 21 and the second robot arm 22 to allow the first robot arm 21 and the second robot arm 22 to carry out each working process in the co-infusion process. In this regard, the co-infusion process section 300 may take, for example, a configuration having one robot arm, a configuration having three or more of robot arms or a configuration having no robot arm as long as it can carry out the co-infusion process.

Figure 6:
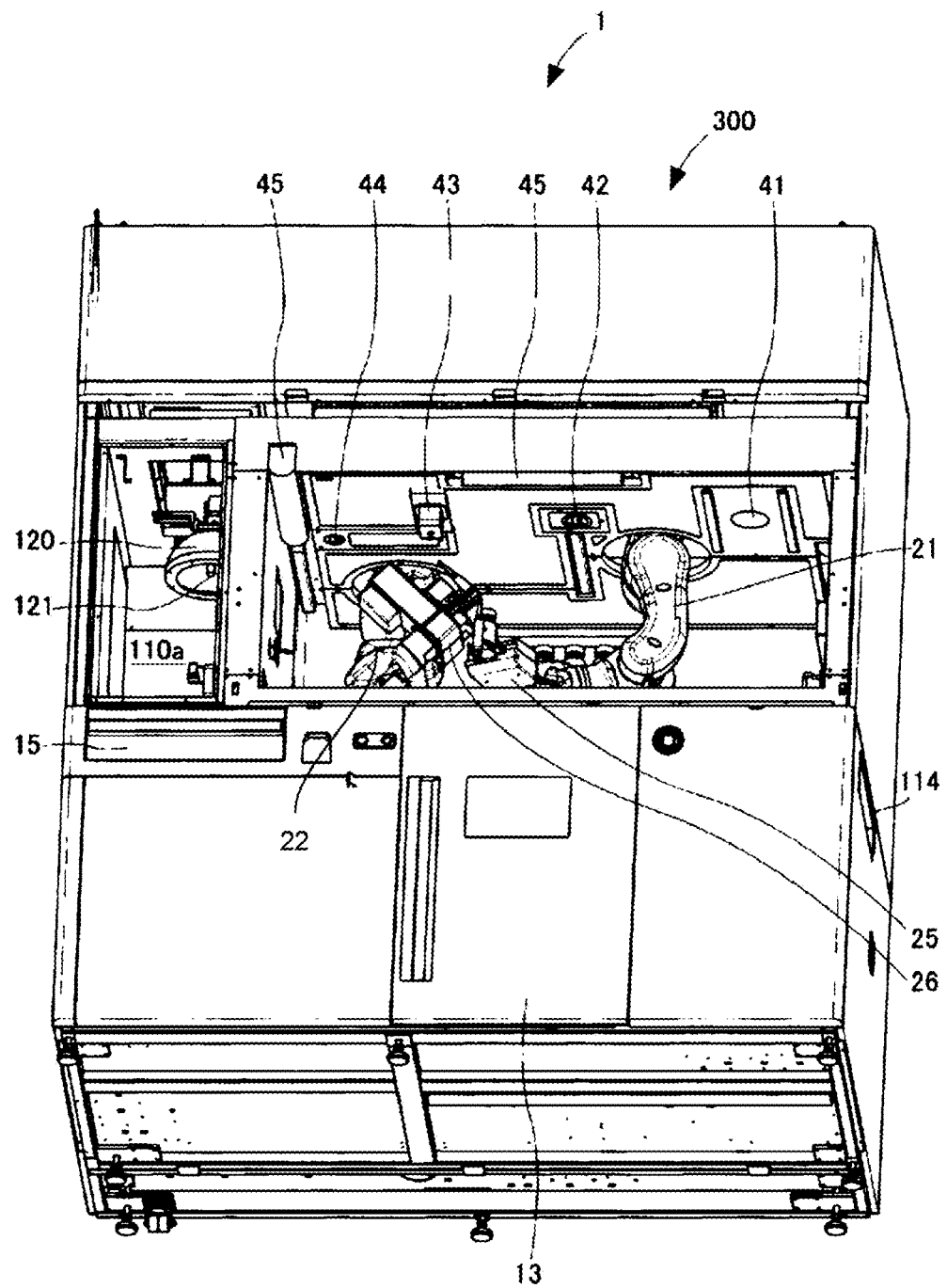
FIG. 6 is a perspective view obtained by seeing the co-infusion apparatus according to the embodiment of the present invention from a lower side.

As shown in FIG. 6, the first robot arm 21 includes a holding member 25 being capable of holding an object such as the medicine container 10 and the injector 11 and is capable of allowing the holding member 25 to be transferred to an arbitrary position within a predetermined movable range. The second robot arm 22 includes a holding member 26 being capable of holding the object such as the medicine container 10 and the injector 11 and carrying out operations for suctioning and injecting the medicine with the injector 11. Each of the first robot arm 21 and the second robot arm 22 is one example of a first driving means and the holding member 26 is one example of a second driving means. Further, the second robot arm 22 is capable of transferring the medicine container 10, the injector 11 or the like to an arbitrary position within a predetermined movable range thereof.

Figure 7:
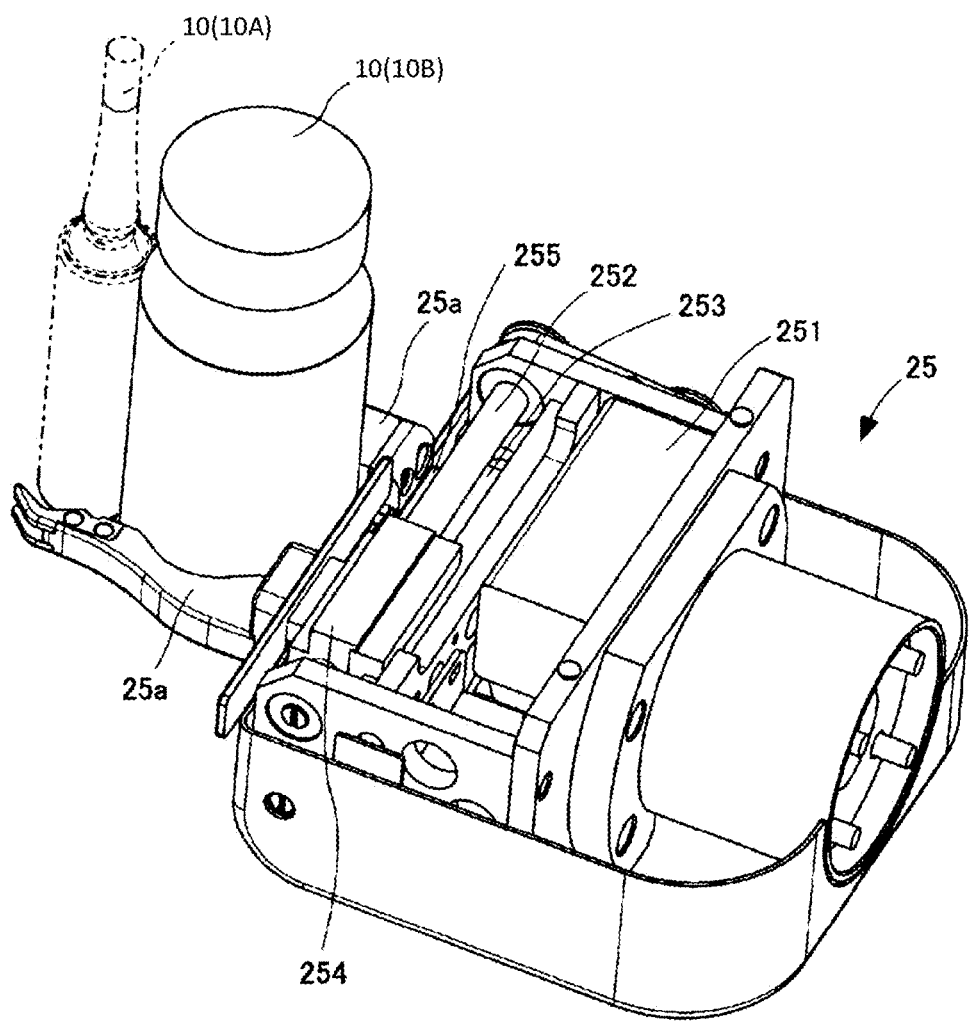
FIG. 7 is a perspective view showing a holding member of a first robot arm of the co-infusion apparatus according to the embodiment of the present invention.

As shown in FIG. 7, the holding member 25 of the first robot arm 21 includes a pair of gripping clicks 25a, a motor 251, two screw shafts 252, 253 to be rotated by the motor 251 and nut blocks 254, 255 respectively screwed with the screw shafts 252, 253. The gripping clicks 25a are respectively fixed to the nut blocks 254, 255. When the nut blocks 254, 255 are transferred by the rotations of the screw shafts 252, 253, the pair of gripping clicks 25a holds and releases the holding member 25 by getting the gripping clicks 25a closer and away from each other.

Further, the pair of gripping clicks 25a constitutes a gripping member having concave portions being suitable for holding the vial bottle 10B and concave portions being suitable for holding the ampule 10A provided on the side of a distal end thereof. Although a condition in which both of the ampule 10A and the vial bottle 10 are held by the gripping member is shown in FIG. 7, the gripping member grips one of the ampule 10A and the vial bottle 10B in practice.

Further, the holding member 25 can hold an injection needle having a cap or the injector 11 with the pair of gripping clicks 25a. In this regard, the second control section 500 can measure a diameter of the injector 11 based on a driving amount of the motor 251 at the time of holding the injector 11 with the pair of gripping clicks 25a of the holding member 25. Thus, the second control section 500 can determine whether or not the injector 11 matches with an injector designated in preparation content information of the preparation data.

Figure 8:
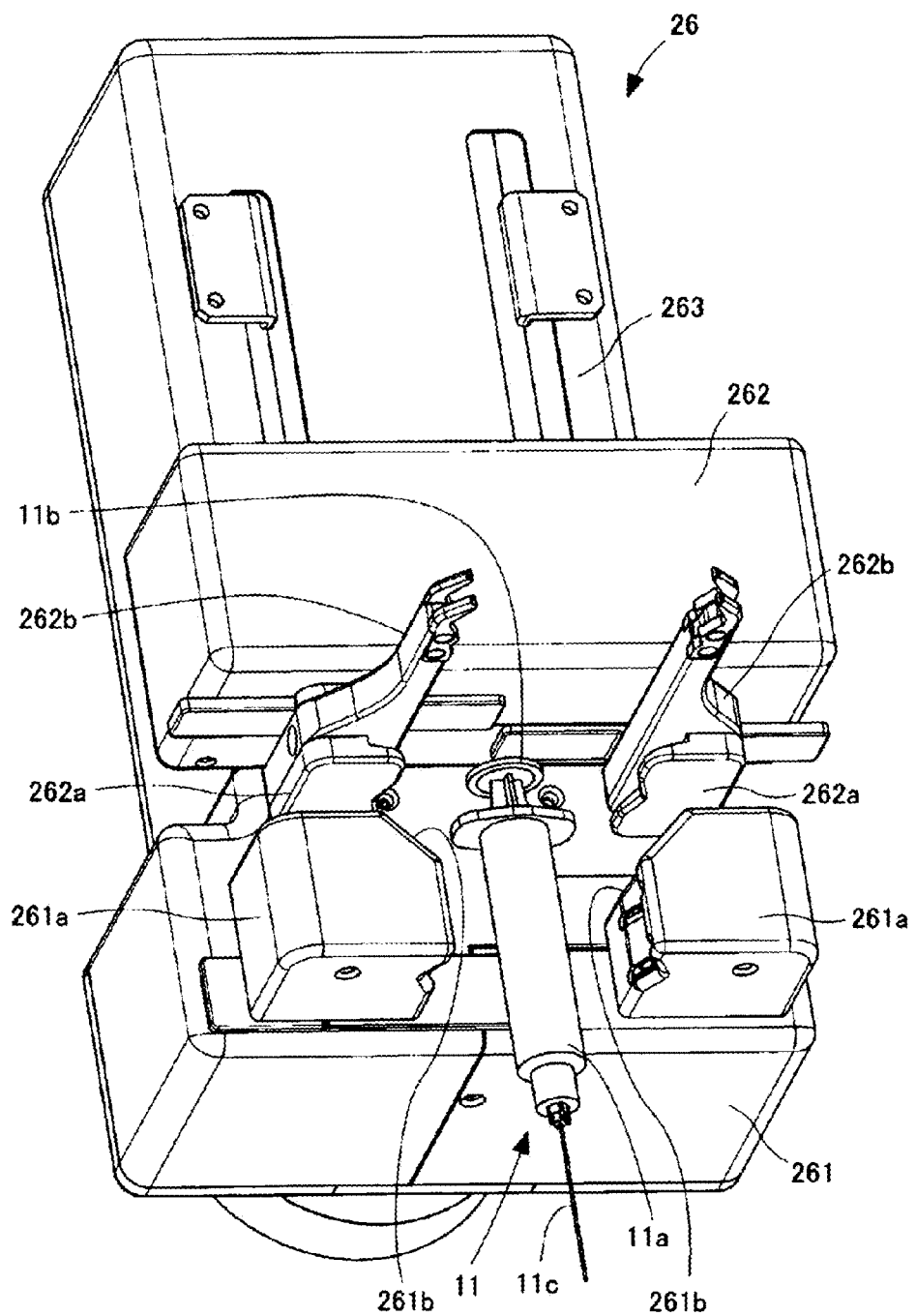
FIG. 8 is a perspective view showing a holding member of a second robot arm of the co-infusion apparatus according to the embodiment of the present invention.

As shown in FIG. 8, the holding member 26 of the second robot arm 22 includes an injector holding member 261, a plunger holding member 262 and a transferring member 263. The injector holding member 261 includes a pair of gripping clicks 261a for holding the syringe 11a of the injector 11. The pair of gripping clicks 261a constitutes a gripping member for holding and releasing the syringe 11a of the injector 11 by getting the pair of gripping clicks 261a closer and away from each other with the same mechanism as a driving mechanism used in the holding member 25. Further, on opposite surfaces of the pair of gripping clicks 261a facing with each other, inclining portions 261b downwardly inclining from upper end surfaces of the gripping clicks 261a toward the opposite surfaces of the gripping clicks 261a are formed.

The plunger holding member 262 includes a pair of gripping clicks 262a for holding a flange portion of a plunger 11b of the injector 11. The pair of gripping clicks 262a constitutes a gripping member for holding and releasing the flange portion of the plunger 11b of the injector 11 by getting the pair of gripping clicks 262a closer and away from each other with the same mechanism as the driving mechanism used in the holding member 25. Gripping clicks 262b are fixed on an upper surface of each of the gripping clicks 262a. The gripping clicks 262b constitute a gripping member for holing other objects such as the medicine container 10 in addition to the injector 11 by getting the pair of gripping clicks 262b closer and away from each other. Further, concave portions for receiving the flange portion of the plunger 11b are formed on upper surfaces of opposite surfaces of the pair of the gripping clicks 262a. Furthermore, tip ends of the pair of gripping clicks 262b protrude toward a more front side more than the pair of gripping clicks 262a. This makes it possible to easily hold an object such as the ampule 10A and the vial bottle 10B with the pair of gripping clicks 262b. In this regard, the gripping clicks 262b may be provided on the gripping clicks 261a.

The transferring member 263 is capable of transferring the plunger holding member 262 in a transferring direction of the plunger 11b of the injector 11. The transferring member 263 transfers the plunger 11b with a driving mechanism such as a motor, a screw shaft rotated by the motor, a nut block screwed with the screw shaft and a guide. The plunger holding member 262 is fixed to the nut block and transferred due to movement of the nut block.

[Tray Conveying Section 110]

A tray conveying section 110 is provided in the co-infusion process section 300. The tray conveying section 110 is used for conveying the tray 101 fed through the tray insertion port 114 provided in a right side end portion of the co-infusion process section 300 in FIG. 6 to a tray conveying terminal portion 110a provided in a left side end portion of the co-infusion process section 300.

FIG. 9 is a planar schematic view showing one example of a conveying path for the tray 101 in the tray conveying section 110. In this regard, pressure in the tray conveying section 110 is set more positive than pressure in the co-infusion process chamber 104. As shown in FIG. 9, the tray conveying section 110 is provided so as to convey the tray 101 with allowing the tray 101 to pass through a rear side of the waste containing chamber 13a located below the co-infusion process chamber 104 and under the waste cover 132a. This makes it possible to access the waste containing chamber 13a from a front side of the co-infusion apparatus 1. Although some of the trays 101 transferred in the tray conveying section 110 are depicted with a dashed-two dotted line in FIG. 9 in order to indicate the conveying path in the tray conveying section 110, this should not be interpreted to mean that a plurality of trays 101 may simultaneously exist in the tray conveying section 110.

An IC reader 101c and an IC reader 15a being capable of reading information from the IC tag 101b provided on the transfusion bag holding member 103 of the tray 101 are provided in the tray conveying section 110. For example, each of the IC reader 101c and the IC reader 15a is an RFID reader for reading information from an RFID tag. The IC reader 101c is provided on a tray conveying start portion 110b into which the tray 101 is loaded through the tray insertion port 114. The IC reader 15a is provided in the tray conveying terminal portion 110a from which the tray 101 is discharged through the tray discharge port 15. In this case, each of the IC reader 101c and the IC reader 15a is one example of a tray reading means.

When the second control section 500 determines that the tray 101 is inserted into the tray conveying start portion 110b through the tray insertion port 114 based on an output from a sensor (not shown in the drawings), the second control section 500 allows the IC reader 101c to read information from the IC tag 101b. Further, when the second control section 500 determines that the tray 101 is inserted into the tray conveying terminal portion 110a based on an output from a sensor (not shown in the drawings), the second control section 500 allows the IC reader 15a to read information from the IC tag 101b. Then, the second control section 500 carries out an after-mentioned tray collating process (see FIG. 28) for determining whether or not the tray 101 is proper or the like according to reading results from the IC reader 101c and the IC reader 15a.

Further, when the second control section 500 determines that the tray 101 reaches to a predetermined position in the tray conveying section 110 through the tray insertion port 114 based on, for example, an output from a sensor, the second control section 500 allows a shutter 111 for communicating and separating between the tray conveying section 110 and the co-infusion process chamber 104 to be slid in a horizontal direction. When the shutter 111 is opened, the object placing member 102 is exposed with respect to the inside of the co-infusion process chamber 104. In FIG. 9, a condition in which the object placing member 102 is exposed with respect to the inside of the co-infusion process chamber 104 is illustrated.

Figure 10:
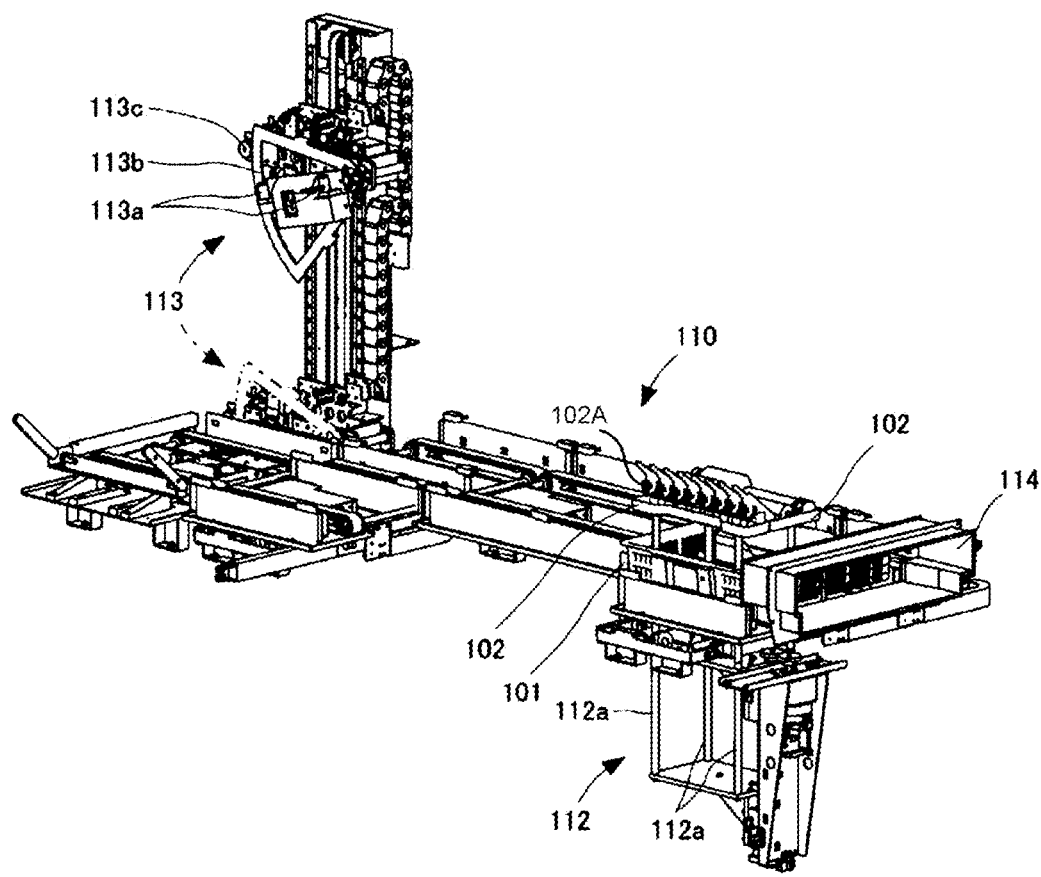
FIG. 10 is a perspective view showing a mechanism of the tray conveying section of the co-infusion apparatus according to the embodiment of the present invention.

As shown in FIG. 10, a tray up-and-down section 112 is provided in the tray conveying section 110. The tray up-and-down section 112 is used for moving up and down the object placing member 102 in the tray 101 transferred into the tray conveying section 110 through the tray insertion port 114. The tray up-and-down section 112 lifts up the object placing member 102 from a lower side toward an upper side with using, for example, driving of four shafts 112a, which are provided so as to be capable of being moved up and down, in a vertical direction.

The second control section 500 allows the tray confirming camera 41 to photograph the object placing member 102 after the tray up-and-down section 112 lifts up the object placing member 102. The tray confirming camera 41 photographs the medicine container 10, the injector 11 and the like placed on the predetermined object placing member 102 from an upper side. In this case, the tray confirming camera 41 is one example of a placing timing photographing means. The second control section 500 carries out an image recognition process with a photographed image photographed by the tray confirming camera 41 to determine whether or not the medicine containers 10, the injectors 11 (the syringes 11a and the injection needles 11c) and the like exist on the object placing member 102 in an amount indicated in the preparation data or the like.

Further, as shown in FIG. 10, a bag up-and-down section 113 for moving up and down the transfusion bag holding member 103 is provided in the tray conveying terminal portion 110a located in a left side space of the co-infusion process chamber 104. The second control section 500 allows the tray 101 to be conveyed to the front of the bag up-and-down section 113 and then allows a hook portion 113a of the bag up-and-down section 113 to hook the engagement hole portion 103a from a lower side. Then, the second control section 500 allows an arc-shaped gear portion 113b on which the hook portion 113a is formed to be rotationally driven with a motor 113c to lift up the transfusion bag holding member 103 and position the co-infusion port of the transfusion bag 12 so as to correspond to the co-infusion communication port 37. Further, the second control section 500 can allow the co-infusion port of the transfusion bag 12 to be directed toward an upper side or a lower side by controlling the motor 113c to drive the bag up-and-down section 113 and incline the transfusion bag holding member 103.

Further, as shown in FIG. 6, a dome light 120 for illuminating the transfusion bag 12 conveyed to the tray conveying terminal portion 110a and a camera for transfusion 121 are provided on an upper side of the tray conveying terminal portion 110a. The camera for transfusion 121 is provided at a central portion in the dome light 120 and reads a barcode provided on a surface of the transfusion bag 12. With this configuration, the second control section 500 can determine whether or not the transfusion bag 12 is proper according to information from the barcode read by the camera for transfusion 121.

[Ampule Cutter 31]

Figure 11:
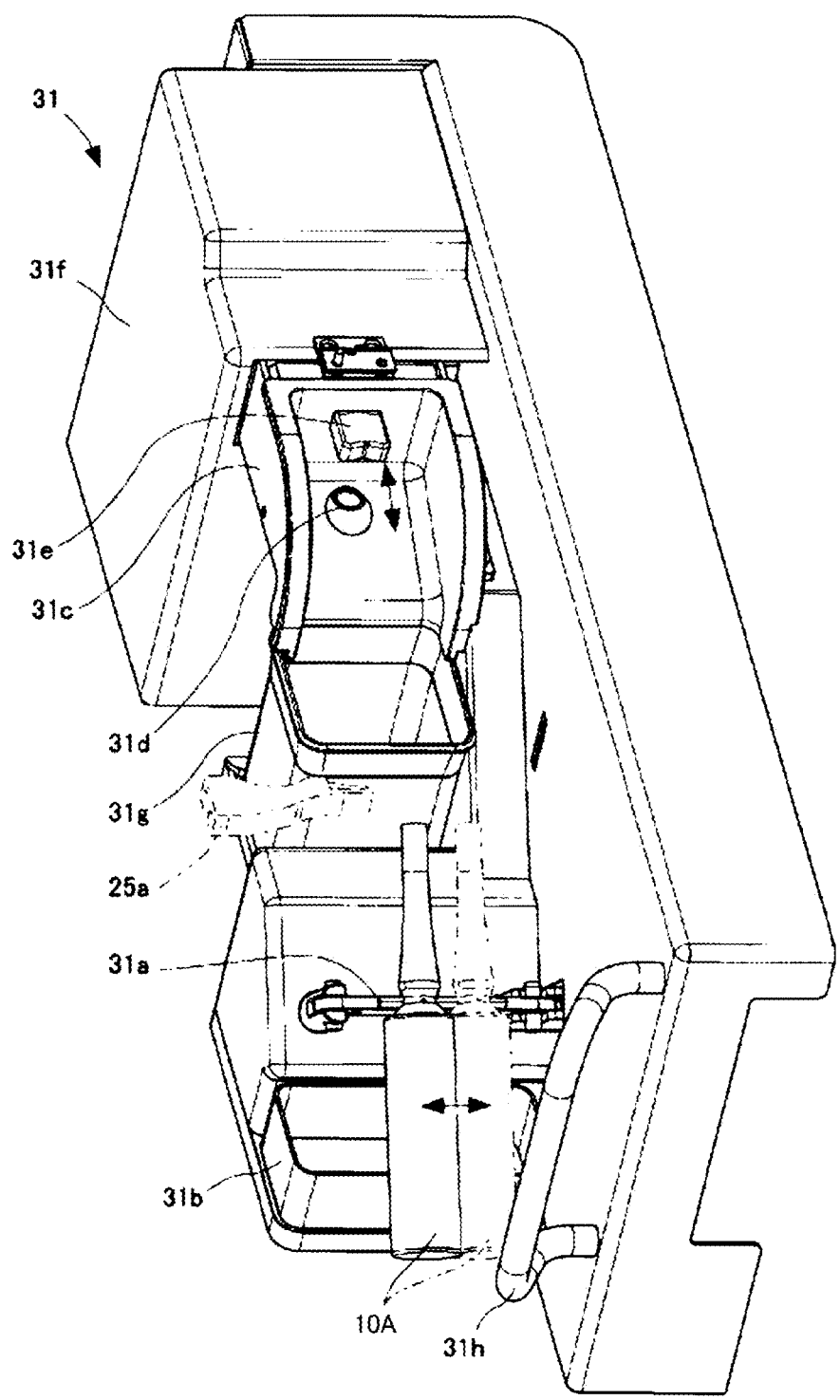
FIG. 11 is a perspective view showing an ampule cutter of the co-infusion apparatus according to the embodiment of the present invention.

As shown in FIG. 11, a rasping member 31a, a dust tray 31b, a head inserting portion 31c, a driving box 31f, a dust box 31g and a gripping member 31h are provided in the ampule cutter 31.

The rasping member 31a is a member for applying a notching work to the neck portion of the ampule 10A. Dusts generated in the notching work using the rasping member 31a fall into the dust tray 31b. Specifically, in the co-infusion apparatus 1, the first robot arm 21 holds the ampule 10A and oscillates the ampule 10A in a state that the neck portion of the ampule 10A makes contact with the rasping member 31a in order to apply the notching work to the neck portion of the ampule 10A.

The head inserting portion 31c has a hole 31d into which a head portion of the ampule 10A to which the notch working has already applied is inserted from a lower side and a pusher 31e located on a lateral side of the head portion of the ampule 10A protruding from the hole 31d toward an upper side. On the other hand, the driving box 31f has a cam provided therein and a driving motor for driving the cam. When the cam is driven by the driving motor, the cam allows the pusher 31e to start a reciprocating motion in a direction in which the pusher 31e gets closer and away from the neck portion of the ampule 10A.

In the co-infusion apparatus 1, the first robot arm 21 holds the ampule 10A with the gripping clicks 25a and inserts the head portion of the ampule 10A into the hole 31d from the lower side so that the head portion positioned upper than the neck portion protrudes toward the upper side. After that, the second control section 500 drives the driving motor of the driving box 31f to move the pusher 31e in a direction for pushing the head portion of the ampule 10A. As a result, the head portion is pushed and broken by the pusher 31e. At this time, the head portion broken by the pusher 31e falls into the dust box 31g. The gripping member 31h is used for allowing the user to grip it at the time of oscillating the ampule cutter 31 along a rail 31i (see FIG. 4) slidably supporting the ampule cutter 31.

[Stirring Device 32]

Figure 12:
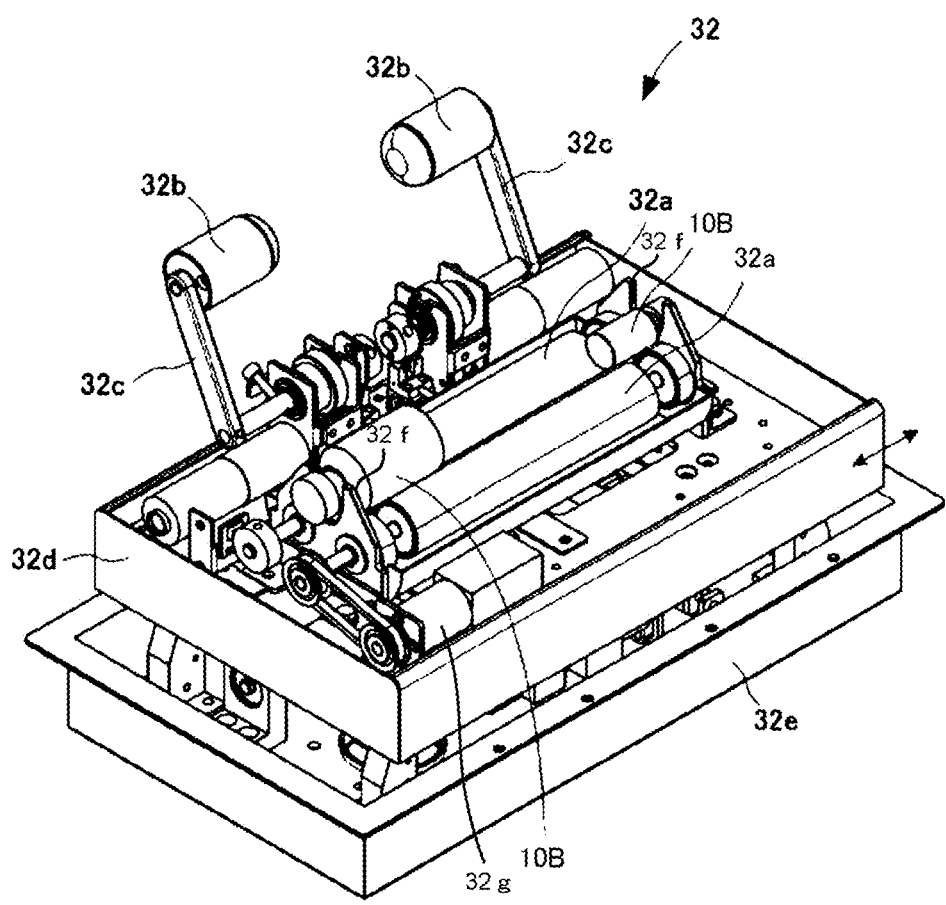
FIG. 12 is a perspective view showing an internal structure of a stirring device of the co-infusion apparatus according to the embodiment of the present invention.

In the case where a medicine such as a powdered medicine (medicinal powder) to which a dissolution process needs to be applied is contained in the vial bottle 10B, the stirring device 32 is used when a mixed medicine is prepared by injecting transfusion, a medicine or the like into the vial bottle 10B to dissolve the medicine. Specifically, as shown in FIG. 12, rollers 32a, pressing members 32b, rotationally supporting members 32c, a supporting plate 32d, a horizontally oscillating mechanism 32e, supporting members 32f, a driving motor 32g and the like are provided in the stirring device 32.

The two rollers 32a are arranged so as to face each other and be separated from each other by a predetermined distance. The one of the rollers 32a is rotationally supported. The other one of the rollers 32a is connected to the driving motor 32g. Each of the rollers 32a has a longitudinal shape extending in an axial direction thereof. In the stirring device 32, it is possible to simultaneously stir two vial bottles 10B respectively placed on both end side portions of the rollers 32a in the axial direction.

The pressing members 32b are used for respectively pressing the vial bottles 10B placed on the rollers 32a from an upper side. The pressing members 32b are driven rollers rotated along with the rotations of the medicine containers 10. The rotationally supporting members 32c allow the pressing members 32b to move in a direction in which the pressing members 32b get closer and away from the medicine containers 10 with a driving motor (not shown in the drawings).

The supporting plate 32d supports the rollers 32a, the pressing members 32b, the rotationally supporting members 32c and the like. The horizontally oscillating mechanism 32e has, for example, a crank mechanism and can oscillate the supporting plate 32d in the axial direction of the rollers 32a.

Each of the supporting members 32f has a U-shaped cutout with which the neck portion of the vial bottle 10B can be mounted on the both end side portions of the rollers 32a in the axial direction thereof. In the case where the vial bottle 10B is placed on the rollers 32a, the neck portion of the medicine container 10 is engaged with the cutout. With this configuration, in the case where the supporting plate 32d is oscillated in the axial direction of the rollers 32a by the horizontally oscillating mechanism 32e, it is possible to oscillate the medicine container 10 following to the oscillation in the axial direction of the rollers 32a, thereby stirring the medicine in the medicine container 10 in a horizontal direction.

On the other hand, when the vial bottle 10B is placed between the two rollers 32a and the driving motor 32g is driven, the medicine container 10 is rotated by the other one of the rollers 32a connected to the driving motor 32g. As a result, the medicine in the medicine container 10 is stirred. At this time, the one of the rollers 32a is also rotated by the rotation of the medicine container 10 in the same direction as the rotational direction of the other one of the rollers 32a. Further, if at least one of the rollers 32a is eccentrically driven, it is also possible to stir the vial bottle 10B placed on the rollers 32a in a vertical direction (an up-and-down direction).

[Placing Shelf 33]

As shown in FIG. 4, the placing shelf 33 is used for temporarily placing the medicine container 10 and the injector 11 in the co-infusion process carried out by the co-infusion apparatus 1. The placing shelf 33 is provided at a position to which both of the first robot arm 21 and the second robot arm 22 can access. The vial bottle 10B is placed on the placing shelf 33 in a state that the vial bottle 10B stands at a predetermined position on the placing shelf 33. On the other hand, an incline holding member for holding the ampule 10A in a state that the ampule 10A is inclined is provided on the placing shelf 33. The ampule 10A is placed on the incline holding member in a state that the ampule 10A is inclined. Further, a neck portion holding hole having a predetermined diameter and in which the neck portion of the injector 11 is engaged is formed on the placing shelf 33. The injector 11 is temporarily placed so that the neck portion of the injector is directed toward a lower side in a state that the injection needle 11c is not attached to the syringe, that is, in a state of only the syringe.

[Placing Member for Rotation 33A]

Although this is not shown in the drawings, a placing member for rotation 33A is used in a working for rotating the injector 11 in a circumferential direction thereof and provided at a position to which the first robot arm 21 can access. For example, a neck portion holding hole having a predetermined diameter and in which the neck portion of the injector 11 is engaged is formed in the placing member for rotation 33A in the same manner as the placing shelf 33. The injector 11 is placed on the placing member for rotation 33A so that the neck portion of the injector 11 is directed toward a lower side in a state that the injection needle 11c is not attached to the syringe, that is, in a state of only the syringe. After the first robot arm 21 places the injector 11 on the placing member for rotation 33A, the first robot arm 21 can rotate the injector 11 by 180 degrees in the circumferential direction thereof. For example, the first robot arm 21 gradually rotates the injector 11 in the circumferential direction thereof until the injector 11 is rotated by 180 degrees by repeatedly carrying out the following steps (a) and (b). (a) After the first robot arm 21 grips the injector 11 and rotates the injector 11 in one direction of the circumferential direction by a predetermined amount, the first robot arm 21 releases the injector 11 to adjust an angle of the first robot arm 21 in the other direction of the circumferential direction by a predetermined amount. (b) The first robot arm 21 again grips the injector 11 to rotate the injector 11 in the one direction of the circumferential direction by a predetermined amount.

[Medicine Reading Section 34]

Figure 13:
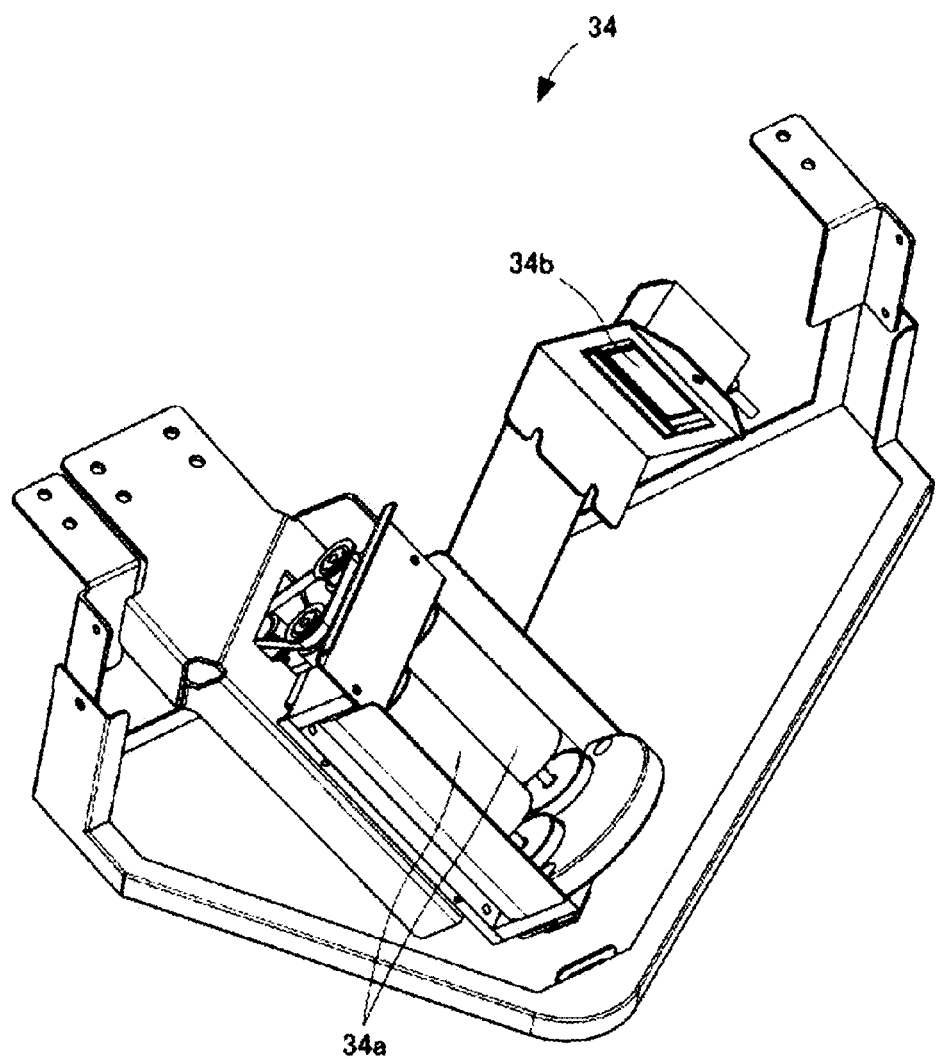
FIG. 13 is a perspective view showing a medicine reading section of the co-infusion apparatus according to the embodiment of the present invention.

The medicine reading section 34 reads a barcode written on a label labeled on the medicine container 10 such as the ampule 10A and the vial bottle 10B and indicating medicine information for a medicine contained in the medicine container 10. Specifically, as shown in FIG. 13, the medicine reading section 34 includes two rollers 34a (one example of a rotation driving means) and a barcode reader 34b (one example of a container reading means). The rollers 34a are arranged so as to face each other and be separated by a predetermined distance. One of the rollers 34a is rotatably supported. The other one of the rollers 34a is connected to a driving motor (not shown in the drawings). The two rollers 34a are driven by the driving motor to rotate the medicine container 10 placed between the rollers 34a in a circumferential direction of the medicine container 10. With this configuration, it is possible to rotate the medicine container 10 in the circumferential direction thereof by 360 degrees, thereby allowing an entire area of the label labelled on the medicine container 10 to be directed toward the barcode reader 34b. Then, the barcode reader 34b reads the barcode from the label on the medicine container 10 rotated by the rollers 34a.

[Weighing Scale 35]

The weighing scale 35 is used for measuring a weight of the injector 11 in the co-infusion process carried out by the co-infusion apparatus 1. A measuring result from the weighing scale 35 is inputted into the second control section 500. The weighing scale 35 is provided in a movable range of the second robot arm 22 and measures the weight of the injector 11 placed on the weighing scale 35 by the second robot arm 22.

[Needle Bending Detecting Section 36]

Figure 14:
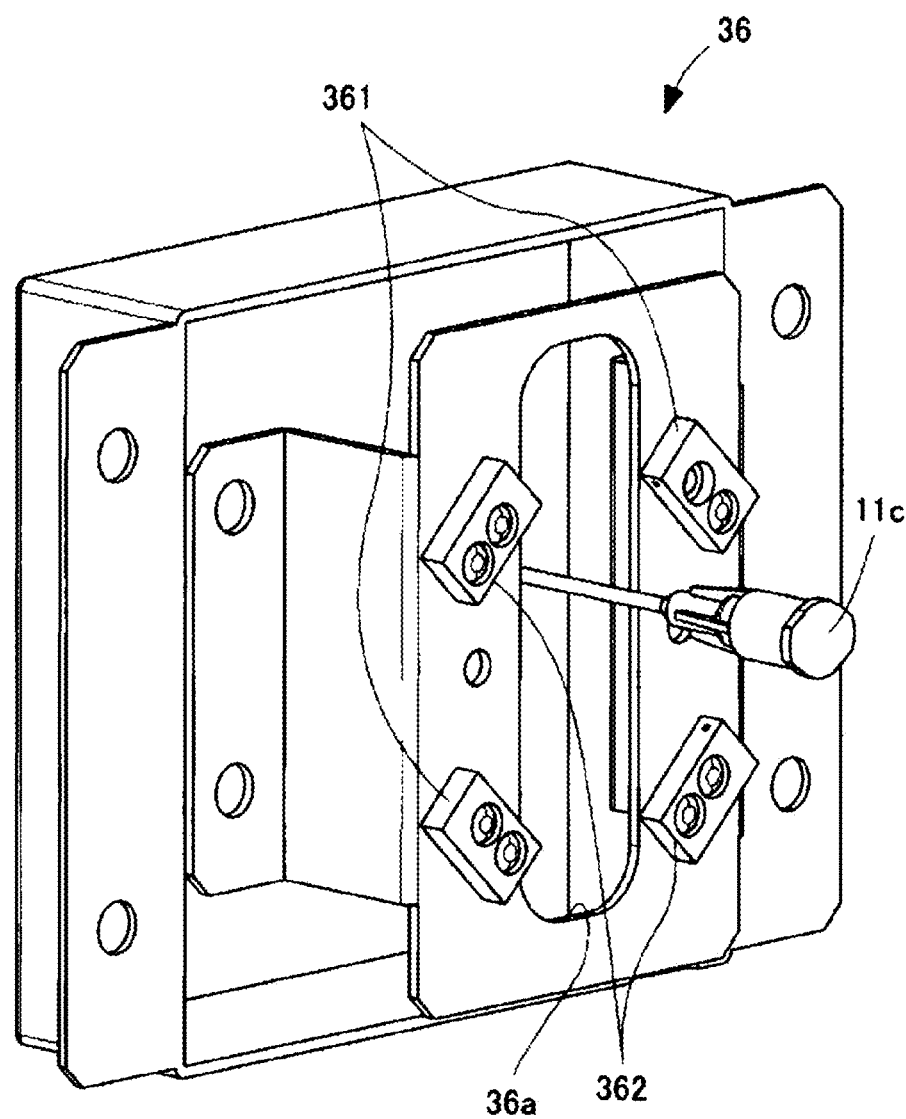
FIG. 14 is a perspective view showing a needle bending detecting section of the co-infusion apparatus according to the embodiment of the present invention.

As shown in FIG. 14, a longitudinal hole 36a in which the injection needle 11c of the injector 11 can be inserted and moved is formed in the needle bending detecting section 36. Further, the needle bending detecting section 36 includes first optical sensors 361 and second optical sensors 362. The first optical sensors 361 are arranged so as to face each other to emit and receive light beams through the longitudinal hole 36a. The second optical sensors 362 are arranged in the same manner as the first optical sensors 361. Further, the first sensors 361 and the second sensors 362 are arranged so that the light beams between the first optical sensors 361 become non-parallel with the light beams between the second optical sensors 362. Detecting results from the first optical sensors 361 and the second optical sensors 362 are inputted into the second control section 500.

Then, the second robot arm 22 inserts the injection needle 11c attached to the injector 11 into the longitudinal hole 36a and moves the injection needle 11c in a vertical direction. At this time, when the light beams between each of the first optical sensors 361 and the second optical sensors 362 are blocked by the injection needle 11c, the first optical sensors 361 and the second optical sensors 362 are turned off. With this configuration, the second control section 500 can detect a bending of the injection needle 11c with using positional information of the injection needle 11c at the time of blocking the light beams. Alternatively, another configuration in which the injection needle 11c is photographed by a camera and the bending of the injection needle is detected by an image recognition method with respect to this photographed image may be considered as another embodiment. In the case where the bending of the injection needle 11c occurs, the second control section 500 allows the second robot arm 22 to adjust a needle tip position, a needle direction or the like of the injection needle 11c at the time of puncturing the transfusion bag 12 with the injection needle 11c based on a bending amount of the injection needle 11c.

[Co-infusion Communication Port 37]

As shown in FIG. 3, the co-infusion communication port 37 is formed in a dome-shaped portion outwardly protruding from a side wall of the co-infusion process chamber 104. Further, a cutout in which the co-infusion port of the transfusion bag 12 is inserted in a vertical direction is formed in the dome-shaped portion. Thus, when the transfusion bag holding member 103 is lifted up, the co-infusion port of the transfusion bag 12 is located into the co-infusion process chamber 104.

[Needle Insertion Confirming Transparent Window 38]

The needle insertion confirming transparent window 38 is a window for visually confirming the transfusion bag 12 in the tray conveying terminal portion 110a from the co-infusion process section 300. The needle insertion confirming transparent window 38 is used at the time of photographing an image for confirming a state that the injection needle 11c of the injector 11 is inserted in the transfusion bag 12.

[Injector Confirming Camera 42]

As shown in FIG. 6, the injector confirming camera 42 is provided on the ceiling of the co-infusion process section 300. The injector confirming camera 42 is used for photographing the injector 11 in order to confirm presence or absence of a medicine suctioned into the injector 11, an amount of the medicine and the like. Although the injector confirming camera 42 may photograph an image in a pre-fixed photographing range R1, the injector confirming camera 42 may be controlled by the second control section 500 to arbitrarily change a position and a size of the photographing range R1. Further, as described below, in the co-infusion apparatus 1, the injector confirming camera 42 photographs, at one time, the injector 11 and the medicine container 10 to provide an inspection image having high reliability. The second control section 500 allows a storage section such as the data storage section 404, the data storage section 504 and a hard disk provided outside the co-infusion apparatus 1 to store the photographed image photographed by the injector confirming camera 42 in order to, for example, inspect whether or not the co-infusion process carried out by the co-infusion apparatus 1 is proper. Then, the second control section 500 allows a display device such as the touch panel monitor 14 and the display 203 to display the photographed image photographed by the injector confirming camera 42 when the user carries out the inspection.

[Injection Needle Attaching and Detaching Device 43]

Figure 15:
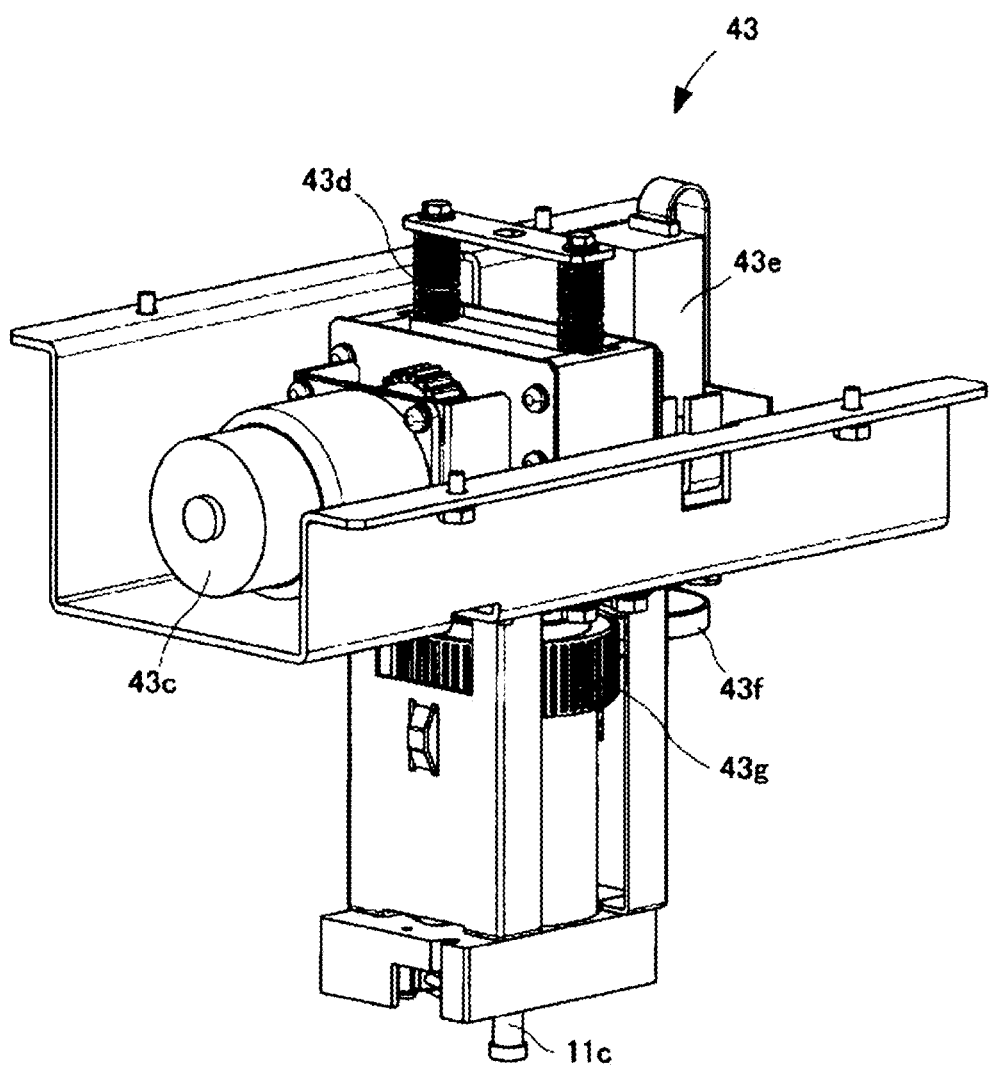
FIG. 15 is a perspective view showing an internal structure of an injection needle attaching and detaching device of the co-infusion apparatus according to the embodiment of the present invention.
Figure 16:
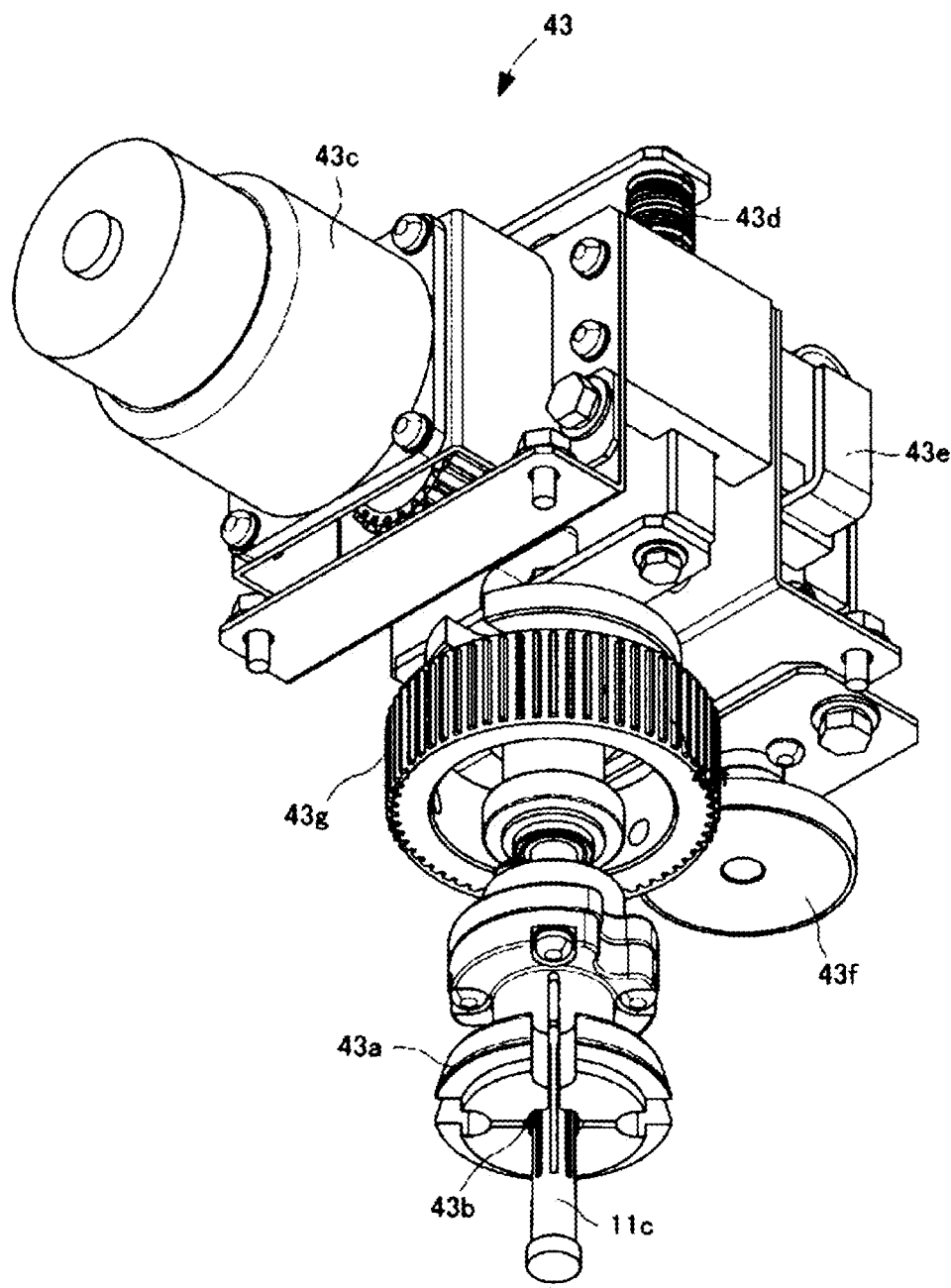
FIG. 16 is another perspective view showing the internal structure of the injection needle attaching and detaching device of the co-infusion apparatus according to the embodiment of the present invention.

As shown in FIGS. 15 and 16, the injection needle attaching and detaching device 43 includes a chuck portion 43a in which cutouts are formed and a hole 43b formed in the chuck portion 43a. A needle tip of an injection needle 11c having a cap is inserted into the hole 43b so that the needle tip of the injection needle 11c is directed toward an upper side. When a motor 43c is driven, the hole 43b of the chuck portion 43a is expanded by a cam mechanism (not shown in the drawings) to insert the injection needle 11c having the cap into the hole 43b. When the driving of the motor 43c is stopped, a holding state for the injection needle 11c having the cap is kept by springs 43d. When a needle rotating motor 43e is driven, a gear 43f and a gear 43g are rotated and then the chuck portion 43a is also rotated to rotate the injection needle 11c having the cap. Further, there formed in each of the cap and the injection needle 11c are ribs which make contact with each other when the cap is rotated in a circumferential direction thereof in a state that the cap is attached to the injection needle 11c. With this configuration, it is possible to rotate the injection needle 11c together with the cap when the cap of the injection needle 11c is rotated by the chuck portion 43a, thereby attaching and detaching the injection needle 11c to/from the syringe 11a. Specifically, the injection needle attaching and detaching device 43 can automatically replace the injection needle 11c attaching to the syringe 11a with another injection needle 11c having a syringe filter used for the case of using the ampule 10A. Further, the injection needle attaching and detaching device 43 can direct the needle tip of the injection needle 11c having the cap toward the upper side. Thus, a tip end aperture of the syringe 11a from which the injection needle 11c has been detached is directed toward the upper side. This makes it possible to prevent liquid from dripping from the aperture of the neck portion of the syringe 11a.

[Needle Insertion Confirming Camera 44]

Figure 17:
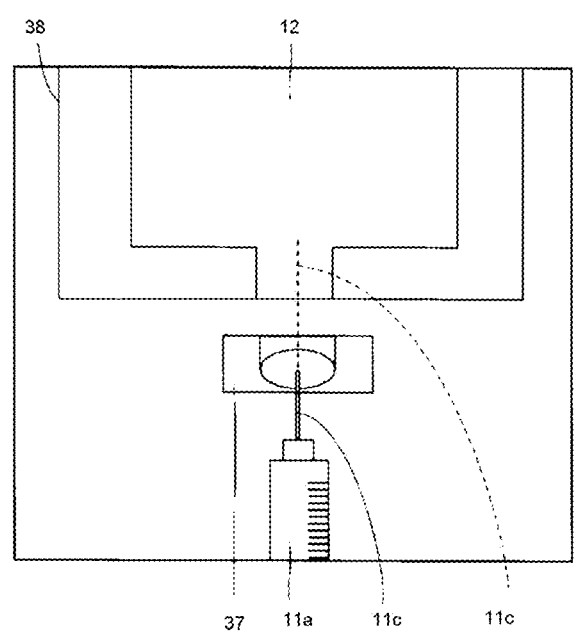
FIG. 17 is a view showing one example of a photographed image of a needle insertion confirming camera of the co-infusion apparatus according to the embodiment of the present invention.

The needle insertion confirming camera 44 photographs the transfusion bag 12 located outside the co-infusion process chamber 104 and the injector 11 in the co-infusion process chamber 104 so that both of the transfusion bag 12 and the injector 11 are located in one image. The second control section 500 allows the needle insertion confirming camera 44 to photograph an image with facing toward a direction of the needle insertion confirming transparent window 38 at the time of puncturing the co-infusion port of the transfusion bag 12 with the injection needle 11c. Then, the photographed image photographed by the needle insertion confirming camera 44 is displayed on the touch panel monitor 14 or the like. FIG. 17 shows one example of the photographed image photographed by the needle insertion confirming camera 44. With this configuration, the user can confirm whether or not a tip end of the injection needle 11c locates in the transfusion bag 12 based on the photographed image. The photographed image is stored in a storage section such as a hard disk provided inside or outside the co-infusion apparatus 1 for a final inspection. When the user operates an OK button on the touch panel monitor 14 displaying the photographed image to determine that the co-infusion process properly completes, the transfusion bag 12 is moved down by the bag up-and-down section 113 to put the transfusion bag 12 back into the tray 101.

[Sterilizing Lamp 45]

The sterilizing lamps 45 are turned on from three hours ago of starting of the co-infusion process, for example. As shown in FIG. 6, one of the two sterilizing lamps 45 is provided at a position between the first robot arm 21 and the second robot arm 22. Thus, an amount of sterilizing light blocked by the first robot arm 21 and the second robot arm 22 becomes small, thereby evenly sterilizing the inside of the co-infusion process chamber 104. Further, there provided in the co-infusion process section 300 is an exhaust system for suctioning air in the co-infusion process chamber 104 through slits 104b (see FIGS. 3 and 4) provided in a lower portion of the side wall of the co-infusion process chamber 104 and discharging the air in the co-infusion process chamber 104 from an exhaust fan (not shown in the drawings) provided on an upper portion of the co-infusion process chamber 104. Further, there provided in the co-infusion process chamber 104 is an air supply system for washing external air taken from an inlet port provided on the ceiling of the co-infusion process chamber 104 to supply the washed external air into the co-infusion process chamber 104 or the like.

[Co-infusion Process]

Next, description will be given to one example of steps of the co-infusion process carried out by the co-infusion process section 300 in the co-infusion apparatus 1. In the co-infusion process, as described below, the second control section 500 controls the first robot arm 21, the second robot arm 22 and the like to suction a medicine from one or more of the medicine containers 10 with the injector 11 based on the preparation data and inject the medicine from the injector 11 into the transfusion bag 12. In this case, the second control section 500 at the time of carrying out a process for controlling the first robot arm 21 and the second robot arm 22 to suction the medicine from the medicine container 10 with the injector 11 is one example of a suctioning control means.

[Co-infusion Process Using the Ampule 10A]

First, description will be given to a basic action of the co-infusion process in the case of injecting a medicine contained in the ampule 10A into the transfusion bag 12.

The second control section 500 allows the IC reader 101c to read identification information for the tray 101 from the IC tag 101b of the tray 101 when the tray 101 is fed into the tray conveying section 110. Then, the second control section 500 allows the shutter 111 to be opened in the case where the identification information for the tray 101 matches with identification information preliminarily associated with the preparation data of the co-infusion process. After that, the second control section 500 allows the tray up-and-down section 112 of the tray conveying section 110 to lift up the object placing member 102 of the tray 101 to expose the object placing member 102 with respect to the co-infusion process chamber 104.

Next, the second control section 500 allows the tray confirming camera 41 to photograph the object placing member 102. Then, the second control section 500 identifies a position and a direction of the object such as the ampule 10A and the injector 11 placed on the object placing member 102 with utilizing an image recognition process based on the photographed image photographed by the tray confirming camera 41. Particularly, the second control section 500 allows the tray confirming camera 41 to photograph the object placing member 102 each time that the ampule 10A or the injector 11 is taken from the object placing member 102 to identify a latest position and a latest direction of the ampule 10A and the injector 11 from the photographed image.

Subsequently, the second control section 500 allows the first robot arm 21 to temporarily place the injector 11 placed on the object placing member 102 exposed with respect to the inside of the co-infusion process chamber 104 onto the placing shelf 33. Further, the second control section 500 allows the first robot arm 21 to set the ampule 10A placed on the object placing member 102 onto the medicine reading section 34. Then, the second control section 500 allows the medicine reading section 34 to read information such as a type of the medicine contained in the ampule 10A and the like.

Further, the second control section 500 allows the first robot arm 21 to set a first injection needle 11c on the injection needle attaching and detaching device 43 and temporarily place a second injection needle 11c on the placing shelf 33. The first injection needle 11c is an injection needle without a syringe filter and the second injection needle 11c is an injection needle having the syringe filter. In this regard, a cap is attached to the injection needle 11c placed on the object placing member 102 and the cap is attached and detached to/from the injection needle 11c by the injection needle attaching and detaching device 43.

Then, the second control section 500 allows the tray up-and-down section 112 of the tray conveying section 110 to move the object placing member 102 down to put the object placing member 102 back into the tray 101 when all of the objects on the object placing member 102 have been taken. In this regard, the second control section 500 confirms whether or not all of the objects on the object placing member 102 have been taken with utilizing the image recognition process based on the photographed image photographed by the tray confirming camera 41.

After that, the second control section 500 allows the shutter 111 to be closed and allows the tray conveying section 110 to convey the tray 101 to the tray conveying terminal portion 110a. Next, the second control section 500 allows the bag up-and-down section 113 of the tray conveying section 110 to position the co-infusion port of the transfusion bag 12 held by the transfusion bag holding member 103 of the tray 101 so as to correspond to the co-infusion communication port 37 formed in the co-infusion process chamber 104.

Then, the second control section 500 allows the second robot arm 22 to transfer the ampule 10A set on the medicine reading section 34 onto the placing shelf 33. Next, the second control section 500 allows the first robot arm 21 to take the injector 11 from the placing shelf 33 to set the injector 11 on the second robot arm 22. Subsequently, the second control section 500 allows the second robot arm 22 to transfer the injector 11 to the injection needle attaching and detaching device 43 to set the injection needle 11c on the injector 11. After that, the second control section 500 allows the second robot arm to transfer the injector 11 to the needle bending detecting section 36 to detect whether or not the bending of the injection needle 11c occurs.

Next, the second control section 500 allows the first robot arm 21 to take the ampule 10A from the placing shelf 33 and then allows the ampule cutter 31 to break the head portion of the ampule 10A. Then, the second control section 500 allows the first robot arm 21 and the second robot arm 22 to make the ampule 10A and the injector 11 get closer with each other to insert the injection needle 11c of the injector 11 into the ampule 10A. After that, the second control section 500 allows the second robot arm 22 to handle the plunger 11b to suction the medicine from the ampule 10A with the injector 11 in an amount that is set in advance by the preparation data.

At this time, the first robot arm 21 and the second robot arm 22 gradually incline postures of the ampule 10A and the injector 11. For example, a certain amount of the medicine is suctioned from the ampule 10A in a state that an opening portion of the ampule 10A is directed toward a vertical upper direction and the injection needle 11c of the injector 11 is directed toward a vertical lower direction, and then the ampule 10A is inclined by about 10 degrees with respect to the vertical direction to form a state that the medicine is transferred to the side of the opening portion (neck portion). With this configuration, it becomes possible to suction the medicine with preventing the medicine from remaining in the ampule 10A as much as possible even if the tip end of the injection needle 11c of the injector 11 does not make contact with a bottom of the ampule 10A.

After that, the second control section 500 controls one or both of the first robot arm 21 and the second robot arm 22 to transfer, into the photographing range R1 of the injector confirming camera 42, the ampule 10A after the medicine has been suctioned and the injector 11 in which the medicine has been suctioned. In this case, the second control section 500 at the time of carrying out such a transferring process is one example of a transfer control means. Then, the second control section 500 allows the injector confirming camera 42 to photograph, at one time, the ampule 10A and the injector 11 to store this photographed image in the data storage section 504 as an inspection image. In this case, the injector confirming camera 42 is one example of a suctioning timing photographing means. For example, the injector confirming camera 42 photographs the predetermined photographing range R1. On the other hand, it may be considered that the second control section 500 can change the photographing range R1 of the injector confirming camera 42 so that the injector confirming camera 42 becomes capable of photographing the ampule 10A and the injector 11 which have been already transferred by the first robot arm 21 and the second robot arm 22 at one time.

Next, the second control section 500 allows the first robot arm 21 and the second robot arm 22 to replace the injection needle 11c of the injector 11. Specifically, the second robot arm 22 transfers the injector 11 to the injection needle attaching and detaching device 43 to attach the cap to the injection needle 11c. Then, the second control section 500 allows the injection needle attaching and detaching device 43 to rotate the cap to remove the injection needle 11c from the injector 11. The removal of the injection needle 11c may be carried out by a rotational motion of the cap due to the first robot arm 21 and the second robot arm 22.

Then, the second control section 500 allows the waste cover 132a to be opened and allows the first robot arm 21 to drop the injection needle 11c held by the injection needle attaching and detaching device 43 into the waste containing chamber 13a to dispose of the injection needle 11c. After that, the second control section 500 allows the first robot arm 21 to set the injection needle 11c having the syringe filter on the injection needle attaching and detaching device 43 from the placing shelf 33. Then, the second control section 500 allows the second robot arm 22 to transfer the injector 11 to the injection needle attaching and detaching device 43 to attach the injection needle 11c to the injector 11. In this case, the second control section 500 also allows the second robot arm 22 to transfer the injector 11 to the needle bending detecting section 36 to detect whether or not the bending of the injection needle 11c occurs. As described above, according to the co-infusion apparatus 1, the injection needle 11c is replaced at the time of suctioning the medicine from the ampule 10A and at the time of injecting the transfusion into the transfusion bag 12. This makes it possible to prevent pieces of the ampule 10A from flowing into the transfusion bag 12.

Then, the second control section 500 allows the second robot arm 22 to puncture the co-infusion port of the transfusion bag 12 conveyed into the tray conveying terminal portion 110a with the injection needle 11c of the injector 11 to inject the mixed medicine in the injector 11 into the transfusion bag 12. On the other hand, the second control section 500 allows the waste cover 132a to be opened and allows the first robot arm 21 to drop the ampule 10A into the waste containing chamber 13a to dispose of the ampule 10A. Further, the second control section 500 allows the second robot arm 22 to transfer the injector 11 to the injection needle attaching and detaching device 43 to attach the cap to the injection needle 11c of the injector 11 and then drop the injector 11 into the waste containing chamber 13a to dispose of the injector 11.

After that, the second control section 500 reads a variety of images photographed by the injector confirming camera 42 or the like from the data storage section 504 to display the photographed images on the touch panel monitor 14. With this configuration, the user can inspect whether or not the co-infusion process has been properly carried out with checking the touch panel monitor 14.

[Co-infusion Process Using the Vial Bottle 10B]

Next, description will be given to a basic action of the co-infusion process for mixing a medicine with transfusion and then injecting the resulted medicine into the transfusion bag 12 in the case where the medicine contained in the vial bottle 10B is a medicine such as a powdered medicine to which a dissolution process needs to be applied.

The second control section 500 allows the IC reader 101c to read identification information for the tray 101 from the IC tag 101b of the tray 101 when the tray 101 is fed into the tray conveying section 110. Then, the second control section 500 allows the shutter 111 to be opened in the case where the identification information for the tray 101 matches with identification information preliminarily associated with the preparation data of the co-infusion process. After that, the second control section 500 allows the tray up-and-down section 112 of the tray conveying section 110 to lift up the object placing member 102 of the tray 101 to expose the object placing member 102 with respect to the co-infusion process chamber 104.

Next, the second control section 500 allows the tray confirming camera 41 to photograph the object placing member 102. Then, the second control section 500 identifies a position and a direction of the object such as the vial bottle 10B and the injector 11 placed on the object placing member 102 with utilizing an image recognition process based on the photographed image photographed by the tray confirming camera 41. Particularly, the second control section 500 allows the tray confirming camera 41 to photograph the object placing member 102 each time that the vial bottle 10B or the injector 11 is taken from the object placing member 102 to identify a latest position and a latest direction of each of the vial bottle 10B and the injector 11 from the photographed image.

Subsequently, the second control section 500 allows the first robot arm 21 to temporarily place the injector 11 placed on the object placing member 102 and exposed with respect to the inside of the co-infusion process chamber 104 onto the placing shelf 33. Further, the second control section 500 allows the first robot arm 21 to set the vial bottle 10B placed on the object placing member 102 onto the medicine reading section 34. Then, the second control section 500 allows the medicine reading section 34 to read information such as a type of the medicine contained in the vial bottle 10B and the like.

Then, the second control section 500 allows the tray up-and-down section 112 of the tray conveying section 110 to move the object placing member 102 down to put the object placing member 102 back into the tray 101 when all of the objects on the object placing member 102 have been taken. In this regard, the second control section 500 confirms whether or not all of the objects on the object placing member 102 have been taken with utilizing the image recognition process based on the photographed image photographed by the tray confirming camera 41.

After that, the second control section 500 allows the shutter 111 to be closed and allows the tray conveying section 110 to convey the tray 101 to the tray conveying terminal portion 110a. Next, the second control section 500 allows the bag up-and-down section 113 of the tray conveying section 110 to position the co-infusion port of the transfusion bag 12 held by the transfusion bag holding member 103 of the tray 101 so as to correspond to the co-infusion communication port 37 formed in the co-infusion process chamber 104.

Then, the second control section 500 allows the second robot arm 22 to transfer the vial bottle 10B set on the medicine reading section 34 onto the placing shelf 33. On the other hand, the second control section 500 allows the first robot arm 21 to set the injection needle 11c of the injector 11 placed on the object placing member 102 on the injection needle attaching and detaching device 43 in parallel with the above transferring process.

Next, the second control section 500 allows the first robot arm 21 to take the injector 11 from the placing shelf 33 to set the injector 11 on the second robot arm 22. Subsequently, the second control section 500 allows the second robot arm 22 to transfer the injector 11 to the injection needle attaching and detaching device 43 to set the injection needle 11c on the injector 11. After that, the second control section 500 allows the second robot arm to transfer the injector 11 to the needle bending detecting section 36 to detect whether or not the bending of the injection needle 11*c* occurs.

Subsequently, the second control section 500 allows the second robot arm 22 to puncture the co-infusion port of the transfusion bag 12 conveyed into the tray conveying terminal portion 110*a* with the injection needle 11*c* of the injector 11 to suction the transfusion from the transfusion bag 12 in an amount of dissolution indicated in the preparation data. On the other hand, the second control section 500 allows the first robot arm 21 to take the vial bottle 10B placed on the placing shelf 33.

Then, the second control section 500 allows the first robot arm 21 and the second robot arm 22 to get the vial bottle 10B and the injector 11 closer with each other to puncture the vial bottle 10B with the injection needle 11*c* of the injector 11. After that, the second control section 500 allows the second robot arm 22 to handle the plunger 11*b* to inject the transfusion in the injector 11 into the vial bottle 10B. With this configuration, the medicine in the vial bottle 10B is dissolved in the transfusion. At this time, postures of the injector 11 and the vial bottle 10B are in a state that the injection needle 11*c* of the injector 11 is directed toward the vertical lower direction and the opening portion of the vial bottle 10B is directed toward the vertical upper direction.

Next, the second control section 500 allows the first robot arm 21 to set the vial bottle 10B in which the transfusion has been injected on the stirring device 32. With this configuration, in the stirring device 32, the medicine and the transfusion in the vial bottle 10B are stirred. After the stirring by the stirring device 32 completes, the second control section 500 allows the first robot arm 21 to take the vial bottle 10B from the stirring device 32.

Then, the second control section 500 allows the first robot arm 21 and the second robot arm 22 to get the vial bottle 10B and the injector 11 closer with each other to puncture the vial bottle 10B with the injection needle 11*c* of the injector 11. After that, the second control section 500 allows the second robot arm 22 to handle the plunger 11*b* to suction the mixed medicine in the vial bottle 10B with the injector 11. At this time, postures of the injector 11 and the vial bottle 10B are in a state that the opening portion of the vial bottle 10B is directed toward the vertical lower direction and the injection needle 11*c* of the injector 11 is directed toward the vertical upper direction.

After that, the second control section 500 controls one or both of the first robot arm 21 and the second robot arm 22 to transfer, into the photographing range R1 of the injector confirming camera 42, the vial bottle 10B after the medicine has been suctioned and the injector 11 in which the medicine has been suctioned. In this case, the second control section 500 at the time of carrying out such a transferring process is one example of a transfer control means. Then, the second control section 500 allows the injector confirming camera 42 to photograph, at one time, the vial bottle 10B and the injector 11 to store this photographed image in the data storage section 504 as an inspection image. In this case, the injector confirming camera 42 is one example of a suctioning timing photographing means. For example, the injector confirming camera 42 photographs the predetermined photographing range R1. On the other hand, it may be considered that the second control section 500 can change the photographing range R1 of the injector confirming camera 42 so that the injector confirming camera 42 becomes capable of photographing the ampule 10A and the injector 11 which have been already transferred by the first robot arm 21 and the second robot arm 22 at one time.

Then, the second control section 500 allows the second robot arm 22 to puncture the co-infusion port of the transfusion bag 12 conveyed into the tray conveying terminal portion 110*a* with the injection needle 11*c* of the injector 11 to inject the mixed medicine in the injector 11 into the transfusion bag 12. On the other hand, the second control section 500 allows the waste cover 132*a* to be opened and allows the first robot arm 21 to drop the vial bottle 10B into the waste containing chamber 13*a* to dispose of the vial bottle 10B. Further, the second control section 500 allows the second robot arm 22 to transfer the injector 11 to the injection needle attaching and detaching device 43 to attach the cap to the injection needle 11*c* of the injector 11 and then drop the injector 11 into the waste containing chamber 13*a* to dispose of the injector 11.

After that, the second control section 500 reads a variety of images photographed by the injector confirming camera 42 or the like from the data storage section 504 to display the photographed images on the touch panel monitor 14. With this configuration, the user can inspect whether or not the co-infusion process has been properly carried out with checking the touch panel monitor 14.

In this regard, it may be considered that the medicine contained in the vial bottle 10B is a medicine such as medicinal solution to which the dissolution process needs not to be applied. Description to the co-infusion process carried out in this case is omitted because the co-infusion process carried out in this case is the same as the co-infusion process carried out in the case where the medicine contained in the vial bottle 10B is the medicine such as the powdered medicine to which the dissolution process needs to be applied except that the process for suctioning the transfusion from the transfusion bag 12 and then injecting the transfusion into the vial bottle 10B to stir the medicine in the vial bottle 10B is not carried out.

[A Variety of Processes of the Second Control Section 500]

Hereinafter, description will be given to details of a variety of processes carried out by the second control section 500 in the co-infusion process. Specifically, the second control section 500 carries out an injector position adjusting process, a container position adjusting process, an inspection control process, a tray collating process, an object taking process, an injection control process and the like which are described below. In this regard, the second control section 500 can substantially-concurrently carry out the after-mentioned various processes in the co-infusion process.

[Injection Position Adjusting Process]

Figure 18:
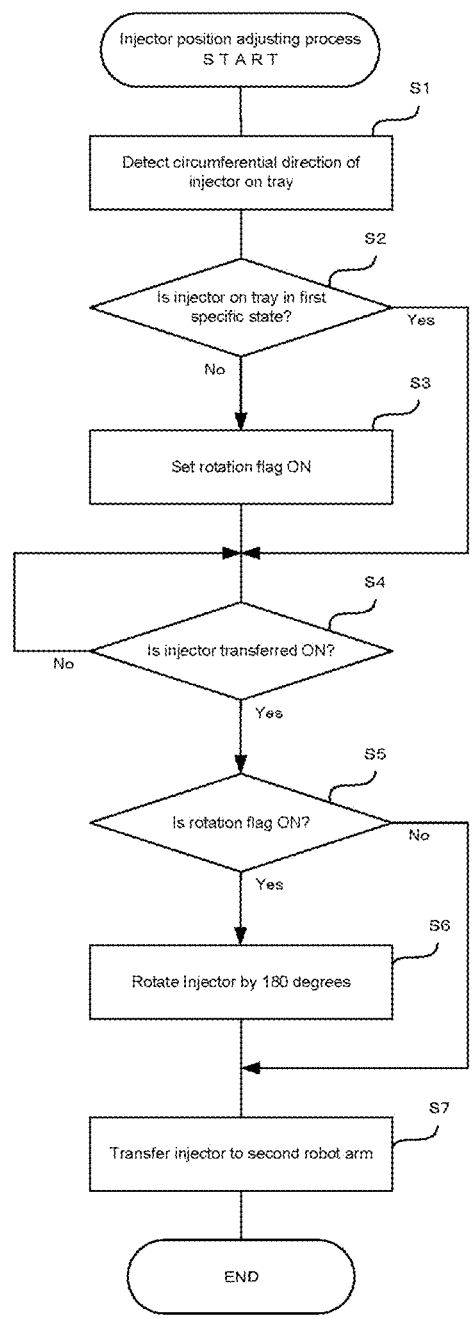
FIG. 18 is a flow chart showing one example of steps of an injector position adjusting process carried out by the co-infusion apparatus according to the embodiment of the present invention.

In the co-infusion process, the second control section 500 carries out the injector position adjusting process for adjusting a circumferential position of the injector 11 held by the second robot arm 22 so that characters of a scale of the injector 11 are located in the photographing range R1 of the injector confirming camera 42 at the time of photographing the inspection image referred to for inspecting whether or not the co-infusion process is properly carried out. The second control section 500 starts the injector position adjusting process when the image for the object placing member 102 is photographed by the tray confirming camera 41. In this case, the second control section 500 at the time of carrying out the injector position adjusting process is one example of an injector position adjusting means. FIG. 18 is a flow chart for showing one example of steps of the injector position adjusting process.

<Step S1>

First, at a step S1, the second control section 500 determines a direction of the syringe 11*a* of the injector 11 placed on the object placing member 102, which is a predetermined placing position, based on the photographed image photographed by the tray confirming camera 41. In this case, the second control section 500 at the time of carrying out the step S1 is one example of a direction detecting means. Specifically, a flange is provided at a tip end of the syringe 11a and the syringe 11a placed on the object placing member 102 is in a state that the characters of the scale are directed toward an upper direction or a lower direction. Thus, the second control section 500 determines whether the injector 11 is placed on the object placing member 102 in a state that the characters of the scale written on the syringe 11a of the injector 11 are directed toward the upper direction (that is a state that the characters of the scale are directed toward the side of the tray confirming camera 41) or the lower direction (the characters of the scale are rotated by 180 degrees in the circumferential direction with respect to the tray confirming camera 41).

The image recognition method based on the photographed image is not particularly limited to a specific method. For example, the second control section 500 may identify the injector 11 corresponding to a standard size indicated in the preparation data with an image matching method. Then, the second control section 500 determines that the characters of the scale of the injector 11 are directed toward the upper direction with applying an OCR (Optical Character Recognition) technique to the image for the injector 11 in the case where characters such as "1", "2" and the like indicating the scale exist on the syringe 11a. Alternatively, in the case where the characters of the scale of the injector 11 are directed toward the lower direction, a reversed character image obtained by reversing the characters indicating the scale is contained in the photographed image photographed by the tray confirming camera 41. Thus, it may be considered that the second control section 500 determines that the characters of the scale of the injector 11 are directed toward the lower direction in the case where the reversed character image exists in the photographed image photographed by the tray confirming camera 41.

In this regard, in the co-infusion apparatus 1, the injector 11 placed on the object placing member 102 is taken by the first robot arm 21 to place it onto the placing shelf 33 and then passed from the first robot arm 21 to the second robot arm 22. At this time, the injector 11 is passed from the first robot arm 21 to the second robot arm 22 in a state that the first robot arm 21 confronts the second robot arm 22. Thus, the front and rear of the surface of the injector 11 is changed between the state that the injector 11 is held by the first robot arm 21 and the state that the injector 11 is held by the second robot arm 22. Hereinafter, a state of the injector 11 placed on the object placing member 102 that the characters of the scale of the injector 11 are located in the photographing range R1 of the injector confirming camera 42 when the injector 11 is transferred into the photographing range R1 of the injector confirming camera 42 by the second robot arm 22 is referred to as "first specific state". Specifically, in the co-infusion apparatus 1, the state that the characters of the scale of the injector 11 placed on the object placing member 102 are directed toward the upper direction is the first specific state. In the case where the injector 11 is in the first specific state in the object placing member 102, the characters of the scale of the injector 11 are directed toward the side of the holding member 25 when the injector 11 is held by the first robot arm 21. Thus, it is impossible to photograph the characters of the scale of the injector 11 in this state with the injector confirming camera 42. In contrast, when the injector 11 is passed from the first robot arm 21 to the second robot arm 22, the characters of the scale of the injector 11 are directed toward the opposite side of the holding member 26. Thus, it becomes possible to photograph the characters of the scale of the injector 11 with the injector confirming camera 42.

<Steps S2 to S3>

At a step S2, the second control section 500 branches the process depending on whether or not the injector 11 in the object placing member 102 is in the first specific state. Specifically, in the case where the injector 11 is not in the first specific state (the case of determining "No" at the step S2), the process shifts to a step S3. At the step S3, the second control section 500 sets a rotation flag, which indicates that a rotating operation for the injector 11 should be carried out, ON. The rotation flag is a flag register provided in the RAM 503 of the second control section 500. On the other hand, in the case where the injector 11 is in the first specific state (the case of determining "Yes" at the step S2), the process shifts to a step S4.

<Step S4>

At the step S4, the second control section 500 waits an arrival of timing of transferring the injector 11 to the second robot arm 22 (the case of determining "No" at the step S4). Then, when the timing of transferring the injector 11 to the second robot arm 22 arrives (the case of determining "Yes" at the step S4), the process shifts to a step S5. In the co-infusion apparatus 1, since the injector 11 is temporarily placed onto the placing shelf 33 by the first robot arm 21, an arrival of timing when the first robot arm 21 passes the injector 11 from the placing shelf 33 to the second robot arm 22 is monitored at the step S4.

<Step S5>

At the step S5, the second control section 500 determines whether or not the rotation flag is ON. In the case where the rotation flag is ON (the case of determining "Yes" at the step S5), the process shifts to a step S6. In the case where the rotation flag is OFF (the case of determining "No" at the step S5), the process shifts to a step S7.

<Step S6>

At the step S6, the second control section 500 controls the first robot arm 21 to rotate the injector 11 in the circumferential direction thereof by 180 degrees with utilizing the placing member for rotation 33A as described above. In this case, the second control section 500 at the time of carrying out the step S6 is one example of an injector rotating means. With this configuration, it is possible to set a direction of the injector 11 to be the same direction as the case where the injector 11 is placed on the object placing member 102 in the first specific state. Thus, according to the co-infusion apparatus 1, it is possible to locate the characters of the scale of the injector 11 in the photographing range R1 of the injector confirming camera 42 when the injector 11 is transferred into the photographing range R1 of the injector confirming camera 42 by the second robot arm 22. In this regard, another configuration in which the injector 11 can be rotated by the second robot arm 22 may be considered as another embodiment.

<Step S7>

After that, at the step S7, the second control section 500 controls the first robot arm 21 and the second robot arm 22 to transfer the injector 11 from the first robot arm 21 to the second robot arm 22.

[Container Position Adjusting Process]

Figure 19:
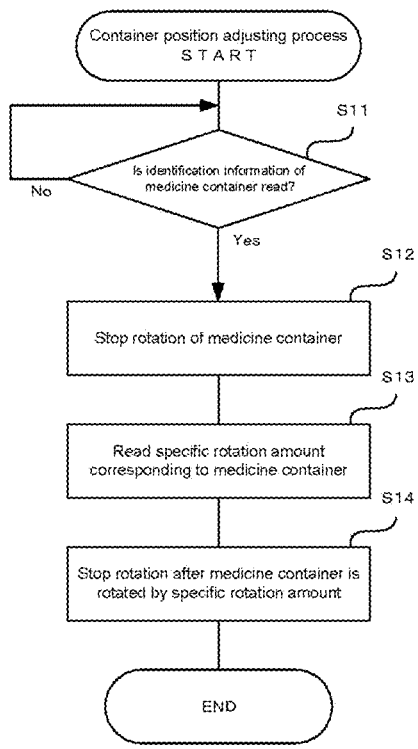
FIG. 19 is a flow chart showing one example of steps of a container position adjusting process carried out by the co-infusion apparatus according to the embodiment of the present invention.

In the co-infusion process, the second control section 500 carries out the container position adjusting process for adjusting a circumferential position of the medicine container 10 so that characters of a medicine name on the medicine container 10 are located in the photographing range R1 of the injector confirming camera 42 at the time of photographing the inspection image referred to for inspecting whether or not the co-infusion process is properly carried out. In this case, the second control section 500 at the time of carrying out the container position adjusting process is one example of a container position adjusting means. FIG. 19 is a flow chart showing one example of steps of the container position adjusting process.

<Step S11>

First, at a step S11, the second control section 500 makes the process stand by until the medicine information is read by the medicine reading section 34 from the barcode of the medicine container 10 (the case of determining "No" at the step S11). Then, when the second control section 500 determines that the medicine information is read by the medicine reading section 34 from the medicine container 10 (the case of determining "Yes" at the step S11), the process shifts to a step S12.

<Step S12>

At the step S12, the second control section 500 allows the driving motor of the roller 34a of the medicine reading section 34 to be stopped to stop the rotation of the medicine container 10.

<Step S13>

At a step S13, the second control section 500 reads a specific rotation amount corresponding to the medicine container 10. Specifically, information on specific rotation amounts for each medicine container 10 is stored in the data storage section 504 of the second control section 500. Each of the specific rotation amounts represents a rotation amount required for setting the medicine container 10 to be in a predetermined second specific state after the barcode of the medicine container 10 is read. The second specific state is a state of the medicine container 10 in the medicine reading section 34 that the medicine name of the medicine container 10 is located in the photographing range R1 of the injector confirming camera 42 when the medicine container 10 is transferred into the photographing range R1 of the injector confirming camera 42 by the first robot arm 21. Specifically, in this embodiment, the second specific state is a state that the medicine name of the medicine container 10 is directed toward the lower direction (a state that the medicine name is directed toward the side of the roller 34a of the medicine reading section 34). With this configuration, the medicine name of the medicine container 10 is directed toward the opposite side of the holding member 25 when the medicine container 10 is held by the first robot arm 21. Thus, it becomes possible to photograph the medicine name with the injector confirming camera 42. In this regard, another configuration in which the second specific state contains not only a state that an entire portion of the medicine name of the medicine container 10 is located in the photographing range R1 but also, for example, a state that a part of the medicine name is located in the photographing range R1 as long as the medicine name of the medicine container 10 can be recognized may be considered as another embodiment.

The information on the specific rotation amount is a driving amount or a driving duration time of the driving motor (not shown in the drawings) of the roller 34a of the medicine reading section 34 or the like. The information on the specific rotation amount is set in advance based on a separation distance between a position of the barcode and a position of the characters of the medicine name in the circumferential direction of the medicine container 10 and a rotational speed of the roller 34a. In this regard, it may be considered that the separation distance between the position of the barcode and the position of the characters of the medicine name is preliminarily registered in the medicine master so as to correspond to each medicine container 10 and the second control section 500 calculates the specific rotation amount for the medicine container 10 in the medicine reading section 34 based on the distance for each time. Further, it may be considered that the specific rotation amount is information stored in the medicine master of the data storage section 404 and the second control section 500 receives the information on the specific rotation amount corresponding to the medicine container 10 from the first control section 400.

<Step S14>

After that, at a step S14, the second control section 500 controls the driving motor (not shown in the drawings) of the roller 34a to rotate the medicine container 10 with the roller 34a by the specific rotation amount and then stop the rotation of the medicine container 10. With this configuration, it is possible to rotate the medicine container 10 by the specific rotation amount and then stop the rotation of the medicine container 10 so that the medicine container 10 is in the second specific state after the medicine information of the medicine container 10 has been read by the barcode reader 34b. In this regard, another configuration which carries out the steps S13 to S14 without stopping the rotation of the medicine container 10 due to the roller 34a by omitting the step S12 may be considered as another embodiment.

As described above, in the co-infusion apparatus 1, the medicine container 10 in the medicine reading section 34 always takes the second specific state. Thus, the characters of the medicine name on the medicine container 10 are located in the photographing range R1 when the medicine container 10 is transferred into the photographing range R1 by the first robot arm 21. Hereinafter, description will be given to the case of locating the medicine name on the medicine container 10 in the photographing range R1, but the circumferential position of the medicine container 10 may be adjusted so that other information such as the barcode of the medicine container 10 and the medicine code of the medicine container 10 is located in the photographing range R1 instead of the medicine name.

[Inspection Control Process]

Figure 20:
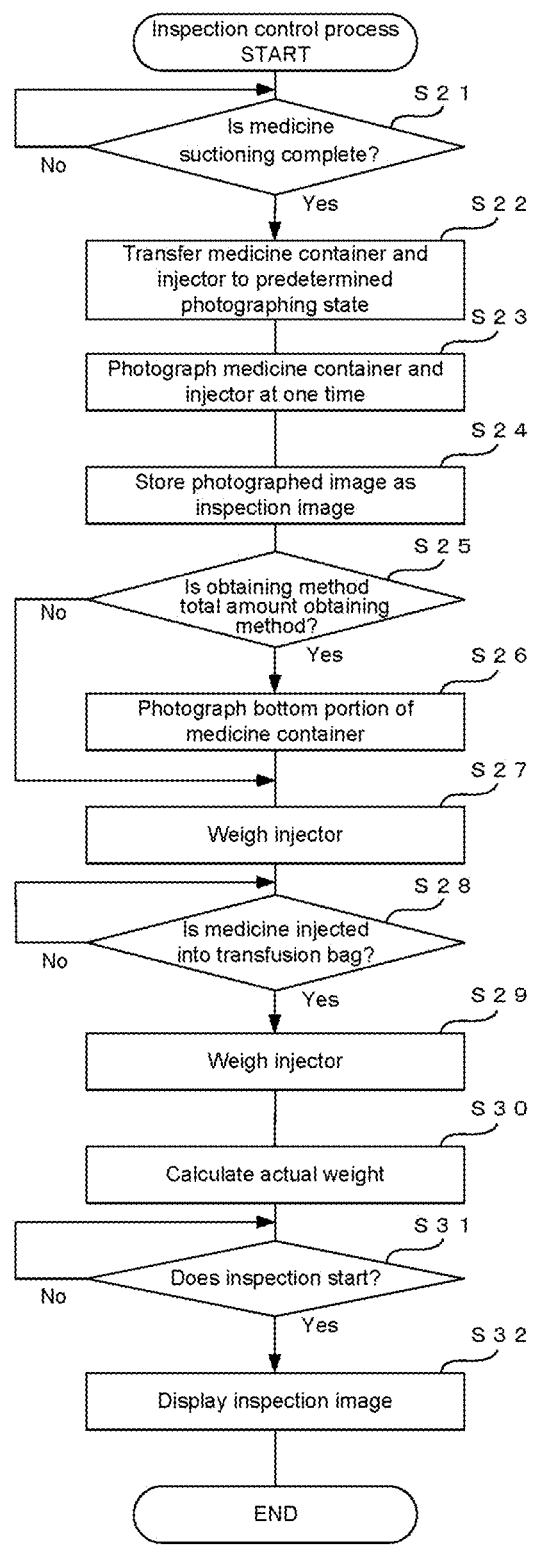
FIG. 20 is a flow chart showing one example of steps of an inspection control process carried out by the co-infusion apparatus according to the embodiment of the present invention.

In the co-infusion process, the second control section 500 carries out the following inspection control process in order to allow the user to carry out the image inspection of the co-infusion process. In this case, the second control section 500 at the time of carrying out the inspection control process is one example of a transfer control means. FIG. 20 is a flow chart showing one example of steps of the inspection control process.

<Step S21>

First, at a step S21, the second control section 500 waits that the injector 11 completes the suctioning of the medicine in the medicine container 10 (the case of determining "No" at the step S21). When the second control section 500 determines that the injector 11 completes the suctioning of the medicine (the case of determining "Yes" at the step S21), the process shifts to a step S22.

<Step S22>

At the step S22, the second control section 500 controls one or both of the first robot arm 21 and the second robot arm 22 to transfer the medicine container 10 after the medicine has been suctioned from the medicine container 10 with the injector 11 and the injector 11 in which the medicine has been suctioned into the photographing range R1 of the injector confirming camera 42. At this time, the second control section 500 allows the first robot arm 21 and the second robot arm 22 to keep holding states of the medicine container 10 and the injector 11 until the medicine container 10 and the injector 11 are photographed by the injector confirming camera 42 after the medicine has been suctioned from the medicine container 10 by the injector 11. Namely, the second control section 500 allows the first robot arm 21 and the second robot arm 22 to transfer, into the photographing range R1, the held medicine container 10 and the held injector 11 without releasing the medicine container 10 and the injector 11 even once. With this configuration, it is possible to enhance the reliability for ensuring the medicine in the injector 11 in the photographed image photographed by the injector confirming camera 42 is the same as the medicine in the medicine container 10.

At this time, due to the injector position adjusting process (see FIG. 18), the position of the injector 11 is adjusted so that the characters of the scale of the injector 11 are located in the photographing range R1 when the injector 11 is transferred into the photographing range R1 by the first robot arm 21. In the same manner, due to the container position adjusting process (see FIG. 19), the position of the medicine container 10 is adjusted so that the characters of the medicine name on the medicine container 10 are located in the photographing range R1 when the medicine container 10 is transferred into the photographing range R1 by the first robot arm 21.

Further, at the step S22, the second control section 500 allows the medicine container 10 and the injector 11 to be arranged in the photographing range R1 so that the characters of the medicine name on the medicine container 10 and the characters of the scale of the injector 11 are directed toward the same direction. Particularly, the second control section 500 allows the medicine container 10 and the injector 11 to be arranged in the photographing range R1 so that vertical directions of the characters of the medicine name on the medicine container 10 and the characters of the scale of the injector 11 are directed toward the same direction as a vertical direction in the photographing range R1.

Figure 21:
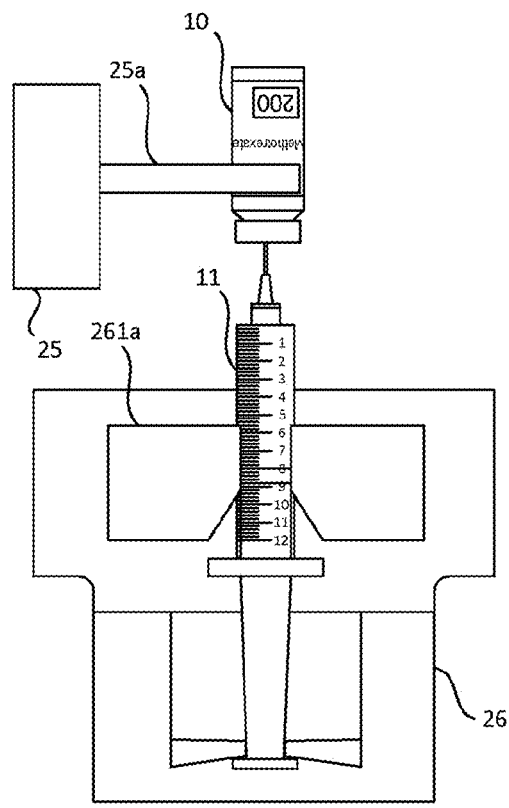
FIG. 21 is a view showing one example of a positional relationship between a medicine container and an injector of the co-infusion apparatus according to the embodiment of the present invention.

FIG. 21 is a view showing one example of a positional relationship between the medicine container 10 and the injector 11.

As shown in FIG. 21, when the medicine is suctioned from the medicine container 10 with the injector 11, the injector 11 is in a state that the injection needle 11c is directed toward the upper direction and the medicine container 10 is in a state that the opening portion of the medicine container is directed toward the lower direction. FIG. 21 is the view showing the positional relationship in the case where the vial bottle 10B is used as the medicine container 10. In the case where the ampule 10A is used as the medicine container 10, the positional relationship between the medicine container 10 and the injector 11 shown in FIG. 21 is reversed.

Figure 22:
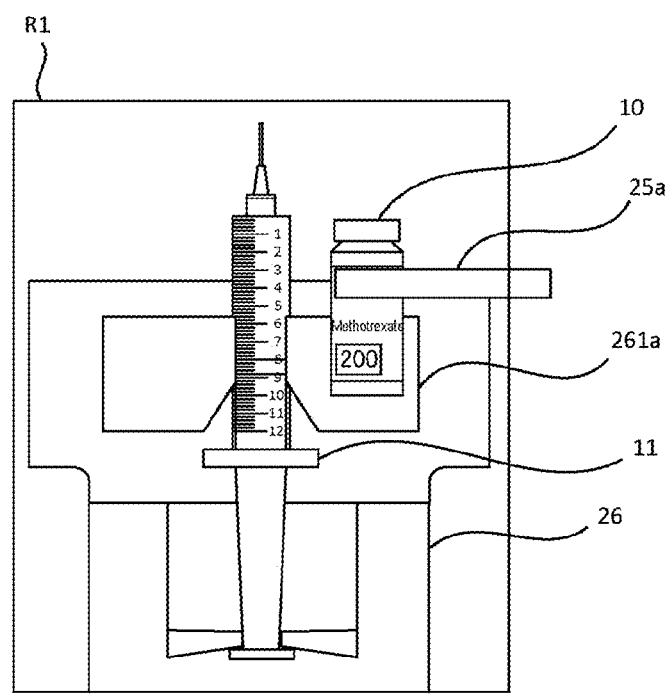
FIG. 22 is another view showing one example of the positional relationship between the medicine container and the injector.

When the suctioning of the medicine from the medicine container 10 with the injector 11 completes, due to the step S22, the medicine container 10 and the injector 11 are transferred at positions so that the medicine container 10 and the injector 11 are located in the photographing range R1 of the injector confirming camera 42 as shown in FIG. 22. Further, the medicine container 10 and the injector 11 allowed to be transferred by the second control section 500 at the step S22 are arranged so that the characters of the medicine name on the medicine container 10 and the characters of the scale of the injector 11 are directed toward the same direction as shown in FIG. 22. Particularly, the vertical directions of the characters of the scale of the injector 11 and the characters of the medicine name on the medicine container 10 are directed toward the same direction as the vertical direction in the photographing range R1. Furthermore, as shown in FIG. 22, the second control section 500 allows the medicine container 10 and the injector 11 to be arranged in the photographing range R1 so that the medicine container 10 and the injector 11 are aligned in a direction perpendicular to a longitudinal direction of the injector 11. With this configuration, it is possible to prevent the size of the photographing range R1 from being long. Of course, another configuration in which the medicine container 10 and the injector 11 are aligned in the longitudinal direction of the injector 11 as shown in FIG. 23 may be considered as another embodiment.

<Step S23>

Next, the second control section 500 controls the injector confirming camera 42 to photograph the photographing range R1 with the injector confirming camera 42. Namely, the second control section 500 allows the medicine container 10 and the injector 11 located in the photographing range R1 to be photographed at one time. With this configuration, it is possible to obtain a highly reliable image as the inspection image for the injector 11 compared with the case where the injector 11 is photographed multiple times and photographed images are synthesized to obtain the inspection image. Further, since the medicine container 10 and the injector 11 are simultaneously photographed, it is possible to ensure reliability for a correspondence relationship between the medicine container 10 and the injector 11 compared with the case where the medicine container 10 and the injector 11 are separately photographed.

<Step S24>

Then, the second control section 500 allows the data storage section 504 to store the photographed image photographed by the injector confirming camera 42 at the step S23 as the inspection image. In this regard, the second control section 500 may allow another server device or the like connected to the co-infusion apparatus 1 through a communication network to store the inspection image.

<Step S25>

Next, the second control section 500 determines whether or not an obtaining method corresponding to the medicine of the medicine container 10 indicated in the preparation data for an adjusted target in the co-infusion process is a whole amount obtaining. The whole amount obtaining is an obtaining method in the case where the medicine in the medicine container 10 is obtained in a whole amount. In addition, a partial amount obtaining for obtaining the medicine in the medicine container 10 in a predetermined amount indicated in the preparation data is known as another obtaining method. The obtaining method for each medicine is preliminarily registered in the medicine master or the like. In the case where the second control section 500 determines that the obtaining method is the whole amount obtaining (the case of determining of "Yes" at the step S25), the process shifts to a step S26. In the case where the second control section 500 determines that the obtaining method is not the whole amount obtaining (the case of determining of "No" at the step S25), the process shifts to a step S27.

In the case where the vial bottle 10B in which a medicine to which the dissolution process needs to be applied is contained is used as the medicine container 10, the transfusion in the transfusion bag 12 is injected into the vial bottle 10B and dissolved and then the whole amount obtaining for obtaining the whole amount of the medicine or the partial amount obtaining for obtaining a part of the medicine is carried out. On the other hand, in the case where the vial bottle 10B or the ampule 10A in which a medicine to which the dissolution process needs not to be applied is contained is used as the medicine container 10, the partial amount obtaining for obtaining the medicine from the vial bottle 10B or the ampule 10A in a medicine amount indicated in the preparation data.

<Step S26>

At the step S26, the second control section 500 controls the first robot arm 21 and the injector confirming camera 42 to photograph a bottom portion of the medicine container 10. In this case, the injector confirming camera is one example of a whole amount obtaining timing photographing means. In this regard, it may be considered that the co-infusion apparatus 1 includes a container photographing camera (whole amount obtaining timing photographing means) provided on a lower surface of the co-infusion process chamber 104 and used for photographing the bottom portion of the medicine container 10 in addition to the injector confirming camera 42.

FIGS. 24(A) and 24(B) are views showing examples of a photographing result at the step S26. Specifically, it may be considered that the second control section 500 controls the first robot arm 21 to change the state of the medicine container 10 in the photographing range R1 of the injector confirming camera 42 to a state that the opening portion of the medicine container 10 is inclined at a predetermined angle with respect to the vertical upper direction as shown in FIG. 24(A) to photograph a side surface of the medicine container 10 with the injector confirming camera 42. With this configuration, in the case where the medicine remains in the medicine container 10, it is possible to confirm a state that the medicine remains on a lower end portion of the medicine container 10 by referring to the photographed image photographed by the injector confirming camera 42. In this regard, it may be considered that the second control section 500 allows the container photographing camera to photograph the bottom surface of the medicine container 10 in the state shown in FIG. 24(A).

Further, it may be considered that the second control section 500 controls the first robot arm 21 to change the state of the medicine container 10 in the photographing range R1 of the injector confirming camera 42 to a state that the bottom surface of the medicine container 10 is located in the photographing range R1 as shown in FIG. 24(B) to photograph the bottom surface of the medicine container 10 with the injector confirming camera 42. With this configuration, in the case where the medicine remains in the medicine container 10, it is possible to photograph a state that the medicine remains in the medicine container 10. Thus, in the case where the medicine remains in the medicine container 10, it is possible to confirm a state that the medicine remains on the bottom surface of the medicine container 10 by referring to the photographed image photographed by the injector confirming camera 42. Further, it is also possible to confirm that a powdered medicine which is not dissolved remains in the medicine container 10 by referring to the photographed image.

Further, it may be considered that the second control section 500 carries out an image processing based on the photographed image for the bottom portion of the medicine container 10 to automatically determine whether or not the medicine remains in the medicine container 10 and report this determining result. For example, the second control section 500 can determine whether or not the medicine remains in the medicine container 10 according to presence or absence of a horizontal line of a liquid surface, which appears in the case where the medicine remains on the bottom portion of the medicine container 10, in the photographed image.

<Step S27>

At the step S27, the second control section 500 controls the second robot arm 22 and the weighing scale 35 to measure a weight of the injector 11 with the weighing scale 35. The weight of the injector 11 weighed at this step S27 is stored in the RAM 503 of the second control section 500 as an after-suctioning weight.

<Step S28>

After that, at a step S28, the second control section 500 waits completion of the injection process for injecting the medicine from the injector 11 into the transfusion bag 12 in the co-infusion process (the case of determining "No" at the step S28). Then, the second control section 500 shifts the process to a step S29 when the injection process for injecting the medicine from the injector 11 into the transfusion bag 12 completes (the case of determining "Yes" at the step S28).

<Step S29>

At the step S29, the second control section 500 controls the second robot arm 22 and the weighing scale 35 to measure a weight of the injector 11 with the weighing scale 35. The weight of the injector measured at this step S29 is stored in the RAM 503 of the second control section 500 as an after-injecting weight.

<Step S30>

Then, at a step S30, the second control section 500 calculates a difference between the after-suctioning weight measured at the step S27 and the after-injecting weight measured at the step S29 to capture a weight of the medicine injected into the transfusion bag 12 in practice. The weight of the medicine calculated at this step S30 is stored in the RAM 503 of the second control section 500 as an actual weight. In this case, the second control section 500 at the time of carrying out this process is one example of a medicine weight capturing means. Further, it may be considered that the second control section 500 captures a difference between a weight of the injector 11 before the medicine is suctioned from the medicine container 10 and a weight of the injector 11 after the medicine has been suctioned from the medicine container 10 as a weight of the medicine injected from the medicine container 10 into the transfusion bag 12.

<Step S31>

After that, at a step S31, the second control section 500 waits start timing of the inspection of the co-infusion process (the case of determining "No" at the step S31). When the start timing of the inspection of the co-infusion process arrives (the case of determining "Yes" at the step S31), the process shifts to a step S32. For example, the start timing of the inspection of the co-infusion process is timing before the transfusion bag 12 is dispensed after the co-infusion process completes. Alternatively, the start timing of the inspection of the co-infusion process may be timing when a selecting operation for selecting the co-infusion process (preparation data) for an inspection target is carried out with respect to the touch panel monitor 14 after a plurality of co-infusion processes have been carried out.

<Step S32>

Figure 25:
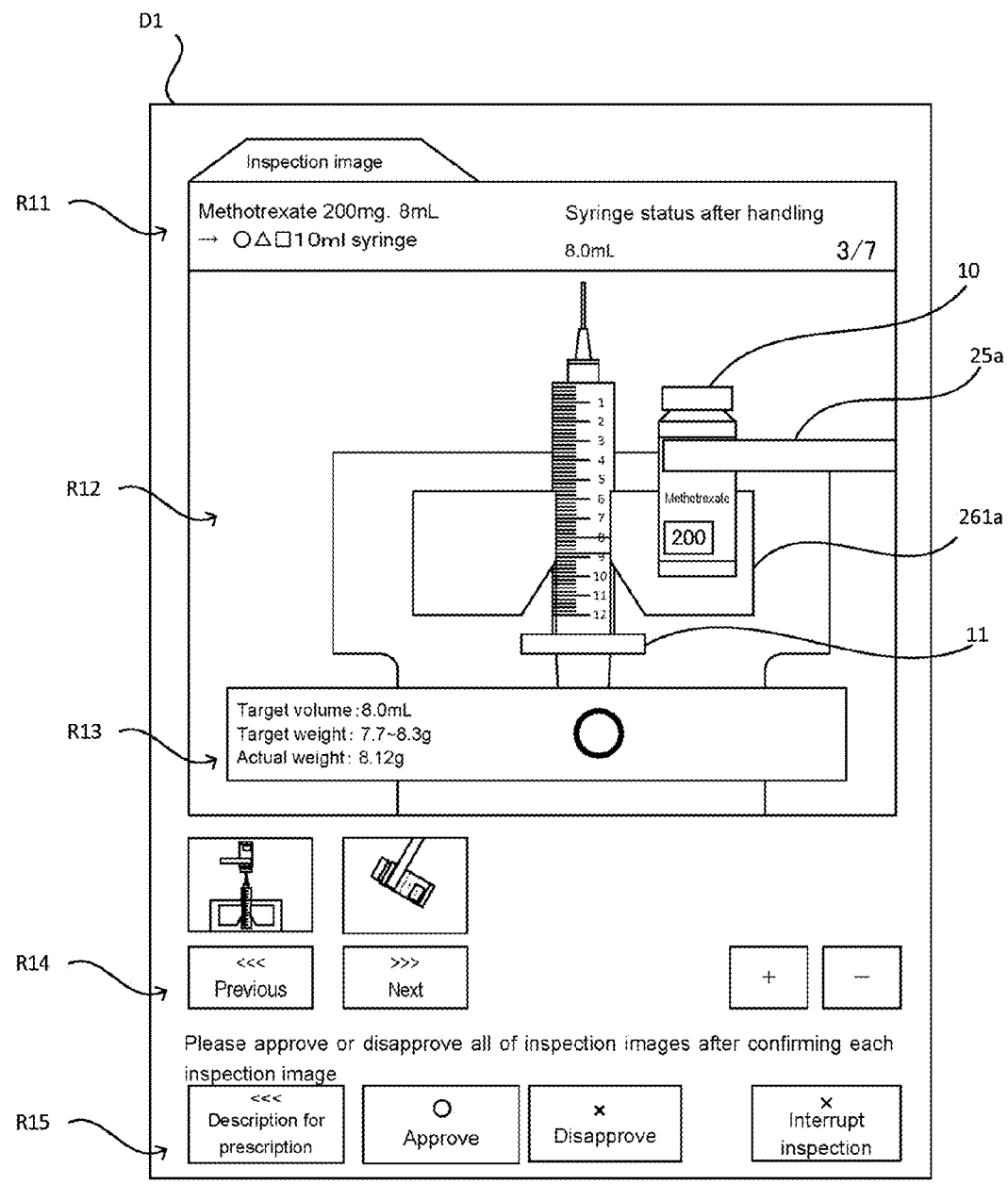
FIG. 25 is a view showing one example of an inspection screen displayed in the inspection control process carried out by the co-infusion apparatus according to the embodiment of the present invention.
Figure 26:
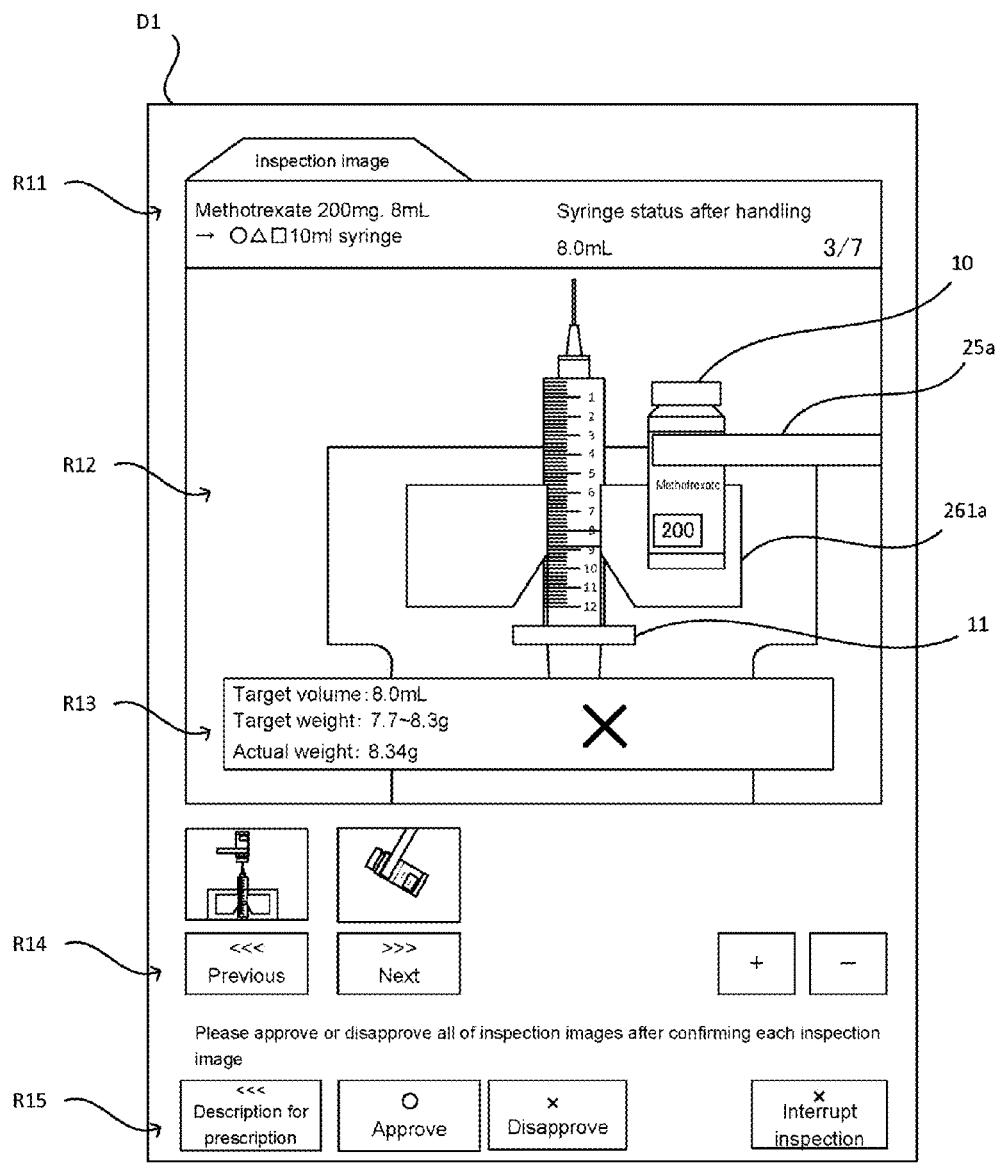
FIG. 26 is another view showing another example of the inspection screen displayed in the inspection control process carried out by the co-infusion apparatus according to the embodiment of the present invention.

At the step S32, the second control section 500 allows the touch panel monitor 14 to display an inspection screen D1 used for carrying out the image inspection of the co-infusion process. FIGS. 25 and 26 are views showing examples of the inspection screen D1. As shown in FIGS. 25 and 26, the inspection screen D1 contains display regions R11 to R13 on which information used for the inspection is displayed.

Further, an operation part R14 for displaying a plurality of images to be inspected in turn and an operation part R15 for carrying out operations such as approval, disapproval and interruption of the inspection are also displayed on the inspection screen D1.

In the display region R11, a medicine name of "Methotrexate 200 mg", a medicine volume of "8 mL" and an injector name of "○△□ 10 ml syringe" indicated in the preparation data are displayed. Further, in the display region R11, a numerical value "8.0 mL" of the scale of the injector 11 calculated based on an actual operation amount of the plunger 11b by the transferring member 263 of the second robot arm 22 is also displayed.

In the display region R12, the image photographed by the injector confirming camera 42 at the step S23 in the inspection control process (see FIG. 20) or the like is displayed as the inspection image. In this case, the second control section 500 at the time of allowing the inspection image to be displayed in the inspection screen D1 is one example of an inspection image display means. As described above, the inspection image in the display region R12 and the information in the display region R11 are together displayed on one screen. This makes it possible to enable an inspector to easily collate the medicine name displayed in the display region R11 with the characters of the medicine name on the medicine container 10 in the inspection image displayed in the display region R12.

Further, in the case where the obtaining method for obtaining the medicine in the co-infusion process is the whole amount obtaining, the second control section 500 allows the image for the bottom surface of the medicine container 10 (see FIG. 24) photographed at the step S26 to be displayed in the display region R12 as the inspection image according to an operation with respect to the operation part R14. This makes it possible for the inspector to determine whether or not the medicine remains in the medicine container 10 by referring to the image for the bottom surface of the medicine container 10 displayed in the display region R12.

In the display region R13, a target volume, a target weight, an actual weight and a weight inspection result are displayed. Specifically, in the display region R13 shown in FIG. 25, a target volume of "8.0 mL", a target weight of "7.7 to 8.3 g", an actual weight of "8.12 g" and a weight inspection result of "○" are displayed. Further, in the display region R12 shown in FIG. 26, a target volume of "8.0 mL", a target weight of "7.7 to 8.3 g", an actual weight of "8.34 g" and a weight inspection result "X" are displayed.

The target volume is a medicine volume contained in the preparation data and a value used as a control index for the operation amount of the plunger 11b by the second robot arm 22. The target weight is a value calculated based on the target volume and a specific weight of the medicine and representing an acceptable range with respect to the weight of the medicine. Further, it may be considered that a weight of the medicine (for example, 8.0 g) corresponding to the target volume and a range of an acceptable error (for example, ±3%) with respect to this weight are displayed instead of the target weight. The actual weight is the weight of the medicine calculated at the step S30 and a value representing the weight of the medicine injected into the transfusion bag 12 in practice.

As described above, the inspection image in the display region R12 and the information in the display region R13 are together displayed on one screen. This makes it possible for the inspector to easily collate the target volume displayed in the display region R13 with the characters of the scale of the injector 11 in the inspection image displayed in the display region R12. Particularly, since the directions of the characters of the medicine name on the medicine container 10 and the characters of the scale of the injector 11 are directed toward the same direction in the inspection image, it is possible to provide a screen which is easy to see for the inspector. Further, since the vertical directions of the characters of the medicine name on the medicine container 10 and the characters of the scale of the injector 11 are directed toward the same direction as the vertical direction in the photographing range R1, the inspector can easily and reliably confirm the characters of the medicine name on the medicine container 10 and the characters of the scale of the injector 11. Thus, it is possible to prevent, for example, an inspection error.

Further, the inspector can confirm whether or not the actual weight, which is the weight of the medicine coinfused from the medicine container 10 into the transfusion bag 12 in the co-infusion process, is in the range for the target weight from one screen of the inspection screen D1 with confirming the medicine name. Further, the second control section 500 determines whether or not the actual weight, which is the weight of the medicine coinfused from the medicine container 10 into the transfusion bag 12 in the co-infusion process, is in the range for the target weight to allow this determining result to be displayed in the display region R12 with a symbol "○" or "X". With this configuration, the inspector can understand the weight inspection result at a glance by referring to the display region R13 displayed together with the display region R12. In this case, the second control section 500 at the time of carrying out such a determining process is one example of a weight inspecting means. Further, it may be considered that a background color of the display region R12 is changed to a blue color in the case where the inspection result is "○" indicating that the inspection result is proper and the background color of the display region R12 is changed to a red color in the case where the inspection result is "X" indicating that the inspection result is improper.

In this regard, the second control section 500 takes into account the specific weight of the medicine at the time of calculating the target weight (g) for the medicine from the target volume (mL) for the medicine. Specifically, the specific weight of each medicine is preliminarily stored in the medicine master of the data storage section 404 of the first control section 400 or the like and the second control section 500 captures information on the specific weight of each medicine from the first control section 400.

In the case where the medicine contained in the medicine container 10 is a medicine such as a liquid medicine to which the dissolution process needs not to be applied, it is possible to calculate the target weight based on the specific weight of the medicine contained in the medicine container 10. In contrast, in the case where the medicine contained in the medicine container 10 is a medicine such as a powdered medicine to which the dissolution process needs to be applied, it is necessary to calculate the target weight with taking into account not only the specific weight of the medicine contained in the medicine container 10 but also a specific weight of a solvent for dissolving the medicine. Thus, in the second control section 500, in addition to the specific weight for each medicine stored in the medicine master, a predetermined specific weight corresponding to each combination of the medicine to which the dissolution process needs to be applied and the solvent used for the dissolution of the medicine is stored in the data storage section 504. More specifically, an amount of the solvent used for the dissolution of the medicine in the medicine container 10 is preliminarily designated for each type of the medicine to be contained in the medicine container 10. Thus, the specific weight corresponding to each combination of the medicine and the solvent is a specific weight corresponding to the case where the medicine is dissolved into the solvent in an amount designated as the solvent amount used for the dissolution of the medicine. With this configuration, the co-infusion apparatus 1 can inspect the amount of the medicine injected into the transfusion bag 12 with utilizing the weight even in the case of dissolving the medicine such as the powdered medicine contained in the vial bottle 10B, to which the dissolution process needs to be applied, into the transfusion and then injecting the medicine into the transfusion bag 12.

On the other hand, the acceptable range is a range predetermined according to, for example, the standard volume of the injector 11 to be used in the co-infusion process. FIG. 27 is a view showing one example of correspondence information defining a relationship between the standard volume of the injector 11 and the acceptable range. As shown in FIG. 27, in the correspondence information, the acceptable range is defined for the standard volume of each injector 11. For example, in the case where the standard volume of the injector 11 is "equal to or more than 5 ml and less than 10 ml", the acceptable range is "±3%" and a value of the acceptable range is "±0.15 ml". Namely, the acceptable range is not defined according to the injection amount of the medicine but defined according to the standard volume of the injector 11. In FIG. 27, acceptable ranges defined by the Health, Labor and Welfare Ministry are shown for references. The acceptable ranges used in the co-infusion apparatus 1 are defined so as to be smaller than the ranges defined by the Health, Labor and Welfare Ministry.

Then, the second control section 500 converts the value of the acceptable range to a weight value based on the specific weight of the medicine. Specifically, in the correspondence information shown in FIG. 27, since the standard volume of the injector 11 to be used in the co-infusion process is "10 ml", the acceptable range is "±3%", that is "±0.3 ml". When the specific weight of the medicine to be used in the co-infusion process is defined as "1", a weight conversion value from the acceptable range of "±0.3 ml" is "±0.3 g". Thus, as shown in FIGS. 25 and 26, in the display region R13, a range of "7.7 to 8.3 g" is displayed as a value of the target weight calculated based on the conversion weight value. Further, in the case where the specific weight of the medicine is "1.1", the weight conversion value is "±0.33 g". Furthermore, another configuration in which a range of "7.7 to 8.3 ml", which is the value of the acceptable range corresponding to the target weight, is displayed in the display region R13 may be considered as another embodiment.

[Tray Collating Process]

Figure 28:
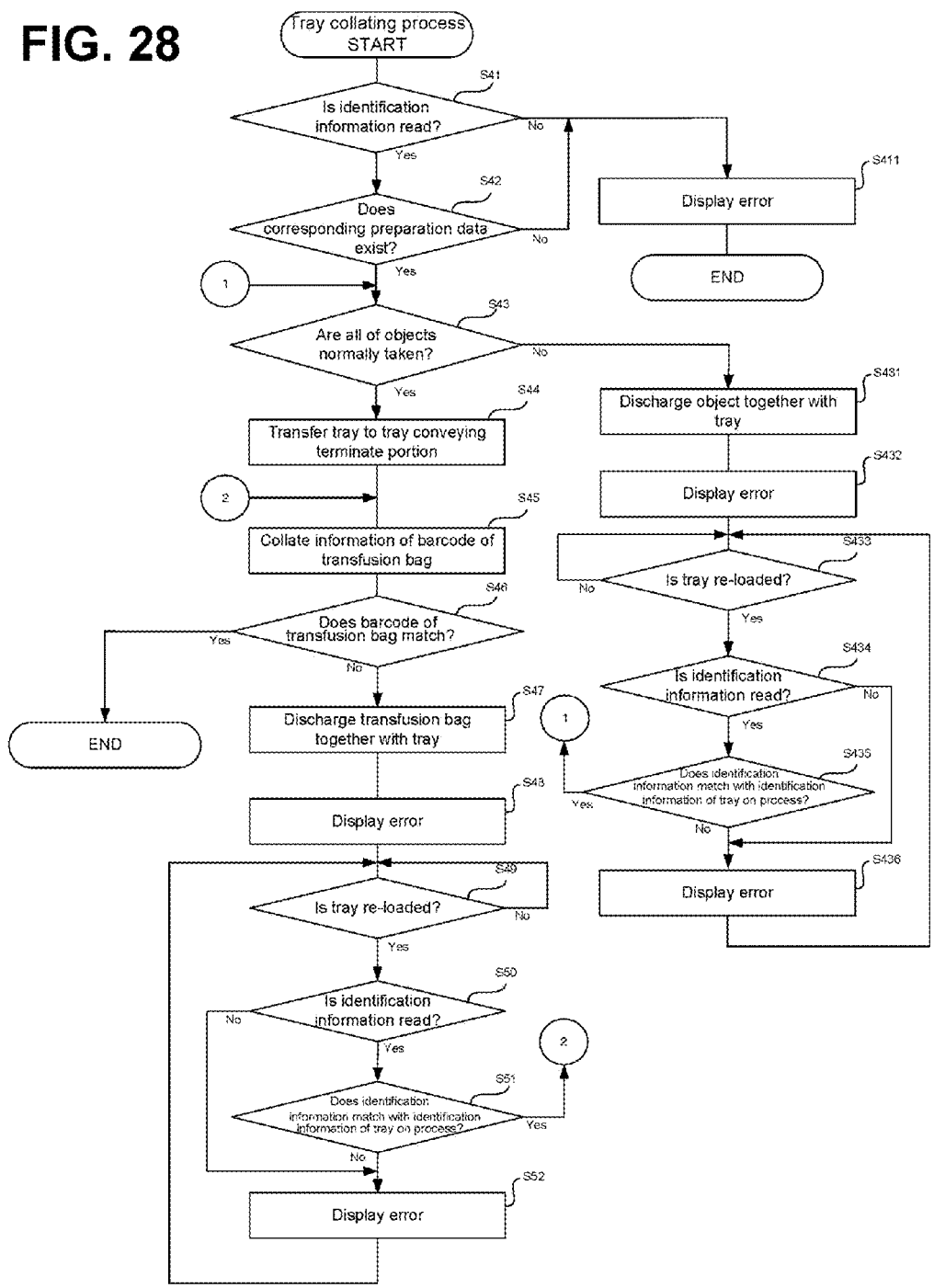
FIG. 28 is a flow chart showing one example of steps of a tray collating process carried out by the co-infusion apparatus according to the embodiment of the present invention.

In the co-infusion process, the second control section 500 carries out the tray collating process for determining whether or not the tray 101 and the object to be placed on the tray 101 are proper. The second control section 500 starts the tray collating process in the case of detecting that the tray 101 is loaded through the tray insertion port 114 with a sensor (not shown in the drawings). In this case, the second control section 500 at the time of carrying out the tray collating process is one example of a collating means. FIG. 28 is a flow chart showing one example of steps of the tray collating process.

<Step S41>

First, at a step S41, the second control section 500 determines whether or not the identification information is read from the IC tag 101*b* of the tray 101 loaded through the tray insertion port 114 by the IC reader 101*c*. In the case of determining that the identification information is read (the case of determining "Yes" at the step S41), the process shifts to a step S42. In the case of determining that the identification information is not read (the case of determining "No" at the step S41), the process shifts to a step S411.

<Step S42>

At the step S42, the second control section 500 determines whether or not there exists the preparation data preliminarily associated with the identification information for the tray 101 read at the step S41. In the case of determining that the preparation data corresponding to the identification information for the tray 101 exists (the case of determining "Yes" at the step S42), the process shifts to a step S43. In the case of determining that the preparation data corresponding to the identification information for the tray 101 does not exist (the case of determining "No" at the step S42), the process shifts to the step S411.

<Step S411>

At the step S411, the second control section 500 allows the touch panel monitor 14 to display an error indication for encouraging the user to remove the tray 101 from the tray insertion port 114. For example, a message such as "Please remove the tray from the tray insertion port" is displayed as the error indication. As described above, in the case where the identification information cannot be read from the tray 101 (the case of determining "No" at the step S41) or in the case where the identification information is not associated with the preparation data (the case of determining "No" at the step S42), the second control section 500 stops the co-infusion process using the tray 101. In a configuration in which the tray 101 has been already conveyed to a position being remote from the tray insertion port 114 at the time of the step S411, the second control section 500 carries out a process for returning the tray 101 to the tray insertion port 114 at the step S411.

<Step S43>

At the step S43, the second control section 500 determines whether or not all of the objects placed on the object placing member 102 are normally taken. Specifically, the second control section 500 allows the first robot arm 21 to take the objects such as the medicine container 10, the syringe 11*a* of the injector 11 and the injection needle 11*c* of the injector 11 placed on the object placing member 102 with collating the objects with the contents of the preparation data. In the case where all of collating results for the objects taken from the object placing member 102 are matched, the second control section 500 determines that all of the objects are normally taken. In the case of determining that all of the objects placed on the object placing member 102 are normally taken (the case of determining "Yes" at the step S43), the process shifts to a step S44. In the case of determining that the objects placed on the object placing member 102 are not normally taken (the case of determining "No" at the step S43), the process shifts to a step S431.

Specifically, the second control section 500 collates the number of the objects identified based on the photographed image photographed by the tray confirming camera 41 with the number of the objects indicated in the preparation data. Further, the second control section 500 collates the type of the syringe 11*a* identified based on the photographed image photographed by the tray confirming camera 41 with the type of the syringe 11*a* contained in the preparation data.

Furthermore, the second control section 500 collates the type of the injection needle 11c identified based on a diameter of the injection needle 11c detected by the needle bending detecting section 36 with the type of the injection needle 11c contained in the preparation data. Furthermore, the second control section 500 collates the medicine information read by the barcode reader 34b in the medicine reading section 34 with the medicine information contained in the preparation data. Then, the second control section 500 determines that the objects placed on the object placing member 102 are not normally taken in the case where the collating results are not matched.

In this regard, even in the case where the type of the object is not completely matched with the content of the preparation data at the time of determining whether or not the object such as the medicine container 10, the syringe 11a and the injection needle 11c is proper at the step S43, it may be considered that the usage of the object which is not matched with the content of the preparation data is approved. For example, in the case where a size of the syringe 11a is larger than a size indicated in the preparation data, it may be considered that the usage of the syringe 11a which is not matched with the content of the preparation data is approved. With this configuration, even in the case where the type of the object is different from the content of the preparation data and in the case where the object is registered in substitute information, it is possible to carry out the co-infusion process with using the object which is not matched with the preparation data but registered in the substitute information.

More specifically, it may be considered that a type of the object which can be substituted is preliminarily registered in the data storage section 504 as the substitute information for each of the medicine container 10, the syringe 11a and the injection needle 11c and the second control section 500 determines whether or not the object is proper based on the substitute information. In this case, it may be considered that combinations of the medicine container 10, the syringe 11a and the injection needle 11c are taken into account and the object which can be substituted under condition of each combination is preliminarily registered in the substitute information. Namely, in the case where the objects such as the medicine container 10, the syringe 11a and the injection needle 11c are matched with one of a plurality of predetermined acceptable patterns, the usage of the object is approved.

<Step S431>

At the step S431, the second control section 500 allows the object whose collating result is not matched at the step S43 to be in a state that the object can be removed from the tray insertion port 114 together with the tray 101. In this case, the second control section 500 at the time of carrying out such a process is one example of a discharge control means. Specifically, the second control section 500 allows the object to be placed back onto the object placing member 102 and then allows the up-and-down section 112 to move the object placing member 102 down to put the object placing member 102 into the tray 101. With this configuration, it becomes possible to remove the object from the tray insertion port 114 together with the tray 101. Further, at the step S431, the second control section 500 may allow the object whose collating result is not matched at the step S43 to be in a state that the object can be removed from the tray discharge port 115 together with the tray 101.

In the case where the collating result of the medicine container 10 is not matched, it may be considered that the second control section 500 allows the first robot arm 21 to keep a holding state of the medicine container 10 and convey the medicine container 10 to a position such as the vicinity of the main door 301 or the injector removing door 302 from which the user can remove the medicine container 10. This enables the user to open the main door 301 or the injector removing door 302 to remove the medicine container 10 held by the holding member 25 of the first robot arm 21. Further, it may be considered that the second control section 500 allows the medicine container 10 to be transferred to a predetermined placing member (not shown in the drawings) used for returning the medicine container 10.

<Step S432>

Then, at a step S432, the second control section 500 allows the touch panel monitor 14 to display the error indication for encouraging the user to remove the tray 101 from the tray insertion port 114. For example, a message such as "Please remove the tray from the tray insertion port and load a proper object" is displayed in the error indication. Further, it is preferable that a list for objects which should be placed on the object placing member 102 is contained in the error indication. For example, it may be considered that the second control section 500 allows the touch panel monitor 14 to display a list of objects contained in the preparation data and display the object whose collating result is not matched so that the user can identify the object whose collating result is not matched. This enables the user to easily understand which object should be placed on the object placing member 102, thereby improving work efficiency of the user.

<Step S433>

After that, at a step S433, the second control section 500 determines whether or not the tray 101 is loaded through the tray insertion port 114 based on a detecting result from a sensor (not shown in the drawings). In the case of determining that the tray 101 is loaded through the tray insertion port 114 (the case of determining "Yes" at the step S433), the process shifts to a step S434. On the other hand, the process waits at the step S433 until the loading of the tray 101 through the tray insertion port 114 is determined (the case of "No" at the step S433). In the case where an operation for cancelling the co-infusion process is carried out with respect to the touch panel monitor 14, the second control section 500 terminates the tray collating process.

<Step S434>

Then, at the step S434, the second control section 500 determines whether or not the identification information is read by the IC reader 101c from the IC tag 101b of the tray 101 which has been loaded through the tray insertion port 114 in the same manner as the step S41. In the case of determining that the identification information is read (the case of determining "Yes" at the step S433), the process shifts to a step S435. In the case of determining that the identification information is not read (the case of determining "No" at the step S433), the process shifts to a step S436.

<Step S435>

At the step S435, the second control section 500 determines whether or not the identification information for the tray 101 is matched with the identification information for the tray 101 allocated to the preparation data for a now-treated target. Namely, the second control section 500 determines whether or not the identification information read at the step S41 is matched with the identification information read at the step S434. With this configuration, it is possible to determine whether or not the identification information read by the IC reader 101c from the subsequent tray 101 subsequently loaded in the co-infusion apparatus 1 after the tray 101 is allowed to be removed at the step S431 is matched with the identification information read by the IC reader 101c from the tray 101 allowed to be removed at the step S431. In the case of determining the identification information for the tray 101 is matched with each other (the case of determining "Yes" at the step S435), the co-infusion process is restarted and the process shifts to the step S43. On the other hand, in the case of determining that the identification information for the tray 101 is not matched with each other (the case of determining "No" at the step S434), the process shifts to the step S436.

<Step S436>

At the step S436, the second control section 500 allows the touch panel monitor 14 to display an error indicating that the identification information for the tray 101 is not matched with the identification information for the tray 101 allocated to the preparation data for the now-treated target to inform it to the user. In this case, the second control section 500 at the time of carrying out such a process is one example of an informing means. For example, a message such as "The tray is improper. Please remove the tray from the tray insertion port and load a proper tray." is displayed as the error. After that, the process shifts to the step S433.

<Step S44>

On the other hand, in the case of determining that all of the objects placed on the object placing member 102 are normally taken (the case of determining "Yes" at the step S43), the second control section 500 allows the tray 101 to be transferred to the tray conveying terminal portion 110a at the subsequent step S44.

<Step S45>

At a step S45, the second control section 500 collates the preparation data with the information of the barcode of the transfusion bag 12 read by the camera for transfusion 121.

<Step S46>

Then, at a step S46, the second control section 500 branches the process depending on the collating result at the step S45. In the case of determining that the transfusion bag 12 is matched with the preparation data (the case of determining "Yes" at the step 46), the tray collating process is terminated. On the other hand, in the case of determining that the transfusion bag 12 is not matched with the preparation data (the case of determining "No" at the step S46), the process shifts to a step S47.

<Step S47>

At the step S47, the second control section 500 allows the transfusion bag 12 whose collating result is not matched at the step S46 to be in a state that the transfusion bag 12 can be removed from the tray discharge port 15 together with the tray 101. In this case, the second control section 500 at the time of carrying out such a process is one example of a discharge control means. Specifically, the second control section 500 allows the bag up-and-down section 113 to move the transfusion bag holding member 103 down to put the transfusion bag 12 back into the tray 101. With this configuration, it is possible to remove the transfusion bag 12 from the tray discharge port 15 together with the tray 101. In the case where a distance between the tray conveying terminal portion 110a and the tray discharge port 15 is large, the second control section 500 carries out a process for conveying the tray 101 to the tray discharge port 15 at the step S47.

<Step S48>

Then, at the step S48, the second control section 500 allows the touch panel monitor 14 to display an error indication for encouraging the use to remove the tray 101 from the tray discharge port 15. For example, a message such as "The tray is improper. Please remove the tray from the tray discharge port, load a proper transfusion bag and insert the tray from the tray discharge port." is displayed in the error indication. With this configuration, the user can place the proper transfusion bag 12 on the tray 101 to re-load the tray 101 from the tray discharge port 15.

<Step S49>

After that, at a step S49, the second control section 500 determines whether or not the tray 101 is re-loaded from the tray discharge port 15 based on a detecting result from a sensor (not shown in the drawings). In the case of determining that the tray 101 is re-loaded from the tray discharge port 15 (the case of determining "Yes" at the step S49), the process shifts to a step S50. On the other hand, the process waits at the step S49 until the tray 101 is re-loaded from the tray discharge port 15 (the case of determining "No" at the step S49). In the case where an operation for cancelling the co-infusion process is carried out with respect to the touch panel monitor 14, the second control section 500 terminates the tray collating process.

<Step S50>

Next, at the step S50, the second control section 500 determines whether or not the identification information is read by the IC reader 15a from the IC tag 101b of the tray 101 loaded from the tray discharge port 15. In the case of determining that the identification information is read (the case of determining "Yes" at the step S50), the process shifts to a step S51. In the case of determining that the identification information is not read (the case of determining "No" at the step S50), the process shifts to a step S52.

<Step S51>

At the step S51, the second control section 500 determines whether or not the identification information for the tray 101 is matched with the identification information for the tray 101 allocated to the preparation data for the now-treated target. Namely, the second control section 500 determines whether or not the identification information read at the step S41 is matched with the identification information read at the step 50. With this configuration, the second control section 500 can determine whether or not the identification information read by the IC reader 101c from the subsequent tray 101 subsequently loaded into the co-infusion apparatus 1 after the tray 101 is allowed to be removed at the step S431 is matched with the identification information read by the IC reader 101c from the tray 101 allowed to be removed at the step S431. In the case of determining that the identification information for the tray 101 is matched with each other (the case of determining "Yes" at the step S51), the co-infusion process is restarted and the process shifts to the step S45. On the other hand, in the case of determining that the identification information is not matched with each other (the case of determining "No" at the step S51), the process shifts to the step S52.

<Step S52>

At the step S52, the second control section 500 allows the touch panel monitor 14 to display an error indicating that the identification information for the tray 101 is not matched with the identification information for the tray 101 allocated to the preparation data for the now-treated target to inform it to the user. In this case, the second control section 500 at the time of carrying out such a process is one example of an informing means. For example, a message such as "The tray is improper. Please remove the tray from the tray discharge port and load a proper tray." is displayed as the error. After that, the process shifts to the step S49. In a configuration in which the tray 101 has been already conveyed to a position being remote from the tray discharge port 15 at the step S52, the second control section 500 carries out a process for returning the tray 101 to the tray discharge port 15 at the step S52.

As described above, in the tray collating process, even in the case where the object or the transfusion bag 12 placed on the tray 101 is improper, it is possible to continue the co-infusion process by placing a proper object or a proper transfusion bag 12 on the tray 101 and loading the tray 101. Further, it is possible to determine whether or not the tray 101 is changed to another tray at the time of re-loading the tray 101, thereby preventing an improper tray form being loaded at the time of re-loading the tray 101. This results in, for example, preventing a medicine corresponding to one patient from being treated as a medicine corresponding to another patient.

[Object Taking Process]

There is a case where one of the objects interferes with the other one or more of the objects on the object placing member 102 when the gripping clicks 25a of the first robot arm 21 take the variety of objects from the object placing member 102 of the tray 101. In order to allow the objects to be taken even in such a case, the second control section 500 carries out the following object taking process. Specifically, the second control section 500 allows the first robot arm 21 to take the medicine containers 10 or the injectors 11 from the object placing member 102 in turn depending on a priority condition predetermined for a condition of the medicine containers 10 or the injectors 11 identified based on the photographing result from the tray confirming camera 41. The second control section 500 starts the object taking process in the case where the image for the object placing member 102 is photographed by the tray confirming camera 41. In this case, the second control section 500 at the time of carrying out the object taking process is one example of a taking control means.

Figure 29:
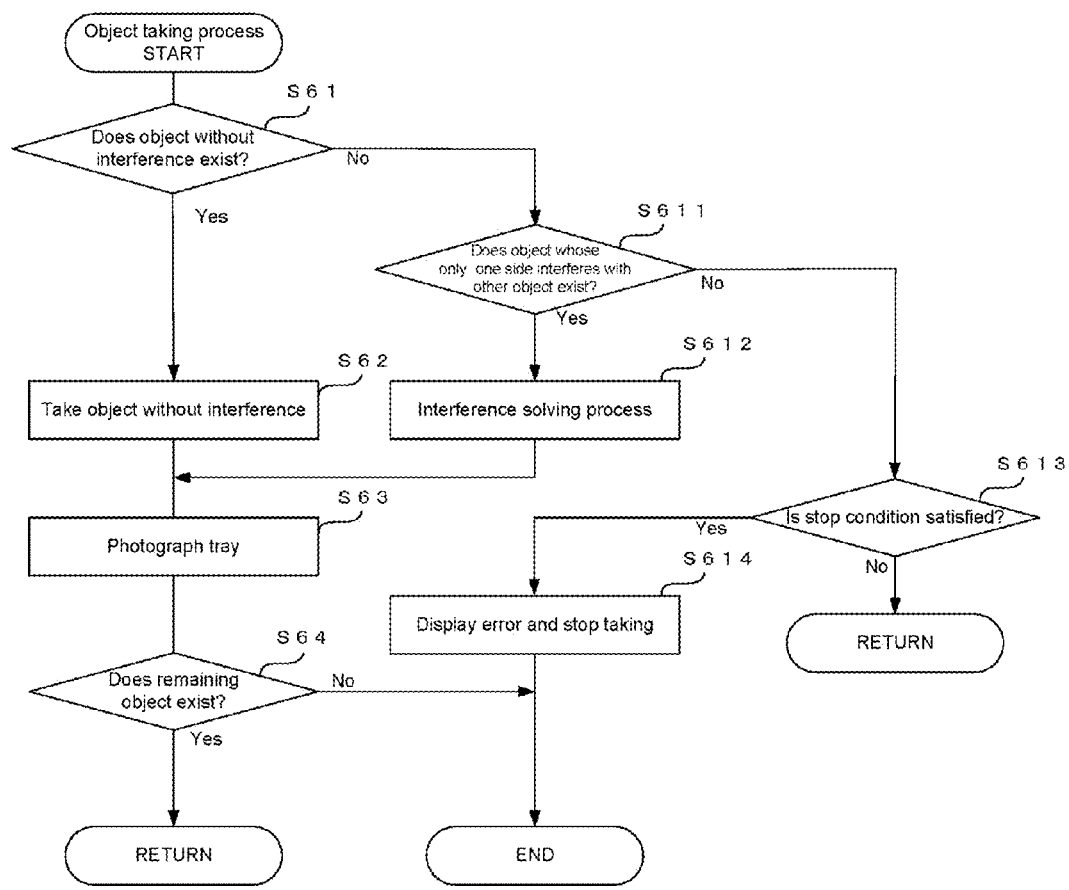
FIG. 29 is a flow chart showing one example of steps of an object taking process carried out by the co-infusion apparatus according to the embodiment of the present invention.
Figure 30A:
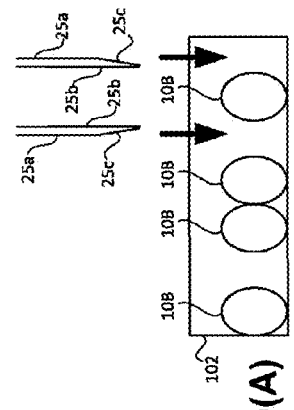
FIG. 30 is a view showing a working example in the object taking process carried out by the co-infusion apparatus according to the embodiment of the present invention.
Figure 30B:
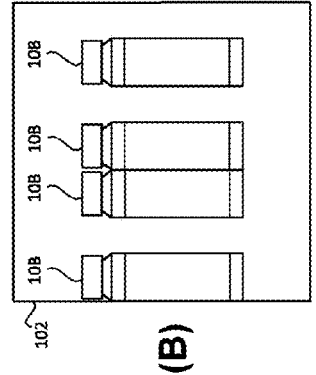
Figure 31A:
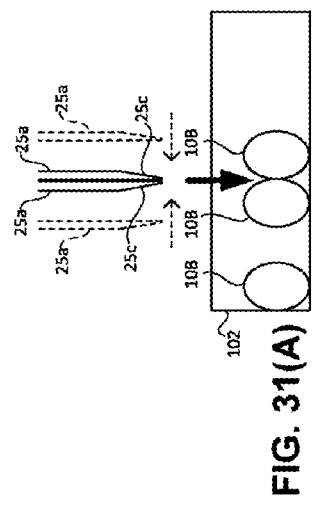
FIG. 31 is another view showing another working example in the object taking process carried out by the co-infusion apparatus according to the embodiment of the present invention.
Figure 31B:
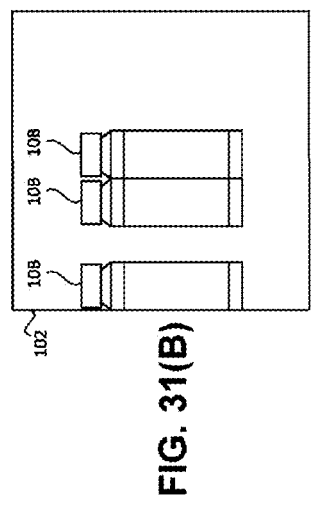
Figure 32A:
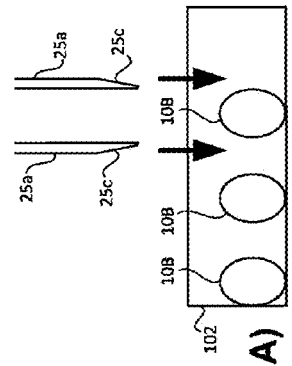
FIG. 32 is another view showing another working example in the object taking process carried out by the co-infusion apparatus according to the embodiment of the present invention.
Figure 32B:
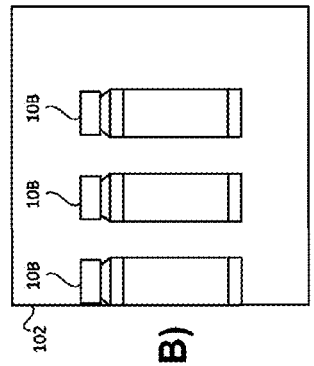

FIG. 29 is a flow chart showing one example of steps of the object taking process. FIGS. 30 to 32 are views showing working examples in the object taking process. FIGS. 30(A), 31(A) and 32(A) are schematic views taken by seeing a condition of the objects in the object placing member 102 from a lateral side. FIGS. 30(B), 31(B) and 32(B) are schematic views taken by seeing the condition of the objects in the object placing member 102 from an upper side.

<Step S61>

First, at a step S61, the second control section 500 determines whether or not one object, which does not interfere with a constituent element (such as a side surface) such as the other one of the objects, a side wall of the object placing member 102 and the supporting member 102A, exists among the objects placed on the object placing member 102 based on the photographed image photographed by the tray confirming camera 41. In the case of determining that the one object without interference exists (the case of determining "Yes" at the step S61), the process shifts to a step S62. In the case of determining that the one object without interference does not exist (the case of determining "No" at the step S61), the process shifts to a step S64.

The word of "interference" means a state that a predetermined gap is not existed between the one object and the other one of the objects or the constituent element of the object placing member 102. Specifically, the gap has a width into which at least the gripping clicks 25a of the first robot arm 21 can be inserted. The second control section 500 identifies a position of each object placed on the object placing member 102 based on information on the medicine container 10, the syringe 11a and the injection needle 11c contained in the preparation data. For example, the second control section 500 identifies the position of each object by utilizing the image matching method between images preliminarily registered for each object and the photographed image.

<Step S62>

At the step S62, the second control section 500 controls the first robot arm 21 to take the object for which the second control section 500 determines that the object does not interfere. For example, in one example shown in FIG. 30, among the plurality of vial bottles 10B, sufficient gaps are existed on both sides of the most-right side vial bottle 10B. Thus, the most-right side vial bottle 10B is preferentially taken by the first robot arm 21.

<Step S63>

At a step S63, the second control section 500 allows the tray confirming camera 41 to photograph the object placing member 102 after the object is taken from the object placing member 102 at the step S62.

<Step S64>

After that, at a step S64, the second control section 500 determines whether or not the object remains in the object placing member 102 based on the photographed image photographed by the tray confirming camera 41 at the step S63. For example, the second control section 500 determines whether or not the object exists in the object placing member 102 based on the photographed image photographed by the tray confirming camera 41. In the case of determining that the object remains in the object placing member 102 (the case of determining "Yes" at the step S64), the process returns to the step S61. On the other hand, in the case of determining that the object does not remain in the object placing member 102 (the case of determining "No" at the step S64), the object taking process is terminated.

<Step S611>

On the other hand, at a step S611, the second control section 500 determines whether or not one object whose only one side interferes with another object exists among the objects placed on the object placing member 102 based on the photographed image photographed by the tray confirming camera 41. In this case, the second control section 500 at the time of carrying out such a process is one example of an interference determining means. In the case of determining that the one object whose only one side interferes with the other object exists (the case of determining "Yes" at the step S611), the process shifts to a step S612. In the case of determining that the one object whose only one side interferes with the other object does not exist (the case of determining "No" at the step S611), the process shifts to a step S613.

<Step S612>

At the step S612, the second control section 500 carries out a process for solving the interference between the two objects for which the second control section 500 determines that only respective sides of the two objects interfere with each other at the step S611 among the objects placed on the object placing member 102. In this case, the second control section 500 at the time of carrying out such a process is one example of a separating means.

Specifically, the second control section 500 allows the gripping clicks 25a of the first robot arm 21 for gripping one of the objects to be inserted between the two objects interfering with each other in a state that the gripping clicks 25a of the first robot arm 21 are closed. With this configuration, the two objects are separated from each other because the two objects are moved with making contact with the gripping clicks 25a. In this embodiment, although the first robot arm 21 is used for separating the two objects, another configuration in which the second robot arm 22 is used for this process depending on a position of the object placing member 102 may be considered as another embodiment.

FIG. 31 shows a state that one vial bottle 10B whose only one side interferes with another vial bottle 10B exists among the plurality of vial bottles 10B. In this case, at the step S612, the second control section 500 allows the gripping clicks 25*a* of the first robot arm 21 to be inserted between the two vial bottles 10B in a state that the gripping clicks 25*a* of the first robot arm 21 are closed to move the two vial bottles 10B in a direction for separating the two vial bottles 10B with each other. With this configuration, it is possible to separate the two vial bottles 10B making contact with each other as shown in FIG. 32. Thus, it becomes possible to take the one of the vial bottles 10B at the step S62 after this process.

In this regard, each of the gripping clicks 25*a* includes a non-slip portion 25*b* for preventing slipping of the object, which is provided on a surface for gripping the object, and an inclining portion 25*c* to be contacted with the object at the time of moving the object, which is provided an outer surface opposite to the surface for gripping the object. For example, the non-slip portion 25*b* has a surface profile having a high frictional coefficient (high resistance). Alternatively, the non-slip portion 25*b* may be a portion to which a sheet having a high frictional coefficient is attached. On the other hand, the inclining portion 25*c* is formed for moving the object with suppressing a load applied to the object caused when the gripping clicks 25*a* are downwardly moved toward the object and make contact with the object. As described above, according to the co-infusion apparatus 1, the gripping clicks 25*a* are inserted between the two objects in a state that the gripping clicks 25*a* are closed. Thus, it is possible to prevent a frictional slide between the non-slip portion 25*b* and the object, thereby preventing pealing of the label of the medicine container 10, breaking of the object and the like. Further, a tip end of each of the gripping clicks 25*a* is formed into a sharply-angled shape because the inclining portion 25*c* is provided. Thus, it is possible to insert the gripping clicks 25*a* between the objects without pressing the objects onto a surface on which the objects are placed even in the case where a diameter of each of the objects is small.

An amount of a moving distance of the gripping clicks 25*a* when the gripping clicks 25*a* are inserted between the two objects is set in advance depending on a distance from an upper end portion to a central portion of one of the two objects to be separated with each other. For example, it may be considered that the amount of the moving distance is equal to ½ times as much as the diameter of the one object whose diameter is larger than that of the other one between the two objects. With this configuration, it is possible to separate the two objects and prevent unnecessary pressure from acting the two objects. Further, it may be considered that, the second control section 500 identifies the one object from the two objects which has a larger space in the direction for separating the two objects with each other based on the photographed image photographed by the tray confirming camera 41 to downwardly move the gripping clicks 25*a* to a position which does not coincide with a central portion between the two objects so that the gripping clicks 25*a* make contact with the identified one object prior to the other one of the two objects.

Further, in the object taking process, description will be given to the case of separating the one object whose only one side interferes with another object from the other object, but another configuration in which a target to be separated is the one object whose only one side interferes with the constituent element of the object placing member 102 may be considered as another embodiment. For example, in the case where the one object whose only one side interferes with the constituent element of the object placing member 102 exists and in the case where a gap between the one object and the constituent element of the object placing member 102 is equal to or larger than a predetermined threshold value, it may be considered that the second control section 500 allows the gripping clicks 25*a* to be inserted between the object and the constituent element of the object placing member 102. For example, the threshold value is set in advance so as to correspond to the diameter of each object. The threshold value represents a separatable value indicating a movable distance for separating the object from the constituent element without pressing the object with the gripping clicks 25*a*.

<Step S613>

On the other hand, at the step S613, the second control section 500 determines whether or not a stop condition for stopping the taking of the object from the object placing member 102 is satisfied based on the photographed image photographed by the tray confirming camera 41. Specifically, the stop condition is whether or not all of the objects placed on the object placing member 102 fall under the category of an object whose one side or both sides interfere with the constituent element of the object placing member 102 or the category of an object whose both sides interfere with other objects. In the case of determining that the stop condition is satisfied (the case of determining "Yes" at the step S613), the process shifts to a step S614. In the case of determining that the stop condition is not satisfied (the case of determining "No" at the step S613), the process returns to the step S61. Further, the stop condition contains whether or not a predetermined stop time elapses from the start of the object taking process. Even in the case where the stop time elapses, the process shifts to the step S614. Furthermore, another configuration in which the step S613 is omitted and the process shifts to the step S614 in the case where the second control section 500 determines that the one object whose only one side interferes with another object does not exist (the case of determining "No" at the step S611) may be considered as another embodiment.

<Step S614>

At the step S614, the second control section 500 allows the touch panel monitor 14 to display an error indication and stops the taking of the object from the object placing member 102. The error indication contains a message indicating that it is impossible to normally take the object in the object placing member 102 and a message for encouraging the user to remove the object placing member 102 from the tray insertion port 114. At this time, the second control section 500 allows the tray up-and-down section 112 to put the object placing member 102 back into the tray 101 to allow the tray 101 to be in a state that the tray 101 can be removed from the tray insertion port 114. For example, the object placing member 102 shown in FIG. 32 is in a state that one vial bottle 10B among the vial bottles 10B makes contact with the side wall of the object placing member 102. Thus, the vial bottle 10B making contact with the side wall of the object placing member 102 is not taken and discharged from the tray insertion port 114 together with the tray 101. This enables the user to re-load the tray 101 through the tray insertion port 114 after solving the interference of the object placed on the object placing member 102.

As described above, according to the object taking process, it is possible to take the one object interfering with another object after separating the one object from the other object. Specifically, the second control section 500 allows the one object on both sides of which predetermined gaps are existed in the photographed image photographed by the tray confirming camera 41 to be taken more preferentially than the other object on one side or both sides of which the gap is not existed in the photographed image photographed by the tray confirming camera 41. Thus, according to the co-infusion apparatus 1, it is possible to separate the objects with each other with utilizing a space existed in the object placing member 102 by preferentially taking the one object which does not interfere with the other object.

[Co-infusion Control Process]

Figure 33:
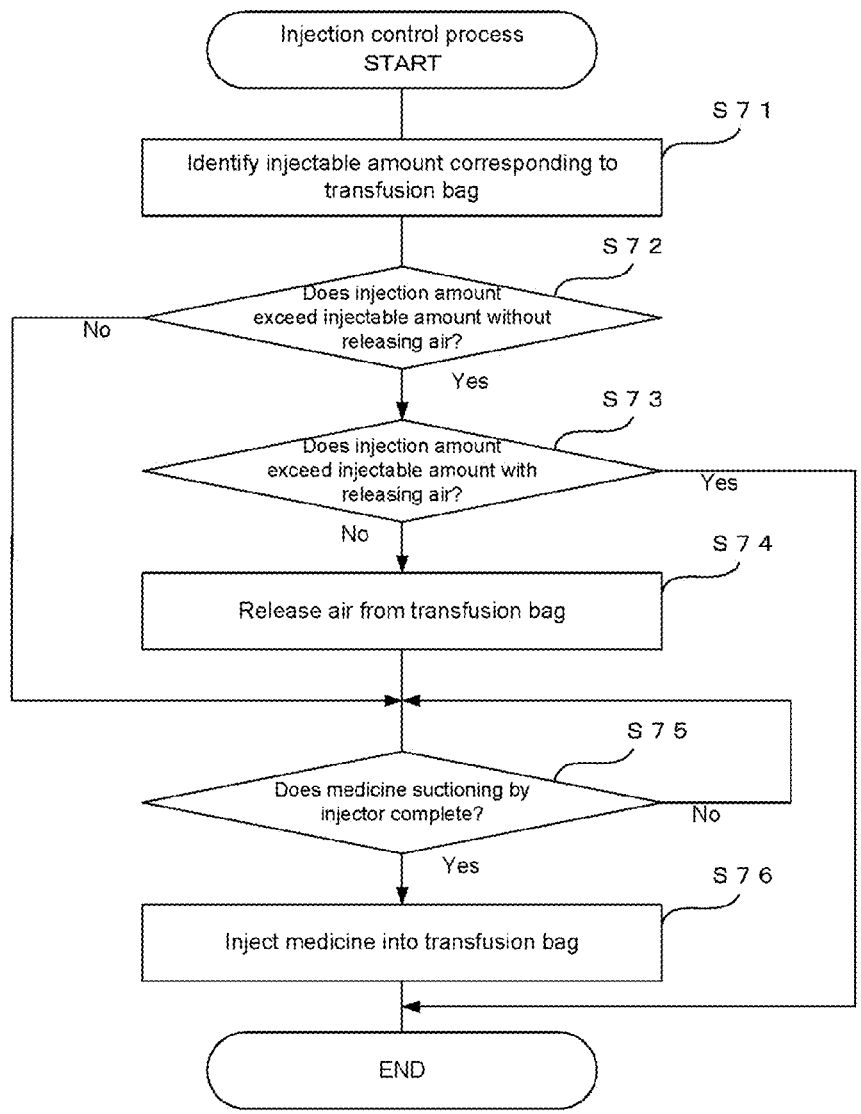
FIG. 33 is a flow chart showing one example of steps of an injection control process carried out by the co-infusion apparatus according to the embodiment of the present invention.

In the co-infusion apparatus 1, the medicine is injected from the injector 11 into the transfusion bag 12 in the co-infusion process. However, there is a risk that pressure inside the transfusion bag 12 becomes positive pressure and the medicine in the transfusion bag 12 squirts from the transfusion bag 12 when the medicine is injected into the transfusion bag 12 in an amount larger than an injectable amount predetermined for the transfusion bag 12. Thus, in the co-infusion apparatus 1, the second control section 500 carries out the injection control process for adjusting an amount of air in the transfusion bag 12 so as to prevent the pressure inside the transfusion bag 12 from being positive pressure in the co-infusion process. In this case, the second control section 500 at the time of carrying out the injection control process is one example of an injection control means. FIG. 33 is a flow chart showing one example of steps of the injection control process.

<Step S71>

First, at a step S71, the second control section 500 identifies the injectable amount corresponding to the transfusion bag 12 to be used. For example, in the medicine master stored in the data storage section 404, transfusion information such as a volume, a shape, a whole amount, an injectable amount without releasing air and an injectable amount with releasing air is stored for each transfusion bag 12. The second control section 500 identifies the injectable amount without releasing air and the injectable amount with releasing air corresponding to the transfusion bag 12 to be used based on the transfusion information. The injectable amount is set in advance as an injection amount which does not make the pressure inside the transfusion bag be positive pressure.

FIG. 34 is a view showing one example of the transfusion information. In the example shown in FIG. 34, in the case where the type of the transfusion bag 12 is "saline A", a volume of the solvent which has been already contained is "100 mL", a whole amount (maximum amount) is "157 mL", an injectable amount without releasing air is "0 mL" and an injectable amount with releasing air is "57 mL". In the case where the type of the transfusion bag 12 is "saline B", a volume of the solvent which has been already contained is "250 mL", a whole amount (maximum amount) is "425 mL", an injectable amount without releasing air is "117.6 mL" and an injectable amount with releasing air is "175 mL". In this regard, as shown in the transfusion information, in the case where the shape of the transfusion bag 12 is "plastic bottle" having a low stretching property such as the case of "saline A", the injectable amount without releasing air and the injectable amount with releasing air are smaller compared with the case where the shape of the transfusion bag 12 is "soft bag" having a high stretching property such as the case of "saline B".

<Step S72>

At a step S72, the second control section 500 determines whether or not the injection amount of the medicine from the injector 11 into the transfusion bag 12 exceeds the injectable amount without releasing air of the transfusion bag 12 identified at the step S71 based on the preparation data. In the case of determining that the injection amount exceeds the injectable amount without releasing air (the case of determining "Yes" at the step S72), the process shifts to a step S73. In the case of determining that the injection amount does not exceed the injectable amount without releasing air (the case of determining "No" at the step S72), the process shifts to a step S75.

<Step S73>

At the step S73, the second control section 500 determines whether or not the injection amount of the medicine from the injector 11 into the transfusion bag 12 exceeds the injectable amount with releasing air of the transfusion bag 12 identified at the step S71 based on the preparation data. In the case of determining that the injection amount does not exceed the injectable amount with releasing air (the case of determining "No" at the step S73), the process shifts to a step S74. On the other hand, in the case of determining that the injection amount exceeds the injectable amount with releasing air (the case of determining "Yes" at the step S73), the second control section 500 terminates the injection control process after displaying an error indication.

In the co-infusion process, in the case where the medicine in the medicine container 10 is dissolved with the transfusion in the transfusion bag 12, the transfusion is suctioned from the transfusion bag 12 and then the medicine dissolved in this transfusion is injected back into the transfusion bag 12. Thus, it may be considered that the second control section 500 determines whether or not the injection amount of the medicine is larger than the injectable amount at the steps S72 and S73 with taking into account an amount of the transfusion suctioned from the transfusion bag 12. For example, it may be considered that the second control section 500 considers a value obtained by subtracting the amount of the transfusion suctioned from the transfusion bag 12 from the injectable amount as the injectable amount to carry out the above determination. With this configuration, it is possible to prevent, for example, an unnecessary process for releasing air (the step S74) from being carried out.

<Step S74>

At the step S74, the second control section 500 controls the second robot arm 22 to suction the air from the transfusion bag 12 with the injector 11 before the medicine is suctioned with the injector 11. Specifically, the second control section 500 controls the motor 113c to drive the bag up-and-down section 113 to incline the transfusion bag holding member 103 so that the co-infusion port of the transfusion bag 12 is directed toward the upper direction. With this configuration, it is possible to gather the air near the co-infusion port of the transfusion bag 12. Then, the second control section 500 allows the second robot arm 22 to insert the injection needle 11c of the injector 11 into the transfusion bag 12 and pull the plunger 11b of the injector 11 to release the air from the transfusion bag 12. For example, an amount of the air released from the transfusion bag 12 is equivalent to an amount of a volume of the medicine amount injected from the injector 11 into the transfusion bag 12 in the co-infusion process. Further, it may be considered that the amount of the air released from the transfusion bag 12 is a predetermined constant amount.

<Step S75>

At the step S75, the second control section 500 waits the completion of the suctioning process for the medicine from the medicine container 10 with the injector 11 in the co-infusion process (the case of determining "No" at the step S75). When the suctioning process for the medicine from the medicine container 10 with the injector 11 completes (the case of determining "Yes" at the step S75), the process shifts to a step S76.

<Step S76>

At the step S76, the second control section 500 controls the second robot arm 22 to inject the medicine from the injector 11 into the transfusion bag 12. At this time, even in the case where the amount of the medicine injected from the injector 11 is larger than the injectable amount without releasing air of the transfusion bag 12, the air in the transfusion bag 12 has been preliminarily released at the step S74. Thus, it is possible to prevent the pressure inside the transfusion bag 12 form being positive pressure, thereby prevent the medicine in the transfusion bag 12 from squirting from the transfusion bag 12.

[Another Example of the Injection Control Process]

Figure 35:
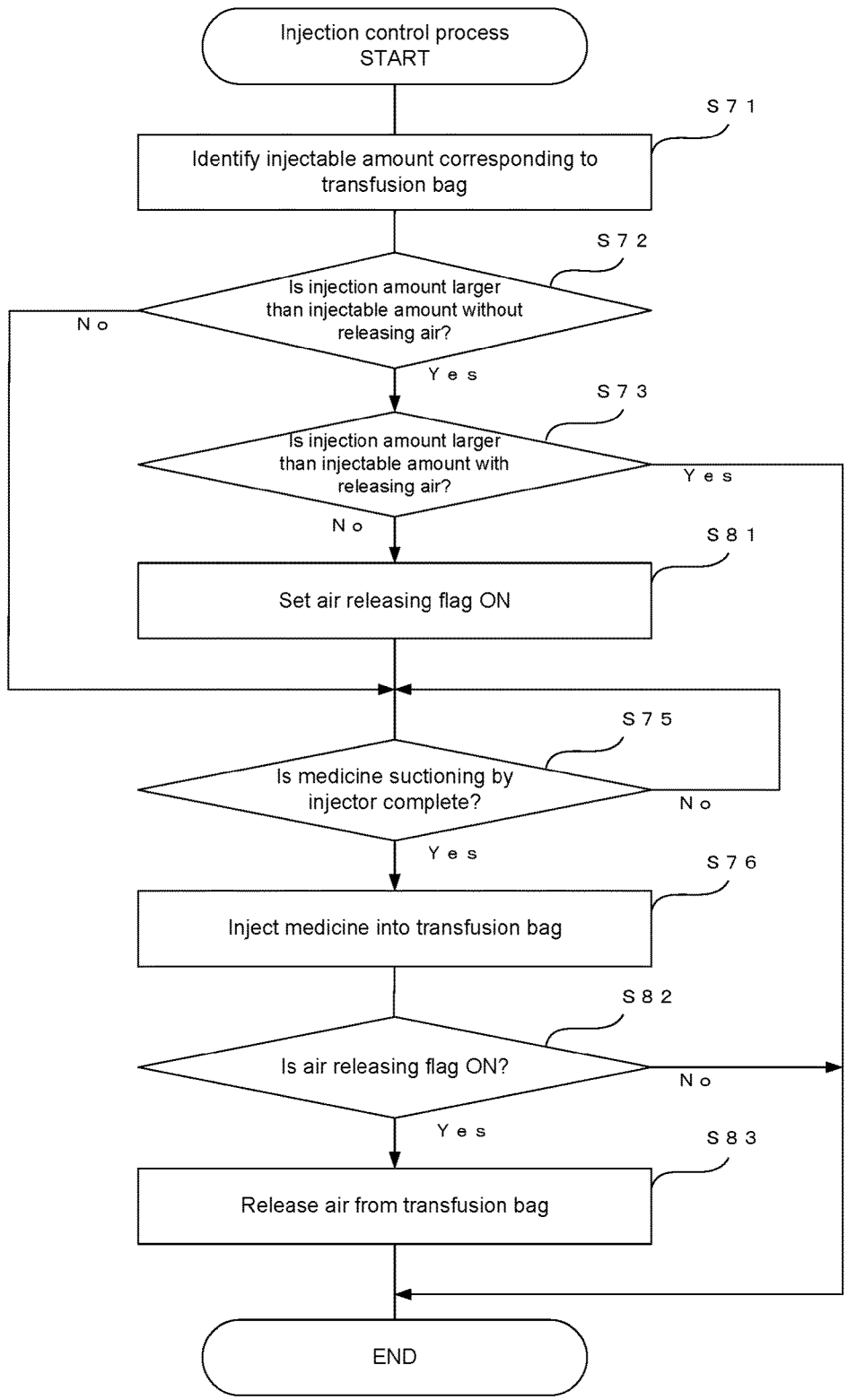
FIG. 35 is a flow chart showing another example of the injection control process carried out by the co-infusion apparatus according to the embodiment of the present invention.

Further, it may be considered that the second control section 500 carries out an injection control process shown in FIG. 35 instead of the above-mentioned injection control process (see FIG. 33). Specifically, in the injection control process shown in FIG. 35, the following steps S81 to S83 are carried out instead of the step S74 to release the air from the transfusion bag 12 with the injector 11 after the medicine is suctioned with the injector 11 and then injected from the injector 11 into the transfusion bag 12.

<Step S81>

At the step S81, the second control section 500 sets a suctioning flag indicating that the suctioning of the air from the transfusion bag 12 needs to be carried out be ON. Namely, the suctioning of the air from the transfusion bag 12 is not carried out at this time. The suctioning flag is a flag register provided in the RAM 503 of the second control section 500.

<Step S82>

After the suctioning of the medicine by the injector 11 completes and then the medicine is injected from the injector 11 into the transfusion bag 12, the second control section 500 determines whether or not the suctioning flag is ON at the step S82. In the case where the suctioning flag is ON (the case of determining "Yes" at the step S82), the process shifts to a step S83. In the case where the suctioning flag is OFF (the case of determining "No" at the step S82), the injection control process is terminated.

<Step S83>

At the step S83, the second control section 500 allows the injector 11 to subsequently suction the air from the transfusion bag 12 with keeping a state that the injection needle 11c of the injector 11 is inserted into the transfusion bag 12. As described above, the air is suctioned at the time of injecting the medicine from the injector 11 into the transfusion bag 12. Thus, it is possible to decrease the number of insertion of the injection needle 11c of the injector 11 into the transfusion bag 12 compared with the case where the air is suctioned from the transfusion bag 12 in advance. In the case of carrying out this injection control process, it may be considered that photographing timing of the needle insertion confirming camera 44 is in a period until the suctioning of the air is started after the medicine is injected from the injector 11 into the transfusion bag 12. With this configuration, it is possible to allow the needle insertion confirming camera 44 to photograph a state that the plunger 11b of the injector 11 is pushed to the last.

As described above, according to the co-infusion apparatus 1, in the case where the injection amount of the medicine to be injected from the injector 11 into the transfusion bag 12 is larger than the injectable amount without releasing air predetermined so as to correspond to the transfusion bag 12, it is possible to release the air from the transfusion bag 12 by carrying out the injection control process. Thus, it is possible to prevent the pressure inside the transfusion bag 12 from being positive pressure, thereby preventing the medicine in the transfusion bag 12 from squirting from the transfusion bag 12.

[Other Functions of the Co-Infusion Apparatus 1]

Hereinafter, description will be given to other functions of the co-infusion apparatus 1. The first control section 400 or the second control section 500 carries out a variety of processes in the co-infusion apparatus 1 to embody the other functions.

[Medicine Suctioning Function in the Case of Using the Ampule 10A]

As described above, the injection needle 11c having the syringe filter is used in the co-infusion apparatus 1 in the case of using the ampule 10A. At this time, a certain type of the syringe filter has a property for allowing air to pass through the syringe filter before water penetrates into the syringe filter and not allowing the air to pass through the syringe after the water penetrates into the syringe filter. Thus, it is important that air does not exist in the injector 11 when the medicine in the injector 11 is injected into the transfusion bag 12 with the injection needle 11c having such a syringe filter. For example, in the case where the air exists in the injector 11, there is a risk that the injector 11 is broken when the second robot arm 22 pushes the plunger 11b of the injector 11.

Thus, in the co-infusion apparatus 1, the second control section 500 controls the injection needle attaching and detaching device 43, the first robot arm 21, the second robot arm 22 and the like to carry out a suctioning action for the medicine from the ampule 10A according to the following steps. With this configuration, it is possible to suction the medicine from the ampule 10A with the injector 11 without remaining the air in the injector 11. FIGS. 36 and 37 are views for explaining steps of the suctioning action for the medicine in the co-infusion process using the ampule 10A. In this regard, description for the needle bending detection of the injection needle 11c and the like is omitted.

<Step S101>

Figures 36A, 36B, 36C:
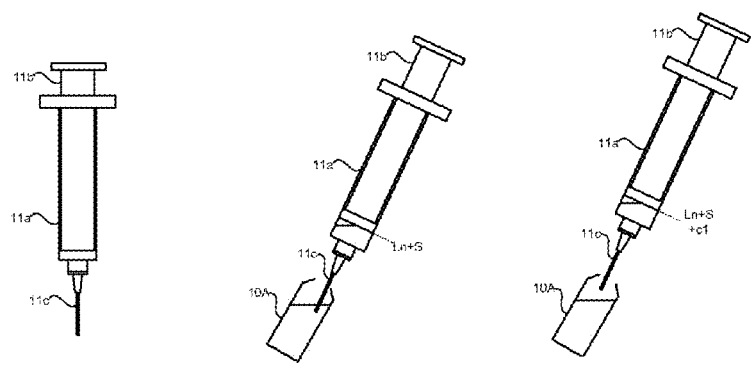
FIG. 36 is a view for explaining steps of a medicine taking action in a co-infusion process in the case of using an ampule carried out by the co-infusion apparatus according to the embodiment of the present invention.

First, at a step S101, the injection needle 11c having no syringe filter is attached to the injector 11 by the injection needle attaching and detaching device 43 and the second robot arm 22 as shown in FIG. 36(A). At this time, although air does not exist in the syringe 11a, air exists between the syringe 11a and the tip end of the injection needle 11c.

<Step S102>

Next, at a step S102, as shown in FIG. 36(B), the second robot arm 22 inserts a needle tip of the injection needle 11c of the injector 11 into the ampule 10A so that the needle tip of the injection needle 11c of the injector is directed toward the lower direction and then pulls the plunger 11b of the injector 11 to suction the medicine from the ampule 10A. At this time, the air existing between the syringe 11a and the tip end of the injection needle 11c flows into the syringe 11a. An initial air amount of the air suctioned into the syringe 11a is defined as "α". When a volume of the medicine to be obtained from the ampule 10A based on the preparation data is defined as "Ln", the second control section 500 pulls the plunger 11b so as to suction the medicine in an amount larger than the volume Ln by a correction amount S. At this time, the scale of the syringe 11a of the injector 11 indicates a value corresponding to "the volume Ln+the correction amount S".

The correction amount S contains the initial air amount α, an adjusting extra amount β and a filter correction amount γ. In the injector 11 (the syringe 11a and the injection needle 11c), the medicine is contained in an amount corresponding to "the volume Ln+the correction amount S—the initial air amount α". The adjusting extra amount β is a value larger than a volume in the injection needle 11c and set in advance as a value used for adjusting the amount of the medicine in the syringe 11a at the after-mentioned step S109. The filter correction amount γ is a value corresponding to a volume in the injection needle 11c having the syringe filter to be attached to the injector 11 and set in advance as an amount of the medicine remaining in the injection needle 11c after the medicine is injected from the injector 11 into the transfusion bag 12. In the case of suctioning the medicine from the plurality of the ampules 10A, air is suctioned in a predetermined amount C at the time of suctioning the medicine from one of the ampules 10A in order to prevent the squirting of the medicine and the predetermined amount C is further added to the scale of the syringe 11a.

<Step S103>

At a step S103, as shown in FIG. 36(C), the second robot arm 22 moves the injector 11 toward the upper direction and then pulls the plunger 11b in a predetermined constant amount c1 in a state that the injection needle 11c is apart from the liquid surface in the ampule 10A. With this configuration, it is possible to prevent liquid leakage from the injector 11. At this time, the scale of the syringe 11a of the injector 11 indicates a value of "the volume Ln+the correction amount S+the constant amount c1".

<Step S104>

Figures 37A, 37B, 37C, 37D, 37E:
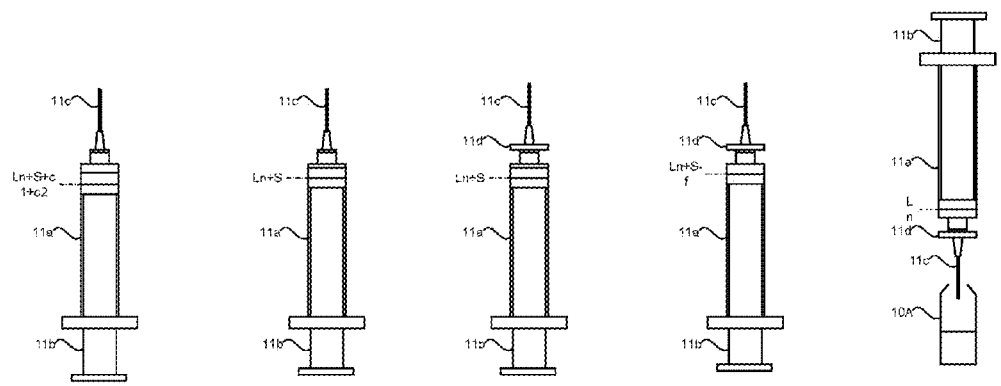
FIG. 37 is another view for explaining the steps of the medicine taking action in the co-infusion process in the case of using the ampule carried out by the co-infusion apparatus according to the embodiment of the present invention.

At a step S104, as shown in FIG. 37(A), the second robot arm 22 directs the tip end of the injection needle 11c of the injector 11 toward the upper direction and then pulls the plunger 11b in a predetermined constant amount c2. The constant amount c2 is an amount enough to suction at least the medicine in the injection needle 11c into the syringe 11a completely. With this configuration, it is possible to suction the medicine in the injection needle 11c of the injector 11 into the syringe 11a, thereby preventing the medicine from squirting from the injector 11 at the time of releasing the air from the injector 11. At this time, the scale of the syringe 11a of the injector 11 indicates a value of "the volume Ln+the correction amount S+the constant amount c1+the constant amount c2".

<Step S105>

At a step S105, the second robot arm 22 rotates the injector 11 around a rotational axis parallel with the horizontal direction one time or multiple times and then directs the needle tip of the injection needle 11c of the injector 11 toward the upper direction. With this configuration, it is possible to gather the air existing in the injector 11 as air bubbles to an upper portion in the injector 11. Further, it may be considered that the air in the injector 11 is gathered to the upper portion in the injector 11 by oscillating the injector 11 or adding vibration to the injector 11.

<Step S106>

At a step S106, as shown in FIG. 37(B), the second robot arm 22 pushes the plunger 11b by an amount corresponding to the constant amount c1 and the constant amount c2 in a state that the tip end of the injection needle 11c of the injector 11 is directed toward the upper direction. With this configuration, it is possible to release the air from the inside of the syringe 11a in the constant amount c1 and the constant amount c2. Since it is necessary to pass the air through the syringe filter to release the air after the injection needle 11c is replaced with an injection needle 11c having a syringe filter, it is necessary to slow down a pushing speed of the plunger 11b. Thus, by releasing the air from the inside of the syringe 11a at the step S105 before the injection needle 11c is replaced with the injection needle 11c having the syringe filter, it is possible to decrease working time. At this time, the scale of the syringe 11a of the injector 11 indicates a value of "the volume Ln+the correction amount S".

<Step S107>

Next, at a step S107, as shown in FIG. 37(C), the injection needle attaching and detaching device 43 and the second robot arm 22 replace the injection needle 11c of the injector 11 with an injection needle 11c having a syringe filter. At this time, a cap covers on the injection needle 11c. As shown in FIG. 37(C), the injection needle 11c having the syringe filter includes a syringe filter 11d. A volume of the whole of the injection needle 11c becomes a value obtained by adding a volume of the syringe filter 11d to a volume of a needle portion of the injection needle 11c.

<Step S108>

Then, at a step S108, as shown in FIG. 37(D), the second robot arm 22 pushes the plunger 11b by an amount larger than the initial air amount α and less than the correction amount S to push out the air in a predetermined amount f in a state that the tip end of the injection needle 11c of the injector 11 is directed toward the upper direction. With this configuration, it is possible to release the air from the inside of the syringe 11a at least in the initial air amount α, thereby allowing the medicine to reach into a part of the injection needle 11c. At this time, the scale of the syringe 11a of the injector 11 indicates a value of "the volume Ln+the correction amount S—the predetermined amount f". Further, at this time, the second robot arm 22 detaches the cap of the injection needle 11c with the injection needle attaching and detaching device 43. Alternatively, the cap of the injection needle 11c may be detached at the after-mentioned step S109.

<Step S109>

After that, at the step S109, as shown in FIG. 37(E), the second robot arm 22 directs the tip end of the injection needle 11c of the injector 11 toward the lower direction to insert the tip end of the injection needle 11c of the injector 11 into an internal space of the ampule 10A and then pushes the plunger 11b until the scale of the syringe 11a reaches a position corresponding to the volume Ln to discharge an extra medicine in the injector 11. In this regard, the second control section 500 can identify the value indicated by the scale of the syringe 11a based on a position of the transferring member 263 of the second robot arm 22.

After the medicine is suctioned from the ampule 10A with the injector 11 according to such steps, the medicine is contained in the syringe 11a of the injector 11 in the amount corresponding to the volume Ln and the injection needle 11c becomes in a state that an inside of the injection needle 11c is filled with the medicine. Thus, since the air does not remain in the syringe 11a of the injector 11, it is possible to prevent the syringe filter 11d from being broken at the time of injecting the medicine from the injector 11 into the transfusion bag 12.

Further, in the injector 11, an inside of the injection needle 11c is filled with the medicine in addition to the inside of the syringe 11a. Thus, the medicine remains in the injection needle 11c of the injector 11 at the time of injecting the medicine from the injector 11 into the transfusion bag 12. However, the medicine contained in the syringe 11a in the volume Ln is injected into the transfusion bag 12. Specifically, since the medicine is suctioned in the adjusting extra amount β with respect to the volume Ln and then an unnecessary amount of the medicine is finally discharged in the afore-mentioned step, it is possible to eliminate influence caused by an individual volume difference of the syringe 11a, the injection needle 11c, the syringe filter 11d or the like. With this configuration, it is possible to suppress, for example, an accidental error of the amount of the medicine to be injected from the medicine container 10 into the transfusion bag 12 with the injector 11. In this regard, another configuration in that the plunger 11b is pulled within a range of the volume of the injection needle 11c after the step S109 in order to prevent liquid leakage from the syringe 11a may be considered as another embodiment.

[Solvent Amount Adjusting Function]

In the above description for the co-infusion apparatus 1, the case where the medicine in the medicine container 10 is injected into the transfusion bag 12 and then the transfusion bag 12 is dispensed is described. On the other hand, as described above, the co-infusion apparatus 1 can dispense the injector 11 in a state that the medicine in the medicine container 10 has been suctioned in the injector 11. At this time, it may be considered that the injector 11 is dispensed in a state that the medicine in the medicine container 10 has been diluted with a solvent in a solvent amount larger than the volume of the medicine container 10. Thus, in the co-infusion apparatus 1, it may be considered that the second control section 500 has the solvent amount adjusting function for controlling the second robot arm 22 to suction the medicine in the medicine container 10 with the injector 11 and then further suction the solvent from the transfusion bag 12 with the injector 11. In this regard, such an adjusting working for the solvent amount is generally referred to as "diluting in cylinder".

Figure 38:
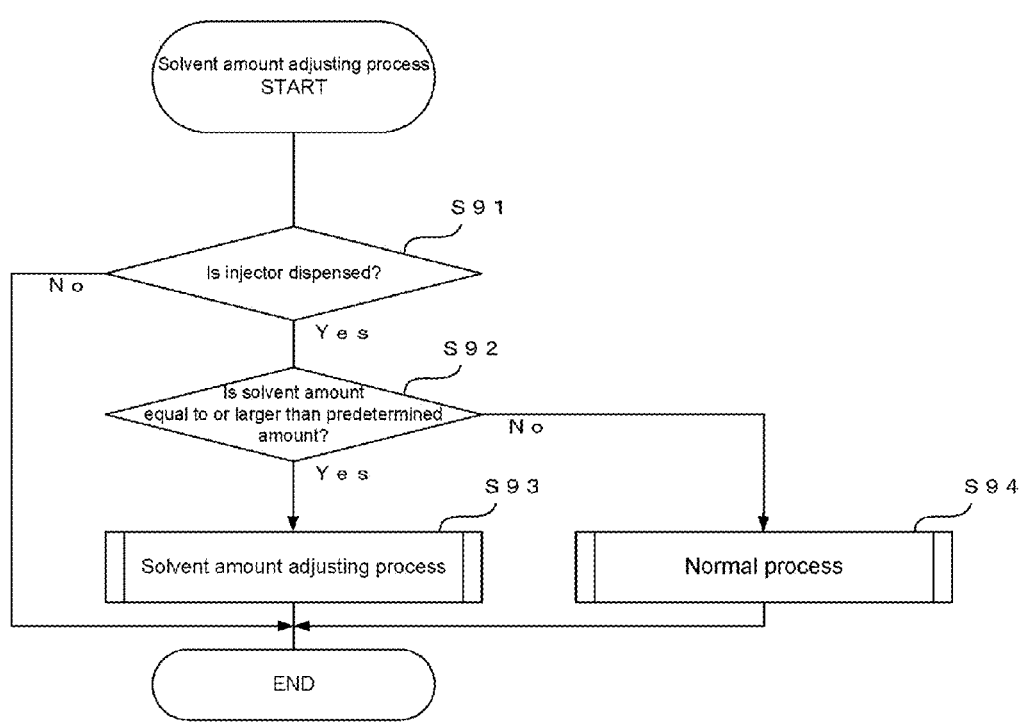
FIG. 38 is a flow chart showing one example of steps of a solvent amount adjusting process carried out by the co-infusion apparatus according to the embodiment of the present invention.

FIG. 38 is a flow chart showing one example of an injector dispensing process carried out by the second control section 500. The injector dispensing process is carried out at the time of carrying out an operation for issuing the preparation data. As shown in FIG. 38, the second control section 500 determines whether or not it is necessary to dispense the injector 11 in a state that the inside of the injector 11 has been filled with the medicine contained in the medicine container 10 based on the preparation data. In the case of determining that it is necessary to dispense the injector 11 (the case of determining "Yes" at a step S91), the second control section 500 allows the process to shifts to a step S92.

Then, at the step S92, the second control section 500 determines whether or not the solvent amount is equal to or larger than the volume of the medicine container 10. In the case of determining that the solvent amount is less than the volume of the medicine container 10 (the case of determining "No" at the step S92), the second control section 500 carries out a normal process for suctioning the medicine in the medicine container 10 with the injector 11 at a step S94. In the case where it is necessary to dissolve or dilute the medicine in the medicine container 10 in the normal process, the medicine in the medicine container 10 is suctioned with the injector 11 after carrying out a process for injecting the solvent suctioned from the transfusion bag 12 with the injector 11 into the medicine container 10 with the injector 11.

On the other hand, in the case where the solvent amount is equal to or larger than the volume of the medicine container 10 (the case of determining "Yes" at the step S92), the second control section 500 carries out the solvent amount adjusting process at a step S93. In the solvent amount adjusting process, the medicine in the medicine container 10 is suctioned with the injector 11 in the same manner as the normal process and then the solvent in the transfusion bag 12 is further suctioned with the injector 11 to adjust the solvent amount in the injector 11.

[Light Shielded Medicine Treating Function]

A medicine which is a preparation target of the co-infusion apparatus 1 contains a medicine such as an anti-cancer medicine (for example, dacarbazine) which should be treated under a light shielding condition (hereinafter, such a medicine is referred to as "light shielded medicine"). In this case, a light shielding container having a light shielding property is used as the medicine container 10 in which the light shielded medicine should be contained. However, there is a problem in that the light shielded medicine is exposed to light until the light shielded medicine is injected from the light shielding container into the transfusion bag 12 with the injector 11 in the co-infusion apparatus 1.

Further, in the case where a pharmacist or the like manually carries out a preparation working, the light shielded medicine is injected into the transfusion bag 12 and then the transfusion bag 12 is contained in a light shielding bag having the light shielding property. In the case of utilizing the co-infusion apparatus 1, the transfusion bag 12 removed from the co-infusion apparatus 1 is manually contained in the light shielding bag in the same manner as the above case. Thus, in the co-infusion apparatus 1, there is a problem in that the lighted shielded medicine contained in the transfusion bag 12 is exposed to light until the transfusion bag 12 is contained in the light shielding bag after the light shielded medicine has been injected from the injector 11 into the transfusion bag 12. Thus, the co-infusion apparatus 1 has a light shielded medicine treating function for suppressing a time duration when the light shielded medicine is exposed to light in the co-infusion process as much as possible in the case where the light shielded medicine is the preparation target of the co-infusion apparatus 1.

Specifically, in the co-infusion apparatus 1, the medicine master stored in the data storage section 404 contains information indicating whether or not each medicine falls under the category of the light shielded medicine. With this configuration, the first control section 400 and the second control section 500 can determine whether or not the medicine of the preparation target contained in the preparation data falls under the category of the light shielded medicine.

Further, in the co-infusion apparatus 1, in the case of carrying out the co-infusion process for the light shielded medicine contained in the preparation data, the first control section 400 informs a message indicating that the preparation target of the co-infusion process falls under the category of the light shielded medicine to the second control section 500. With this configuration, the second control section 500 can turn off illuminating elements (not shown in the drawings) in the co-infusion process chamber 104 before the tray 101 on which the light shielded medicine is set is conveyed into the co-infusion process chamber 104. With this configuration, it is possible to suppress light exposed to the light shielded medicine at the time of carrying out the co-infusion process for the light shielded medicine in the co-infusion process chamber 104.

In this regard, an illumination is required in the co-infusion apparatus 1 for photographing states of the light shielding container (medicine container 10), the injector 11, the transfusion bag 12 or the like in the co-infusion process chamber 104 to carry out the image inspection of the co-infusion process. For responding to this requirement, the second control section 500 temporarily turns on the illuminating elements (not shown in the drawings) in the co-infusion process chamber 104 at the time of photographing the inspection image. With this configuration, it is possible to carry out the image inspection of the co-infusion process for the light shielded medicine with suppressing irradiation of light to the light shielded medicine.

Further, it may be considered that the user preliminarily puts the transfusion bag 12 in the light shielding bag 12 to set the transfusion bag 12 on the tray 101 in a state that only the co-infusion port of the transfusion bag 12 is exposed out of the light shielding bag 12 at the time of setting the transfusion bag 12 on the tray 101. With this configuration, it is possible to suppress light exposed to the light shielded medicine after the light shielded medicine has been injected into the transfusion bag 12. In this case, the information such as the barcode attached to the surface of the transfusion bag 12 cannot be read by the camera for transfusion 121 of the tray conveying terminal portion 110a. Thus, it may be considered that the second control section 500 turns off the collating function utilizing the barcode of the transfusion bag 12. Further, it may be considered that the same information as the barcode of the transfusion bag 12 is attached to an outer surface of the light shielding bag. In the case of carrying out the co-infusion process for the light shielded medicine contained in the preparation data, the second control section 500 turns off the dome light 120. With this configuration, it is possible to further suppress light from being exposed to the light shielded medicine in the tray conveying terminal portion 110a.

On the other hand, it may be considered that the user sets the transfusion bag 12 on the tray 101 according to the normal process without putting the transfusion bag 12 in the light shielding bag. In this case, the second control section 500 turns on the dome light 120 to photograph the barcode of the transfusion bag 12 with the camera for transfusion 121 and then turns off the dome light 120 before the light shielded medicine is injected into the transfusion bag 12. With this configuration, it is possible to suppress light from being exposed to the light shielded medicine after the light shielded medicine is injected into the transfusion bag 12.

[Second Embodiment]

As described above, in the co-infusion process using the medicine container 10 carried out by the co-infusion apparatus 1, the weight of the medicine suctioned from the medicine container 10 and injected into the transfusion bag 12 with the injector 11 is measured based on the weight of the injector 11. Specifically, the second control section 500 calculates, as the weight of the medicine suctioned from the medicine container 10 and injected into the transfusion bag 12 with the injector 11, the difference between the weight of the injector 11 after the medicine has been suctioned from the medicine container 10 and the weight of the injector 11 after the medicine has been injected into the transfusion bag 12. In this regard, it may be considered that the second control section 500 calculates, as the weight of the medicine injected from the medicine container 10 into the transfusion bag 12, the weight of the injector 11 before the medicine is suctioned from the medicine container 10 and the weight of the injector 11 after the medicine has been suctioned from the medicine container 10.

Further, in the co-infusion process using the vial bottle 10B as the medicine container 10, there is a case where a weight of the transfusion suctioned from the transfusion bag 12 and injected into the vial bottle 10B with the injector 11 is measured. Specifically, by weighing the injector 11 after the transfusion has been suctioned from the transfusion bag 12 with the weighing scale 35 and weighing the injector 11 after the transfusion has been injected into the vial bottle 10B with the weighing scale 35, it is possible to calculate the weight of the transfusion injected into the vial bottle 10B with the injector 11 from a difference between these obtained weights. The weight of the transfusion injected into the vial bottle 10B with the injector 11 is used as an evidence for the weight of the transfusion injected into the vial bottle 10B, used for determining whether or not the amount of the transfusion injected into the vial bottle 10B is proper, or used for calculating a concentration of a powdered medicine (medicinal powder) in the transfusion when the powdered medicine contained in the vial bottle 10B is dissolved into the transfusion or the like.

In the co-infusion apparatus 1 (see FIG. 4), the weighing scale 35 is not provided in the movable range of the first robot arm 21 being capable of transferring the vial bottle 10B but in a movable range of the second robot arm 22 being capable of transferring and handling the injector 11. Thus, the process for weighing the weight of the injector 11 with the weighing scale 35 is carried out by the second robot arm 22. Even assuming the case of weighing a weight of the vial bottle 10B with the weighing scale 35, a process for weighing the weight of the vial bottle 10B is also carried out by the second robot arm 22.

However, in the co-infusion process, the second robot arm 22 carries out a variety of processes regarding the injector 11 such as the process for suctioning the transfusion from the transfusion bag 12 with the injector 11 in series in addition to the process for weighing the injector 11. Thus, there is a risk that the process for weighing the injector 11 with the second robot arm 22 leads to a factor making a required time of the co-infusion process longer.

In contrast, description will be given to a configuration of this embodiment which can measure the weight of the transfusion injected into the vial bottle 10B with shortening the required time of the co-infusion process.

Hereinafter, description will be given to a co-infusion apparatus 1A according to this embodiment with reference to FIGS. 39 to 44. In this regard, since the same names and the same reference signs are used for the same components of the co-infusion apparatus 1A as those of the co-infusion apparatus 1, description for the same components is omitted. The constituent components and the process steps of the co-infusion apparatus 1 and the co-infusion apparatus 1A described in the description for each embodiment of the present invention can be arbitrarily combined with each other.

[Configuration of the Co-infusion Apparatus 1A]

Figure 39:
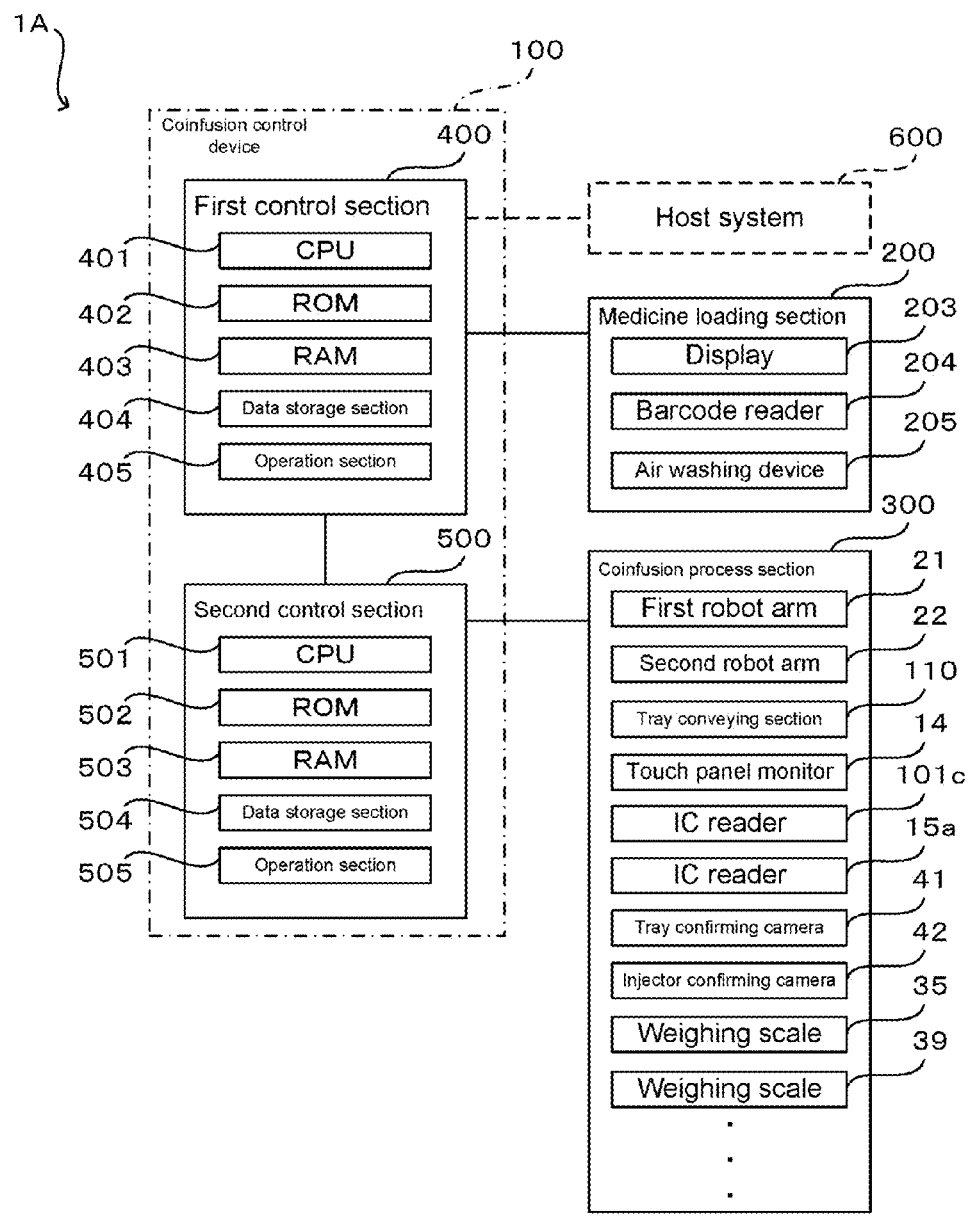
FIG. 39 is a block diagram showing a system configuration of a co-infusion apparatus according to another embodiment of the present invention.
Figure 40:
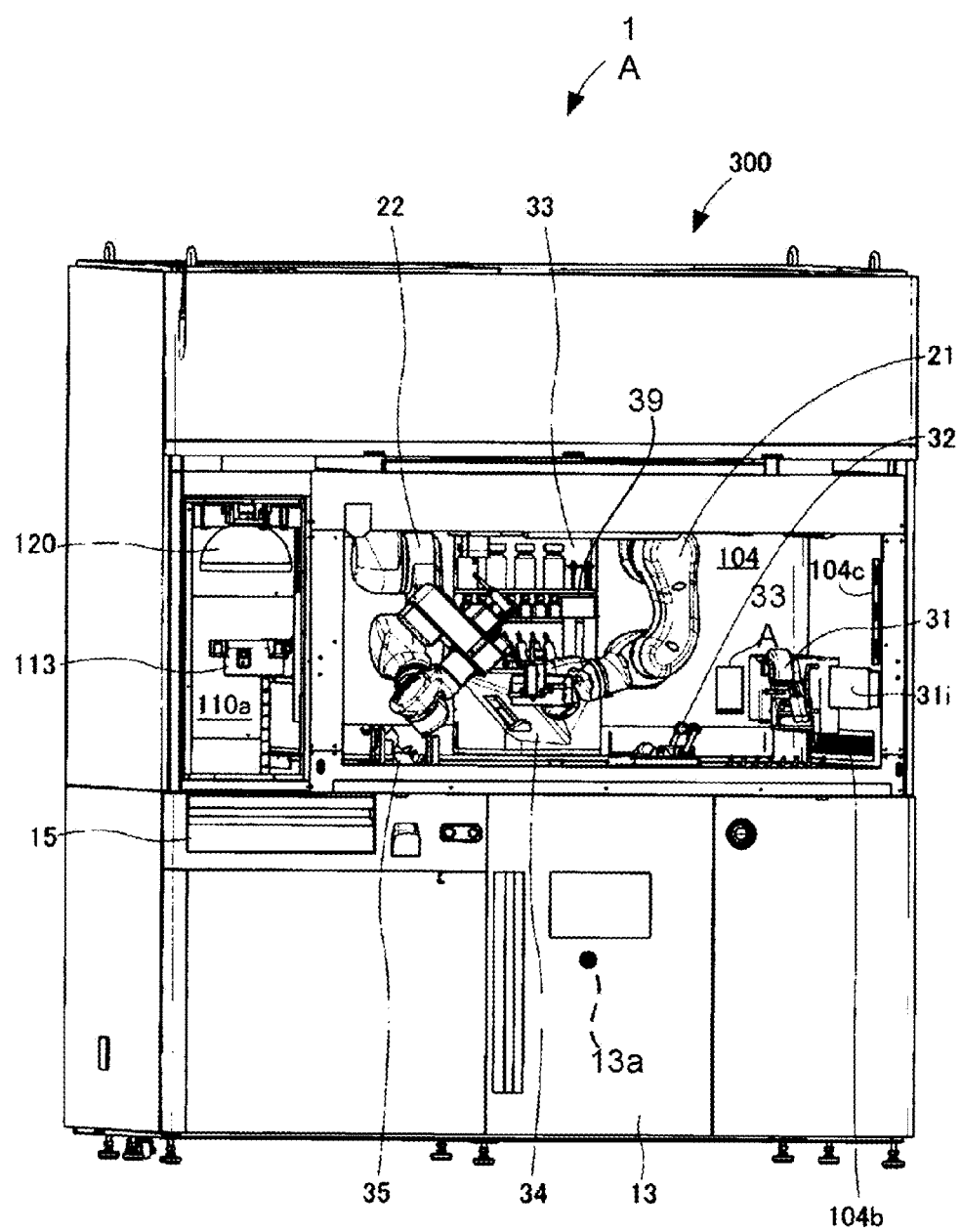
FIG. 40 is a front view showing a state that a main door and a part of a front wall of the co-infusion apparatus according to the other embodiment of the present invention are removed.

As shown in FIGS. 39 and 40, the co-infusion apparatus 1A includes a weighing scale 39 (one example of a weighing device) in addition to the constituent components of the co-infusion apparatus 1. The weighing scale 39 is provided in the movable range of the first robot arm 21 and at a position in the vicinity of a rear surface of the co-infusion apparatus 1A in which the placing shelf 33 is provided. With this configuration, the weighing scale 39 can weigh the object such as the vial bottle 10B and the injector 11 to be transferred by the first robot arm 21. In this regard, a weighing result from the weighing scale 39 is inputted into the second control section 500.

Further, an arrangement of the weighing scale 39 is not limited to the position in the vicinity of the placing shelf 33 shown in FIG. 40 as long as the weighing scale 39 is provided in the movable range of the first robot arm 21 and at a position at which the weight of the vial bottle 10B to be transferred by the first robot arm 21 can be measured. For example, it may be considered that the weighing scale 39 is provided in the placing shelf 33 or in the vicinity of the stirring device 32, the medicine reading section 34 or the like. Furthermore, the weighing scale 39 may be arranged in a movable range common to the first robot arm 21 and the second robot arm 22.

Further, another configuration in which a weighing device is provided in the first robot arm 21 instead of the weighing scale 39 may be considered as another embodiment. Specifically, it is possible to consider a configuration in which a weighing device being capable of weighing the object such as the medicine container 10 and the injector 11 held by the holding member 25 is embedded in the first robot arm 21. With this configuration, it is possible to weigh the object, which is a weighing target, such as the medicine container 10 and the injector 11 with keeping a state that the first robot arm 21 holds the object. Thus, it is possible to omit, for example, a working process for setting the object on the weighing scale 39 and a working process for again holding the object set on the weighing scale 39 after the object has been weighed, thereby significantly shortening the required time of the co-infusion process.

Since the co-infusion apparatus 1A includes the two weighing scales (the weighing scale 35 and the weighing scale 39), it is possible to concurrently allow the weighing scale 35 to weigh the object such as the injector 11 to be transferred by the second robot arm 22 and allow the weighing scale 39 to weigh the object such as the vial bottle 10B to be transferred by the first robot arm 21. On the other hand, another configuration in which one weighing device is provided in the movable range common to the first robot arm 21 and the second robot arm 22 and the one weighing device is used for weighing the vial bottle 10B and the injector 11 may be considered as another embodiment.

[Co-infusion Process in the Co-infusion Apparatus 1A]

Next, with reference to FIGS. 41 and 42, description will be given to a first robot arm control process and a second robot arm control process carried out by the second control section 500 in the co-infusion process carried out by using the vial bottle 10B. Further, the following description will be given to actions of the first robot arm 21 and the second robot arm 22 in this case with reference to FIGS. 43 and 44. In this regard, description for the co-infusion process carried out by using the ampule 10A in the co-infusion apparatus 1A is omitted because it is the same as that of the co-infusion apparatus 1. Further, the second control section 500 can carry out the injector position adjusting process (see FIG. 18), the container position adjusting process (see FIG. 19), the inspection control process (see FIG. 20), the tray collating process (see FIG. 28), the object taking process (see FIG. 29), the injection control process (see FIG. 33 or 35), the solvent amount adjusting process (see FIG. 38) and the like along with the co-infusion process.

The second control section 500 starts the first robot arm control process and the second robot arm control process after the object such as the vial bottle 10B and the injector 11 has been taken from the tray 101 fed into the tray conveying section 110. The first robot arm control process and the second robot arm control process are concurrently carried out by the second control section 500. The CPU 501 of the second control section 500 contains one or more of processors and the second control section 500 can carry out parallel processing for a plurality of processes with the one or more of processors. The parallel processing carried out by the second control section 500 contains a process for using the one processor to substantially-parallel carry out a variety of processes with switching the variety of processes in turn and a process for using the plurality of processors to simultaneously carry out a variety of processes by diving and allocating the variety of processes to the plurality of processors.

[First Robot Arm Control Process]

First, description will be given to one example of the first robot arm control process carried out by the second control section 500 with reference to FIG. 41.

<Step S1001>

At a step S1001, the second control section 500 controls the first robot arm 21 to transfer the vial bottle 10B on the weighing scale 39 to carry out a first weighing process for weighing the vial bottle 10B with the weighing scale 39 before the transfusion is injected into the vial bottle 10B. Namely, in the co-infusion apparatus 1A, the weight of the vial bottle 10B is measured by using the first robot arm 21 without using the second robot arm 22. At this time, in the co-infusion apparatus 1A, the second control section 500 carries out the first weighing process of the step S1001 in parallel with a first transfusion suctioning process of the after-mentioned step S2001 (see FIG. 42).

<Step S1002>

Next, at a step S1002, the second control section 500 determines whether or not the stirring device 32 is available. Specifically, since the stirring device 32 includes the two supporting members 32*f* as described above, the stirring device 32 can simultaneously stir two vial bottles 10B. Hereinafter, among the supporting members 32*f*, one of the supporting members 32*f* is referred to as "first stirring section 32/1" and the other one of the supporting members 32*f* is referred to as "second stirring section 32/2". In this regard, the stirring device 32 may take a configuration being capable of simultaneously stirring three or more of vial bottles 10B.

At the step S1002, the second control section 500 determines that the stirring device 32 is not available in the case where the vial bottles 10B are respectively set on both of the first stirring section 32/1 and the second stirring section 32/2. Further, the second control section 500 determines that the stirring device 32 is available in the case where the vial bottle 10B is not set on at least one of the first stirring section 32/1 and the second stirring section 32/2.

For example, a first stirring flag and a second stirring flag respectively indicating whether or not the first stirring section 32/1 and the second stirring section 32/2 are available are provided in the RAM 503. The second control section 500 sets the first stirring flag or the second stirring flag "1" at the time of setting the vial bottle 10B on the first stirring section 32/1 or the second stirring section 32/2 at the after-mentioned step S1008 or S1071. Further, initial values of the first stirring flag and the second stirring flag are "0". The second control section 500 resets values of the first stirring flag and the second stirring flag at the time of removing the vial bottles 10B from the first stirring section 32/1 and the second stirring section 32/2. With this configuration, the second control section 500 can determine whether or not the first stirring section 32/1 and the second stirring section 32/2 are available by referring to the values of the first stirring flag and the second stirring flag.

In the case of determining that the stirring device 32 is available (the case of determining "Yes" at the step S1002), the process shifts to a step S1003. In the case of determining that the stirring device 32 is not available (the case of determining "No" at the step S1002), the process shifts to a step S1010.

<Step S1003>

At the step S1003, the second control section 500 controls the first robot arm 21 to operate the first robot arm 21 together with the second robot arm 22 controlled at the after-mentioned step S2003 (see FIG. 42) to carry out an injection process for injecting the transfusion into the vial bottle 10B with the injector 11. With this configuration, the medicine contained in the vial bottle 10B is dissolved by the transfusion. Hereinafter, the transfusion in which the medicine has been dissolved in the vial bottle 10B is referred to as "medicinal solution".

As described above, in the co-infusion apparatus 1A, the injection process for injecting the transfusion into the vial bottle 10B at the step S1003 is not carried out and the process stands by at the step S1002 in the case where the stirring device 32 is not available. On the other hand, the step S1003 is carried out on condition that the stirring device 32 is available. Namely, if the stirring device 32 is not in a state that the stirring device 32 can start to stir the vial bottle 10B after the transfusion has been injected into the vial bottle 10B, the injection of the transfusion into the vial bottle 10B is not carried out. Thus, it is possible to suppress poor dissolving of the medicine or the like caused by congelation of the medicine in the vial bottle 10B generated in the case where the vial bottle 10B is left for a long term as it stands after the transfusion has been injected into the vial bottle 10B.

<Step S1004>

At a step S1004, the second control section 500 controls the first robot arm 21 to transfer the vial bottle 10B on the weighing scale 39 to carry out the second weighing process for weighing the vial bottle 10B with the weighing scale 39 after the transfusion has been injected into the transfusion. Even in this case, the weight of the vial bottle 10B is measured by using the first robot arm 21 without using the second robot arm 22 in the same manner as the step S1001.

<Step S1005>

At a step S1005, the second control section 500 calculates the difference between the weight of the vial bottle 10B which is the weighing result at the step S1001 and the weight of the vial bottle 10B which is the weighing result at the step S1004. With this configuration, the second control section 500 captures the difference as the weight of the transfusion injected from the injector 11 into the vial bottle 10B. In this case, the second control section 500 at the time of carrying out the step S1005 is one example of a transfusion weight capturing means. As described above, in the co-infusion apparatus 1A, it is possible to measure the weight of the transfusion injected into the vial bottle 10B from the weights of the vial bottle 10B before and after the transfusion is injected into the vial bottle 10B. Thus, it is unnecessary to use the second robot arm 22 to measure the weight of the injector 11 in order to capture the weight of the transfusion injected into the vial bottle 10B.

Further, in the co-infusion apparatus 1A, a specific weight for each type of the transfusion contained in the transfusion bag 12 is stored in the medicine master of the data storage section 504. Thus, the second control section 500 can calculate an amount of the transfusion injected into the vial bottle 10B based on the medicine master, the type of the transfusion in the transfusion bag 12 and the weight of the transfusion captured at the step S1005. With this configuration, for example, the second control section 500 can set the amount of the transfusion injected into the vial bottle 10B as an amount of the medicinal solution to be suctioned from the vial bottle 10B.

<Step S1006>

At a step S1006, the second control section 500 stops the driving of the stirring device 32. In the case where the stirring device 32 has been already stopped, the process shifts to a step S1007 without any change. In the case where the stirring device 32 takes a configuration being capable of individually carrying out on/off control of the stirring of a plurality of vial bottles 10B, it is unnecessary to stop the driving of the stirring device 32.

<Step S1007>

At a step S1007, the second control section 500 determines whether or not the first stirring section 32/1 is available. In the case of determining that the first stirring section 32/1 is available (the case of determining "Yes" at the step S1007), the process shifts to the step S1008. In the case of determining that the first stirring section 32/1 is not available (the case of determining "No" at the step S1007), the process shifts to the step S1071.

<Step S1008, S1071>

At the step S1008, the second control section 500 controls the first robot arm 21 to set the vial bottle 10B after the weight of the vial bottle 10B has been measured with the weighing scale 39 on the first stirring section 32/1 to carry out the stirring process for stirring the vial bottle 10B. Further, at the step S1071, the second control section 500 controls the first robot arm 21 to set the vial bottle 10B after the weight of the vial bottle 10B has been measured with the weighing scale 39 on the second stirring section 32/2 to carry out the stirring process for stirring the vial bottle 10B.

<Step S1009>

Then, at a step S1009, the second control section 500 allows the stirring device 32 to start to drive. With this configuration, the stirring device 32 stirs the transfusion and the medicine contained in the vial bottle 10B to produce the sufficiently-mixed transfusion. In the case where the stirring device 32 has already driven, the process shifts to a step S1010 without any change.

<Step S1010>

At a step S1010, the second control section 500 determines whether or not the stirring of the first stirring section 32/1 completes. Specifically, the second control section 500 starts to measure a stirring time of the first stirring section 32/1 when the driving of the stirring device 32 is started after the vial bottle 10B has been set on the first stirring section 32/1 at the step S1008. In the same manner, the second control section 500 starts to measure a stirring time of the second stirring section 32/2 when the driving of the stirring device 32 is started after the vial bottle 10B has been set on the second stirring section 32/2 at the step S1071. Then, the second control section 500 determines that the stirring of the first stirring section 32/1 or the second stirring section 32/2 completes in the case where a measured time corresponding to the first stirring section 32/1 or the second stirring section 32/2 reaches to a predetermined stirring time. In this regard, the stirring time is set in advance according to the type, the amount and the like of the medicine contained in the vial bottle 10B. While the driving of the stirring device 32 is stopped, measuring of the stirring times of the first stirring section 32/1 and the second stirring section 32/2 are also temporarily stopped.

In the case of determining that the stirring of the first stirring section 32/1 completes (the case of determining "Yes" at the step S1010), the process shifts to a step S1011. In the case of determining that the stirring of the first stirring section 32/1 does not complete (the case of determining "No" at the step S1010), the process shifts to a step S1013.

<Steps S1011 to S1012>

At the step S1011, the second control section 500 stops the driving of the stirring device 32. Then, at a step S1012, the second control section 500 controls the first robot arm 21 to take the vial bottle 10B from the first stirring section 32/1 of the stirring device 32 and operate the first robot arm 21 together with the second robot arm 22 controlled at the after-mentioned step S2041 (see FIG. 42) to suction the medicinal solution from the vial bottle 10B with the injector 11.

<Step S1013>

On the other hand, at the step S1013, the second control section 500 determines whether or not the stirring of the second stirring section 32/2 completes. In the case of determining that the stirring of the second stirring section 32/2 completes (the case of determining "Yes" at the step S1013), the process shifts to a step S1014. In the case of determining that the stirring of the second stirring section 32/2 does not complete (the case of determining "No" at the step S1013), the process shifts to a step S1016.

<Steps S1014 to S1015>

At the step S1014, the second control section 500 stops the driving of the stirring device 32. Then, at a step S1015, the second control section 500 controls the first robot arm 21 to take the vial bottle 10B from the second stirring section 32/2 of the stirring device 32 and operate the first robot arm 21 together with the second robot arm 22 controlled at the after-mentioned step S2031 (see FIG. 42) to suction the medicinal solution from the vial bottle 10B with the injector 11.

<Step S1016>

After that, at the step S1016, the second control section 500 determines whether or not another vial bottle 10B to be subsequently used exists based on the preparation data. For example, at the step S1016, the second control section 500 determines that the other vial bottle 10B to be subsequently used exists in the case of carrying out a preparation working using a plurality of vial bottles 10B based on one preparation data or in the case of continuously carrying out a plurality of preparation workings for a plurality of preparation data using the vial bottle 10B.

In the case of determining that the other vial bottle 10B to be subsequently used exists (the case of determining "Yes" at the step S1016), the process returns to the step S1001 and then the same process described above is carried out for the other vial bottle 10B to be subsequently used. In the case of determining that the other vial bottle 10B to be subsequently used does not exist (the case of determining "No" at the step S1016), the process shifts to a step S1017.

<Step S1017>

At the step S1017, the second control section 500 determines whether or not the vial bottle 10B remains on the first stirring section 32/1 or the second stirring section 32/2 of the stirring device 32. In the case of determining that the vial bottle 10B remains on the first stirring section 32/1 or the second stirring section 32/2 (the case of determining "Yes" at the step S1017), the process shifts to the step S1009 and then the stirring for the remaining vial bottle 10B is restarted by the stirring device 32. In the case where that the stirring device 32 has been already driven, the process shifts to the step S1010 without any change. On the other hand, in the case of determining that any vial bottle 10B does not remain on the first stirring section 32/1 and the second stirring section 32/2 (the case of determining "No" at the step S1017), the first robot arm control process is terminated.

[Second Robot Arm Control Process]

Next, description will be given to one example of the second robot arm control process carried out by the second control section 500 with reference to FIG. 42.

<Step S2001>

At a step S2001, the second control section 500 controls the second robot arm 22 to carry out the first transfusion suctioning process for suctioning the transfusion from the transfusion bag 12 with the injector 11 in a necessary amount based on the preparation data. At this time, in the co-infusion apparatus 1A, the weight of the vial bottle 10B is measured at the step S1001 (see FIG. 41) by using the first robot arm 21. With this configuration, the second robot arm 22 can allow the injector 11 to suction the transfusion from the transfusion bag 12 while the first robot arm 21 weighs the vial bottle 10B. Namely, in the co-infusion apparatus 1A, the second control section 500 concurrently carries out the first transfusion suctioning process at the step S2001 and the first weighing process (see FIG. 41: step S1001) at the step S1001.

<Step S2002>

Figure 41:
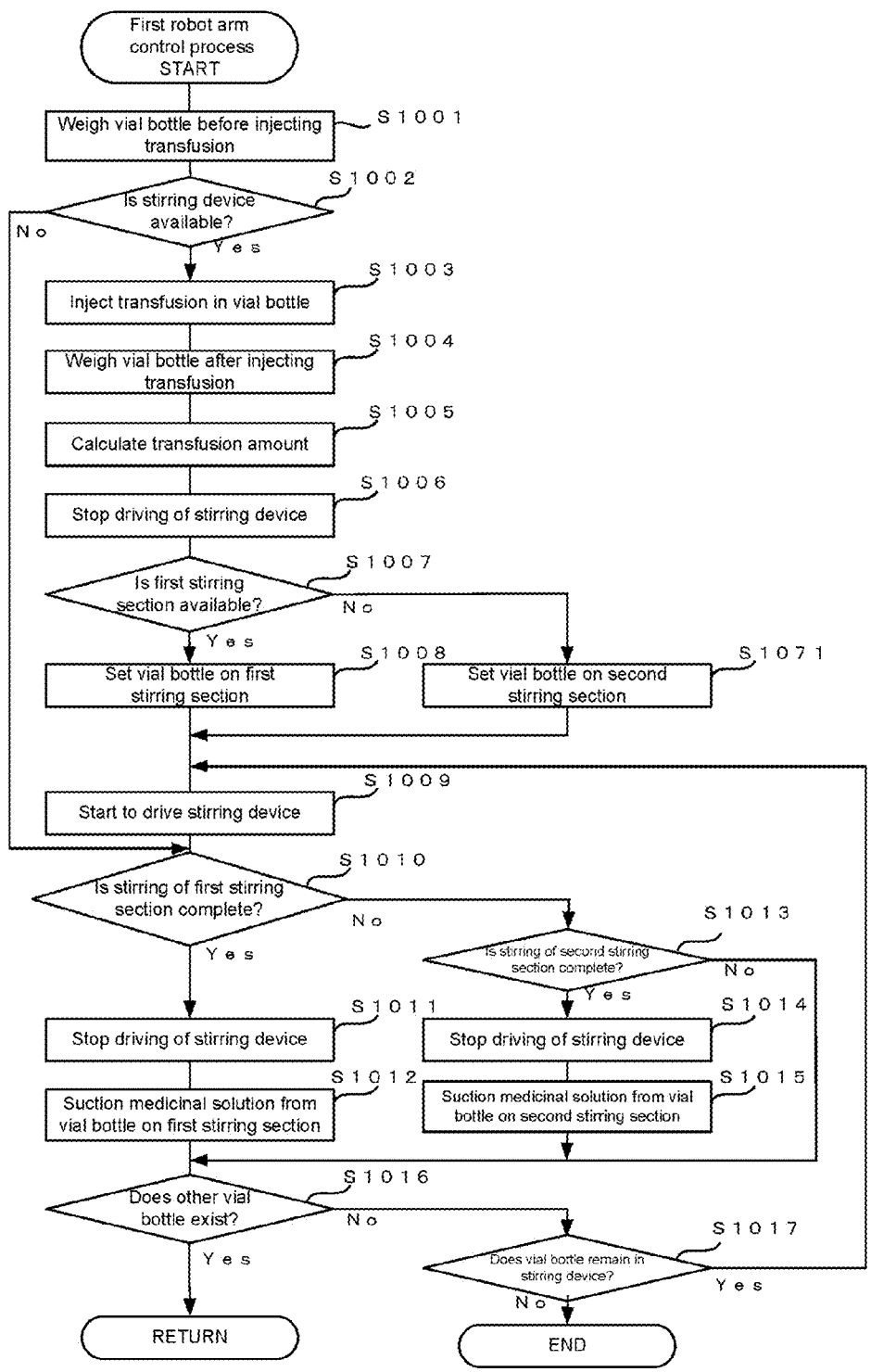
FIG. 41 is a flow chart for explaining one example of a first robot arm control process carried out by the co-infusion apparatus according to the other embodiment of the present invention.

Next, at a step S2002, the second control section 500 determines whether or not the stirring device 32 is available in the same manner as the step S1002 (see FIG. 41). In the case of determining that the stirring device 32 is available (the case of determining "Yes" at the step S2002), the process shifts to a step S2003. In the case of determining that the stirring device 32 is not available (the case of determining "No" at the step S2002), the process shifts to a step S2004.

<Step S2003>

At the step S2003, the second control section 500 controls the second robot arm 22 to operate the second robot arm 22 together with the first robot arm 21 controlled at the step S1003 (see FIG. 41) to carry out the injection process for injecting the transfusion into the vial bottle 10B with the injector 11. As described above, in the co-infusion apparatus 1A, in the case where the stirring device 32 is not available after the transfusion has been suctioned from the transfusion bag 12 into the injector 11 (the case of determining "No" at the step S2002), the injection process for injecting the transfusion into the vial bottle 10B is not carried out and the process stands by at the step S2002. Namely, the step S2003 is carried out on condition that the stirring device 32 is available.

<Step S2004>

At the step S2004, the second control section 500 determines whether or not the stirring for the vial bottle 10B on either the first stirring section 32/1 or the second stirring section 32/2 of the stirring device 32 completes in the same manner as the step S1010 and the step S1013 (see FIG. 41). In the case of determining that the stirring for the vial bottle 10B in the stirring device 32 completes (the case of determining "Yes" at the step S2004), the process shifts to a step S2041. In the case of determining that the stirring for the vial bottle 10B in the stirring device 32 does not complete (the case of determining "No" at the step S2004), the process shifts to a step S2005.

<Step S2005>

At the step S2005, the second control section 500 determines whether or not the other vial bottle 10B to be subsequently used exists based on the preparation data in the same manner as the step S1016 (see FIG. 41). In the case where the other vial bottle 10B to be subsequently used exists (the case of determining "Yes" at the step S2005), the process returns to the step S2001 and the same process described above is carried out for the other vial bottle 10B to be subsequently used. In the case of determining that the other vial bottle 10B to be subsequently used does not exist (the case of determining "No" at the step S2005), the process shifts to the step S2004.

<Step S2041>

At the step S2014, the second control section 500 controls the second robot arm 22 to operate the second robot arm 22 together with the first robot arm 21 controlled at the step S1012 or the step S1015 (see FIG. 41) to suction the medicinal solution from the vial bottle 10B with the injector 11. In this regard, it may be considered that the second control section 500 sets the amount of the medicinal solution suctioned from the vial bottle 10B with the injector 11 based on the weight of the transfusion captured at the step S1005. In this case, the second control section 500 at the time of carrying out such a process is one example of a suctioning amount setting means.

<Step S2042>

Then, at a step S2042, the second control section 500 controls the second robot arm 22 to carry out a bag injection process for injecting the medicinal solution suctioned into the injector 11 at the step S2041 into the transfusion bag 12.

<Step S2043>

After that, at a step S2043, the second control section 500 determines whether or not the other vial bottle 10B to be subsequently used exists based on the preparation data in the same manner as the step S2005. In the case of determining that the other vial bottle 10B to be subsequently used exists (the case of determining "Yes" at the step S2043), the process returns to the step S2003 and the same process described above is carried out for the other vial bottle 10B to be subsequently used. In the case of determining that the other vial bottle 10B to be subsequently used does not exits (the case of determining "No" at the step S2043), the process shifts to a step S2044.

<Step S2044>

At the step S2044, the second control section 500 determines whether or not the vial bottle 10B remains on the first stirring section 32f1 or the second stirring section 32f2 of the stirring device 32. In the case of determining that the vial bottle 10B remains on the first stirring section 32f1 or the second stirring section 32f2 (the case of determining "Yes" at the step S2044), the process shifts to the step S2004. On the other hand, in the case of determining that any vial bottle 10B does not remain on the first stirring section 32f1 and the second stirring section 32f2 (the case of determining "No" at the step S2044), the second robot arm control process is terminated.

[Actions of the First Robot Arm 21 and the Second Robot Arm 22 in a Co-Infusion Action]

Figure 43:
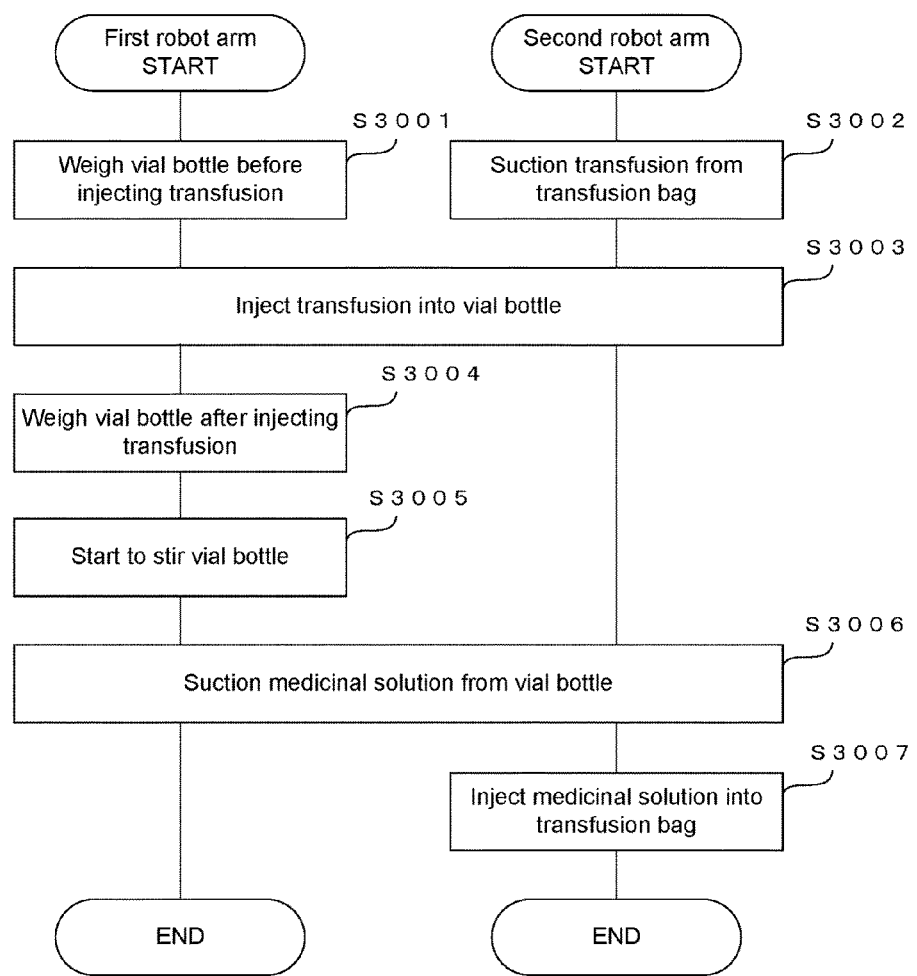
FIG. 43 is a flow chart for explaining working examples of a first robot arm and a second robot arm in the co-infusion apparatus according to the other embodiment of the present invention.
Figure 44:
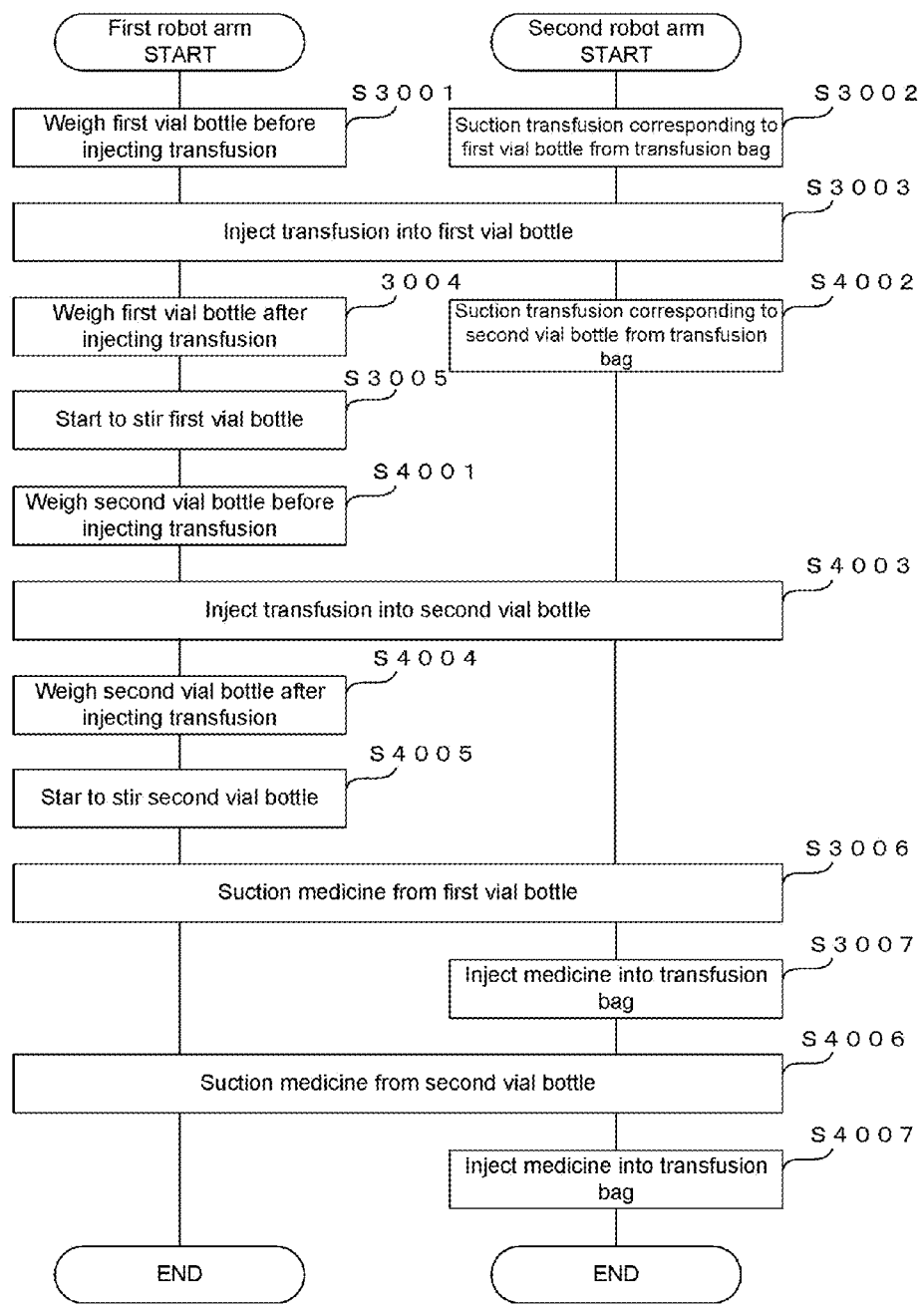
FIG. 44 is another flow chart for explaining other working examples of the first robot arm and the second robot arm in the co-infusion apparatus according to the other embodiment of the present invention.

Subsequently, description will be given to an outline of actions of the first robot arm 21 and the second robot arm 22 ordered in time series in the case of carrying out the first robot arm control process and the second robot arm control process with reference to FIGS. 43 and 44. In this regard, vertical directions in FIGS. 43 and 44 represent a time-series flow.

[Co-infusion Process in the Case where the Number of the Vial Bottles 10B is One]

First, description will be given to working examples of the first robot arm 21 and the second robot arm 22 in the case of carrying out the co-infusion process using one vial bottle 10B with reference to FIG. 43.

<Steps S3001, S3002>

First, at a step S3001, the first robot arm 21 allows the weighing scale 39 to weigh the vial bottle 10B before the transfusion is injected into the vial bottle 10B. At a step S3002, the second robot arm 22 allows the injector 11 to suction the transfusion from the transfusion bag 12. Actions of the step S3001 and the step S3002 are concurrently carried out by concurrently carrying out the first weighing process (See FIG. 41: Step S1001) and the first transfusion suctioning process (see FIG. 42: step S2001).

Thus, since the first weighing process and the first transfusion suctioning process are concurrently carried out in the co-infusion apparatus 1A, it is possible to efficiently progress the co-infusion process, thereby shortening the required time of the co-infusion process. In this case, the second control section 500 at the time of concurrently carrying out the first weighing process and the first transfusion suctioning process is one example of a first control means.

<Step S3003>

Next, at a step S3003, the first robot arm 21 and the second robot arm 22 are operated together to inject the transfusion into the vial bottle 10B with the injector 11. The second control section 500 carries out the injection process (step S1003 and step S2003) to carry out an action of the step S3003. In this case, the second control section 500 at the time of carrying out the injection process is one example of a second control means.

<Step S3004>

At a step S3004, the first robot arm 21 allows the weighing scale 39 to weigh the vial bottle 10B after the transfusion has been injected into the vial bottle 10B. The second control section 500 carries out the second weighing process (step S1004) to carry out an action of the step S3004. In this case, the second control section 500 at the time of carrying out the second weighing process is one example of a second control means.

<Step S3005>

Subsequently, at a step S3005, the first robot arm 21 transfers the vial bottle 10B to the stirring device 32 to stir the vial bottle 10B with the stirring device 32. The second control section 500 carries out the stirring process (step S1008 and step S1071) to carry out an action of the step S3005.

<Step S3006>

After that, at a step S3006, the first robot arm 21 and the second robot arm 22 are operated together to suction the medicinal solution from the vial bottle 10B with the injector 11.

<Step S3007>

Then, at a step S3007, the medicinal solution suctioned form the vial bottle 10B with the injector 11 is injected into the transfusion bag 12 by the second robot arm 22. The second control section 500 carries out the bag injection process (step S2042) to carry out an action of the step S3007.

[Co-infusion Process in the Case where the Number of the Vial Bottles 10B is Two]

Next, description will be given to working examples of the first robot arm 21 and the second robot arm 22 in the case of carrying out the co-infusion process using two vial bottles 10B with reference to FIG. 44. In this regard, since the same reference signs are used for the same steps of the co-infusion process as those of the co-infusion process described with reference to FIG. 43, description for the same steps is omitted.

<Step S4001>

In the case where the two vial bottles 10B are used in the co-infusion process, the first robot arm 21 allows the weighing scale 39 to weigh the second vial bottle 10B before the transfusion is injected into the second vial bottle 10B (step S4001) after carrying out the step S3005. The second control section 500 carries out the first weighing process (see FIG.

41: step S1001) corresponding to the second vial bottle 10B to carry out an action of the step S4001.

<Step S4002>

On the other hand, in the case where the two vial bottle 10B are used in the co-infusion process, the second robot arm 22 allows the injector 11 to suction the transfusion corresponding to the second vial bottle 10B from the transfusion bag 12 (step S4002) after carrying out the step S3003. The second control section 500 carries out the step S2001 to carry out an action of the step S4002. In this case, the process for carrying out the step S2001 to suction the transfusion corresponding to the second vial bottle 10B from the transfusion bag 12 is one example of a second transfusion suctioning process and the second control section 500 at the time of carrying out the second transfusion suctioning process is one example of a third control means.

At this time, the first transfusion suctioning process (step S4002) for the second vial bottle 10B, the second weighing process (step S3004) for the first vial bottle 10B, the stirring process (step S3005) for the first vial bottle 10B and the first weighing process (step S4001) for the second vial bottle 10B are concurrently carried out. Thus, it is possible to more efficiently progress the co-infusion process, thereby shortening the required time of the co-infusion process using the plurality of vial bottle 10B.

<Step S4003>

After that, at a step S4003, the first robot arm 21 and the second robot arm 22 are operated together in the same manner as the step S3003 to inject the transfusion into the second vial bottle 10B with the injector 11.

<Steps S4004, S4005>

Further, at steps S4004 and S4005, the first robot arm 21 allows the weighing scale 39 to weigh the second vial bottle 10B after the transfusion has been injected into the second vial bottle 10B and then transfers the second vial bottle 10B to the stirring device 32 to allow the stirring device 32 to stir the second vial bottle 10B in the same manner as the steps S3004 and S3005.

<Step S4006>

Then, at a step S4006, the first robot arm 21 and the second robot arm 22 are operated together in the same manner as the step S3006 to suction the medicinal solution from the second vial bottle 10B with the injector 11.

<Step S4007>

At a step S4007, the second robot arm 22 allows the injector 11 to inject the medicinal solution suctioned from the second vial bottle 10B into the transfusion bag 12 in the same manner as the step S4007.

As described above, in the co-infusion apparatus 1A according to this embodiment, the vial bottle 10B is weighed by using the first robot arm 21, which stands by when the transfusion is suctioned from the transfusion bag 12 due to the second robot arm 22, to calculate the weight of the transfusion injected into the vial bottle 10B. Thus, in the co-infusion apparatus 1A, it is possible to capture the weight of the transfusion injected into the vial bottle 10B and shorten the required time of the co-infusion process compared with the case where the second robot arm 22 carries out the process for measuring the weight of the injector 11 or the vial bottle 10B.

[Third Embodiment]

In the case of carrying out the co-infusion process using the plurality of vial bottles 10B, in the co-infusion apparatus 1A, it may be considered that the transfusion is suctioned from the transfusion bag 12 in a necessary amount corresponding to each vial bottle 10B for each time when the transfusion is individually injected into each vial bottle 10B with the injector 11. However, in the case of carrying out such a process, there is a problem in that it is necessary to carry out the suctioning of the transfusion from the transfusion bag 12 with the injector 11 multiple times corresponding to the number of the vial bottles 10B and thereby the required time of the co-infusion process becomes longer.

In contrast, in the co-infusion apparatus 1A, it may be considered that the transfusion is suctioned from the transfusion bag 12 with the injector 11 at one time in a total necessary amount corresponding to all of the plurality of vial bottles 10B and then the transfusion is distributed from the injector 11 into each vial bottle 10B in a necessary amount corresponding to each vial bottle 10B. In this case, it is only necessary to carry out the suctioning of the transfusion from the transfusion bag 12 with the injector 11 multiple times less than the number of the vial bottles 10B. This results in shortening the required time of the co-infusion process. Further, after that, a medicinal solution in the plurality of vial bottles 10B is suctioned by the injector 11 in turn and injected into the transfusion bag 12. Hereinafter, in this embodiment, description will be given to an exemplary case of carrying out the co-infusion process using a vial bottle 10B1 and a vial bottle 10B2 which are two vial bottles 10B in which a medicine such as a powdered medicine has been contained. Further, description will be given to the case where the whole amount of the medicine in the vial bottle 10B1 and the vial bottle 10B2 is used in the co-infusion process. In this regard, the number of the vial bottles 10B is not limited to two.

Here, description will be given to a method for distributing the transfusion from the injector 11 into the two vial bottles 10B1, 10B2 with reference to FIG. 45. Specifically, the following description will be given to the case where 10 ml of the transfusion is suctioned from the transfusion bag 12 with the injector 11 and 5 ml of the transfusion is distributed and injected from the injector 11 into each of the vial bottles 10B1, 10B2.

Figure 45A:
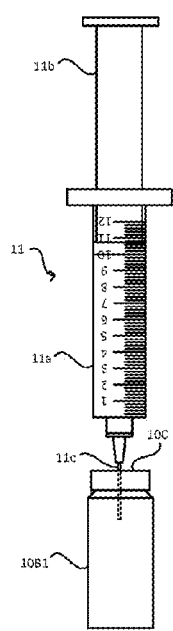
FIG. 45 is a view showing a state of an injection process and a state of a suctioning process in the co-infusion apparatus according to the other embodiment of the present invention.
Figure 45B:
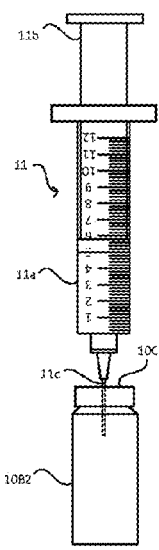

At first, as shown in FIG. 45(A), 5 ml of the transfusion is injected from the injector 11 into the vial bottle 10B1 in a state that 10 ml of the transfusion has been suctioned from the transfusion bag 12 with the injector 11. Next, as shown in FIG. 45(B), 5 ml of the remaining transfusion is injected from the injector 11 into the vial bottle 10B2 in a state that 5 ml of the transfusion remains in the injector 11. At the time of injecting the transfusion from the injector 11 into each of the vial bottles 10B1, 10B2, the injector 11 and the vial bottles 10B1, 10B2 are in a state that the injection needle 11c of the injector 11 is directed toward the lower direction and a rubber plug 10C of each of the vial bottles 10B1, 10B2 is directed toward the upper direction as shown in FIGS. 45(A) and 45(B).

Figure 45C:
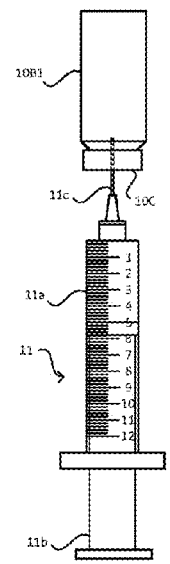
Figure 45D:
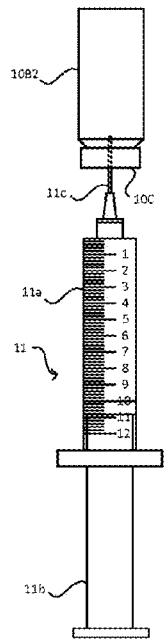

After the stirring for the vial bottle 10B1 completes, 5 ml of the medicinal solution in which the medicine has been dissolved is suctioned from the vial bottle 10B1 with the injector 11 as shown in FIG. 45(C). Further, after the stirring for the vial bottle 10B2 completes, 5 ml of the medicinal solution in which the medicine has been is also suctioned from the vial bottle 10B2 with the injector 11 as shown in FIG. 45(D). At the time of suctioning the medicinal solution from each of the vial bottles 10B1, 10B2 with the injector 11, the injector 11 and the vial bottles 10131, 10B2 are in a state that the injection needle 11c of the injector 11 is directed toward the upper direction and the rubber plug 10C of each of the vial bottles 10B1, 10B2 is directed toward the lower direction as shown in FIGS. 45(C) and 45(D).

In this regard, in the case of injecting the transfusion from the injector 11 into each of the vial bottles 10B1, 10B2 without any technical consideration, pressure in each of the vial bottles 10B1, 10B2 becomes positive pressure and the medicinal solution in each of the vial bottles 10B1, 10B2 becomes likely to leak from each of the vial bottles 10B1, 10B2. Thus, after the injection needle 11c of the injector 11 has been inserted into the rubber plug 10C of each of the vial bottles 10B1, 10B2, the plunger 11b of the injector 11 is handled to suction air from each of the vial bottles 10B1, 10B2 in a predetermined amount. As a result, the pressure in each of the vial bottles 10B1, 10B2 becomes negative pressure. Then, the plunger 11b of the injector 11 is handled to inject the transfusion from the injector 11 into each of the vial bottles 10B1, 10B2. By carrying out such a series of injection processes one time or multiple times, it is possible to inject the transfusion into each of the vial bottles 10B1, 10B2 in the necessary amount corresponding to each of the vial bottles 10B1 and 10B2.

However, in the case of carrying out such an injection process, there is a case where a variation occurs in the amount of the transfusion injected from the injector into the vial bottle 10B1 depending on change of the pressure in the vial bottle 10B1 or the like. For example, it may be considered that while an ideal value of the amount of the transfusion to be injected into each of the vial bottles 10B1, 10B2 is 5 ml, actual amounts of the transfusion injected into the vial bottles 10B1, 10B2 in practice become respectively 4.75 ml and 5.25 ml.

Thus, in the case of carrying out this type of injection process, a suctioning process for suctioning the transfusion from the vial bottle 10B1 in an amount slightly larger than the ideal value of the transfusion to be injected into the vial bottle 10B1 is carried out at the time of suctioning the medicinal solution from the vial bottle 10B1. With this configuration, even in the case where the variation occurs in the amount of the transfusion injected in the vial bottle 10B in practice, it is possible to obtain the whole amount of the transfusion in the vial bottle 10B1. For example, it may be considered that 5.5 ml of the transfusion including 5 ml of the transfusion and 10% of the extra amount predetermined with respect to 5 ml of the transfusion is suctioned.

However, if the suctioning process for suctioning the transfusion in an amount larger than the predetermined amount (ideal amount) by the extra amount is carried out, there is a case where extra air (in this case, 1 ml of air) is contained in the injector 11 after the medicinal solution has been suctioned from the vial bottle 10B1 and the vial bottle 10B2. As a result, it becomes difficult to accurately understand the amount of the medicinal solution in the injector 11 even by referring to the scale of the injector 11.

Specifically, in the co-infusion apparatus 1A, there is a case where the image of the scale of the injector 11 is photographed as an evidence for indicating that the medicinal solution is suctioned from the vial bottle 10B1 and the vial bottle 10B2 with the injector 11 in the necessary amount. In this case, it is necessary to carry out a process for discharging the extra air from the injector 11 before the scale of the injector 11 is photographed. At this time, in order to discharge the extra air from the injector 11, it is necessary to slowly handle the plunger 11b in a state that the injection needle 11c of the injector 11 is directed toward the upper direction so that the medicinal solution does not leak from the injector 11. Thus, there is a problem in that the required time of the co-infusion process becomes longer due to the process for discharging the extra air from the injector 11.

Further, an injector having a size (volume) preliminarily selected according to the suctioning amount required in the co-infusion process is used as the injector 11. However, in the configuration in which the injector 11 suctions the extra amount as described above, it is necessary to select the size of the injector 11 with considering that the extra amount is suctioned. Particularly, there is a risk that it becomes necessary to select the injector 11 having a size larger than an originally required size by one level only for suctioning the extra amount with the injector 11. However, since an individual difference of the injector 11 tends to increase as the size of the injector 11 increases, it is preferable to use the injector 11 having a size as small as possible.

Figure 42:
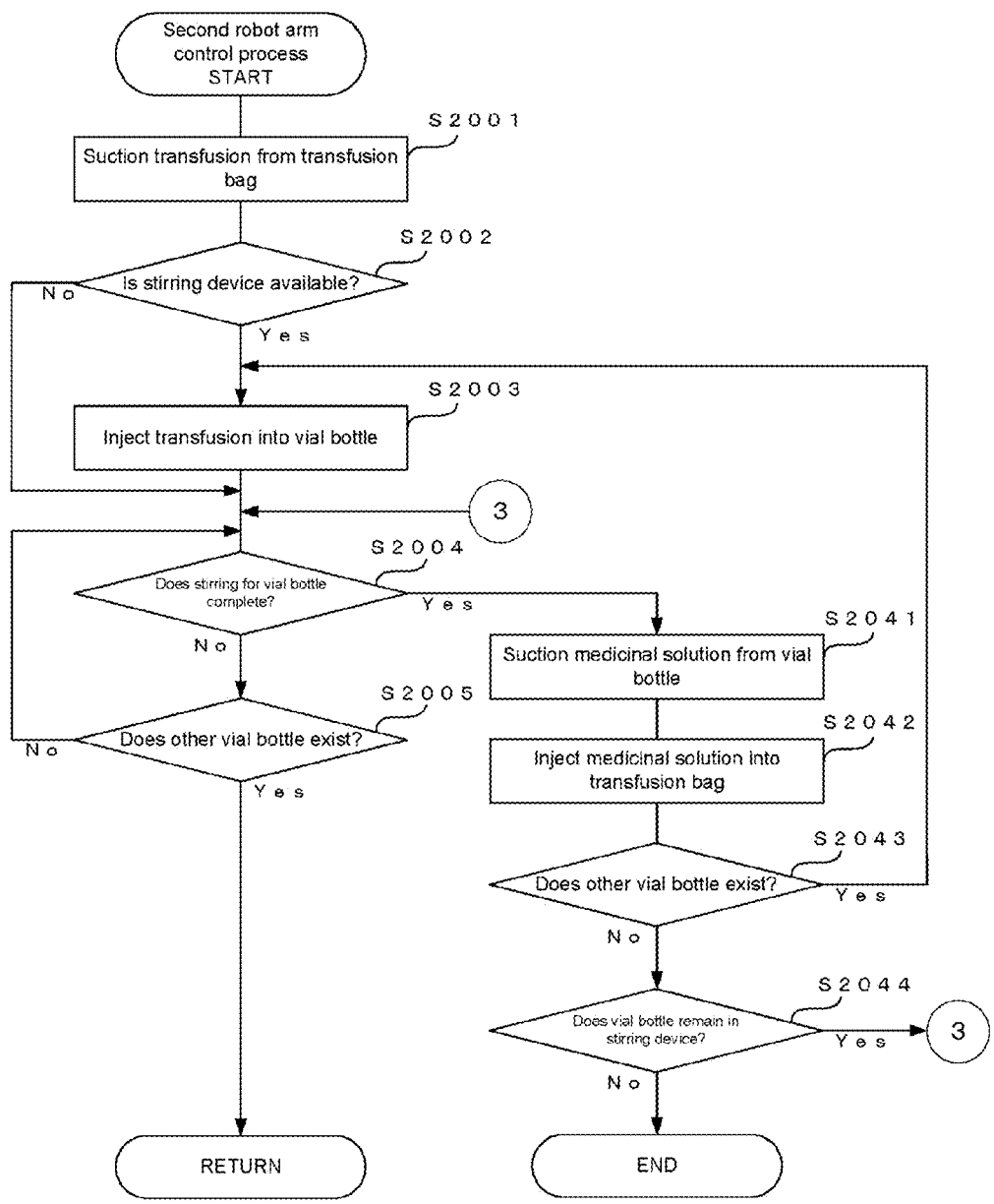
FIG. 42 is a flow chart for explaining one example of a second robot arm control process carried out by the co-infusion apparatus according to the other embodiment of the present invention.
Figure 46:
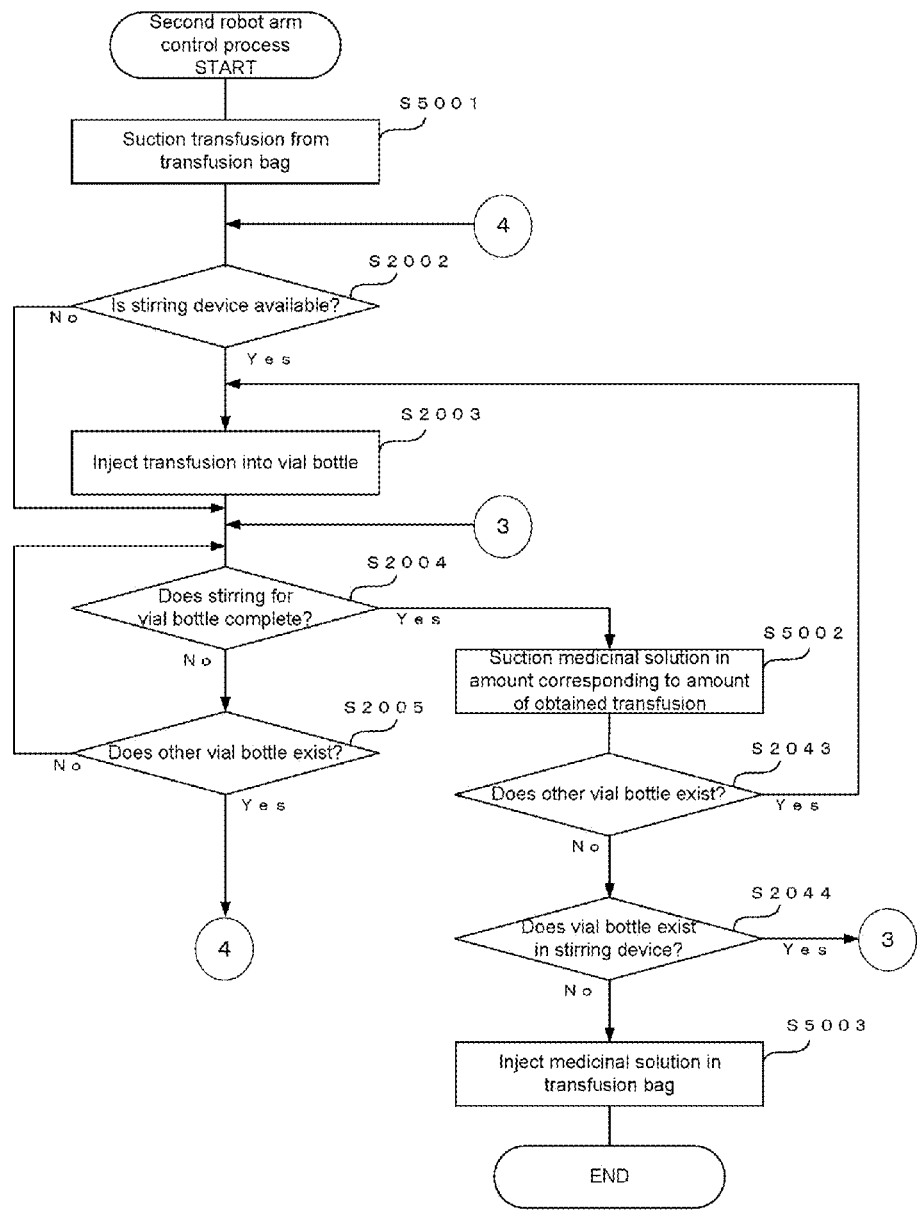
FIG. 46 is another flow chart for explaining another example of the second robot arm control process carried out by the co-infusion apparatus according to the other embodiment of the present invention

In contrast, in the co-infusion apparatus 1A according to this embodiment, the second control section 500 carries out a second robot arm control process shown in FIG. 46 instead of the second robot arm control process shown in FIG. 42. With this configuration, in the co-infusion apparatus 1A, it becomes possible to shorten the required time of the co-infusion process in the case of suctioning the medicinal solution from the plurality of vial bottles 10B after the transfusion has been distributed into the plurality of vial bottles 10B with the injector 11 and use the injector 11 having a size as small as possible.

[Second Robot Arm Control Process]

Hereinafter, description will be given to one example of the second robot arm control process carried out by the second control section 500 in the co-infusion apparatus 1A according to this embodiment with reference to FIG. 46. In this regard, since the same reference signs are used for the same steps as those of the second robot arm control process shown in FIG. 42, description for the same steps is omitted.

<Step S5001>

At first, at a step S5001 in the second robot arm control process, the second control section 500 controls the second robot arm 22 to suction the transfusion from the transfusion bag 12 with the injector 11 in a total amount of the transfusion to be injected into the plurality of vial bottles 10B.

In the above-mentioned example, 10 ml of the transfusion to be injected into the vial bottles 10B1, 10B2 is suctioned from the transfusion bag 12 with the injector 11 in total. Then, at the subsequent step S2003, 5 ml of the transfusion is injected into the vial bottle 10B1 with the injector 11. At the step S1005, the weight of the transfusion which has been injected into the vial bottle 10B1 is captured. After the injection of the transfusion into the vial bottle 10B1 completes, 5 ml of the transfusion is injected into the vial bottle 10B2 with the injector 11 at the step S2003 in the same manner as the vial bottle 10B1. At the step S1005, the weight of the transfusion which has been injected into the vial bottle 10B2 is captured. The weight of the transfusion in each of the vial bottles 10B1, 10B2 captured at the step S1005 is stored in the RAM 503 or the data storage section 504.

<Step S5002>

After that, when the stirring for the vial bottle 10B completes at the step S2004 (in the case of determining "Yes" at the step S2004), the process shifts to a step S5002. At the step S5002, the second control section 500 allows the injector 11 to suction the medicinal solution from the vial bottle 10B. Specifically, at the step S5002, the second control section 500 sets the amount of the medicinal solution to be suctioned from the vial bottle 10B as an amount of the medicinal solution based on the weight of the transfusion calculated at the step S1005 (see FIG. 41), that is, the weight of the transfusion which has been injected into the vial bottle 10B and allows the injector 11 to suction the medicinal solution from the vial bottle 10B in the set amount of the medicinal solution.

<Step S5003>

Then, in the co-infusion apparatus 1A, after the same process is applied to each vial bottle 10B to suction the medicinal solution contained in each vial bottle 10B with the injector 11 (the case of determining "Yes" at the step S2044), the process shifts to a step S5003. At the step S5003, the second control section 500 controls the second robot arm 22 to inject the medicinal solution in the injector 11 into the transfusion bag 12. At this time, the medicinal solution contained in the injector 11 has been suctioned from each vial bottle 10B according to the weighing result for each vial bottle 10B without an error.

Thus, extra air is not contained in the injector 11 and it is unnecessary to discharge the extra air from the injector 11. Therefore, it is possible to shorten the required time of the co-infusion process and match the scale of the injector 11 with a predetermined necessary amount. In addition, since air does not exist in the injector 11, it is possible to confirm a state that the amount of the transfusion in the injector 11 coincides with the necessary amount by referring to the scale of the injector 11 photographed in the inspection control process (see FIG. 20) or the like. Further, since the co-infusion apparatus 1A needs not to suction the extra amount with the injector 11, it is possible to use the injector 11 having a higher accuracy and a smaller size than the case of suctioning the extra amount as described above.

In the co-infusion process carried out in the co-infusion apparatus 1A, it may be considered that a whole amount of the medicine is obtained from the vial bottle 10B1 of the vial bottles 10B1, 10B2 and a part of the medicine is obtained from the vial bottle 10B2. In this case, since the whole amount of the medicine is obtained from the vial bottle 10B1, the amount of the transfusion to be injected into the vial bottle 10B1 may be equal to or larger than a specific amount that is set in advance for the case of using the medicine in the vial bottle 10B1. On the other hand, since a part of the medicine is obtained from the vial bottle 10B2, it is necessary to obtain the medicine from the vial bottle 10B2 in the necessary amount by controlling the amount of the transfusion to be injected into the vial bottle 10B2 and the amount of the medicinal solution to be obtained from the vial bottle 10B2 at high accuracy.

On the other hand, in this embodiment, at the step S5003, the medicinal solution is continuously suctioned from the vial bottle 10B1 and the vial bottle 10B2 with the injector 11 and injected into the transfusion bag 12. With this configuration, it is possible to reduce the number of the insertion of the injection needle 11c of the injector 11 into the transfusion bag 12 compared with the case of individually suctioning the medicinal solution from each of the vial bottle 10B1 and the vial bottle 10B2 with the injector 11 to inject the medicinal solution in the transfusion bag 12, thereby shortening the required time of the co-infusion process.

However, in this case, there is a risk that the medicinal solution suctioned from the vial bottle 10B1 into the injector 11 flows into the vial bottle 10B2 during the step for continuously suctioning the medicinal solution from the vial bottle 10B2 with the injector 11 after the medicinal solution has been suctioned form the vial bottle 10B1 with the injector 11. Thus, in the case where a concentration of the medicinal solution in the vial bottle 10B1 differs from a concentration of the medicinal solution in the vial bottle 10B2, there is a risk that the necessary amount of the medicine is not contained in the medicinal solution even if the predetermined total amount of the medicinal solution is suctioned from the vial bottle 10B1 and the vial bottle 10B2 with the injector 11.

Namely, in the co-infusion apparatus 1A, since it is only necessary to obtain the whole amount of the medicine from the vial bottle 10B1, it may be considered under normal condition that the transfusion is injected into the vial bottle 10B1 in an amount equal to or larger than the predetermined specific amount and the injector 11 is handled so that the injector 11 can sufficiently suction the transfusion in the amount equal to or larger than the specific amount. Specifically, in the case where a human operator manually carries out a working for obtaining a part of the medicine from the vial bottle 10B1, it is necessary to carry out a working for handling the injector 11 in a careful manner to inject the transfusion into the vial bottle 10B1 in the predetermined amount. On the other hand, in the case of obtaining the whole amount of the medicine from the vial bottle 10B1, it is commonly carried out that the transfusion is injected into the vial bottle 10B1 in an amount larger than the specific amount by a certain extra amount and the whole amount of the medicinal solution in the vial bottle 10B1 is obtained in order to reduce time and effort of the operator for handling the injector 11. Thus, even in the co-infusion apparatus 1A, it may be considered that the transfusion is injected into the vial bottle 10B in an amount larger than the specific amount by an extra amount in the same manner as the case where the operator manually obtains the whole amount of the medicine from the vial bottle 10B1.

In contrast, in the co-infusion apparatus 1A, since the second robot arm 22 is controlled by the second control section 500, it is possible to easily and highly-accurately control the suctioning amount and the injection amount of the injector 11 compared with the case where the operator manually carries out such a working. Thus, in the co-infusion apparatus 1A, it may be considered that the second control section 500 sets the amount of the transfusion to be injected into the vial bottle 10B1 and the vial bottle 10B2 so that the concentrations of the medicinal solution in the vial bottle 10B1 and the vial bottle 10B2 become equal to each other even in the case where the whole amount of the medicine is obtained from the vial bottle 10B1. With this configuration, since the concentrations of the medicinal solution produced in the vial bottle 10B1 and the vial bottle 10B2 become equal to each other, it is possible to accurately suction the medicinal solution in which the necessary amount of the medicine is contained with the injector 10 even in the case where the medicinal solution is suctioned from which one of the vial bottle 10B1 and the vial bottle 10B2 in first.

For example, a case where 1 g of the medicine is contained in the vial bottle 10B1, 200 mg of the medicine is contained in the vial bottle 10B2, the specific amount of the transfusion in the case of using the vial bottle 10B1 is equal to or larger than 25 ml and the specific amount of the transfusion in the case of using the vial bottle 10B2 is equal to or larger than 5 ml is assumed. In addition, it is assumed that the necessary amount of the medicine to be contained in the medicinal solution to be suctioned with the injector 10 is 1.1 g. In this case, the second control section 500 controls the second robot arm 22 to suction 30 ml of the transfusion from the transfusion bag 12 with the injector 11 and then inject 25 ml of the transfusion into the vial bottle 10B1 and 5 ml of the transfusion into the vial bottle 10B2. With this configuration, the concentrations of the medicinal solution in the vial bottle 10B1 and the vial bottle 10B2 become equal to each other. Thus, the second control section 500 can allow the injector 10 to suction total 27.5 ml of the medicinal solution from the vial bottle 10B1 and the vial bottle 10B2 in random order to obtain 1.1 g of the medicine, which is the necessary amount of the medicine, and inject the necessary amount of the medicine into the transfusion bag 12.

[Fourth Embodiment]

Figure 47:
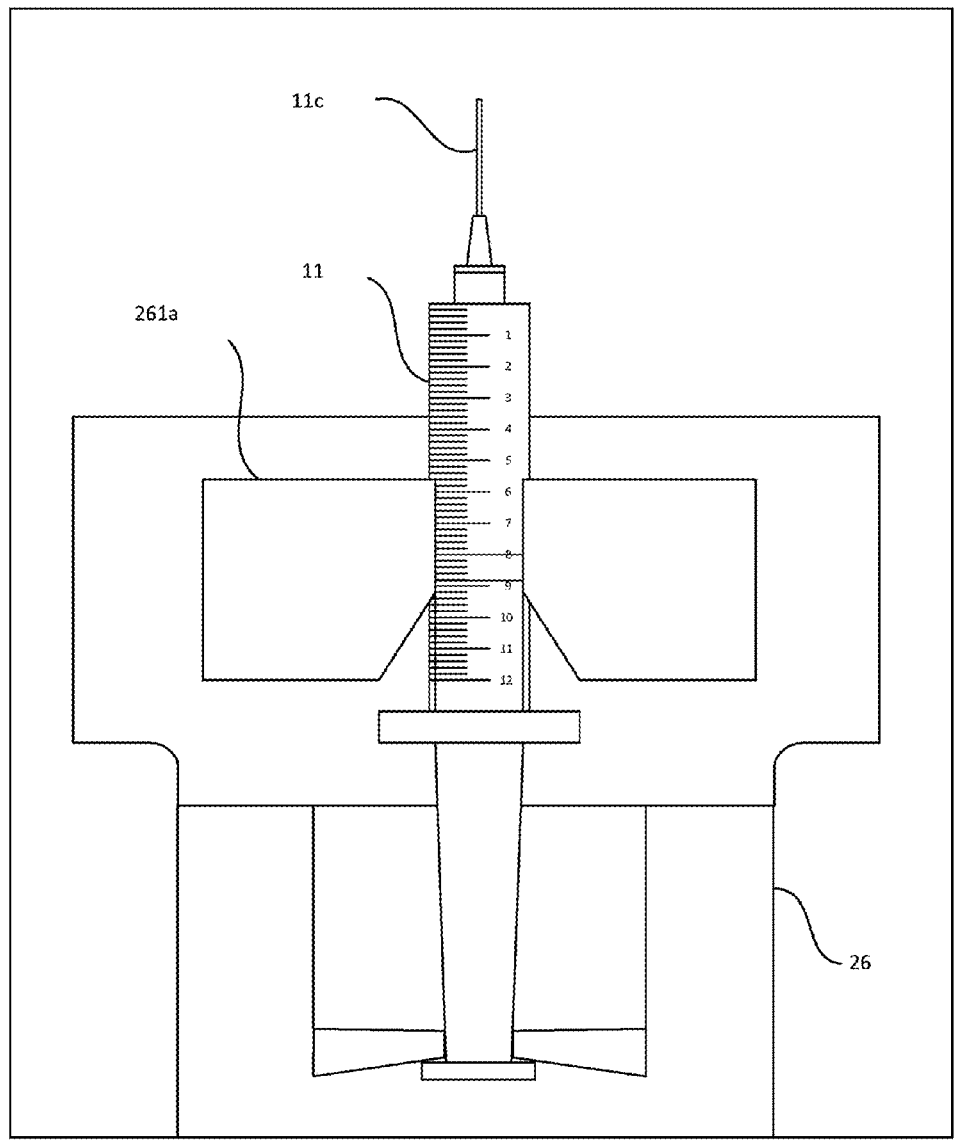
FIG. 47 is a view showing one example of an image of the injector photographed by the co-infusion apparatus according to the other embodiment of the present invention.

In this regard, in the co-infusion apparatus 1A, it may be considered that the scale of the injector 11 is photographed in a state that the injection needle 11c of the injector 11 is pulled out from the vial bottle 10B after the medicinal solution has been suctioned from the vial bottle 10B with the injector 11. For example, the photographing for the scale of the injector 11 is carried out at the step S23 of the inspection control process (see FIG. 20) or the like. Although the step S23 has been already described for the case where the vial bottle 10B and the injector 11 are photographed at one time, the photographing for the scale of the injector 11 is not limited thereto. It may be considered that only the injector 11 is photographed as shown in FIG. 47. Further, in the case where the medicinal solution is continuously suctioned from the plurality of vial bottles 10B with the injector 11, the injector 11 is photographed every time when the medicinal solution is suctioned from each vial bottle 10B or after the medicinal solution has been suctioned from all of the vial bottles 10B.

In the case of pulling out the injection needle 11c of the injector 11 from the vial bottle 10B at the time of photographing the scale of the injector 11, it is necessary to slightly pull the plunger 11b of the injector 11 to suction air into the injector 11 in order to prevent the medicinal solution from leaking from the injection needle 11c of the injector 11. However, in a state that the plunger 11b of the injector 11 is slightly pulled and thereby extra air exists in the injector 11, the scale of the injector 11 does not coincide with the predetermined necessary amount. Thus, it is necessary to slightly push the plunger 11b of the injector 11 to release the extra air from the injector 11 before the injector 11 is photographed after the injection needle 11c of the injector 11 has been pulled out from the vial bottle 10B. At this time, it is necessary to slowly carry out a step for pushing the plunger 11b of the injector 11 in order to prevent the medicinal solution from leaking from the injection needle 11c of the injector 11. Thus, this step for pushing the plunger 11b of the injector 11 requires a lot of time. Further, after the scale of the injector 11 has been photographed, it is necessary to return the plunger 11b of the injector 11 to a state that the plunger 11b is slightly pulled in order to prevent the medicinal solution from leaking from the injection needle 11c of the injector 11 at the time of transferring the injector 11. This leads to a problem in that the required time of the co-infusion process becomes longer due to the process for photographing the scale of the injector 11.

Thus, in the co-infusion apparatus 1A according to this embodiment, the second control section 500 controls the first robot arm 21 and the second robot arm 22 to photograph the scale of the injector 11 with the injector confirming camera 42 in a state that the injection needle 11c of the injector 11 is inserted into the vial bottle 10B. In this case, the second control section 500 at the time of carrying out such a process is one example of a photographing control means.

Specifically, it may be considered that the second control section 500 allows the injector 11 to suction the medicinal solution from the vial bottle 10B in the photographing range R1 of the injector confirming camera 42. Alternatively, it may be considered that the second control section 500 allows the vial bottle 10B and the injector 11 to be transferred into the photographing range R1 of the injector confirming camera 42 after the medicinal solution has been suctioned from the vial bottle 10B with the injector 11 in another area.

Figure 48:
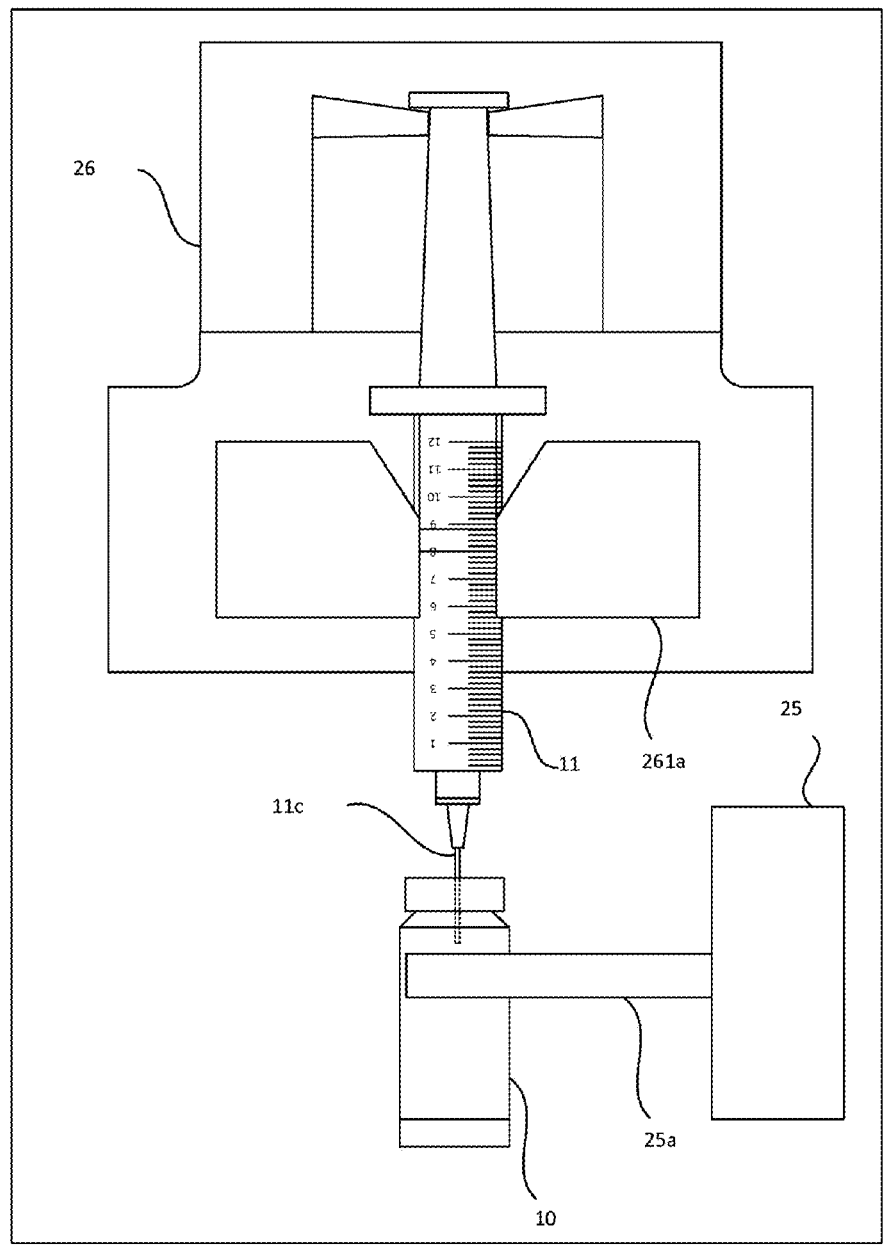
FIG. 48 is a view showing one example of an image of the injector and the medicine container photographed by the co-infusion apparatus according to the other embodiment of the present invention.

FIG. 48 is a view showing one example of an image photographed by the injector confirming camera 42. Specifically, as shown in FIG. 48, the second control section 500 controls the first robot arm 21 and the second robot arm 22 to photograph the scale of the injector 11 with the injector confirming camera 42 in a state that the injection needle 11c of the injector 11 is directed toward the lower direction and the rubber plug 11C of the vial bottle 10B is directed toward the upper direction. Namely, the second control section 500 first controls the first robot arm 21 and the second robot arm 22 to carry out an injection process for injecting the transfusion into the vial bottle 10B with the injector 11 in a state that the rubber plug 10C of the vial bottle 10B is directed toward the upper direction and the injection needle 11c of the injector 11 is directed toward the lower direction. Then, the second control section 500 controls the first robot arm 21 and the second robot arm 22 to carry out a suctioning process for suctioning the transfusion from the vial bottle 10B with the injector 11 in a state that the rubber plug 10C of the vial bottle 10B is directed toward the lower direction and the injection needle 11c of the injector 11 is directed toward the upper direction. In this case, the second control section 500 at the time of carrying out such an injection process and a suctioning process is one example of a fifth control means. After that, the second control section 500 allows vertical positions of the injector 11 and the vial bottle 10B to be inverted in a state that the injection needle 11c of the injector 11 is inserted into the vial bottle 10B and then allows the injector 11 to be photographed. Then, the second control section 500 controls the second robot arm 22 to suction extra air with the injector 11 in order to prevent a liquid leakage from the injector 11 and then controls one or both of the first robot arm 21 and the second robot arm 22 to pull out the injection needle 11c of the injector 11 from the vial bottle 10B.

As described above, in the co-infusion apparatus 1A according to this embodiment, the injector 11 is photographed without pulling out the injection needle 11c of the injector 11 from the vial bottle 10B and with keeping a state that the injection needle 11c of the injector 11 is inserted into the vial bottle 10B. Thus, it is unnecessary to carry out the step for discharging the extra air from the injector 11 and the step for suctioning the extra air with the injector 11 again as described above, thereby suppressing a delay of the co-infusion process caused by the process for photographing the scale of the injector 11.

In this regard, another configuration in which the second control section 500 controls the first robot arm 21 and the second robot arm 22 to photograph the scale of the injector 11 with the injector confirming camera 42 in a state that the injection needle 11c of the injector 11 is directed toward the upper direction and the rubber plug 11C of the vial bottle 10B is directed toward the lower direction may be considered as another embodiment. Namely, it may be considered that the second control section 500 allows the injector 11 to suction the medicinal solution from the vial bottle 10B and then allows the injector 11 to be photographed with keeping the state of the injector 11.

In this case, the second control section 500 controls the first robot arm 21 and the second robot arm 22 to rotate the injector 11 and the vial bottle 10B to direct the injection needle 11c of the injector 11 toward the lower direction and direct the rubber plug 11C of the vial bottle 10B toward the upper direction. Then, the second control section 500 allows the injector 11 to suction extra air in order to prevent the liquid leakage from the injector 11 and then controls one or both of the first robot arm 21 and the second robot arm 22 to pull out the injection needle 11c of the injector 11 from the vial bottle 10B.

[Fifth Embodiment]

In this regard, in the co-infusion apparatus 1A, in the case of injecting the transfusion from the injector 11 into the vial bottle 10B, the case of suctioning the medicinal solution from the vial bottle 10B with the injector 11 or the like, there is a case where the injection needle 11c of the injector 11 is inserted into the rubber plug 10C of the vial bottle 10B multiple times. At this time, if the injection needle 11c of the injector is inserted at the same position or the neighborhood position on the rubber plug 10C of the vial bottle 10B multiple times, this leads to a problem known as a coring problem in that a part of the rubber plug 10C is scraped off. As a result, the medicinal solution becomes likely to leak from the rubber plug 10C of the vial bottle 10B.

In contrast, in this embodiment, the second control section 500 changes a insertion position of the injection needle 11c with respect to the rubber plug 10C to a position differing each time in the case where the injection needle 11c of the injector 11 is inserted into the rubber plug 10C of the vial bottle 10B multiple times. In this case, the second control section 500 at the time of carrying out such a process is one example of a fourth control means. More specifically, the second control section 500 sets a central position of the rubber plug 10C and one or more of separated positions separated from each other in a radial direction from the central position as the insertion positions of the injection needle 11c. In the case where the injection needle 11c is inserted into the rubber plug 10C multiple times, a plurality of insertion positions of the injection needle 11c need not to contain the central position of the rubber plug 10C as long as the plurality of insertion positions of the injection needle 11c contains the separated positions separated from each other in the radial direction on the rubber plug 10C.

FIGS. 49(A) and 49(B) are planar views of the rubber plug 10C of the vial bottle 10B and show examples of the insertion positions on the rubber plug 10C. In the example shown in FIG. 49(A), the second control section 500 sets a central position P1 of the rubber plug 10C as an insertion position for the first time when the injection needle 11c of the injector 11 is inserted into the rubber plug 10C at the first time. After that, the second control section 500 sets a separated position P2 separated from the central position P1 of the rubber plug 10C by a predetermined distance d11 in an outward radial direction as the insertion position for the second time when the injection needle 11c of the injector 11 is inserted into the rubber plug 10C at the second time. Further, the second control section 500 sets a separated position P3 separated from the separated position P2 by the predetermined distance d11 in the outward radial direction as the insertion position for the third time when the injection needle 11c of the injector 11 is inserted into the rubber plug 10C at the third time. With this configuration, the second control section 500 can set the insertion positions on the rubber plug 10C to be different positions differing each time regardless of a rotational position of the vial bottle 10B in a circumferential direction thereof.

Further, it may be considered that the second control section 500 detects a rotation stop position of the vial bottle 10B in the circumferential direction to set different positions separated from each other on the same circle on the rubber plug 10C as the plurality of insertion positions. More specifically, the second control section 500 carries out the same process as the injector position adjusting process (see FIG. 18) when the injection needle 11c of the injector 11 is inserted into the rubber plug 10C of the vial bottle 10B to change (adjust) the posture of the vial bottle 10B to a posture for allowing the second control section 500 to identify the rotation stop position of the vial bottle 10B in the circumferential direction.

For example, the second control section 500 allows the vial bottle 10B to be rotated until the medicine information is read from the barcode on the vial bottle 10B by the medicine reading section 34. Then, the second control section 500 stops the driving of the driving motor of the roller 34a of the medicine reading section 34 when the barcode on the vial bottle 10B is read to stop the rotation of the vial bottle 10B. In this case, the second control section 500 at the time of carrying out such a process is one example of a container position adjusting means. With this configuration, it is possible to stop the vial bottle 10B in a predetermined stop posture which allows the barcode to be read.

Thus, based on the predetermined stop posture of the vial bottle 10B, the second control section 500 can identify the rotation stop position of the vial bottle 10B in the circumferential direction thereof when the vial bottle 10B is held by the second robot arm 22. In this regard, it may be considered that the second control section 500 sets each of the insertion positions based on the rotation stop position of the vial bottle 10B in the circumferential direction thereof. Further, it may be considered that the second control section 500 allows the vial bottle 10B to be rotated by a predetermined specific rotation amount and then stops the rotation of the vial bottle 10B in the same manner as the container position adjusting process (see FIG. 19) after the barcode on the vial bottle 10B has been read in order to stop the vial bottle 10B in the predetermined stop posture.

In the example shown in FIG. 49(B), the second control section 500 sets a position P11 on the rubber plug 10C as the insertion position for the first time when the injection needle 11c of the injector 11 is inserted into the rubber plug 10C at the first time. After that, the second control section 500 sets a position P12 separated from the position P11 of the rubber plug 10C in a circumferential direction of a concentric circle Q1 concentrically with an external circles of the rubber plug 10C as the insertion position for the second time when the injection needle 11c of the injector 11 is inserted into the rubber plug 10C at the second time. Further, the second control section 500 sets a position P13 separated from the position P12 in the circumferential direction of the concentric circle Q1 as the insertion position for the third time in the case where the injection needle 11c of the injector 11 is inserted into the rubber plug 10C at the third time. With this embodiment, the second control section 500 can set the insertion positions on the rubber plug 10C to be different positions differing each time.

As described above, in the co-infusion apparatus 1A according to this embodiment, it is possible to insert the injection needle 11c into the rubber plug 10C at different positions on the rubber plug 10C differing from each other and separated from each other by a predetermined distance even in the case where the injection needle 11c of the injector 11 is inserted into the rubber plug 10C of the vial bottle 10B multiple times. Thus, in the co-infusion apparatus 1A, it is possible to suppress the coring problem from occurring, thereby suppressing the liquid leakage from the vial bottle 10B compared with the case where the injection needle 11c is inserted into the rubber plug 10C at the same position or in the vicinity of the same position multiple times.

Further, it may be considered from the second control section 500 changes the time duration from the reading for the barcode on the vial bottle 10B by the medicine reading section 34 until the stopping for the driving motor of the roller 34a of the medicine reading section 34 every time when the injection needle 11c is inserted into the rubber plug 10C to change the rotation stop position of the vial bottle 10B every time when the injection needle 11c is inserted into the vial bottle 10B. With this configuration, it is also possible to insert the injection needle 11c into the rubber plug 10C at different positions differing from each other and separated from each other by a predetermined distance in the case where the injection needle 11c of the injector 11 is inserted into the rubber plug 10C of the vial bottle 10B multiple times.

[Sixth Embodiment]

In the co-infusion apparatus 1A, the transfusion bag holding member 103 is transferred in the tray conveying terminal portion 110a (see FIG. 9) by the bag up-and-down section 113 so that the co-infusion port of the transfusion bag 12 is positioned so as to correspond to the co-infusion communication port 37. At this time, it is possible to take a configuration in which the bag up-and-down section 113 can move the transfusion bag holding member 103 in the upper direction and move the transfusion bag holding member 103 in a horizontal direction so as to direct the transfusion bag holding member 103 toward the co-infusion communication port 37. Of course, it is also possible to take a configuration in which a mechanism being capable of slidably moving the transfusion bag holding member 103 is provided separately from the bag up-and-down section 113.

In this regard, in the transfusion bag holding member 103, the co-infusion port of the transfusion bag 12 is fixed by the chuck member 140 (see FIG. 5). However, there is a risk that the transfusion bag 12 is not fixed at a normal position by the chuck member 140. In this case, there is a risk that the transfusion bag 12 interferes with other constituent components or a risk that the injection of the transfusion into the transfusion bag 12 with the injector 11 is not normally carried out, for example. Thus, it may be considered that the co-infusion apparatus 1A includes a configuration for determining whether or not a fixing position of the transfusion bag 12 in the transfusion bag holding member 103 is normal. Hereinafter, description will be given to one example of such a configuration.

Specifically, the co-infusion apparatus 1A according to this embodiment includes a co-infusion port detecting means such as an optical sensor for detecting that the co-infusion port of the transfusion bag 12 held by the transfusion bag holding member 103 reaches to a predetermined position when the transfusion bag holding member 103 is transferred. Further, the second control section 500 determines whether or not a required time from the start of the transferring of the transfusion bag holding member 103 until the detection of the co-infusion port of the transfusion bag 12 due to the co-infusion port detecting means is within a predetermined acceptable range. Then, the second control section 500 determines that the transfusion bag 12 is not fixed at the normal position by the chuck member 140 in the case of determining that the required time is not in the acceptable range to stop the transferring of the transfusion bag holding member 103.

In more detail, in the co-infusion apparatus 1A, the acceptable range corresponding each transfusion bag 12 is stored in the transfusion information of the medicine master stored in the data storage section 404. The acceptable range is set in advance as a required time from the start of the transferring of the transfusion bag holding member 103 until the detection of the co-infusion port of the transfusion bag 12 due to the co-infusion port detecting means in the case where the transfusion bag 12 is normally fixed in the transfusion bag holding member 103. Then, the second control section 500 reads the acceptable range corresponding to each type of the transfusion bag 12 from the transfusion information to determine whether or not the transfusion bag 12 is normally fixed in the transfusion bag holding member 103 depending on whether or not the required time is in the acceptable range. With this configuration, in the co-infusion apparatus 1A, it is possible to suppress, for example, the risk that the transfusion bag 12 interferes with the other constituent components, thereby normally carrying out the injection of the transfusion into the transfusion bag 12 with the injector 11.

[Seventh Embodiment]

Figure 50:
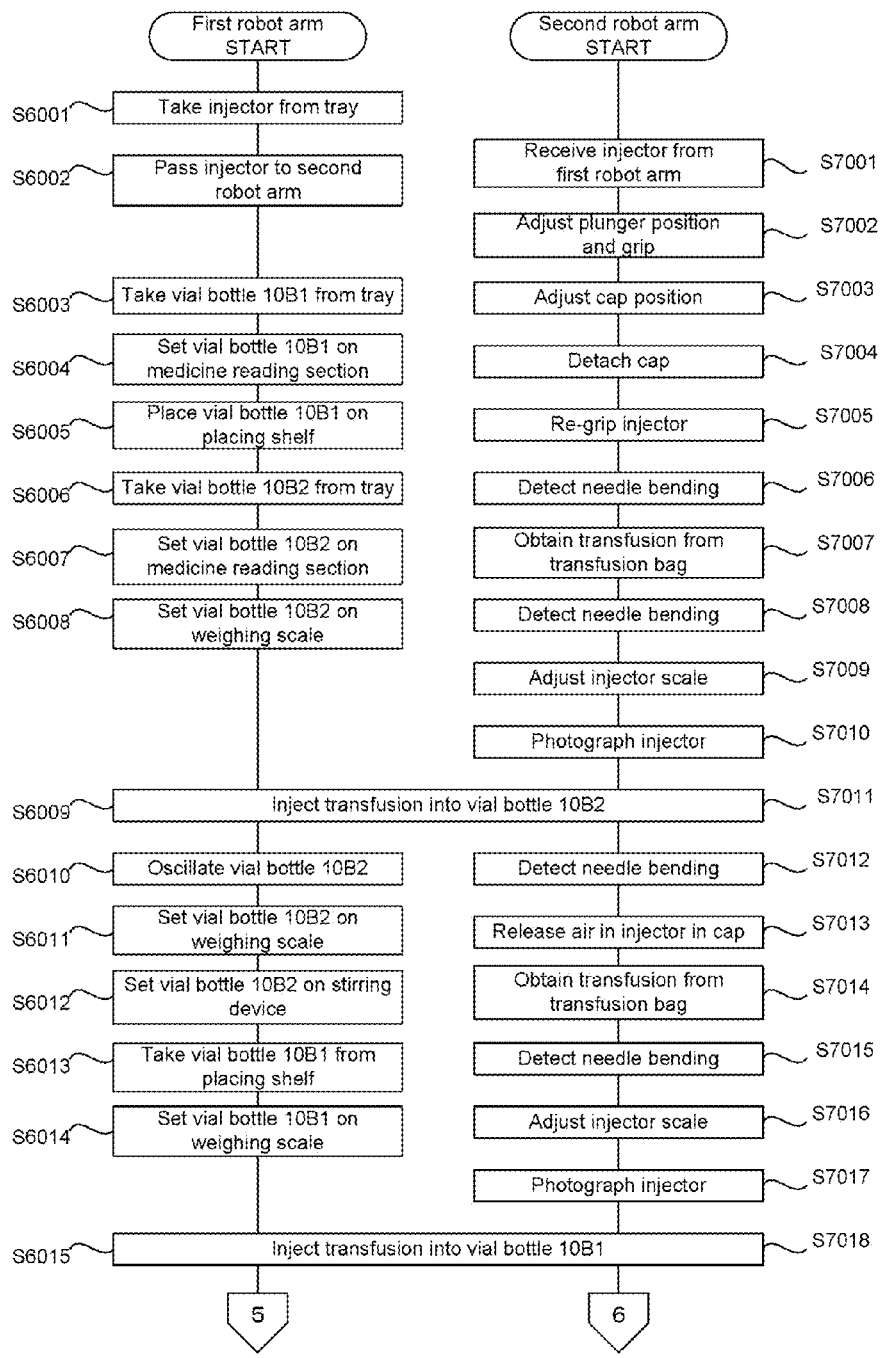
FIG. 50 is a flow chart for explaining a co-infusion action in the co-infusion apparatus according to the other embodiment of the present invention.
Figure 51:
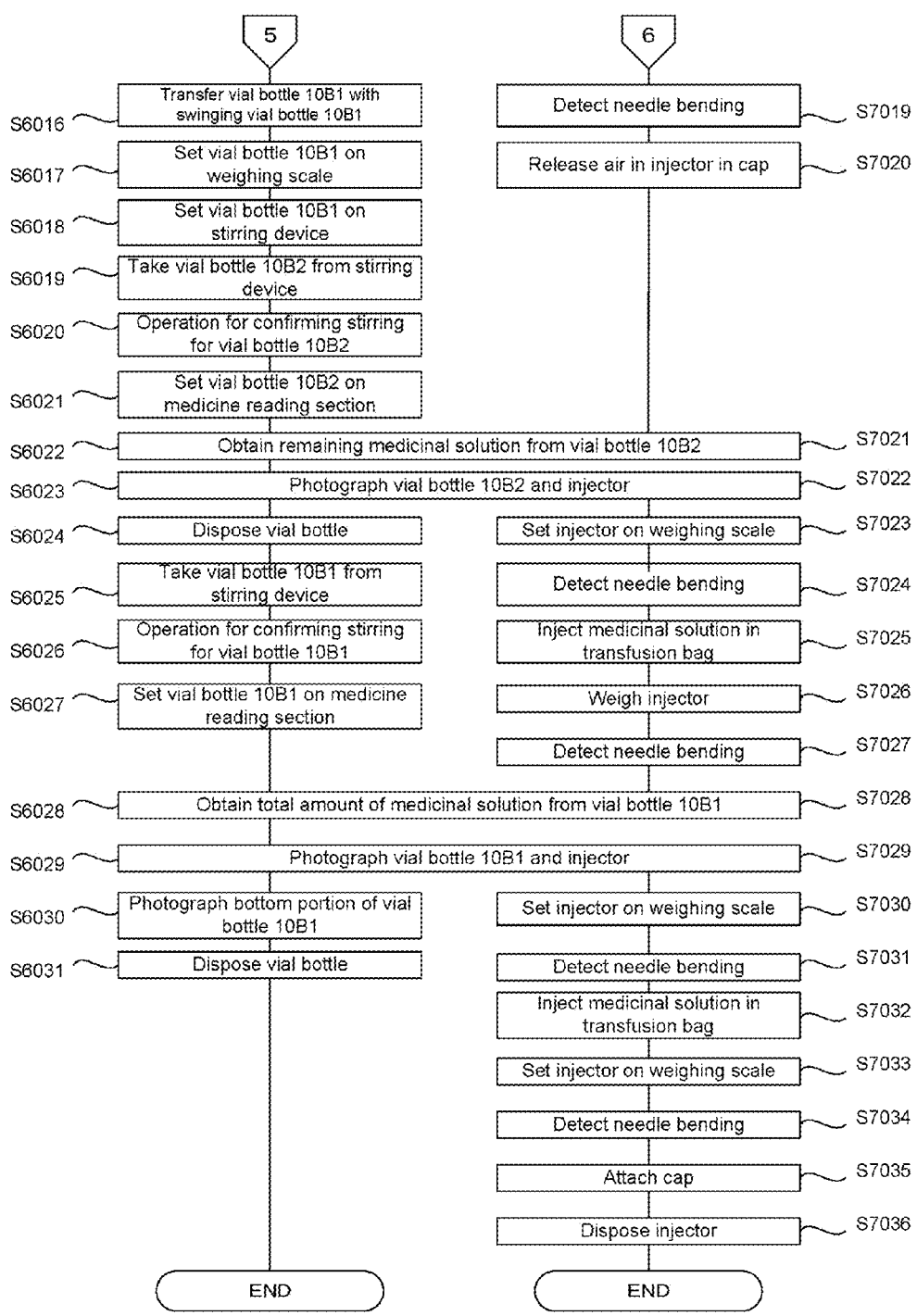
FIG. 51 is another flow chart for explaining the co-infusion action in the co-infusion apparatus according to the other embodiment of the present invention.

In this embodiment, description will be given to another example of the co-infusion action carried out by allowing the second control section 500 to control the first robot arm 21 and the second robot arm 22 in the co-infusion apparatus 1A. FIGS. 50 and 51 are views for explaining a flow of the co-infusion action. Each left side of FIGS. 50 and 51 shows an action of the first robot arm 21 and each right side of FIGS. 50 and 51 shows an action of the second robot arm 22. In FIGS. 50 and 51, the process proceeds toward the lower direction with the passage of the time.

Specifically, description in this embodiment will be given to the case where one type of powdered medicine is contained in two vial bottles 10B1, 10B2 and a co-infusion action for dissolving the powdered medicine in the two vial bottles 10B1, 10B2 into the transfusion and then injecting the medicinal solution into the transfusion bag 12 is carried out. Further, it is assumed that the whole amount obtaining for obtaining a whole amount of the powdered medicine is carried out for the vial bottle 10B1 and the partial amount obtaining for obtaining a part of the powdered medicine is carried out for the vial bottle 10B2.

In this regard, in the co-infusion apparatus 1A, it may be considered that the syringe 11a and the injection needle 11c are separately set on the tray 101 and the injection needle 11c is attached to the syringe 11a by using the injection needle attaching and detaching device during the co-infusion action. The injection needle attaching and detaching device 43 is also used for detaching a cap 11e of the injection needle 11c of the injector 11 and can hold the cap 11e which has been detached from the injector 11. In this case, the injection needle attaching and detaching device 43 is one example of a cap attaching and detaching means.

On the other hand, in the case where the injection needle 11c is attached to the syringe 11a in the co-infusion apparatus 1A, there is a risk that connecting portions of the syringe 11a and the injection needle 11c are contaminated before the tray 101 is loaded into the co-infusion apparatus 1A. For example, when the syringe 11a and the injection needle 11c before connecting are set on the tray 101 by a pharmacist or the like, there is a risk that the connecting portion of the syringe 11a or the connecting portion of the injection needle 11c makes contact with the tray 101 or the like and dusts or the like adhere to the connecting portion of the syringe 11a or the connecting portion of the injection needle 11c. Further, in the case where the syringe 11a and the injector 11 are connected with each other in the co-infusion apparatus 1A, a working time for attaching the injection needle 11c to the syringe 11a during the co-infusion action is also required. Thus, it may be considered that the injector 11 is set on the tray 101 in a state that the injection needle 11c has been already attached to the syringe 11a. With this configuration, it is possible to prevent the connecting portions of the syringe 11a and the injection needle 11c from being contaminated and it becomes unnecessary to carry out an action for attaching the injection needle 11c to the syringe 11a during the co-infusion action. In this embodiment, description will be given to the co-infusion action in the case where the tray 101 on which the injector 11 is set in a state that the injection needle 11c has been already attached to the syringe 11a is loaded into the co-infusion apparatus 1A.

<Steps S6001 to S6002, S7001>

At first, the first robot arm 21 takes the injector 11 from the tray 101 (S6001). Then, the first robot arm 21 passes the injector 11 to the second robot arm 22 (S6002) and the second robot arm 22 receives the injector 11 from the first robot arm 21 (S7001).

<Step S7002>

Next, the second robot arm 22 adjusts a position of the plunger 11b of the injector 11 and grips the plunger 11b with the gripping clicks 262a of the holding member 262 (S7002). Specifically, it may be considered that the plunger 11b of the injector 11 set on the tray 101 is not completely pushed down. For example, if a rubber at a tip end of the plunger 11b is pressured and contacted with a tip end of the syringe 11a in the injector 11, there is a risk that the rubber of the plunger 11b deteriorates. Thus, in order to avoid the deterioration of the rubber of the plunger 11b, the plunger 11b may be in a state that the plunger 11b is not pushed down to the end of the syringe 11a before the injector 11 is used.

Thus, in the co-infusion apparatus 1A, the second robot arm 22 carries out an action for pushing down the plunger 11b toward the side of the tip end of the syringe 11a to the end at the step S7002. Specifically, it may be considered that the second robot arm 22 uses the gripping clicks 261a of the injector holding member 261 to hold the syringe 11a of the injector 11 and uses the transferring member 263 of the plunger holding member 262 to adjust the position of the plunger 11b with keeping this holding state of the syringe 11a. With this configuration, it is possible to utilize the action for holding the syringe 11a of the injector 11 inevitably carried out by the second robot arm 22, thereby shortening the working time for eliminating a gap between the plunger 11b and the syringe 11a.

Figure 52A:
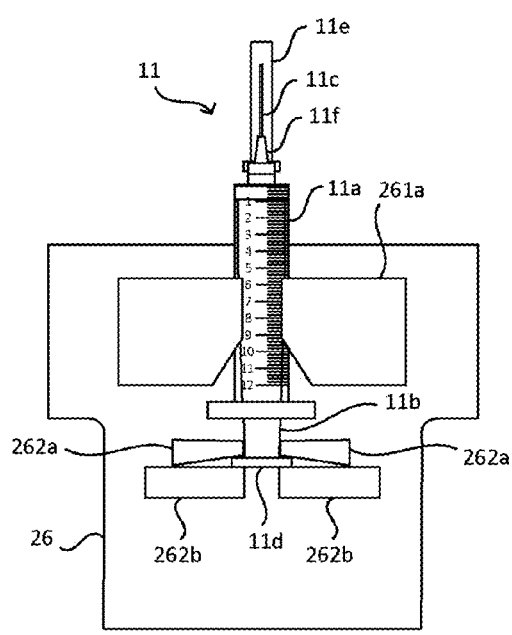
FIG. 52 is a view for explaining a plunger position adjusting process in the co-infusion apparatus according to the other embodiment of the present invention.

At this time, it may be considered that the action for eliminating the gap is carried out in a state that the flange portion of the plunger 11b is gripped by the gripping clicks 262a. However, in the co-infusion apparatus 1A, the pair of gripping clicks 262a grips the flange portion 11d of the plunger 11b by utilizing concave portions formed between the gripping clicks 262a and the gripping clicks 262b as shown in FIG. 52(A). Thus, if a positional relationship between the plunger 11b and the syringe 11a does not match with a predetermined positional relationship, there is a risk that the flange portion 11d of the plunger 11b does not engage with the concave portions and it becomes impossible to grip the flange of the plunger 11b with the gripping clicks 262a.

Figure 52B:
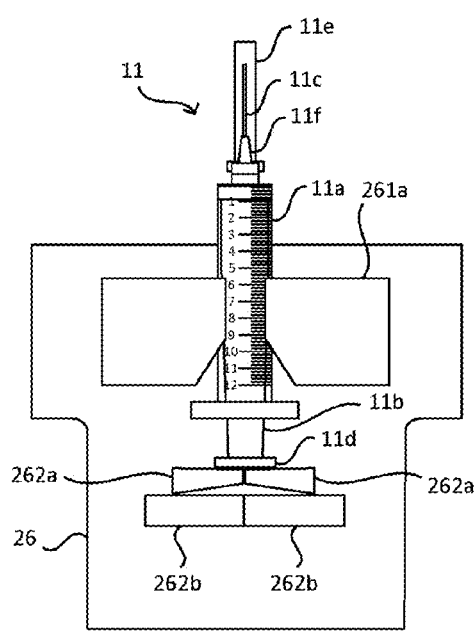

Thus, it may be considered that the action for eliminating the gap is carried out by pushing the pair of gripping clicks 262a toward the flange of the plunger 11b to push down the plunger 11b into the syringe 11a in a state that the pair of gripping clicks 262a is closed as shown in FIG. 52(B). In this regard, the second control section 500 can determine that the plunger 11b of the injector 11 is pushed down into the syringe 11a completely in the case where, for example, a torque caused in the motor for driving the transferring member 263 reaches a predetermined value.

With this configuration, even in the case where an initial position of the plunger 11b is out of a position from which the pair of gripping clicks 262a can grip the flange portion 11d of the plunger 11b, it is possible to eliminate the gap, thereby allowing the pair of gripping clicks 262a to grip the flange portion 11d of the plunger 11b as shown in FIG. 52(A). Further, it is possible to prevent a position of a starting point (position of original point) for suctioning the transfusion or the medicinal solution from shifting due to the gap, thereby carrying out an accurate suctioning action.

<Step S7003>

Next, the second robot arm 22 carries out a position adjusting step for the cap 11e which has been already attached to the injection needle 11c of the injector 11 (S7003). Hereinafter, description will be given to the position adjusting step for the cap 11e of the injection needle 11c with reference to FIGS. 53 and 54.

As described above, in the co-infusion apparatus 1A, the injector 11 is assembled by attaching the injection needle 11c to the syringe 11a before the tray 101 is loaded into the co-infusion apparatus 1A. At this time, as shown in the injection needle 11c in FIG. 52(A), the cap 11e is attached to a needle base 11f of the injection needle 11c and the injection needle 11c can be rotationally moved together with the cap 11e in an integrated manner. The cap 11e is attached to the injection needle 11c by engaging the cap 11e with an outer peripheral surface of the needle base 11f. For example, the number of contacting points between the cap 11e and the needle base 11f is three or four. When the cap 11e is rotated to rotate the needle base 11f, the needle base 11f of the injection needle 11c is screwed with the tip end of the syringe 11a.

However, there is a risk that the cap 11e is inclined with respect to a center of the syringe 11a in a state that the injection needle 11c has been already attached to the syringe 11a and a central position of a tip end of the cap 11e is out of the center of the syringe 11a. On the other hand, in the co-infusion apparatus 1A, the second control section 500 allows the cap 11e to be inserted into an aperture of the injection needle attaching and detaching device 43 in a state that a center of the gripping clicks 261a for gripping the syringe 11a coincides with a center of the aperture of the injection needle attaching and detaching device 43. Thus, if the cap 11e is inserted into the injection needle attaching and detaching device 43 in a state that the central position of the tip end of the cap 11e is out of the center of the syringe 11a, there is a risk that the cap 11e makes contact with a marginal portion of the aperture of the injection needle attaching and detaching device 43. In contrast, in the co-infusion apparatus 1A, the position adjusting step for the cap 11e is carried out according to the following configuration and action.

Figure 53:
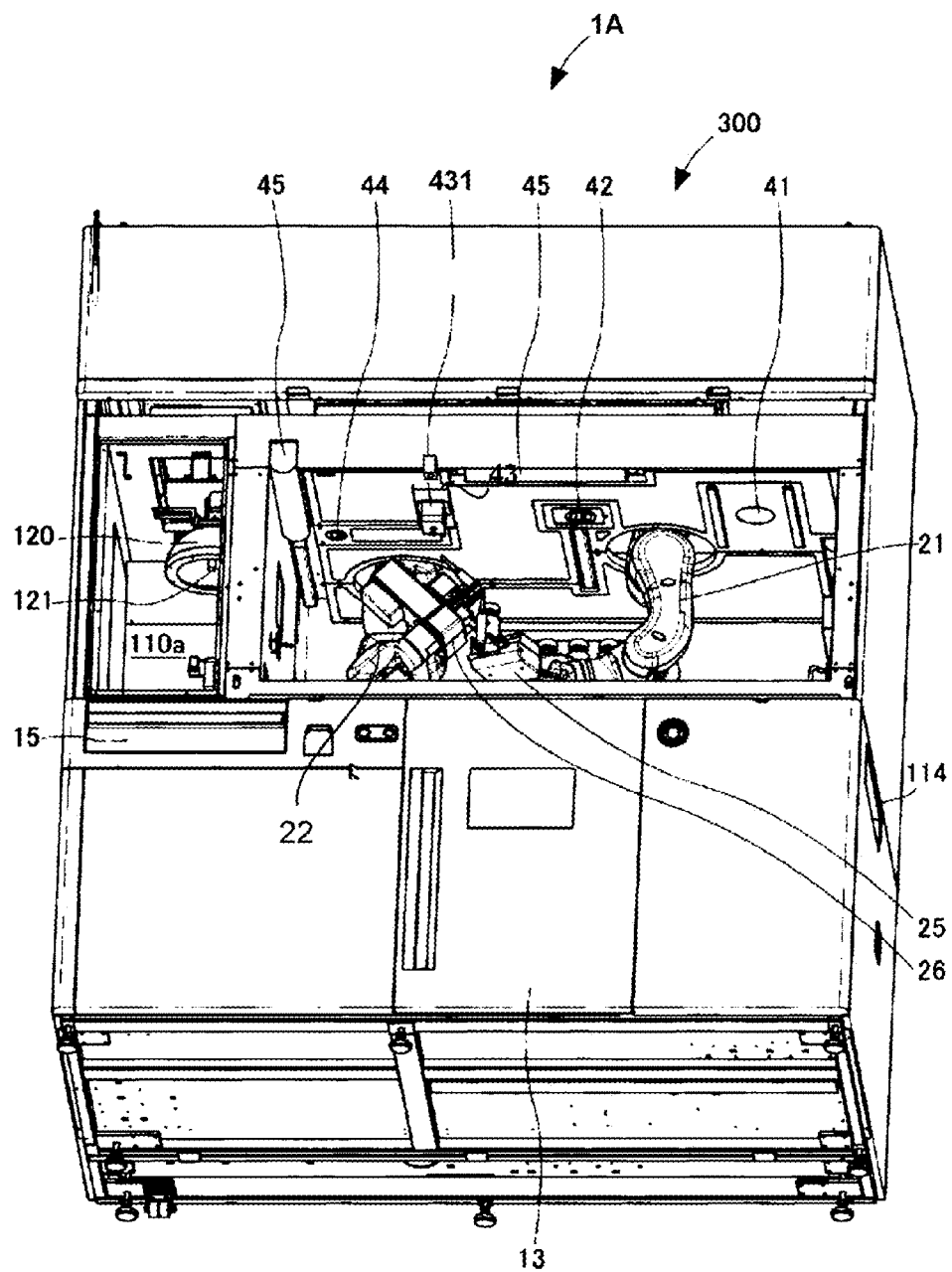
FIG. 53 is a view for explaining a cap position adjusting process in the co-infusion apparatus according to the other embodiment of the present invention.
Figure 54A:
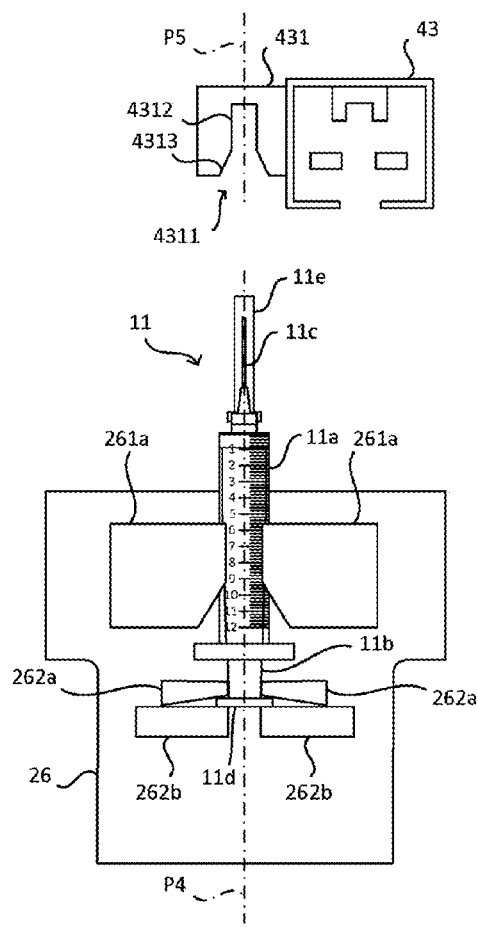
FIG. 54 is another view for explaining the cap position adjusting process in the co-infusion apparatus according to the other embodiment of the present invention.

At first, in the co-infusion apparatus 1A, a cap correcting member 431 used in the position adjusting step for the cap 11e is provided in parallel with the injection needle attaching and detaching device 43 as shown in FIGS. 53 and 54. As shown in FIG. 54(A), the cap correcting member 431 is a cylindrical bottomed member having an opening portion 4311, a criterion portion 4312 and a tapered portion 4313. A central axis of the cap correcting member 431 is a center P5.

A circular aperture having a diameter larger than an outer diameter of the cap 11e of the injector 11 is formed in the opening portion 4311. A cylindrical space used as a criterion of the position adjustment for the cap 11e is formed in the criterion portion 4312. The criterion portion 4312 has an inner diameter equal to or slightly larger than the outer diameter of the cap 11e. The tapered portion 4313 is formed into a mortar-like shape gradually expanding from the criterion portion 4312 toward the opening portion 4311.

Figure 54B:
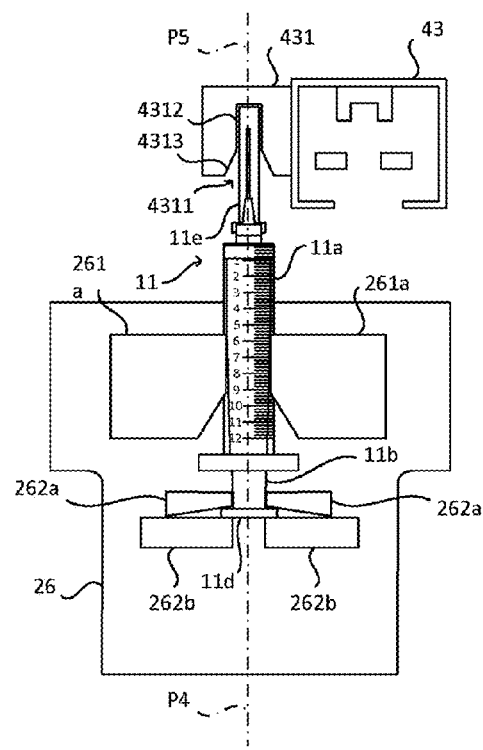

In the co-infusion apparatus 1A, the second control section 500 allows the position of the second robot arm 22 to be adjusted so that a center P4 of the gripping clicks 261a and the gripping clicks 262a coincides with a center P5 of the cap correcting member 431 as shown in FIG. 54(A). Then, the second control section 500 controls the second robot arm 22 to insert the cap 11e of the injector 11 into the cap correcting member 431 as shown in FIG. 54(B). For example, the second control section 500 allows the second robot arm 22 to be transferred by a transferring amount set in advance as a transferring amount for inserting the tip end of the cap 11e into the criterion portion 4312. In this regard, it may be considered that the second control section 500 determines that the tip end of the cap 11e is inserted into the criterion portion 4312 in the case where a torque caused in the motor for driving the second robot arm 22 reaches a predetermined value.

Further, the second control section 500 allows the gripping clicks 261a to reduce gripping force with respect to the syringe 11a after the cap 11e has been inserted into the cap correcting member 431, while the cap 11e is inserted into the cap correcting member 431 or before the cap 11e is inserted into the cap correcting member 431 to give a degree of freedom to the syringe 11a. Since the gripping clicks 262b keep a holding state of the flange of the plunger 11b, the syringe 11a does not drop. Further, it may be considered that both of the gripping clicks 261a and the gripping clicks 262a reduce the gripping force with respect to the syringe 11a as long as the gripping clicks 261a and the gripping clicks 262a can keep holding the syringe 11a.

In the case where the central position of the tip end of the cap 11e coincides with the center P4 and the center P5, the cap 11e is inserted into the criterion portion 4312 without a contact between the cap 11e and the tapered portion 4313. On the other hand, in the case where the central position of the tip end of the cap 11e does not coincide with the center P4 and the center P5 due to a misalignment of an attaching state between the injection needle 11c and the syringe 11a or the like, the tip end of the cap 11e is inserted until the criterion portion 4312 with keeping the contact between the tip end of the cap 11e and the tapered portion 4313. Thus, it is possible to correct a misalignment of an attaching state among the cap 11e, the injection needle 11c and the syringe 11a or the like, thereby matching the central position of the tip end of the cap 11e with the center P4 and the center P5.

Then, the second control section 500 allows the gripping clicks 261a to again grip the syringe 11a in a state that the cap 11e is inserted into the cap correcting member 431 and the misalignment of the attaching state among the cap 11e, the injection needle 11c and the syringe 11a or the like is corrected. After that, the second control section 500 controls the second robot arm 22 to remove the cap 11e from the cap correcting member 431.

<Steps S7004 to S7005>

Next, the second robot arm 22 inserts the cap 11e into the injection needle attaching and detaching device 43 to detach the cap 11e from the injector 11 (S7004) and then again grips the injector 11 (S7005).

Figure 55A:
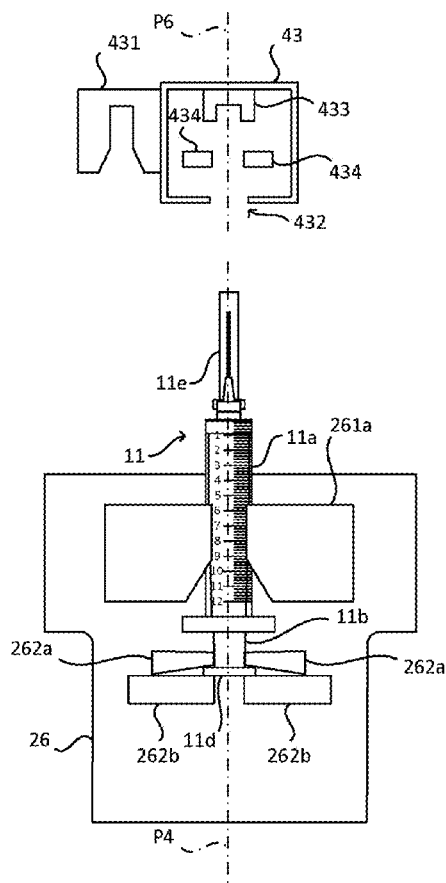
FIG. 55 is a view for explaining a cap detaching process in the co-infusion apparatus according to the other embodiment of the present invention.
Figure 55B:
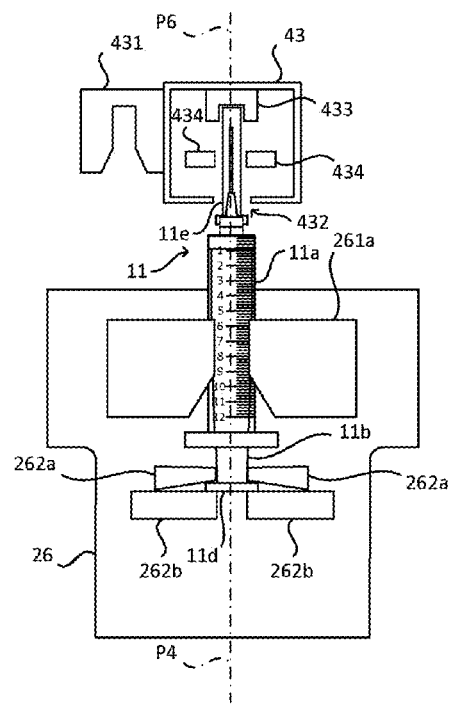

In the co-infusion apparatus 1A, the injection needle attaching and detaching device 43 includes an opening portion 432 in which a circular aperture into which the cap 11e should be inserted is formed, a pressed portion 433 having a circular concave portion to which the tip end of the cap 11e should be pressed and a pair of gripping members 434 being capable of gripping the cap 11e as shown in FIG. 55(A). In the injection needle attaching and detaching device 43, a center of the aperture of the opening portion 432 and a center of the concave portion of the pressed portion 433 are located on a center P6. The pressed portion 433 and the pair of gripping members 434 are supported so that the pressed portion 433 and the pair of gripping members 434 can be rotated around the center P6 serving as a rotational axis thereof by a rotating mechanism (not shown in the drawings).

Then, in the co-infusion apparatus 1A, the second control section 500 allows the position of the second robot arm 22 to be adjusted so that the center P4 of the gripping clicks 261a and the gripping clicks 262a coincides with the center P6 of the injection needle attaching and detaching device 43 as shown in FIG. 55(A). Then, the second control section 500 controls the second robot arm 22 to insert the cap 11e of the injector 11 into the injection needle attaching and detaching device 43. For example, the second control section 500 allows the second robot arm 22 to be transferred by a transferring amount set in advance as a transferring amount for inserting the tip end of the cap 11e into the pressed portion 433. In this regard, it may be considered that the second control section 500 determines that the tip end of the cap 11e is inserted into the pressed portion 433 in the case where a torque caused in the motor for driving the second robot arm 22 reaches a predetermined value.

In the co-infusion action, since the position adjustment for the cap 11e of the injector 11 has been already carried out at the step S7003, the central position of the tip end of the cap 11e coincides with the center P4. Thus, the tip end of the cap 11e is normally inserted into the pressed portion 433 without a contact between the tip end of the cap 11e and a marginal portion of the aperture of the opening portion 432. Then, the second control section 500 allows the pair of gripping members 434 to be driven to grip the cap 11e. At this time, the second control section 500 allows the gripping clicks 261a to reduce the gripping force with respect to the syringe 11a to give the degree of freedom to the syringe 11a and then allows the gripping clicks 261a to again grip the syringe 11a to again hold the syringe 11a. After that, the second control section 500 allows the second robot arm 22 to separate the injector 11 from the injection needle attaching and detaching device 43 to detach the cap 11e from the syringe 11a. After that, in the injection needle attaching and detaching device 43, the gripping members 434 keep holding the cap 11e.

In this embodiment, although description will be given to the case where the injection needle attaching and detaching device 43 and the cap correcting member 431 are separately provided in the co-infusion apparatus 1A, another configuration in which the injection needle attaching and detaching device 43 further has the function of the cap correcting member 431 may be considered as another embodiment. Specifically, another configuration in which the same tapered portion as the tapered portion 4313 is formed in the marginal portion of the aperture of the opening portion 432 of the injection needle attaching and detaching device 43 and the cap 11e which should be inserted into the opening portion 432 is guided to the pressed portion 433 by the tapered portion may be considered as another embodiment. With this configuration, it is possible to shorten the required time of the co-infusion action.

In this regard, even in the case where the cap 11e is inserted into the injection needle attaching and detaching device 43 and the tip end of the cap 11e is inserted into the pressed portion 433, there is a case where a center P7 of a rear end of the cap 11e does not coincide with the center P6 of the injection needle attaching and detaching device 43. Thus, it may be considered that the second control section 500 allows the first robot arm 21 to carry out a position adjustment for matching the center P7 of the rear end of the cap 11e with the center P6 of the injection needle attaching and detaching device 43 (see FIG. 55(a)) at the time of carrying out the steps S7004 and the S7005.

Figure 56A:
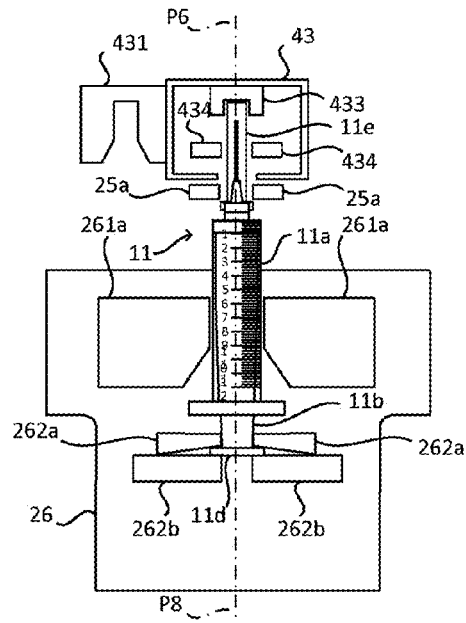
FIG. 56 is another view for explaining the cap detaching process in the co-infusion apparatus according to the other embodiment of the present invention.

Specifically, after the cap 11e has been inserted into the pressed portion 433, the second control section 500 allows the gripping clicks 261a to reduce the gripping force with respect to the syringe 11a to give the degree of freedom to the syringe 11a as shown in FIG. 56(A). Since the gripping clicks 262b keep a gripping state of the flange portion 11d of the plunger 11b, the syringe 11a does not drop. Further, it may be considered that both of the gripping clicks 261a and the gripping clicks 262a reduce the gripping force with respect to the syringe 11a as long as the gripping clicks 261a and the gripping clicks 262a can keep holding the syringe 11a.

Figure 56B:
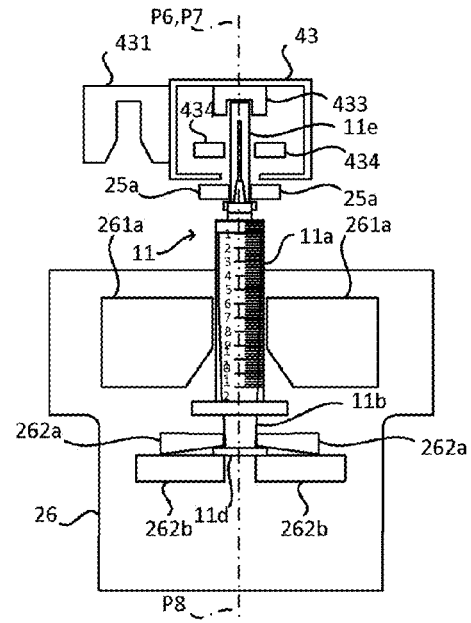

Then, the second control section 500 allows the gripping clicks 25a of the first robot arm 21 to grip a rear end portion of the cap 11e in a longitudinal direction thereof which protrudes from the opening portion 432 of the injection needle attaching and detaching device 43 as shown in FIG. 56(B). At this time, the second control section 500 allows a center of the gripping clicks 25a of the first robot arm 21 to be matched with the center P6 of the injection needle attaching and detaching device 43. With this configuration, it is possible to match the center P7 of the rear end of the cap 11e supported by the pressed portion 433 of the injection needle attaching and detaching device 43 with the center P6 of the injection needle attaching and detaching device 43.

Figure 56C:
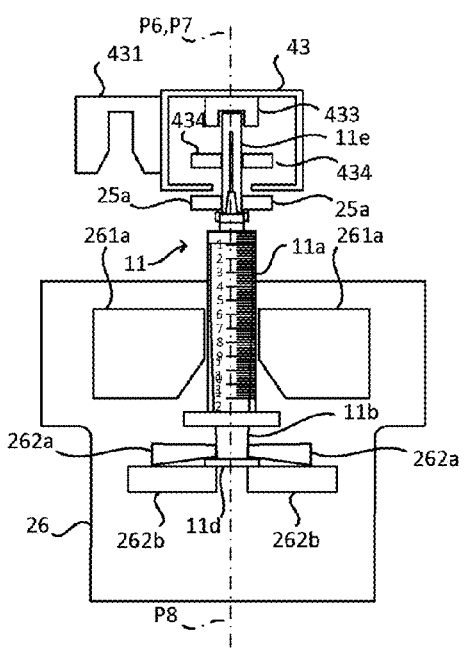
Figure 56D:
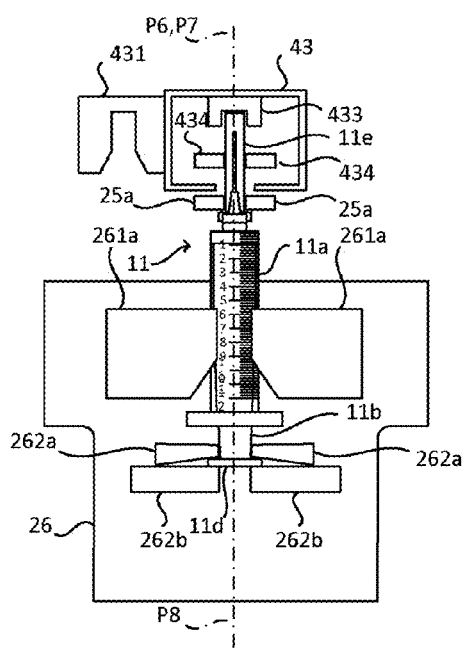

Next, the second control section 500 allows the gripping members 434 of the injection needle attaching and detaching device 43 to grip a central portion of the cap 11e in the longitudinal direction thereof as shown in FIG. 56(C). Then, the second control section 500 allows the gripping clicks 261a of the second robot arm 22 to again grip the syringe 11a as shown in FIG. 56(D). In this regard, these two steps may be carried out in parallel or in reverse order. After that, the second control section 500 allows the gripping clicks 25a of the first robot arm 21 to release the gripping for the cap 11e and allows the second robot arm 22 to be transferred to separate the injector 11 from the injection needle attaching and detaching device 43 to detach the cap 11e from the injector 11.

As described above, the center P7 of the rear end of the cap 11e coincides with the center P6 of the injection needle attaching and detaching device 43. Thus, after that, the second control section 500 can allow the injection needle 11c to be normally inserted into the cap 11e when the injection needle 11c of the syringe 11a is again inserted into the cap 11e. Specifically, the second control section 500 controls the second robot arm 22 so that the tip end of the injection needle 11c which can be recognized based on the detecting result from the needle bending detecting section 36 is located on the center P7 of the cap 11e to insert the injection needle 11c into the cap 11e. With this configuration, it is possible to prevent the injection needle 11c from making contact with a marginal portion of an aperture of the cap 11e.

In this regard, it may be considered that the processes at the steps S7002 to S7005 are carried out for each injector 11. For example, in the case where the medicinal solution is obtained from the vial bottle 10B in which different types of powdered medicine are contained, the processes at the steps S7002 to S7005 are carried out at the time of carrying out the co-infusion action for each vial bottle 10B. Further, even in the case where the medicine contained in the vial bottle 10B is liquid, the processes at the steps S7002 to S7005 are carried out in the same manner. In addition, a variety of process steps in the co-infusion action described here can be carried out in the co-infusion action in the case where the medicine contained in the vial bottle 10B is liquid, as needed.

<Step S6003 to S6005>

On the other hand, the first robot arm 21 takes the first vial bottle 10B1 from the tray 101 (S6003) and then sets the vial bottle 10B1 on the medicine reading section 34 (S6004). With this configuration, it is possible to read the type of the medicine in the vial bottle 10B1 with the medicine reading section 34. After that, the first robot arm 21 places the vial bottle 10B1 on the placing shelf 33 (S6005).

<Steps S6006 to S6008>

Subsequently, the first robot arm 21 takes the second vial bottle 10B2 from the tray 101 (S6006) and then sets the vial bottle 10B2 on the medicine reading section 34 (S6007). With this configuration, it is possible to read the type of the medicine in the vial bottle 10B2 with the medicine reading section 34. After that, the first robot arm 21 sets the vial bottle 10B2 on the weighing scale 39 (S6008). With this configuration, it is possible to weigh the weight of the vial bottle 10B2 with the weighing scale 39. In this regard, in the case where the weighing due to the weighing scale 39 is carried out, the subsequent action of the first robot arm 21 proceeds after a weighing value of the weighing scale 39 stabilizes and it is confirmed that the weighing value is in a predetermined range. This can be applied to other subsequent actions of the first robot arm 21. Of course, in the case where there is an action which can be carried out by the first robot arm 21 without affecting to the now-weighted target of the weighing scale 39 during the weighing due to the weighing scale 39, such an action may be carried out.

<Steps S7006 to S7008>

In addition, the second robot arm 22 transfers the injector 11 to the needle bending detecting section 36 (S7006) to detect a needle bending state of the injection needle 11c of the injector 11 and then obtains the transfusion from the transfusion bag 12 with the injector 11 in a necessary amount (S7007). At this time, when the transfusion is suctioned from the transfusion bag 12 with the injector 11, the postures of the injector 11 and the transfusion bag 12 are controlled so that the tip end of the injection needle 11c of the injector 11 is directed toward the upper direction upper than a horizontal line and the co-infusion port of the transfusion bag 12 is directed toward the lower direction lower than the horizontal line. On the other hand, after the transfusion has been obtained from the transfusion bag 12 in the necessary amount, the second robot arm 22 transfers the tip end of the injection needle 11c into an air layer in the transfusion bag 12 to suction the air in the transfusion bag 12 with the injector 11 in a predetermined amount and then pulls off the injection needle 11c from the transfusion bag 12. For example, the second control section 500 controls the postures of the transfusion bag 12 and the injector 11 by allowing the bag up-and-down section 113 to be driven to incline the transfusion bag holding member 103 so that the co-infusion port of the transfusion bag 12 is directed toward the upper direction upper than the horizontal line and controlling the second robot arm 22 to direct the tip end of the injection needle 11c of the injector 11 toward the lower direction lower than the horizontal line. With this configuration, it is possible to locate the tip end of the injection needle 11c in the air layer in the transfusion bag 12. When the plunger 11b in this state is pulled to transfer the transfusion in the injection needle 11c of the injector 11 into the syringe 11a, a gas layer is generated in the injection needle 11c. Thus, for example, it is possible to prevent the transfusion from dropping from the injection needle 11c when the injection needle 11c is pulled out from the transfusion bag 12. After that, the second robot arm 22 again transfers the injector 11 to the needle bending detecting section 36 (S7008) to detect the needle bending state of the injection needle 11c of the injector 11.

<Steps S7009 to S7010>

Next, the second robot arm 22 carries out an action for matching the scale of the syringe 11a with the necessary amount of the transfusion which has been obtained at the step S7007 (S7009). Specifically, the second robot arm 22 allows the injector 11 to suction air in a predetermined amount in a state that the tip end of the injection needle 11c of the syringe 11a is directed toward the vertical upper direction and then directs the tip end of the injection needle 11c toward the vertical lower direction once to gather air bubbles in the syringe 11a. After that, the second robot arm 22 allows the injection needle 11c of the syringe 11a to be inserted into the cap 11e held by the injection needle attaching and detaching device 43 and pushes the plunger 11b in this state in a predetermined amount to discharge the air in the syringe 11a. With this configuration, in the syringe 11a, the position of the scale indicated by a tip end of the rubber of the plunger 11b is matched with the necessary amount of the transfusion which has been obtained at the step S7007. Then, the second robot arm 22 transfers the injector 11 into the photographing range of the injector confirming camera 42 (S7010). At this time, the second control section 500 allows the injector confirming camera 42 to photograph the injector 11. As described above, at the step S7009, the air which has been suctioned in the syringe 11a for the purpose of preventing the transfusion from dropping from the injection needle 11c when the injection needle 11c is pulled out from the transfusion bag 12 is discharged. Thus, it is possible to prevent the transfusion from dropping when the injection needle 11c is pulled out from the injection needle 11c and store the position of the scale indicated by the tip end of the rubber of the plunger 11b as an image in a state that the position of the scale is matched with the scale corresponding to the necessary amount of the transfusion when the injector 11 is photographed.

<Steps S6009, S7011>

After that, the first robot arm 21 and the second robot arm 22 carry out an injection process for injecting the transfusion in the injector 11 into the vial bottle 10B2 (S6009, S7011). In the injection process, the second control section 500 controls the first robot arm 21 and the second robot arm 22 to direct the opening portion of the vial bottle 10B2 toward the upper direction and direct the tip end of the injector 11 toward the lower direction. At this time, the second control section 500 allows the injection needle 11c of the injector 11 to be inserted into the rubber plug 10C of the vial bottle 10B2. Subsequently, the second control section 500 controls the holding member 26 to alternately carry out a first replacement process for suctioning air from the vial bottle 10B2 with the injector 11 and a second replacement process for injecting the transfusion in the injector 11 into the vial bottle 10B2. In this case, the second control section 500 at the time of carrying out a process for carrying out the injection process is one example of a sixth control means.

<Steps S6010 to S6011>

In this regard, if the transfusion which has been injected in the vial bottle 10B2 is left for a long term, a so-called stacking phenomenon that the powdered medicine in the vial bottle 10B2 coagulates occurs. This results in the case where the powdered medicine becomes not likely to dissolve even if the subsequent stirring step is carried out. Thus, in the co-infusion action, the first robot arm 21 carries out a oscillating action for oscillating the vial bottle 10B2 after the transfusion has been injected into the vial bottle 10B2 (S6010). For example, it may be considered that the first robot arm 21 has a predetermined rotational axis and rotates the vial bottle 10B2 in a predetermined angle range around the predetermined rotational axis. With this configuration, it is possible to prevent the powdered medicine from coagulating immediately after the transfusion has been injected into the vial bottle 10B2. In this regard, the oscillating action for oscillating the vial bottle 10B2 is not limited thereto as long as it can facilitate the dissolution of the powdered medicine into the transfusion in the vial bottle 10B2.

After that, the first robot arm 21 sets the vial bottle 10B2 on the weighing scale 39 (S6011). At this time, the weight of the vial bottle 10B is weighed by the weighing scale 39. Then, the first robot arm 21 takes the vial bottle 10B2 from the weighing scale 39 to set the vial bottle 10B2 on the stirring device 32 (S6012). With this configuration, the stirring for the vial bottle 10B2 is started.

Further, it may be considered that the first robot arm 21 carries out the oscillating action at the step S6010 in parallel with one or both of the step S6011 and the step S6012. Namely, it may be considered that the first robot arm 21 carries out the oscillating action for oscillating the vial bottle 10B2 at the step S7010 while the vial bottle 10B2 is being transferred to the weighing scale 39 at the step S7011 or while the vial bottle 10B2 is being transferred to the stirring device 32 at the step S7012. With this configuration, it is possible to stir the medicinal solution in the vial bottle 10B2 without delaying the required time of the co-infusion action.

Further, it may be considered that the second control section 500 decides whether or not the oscillating action at the step S7010 should be carried out depending on the type of the medicine contained in the vial bottle 10B2. In this regard, it may be considered that a relationship between the type of the medicine and the decision for the oscillating action is preliminarily registered in the medicine master or the like. Specifically, in the case where the medicine contained in the vial bottle 10B2 is a medicine which is likely to bubble, it may be considered that the oscillating action is not carried out or the oscillating action is slowly carried out. In addition, in the case where the medicine contained in the vial bottle 10B2 is a medicine to which the transfusion needs to be gradually penetrated, it may be also considered that the oscillating action is not carried out or the oscillating action is slowly carried out.

<Steps S6013 to S6014>

Next, the first robot arm 21 takes the vial bottle 10B1 from the placing shelf 33 (S6013) to set the vial bottle 10B1 on the weighing scale 39 (S6014). At this time, the weight of the vial bottle 10B1 is weighed by the weighing scale 39.

<Step S7012 to S7013>

Further, the second robot arm 22 again transfers the injector 11 to the needle bending detecting section 36 (S7012) to detect the needle bending state of the injection needle 11c of the injector 11. After that, the second robot arm 22 carries out an air releasing action for the syringe 11a (S7013). The air releasing action is an action for discharging air which has been suctioned from the vial bottle 10B2 at the first replacement process of the step S6009 and the step S7011 and remained in the syringe 11a. In this regard, it may be considered that the air releasing action for the syringe 11a is carried out in the transfusion bag 12 at the time of obtaining the transfusion from the transfusion bag 12, but there is a case where the pressure in the transfusion bag 12 becomes positive pressure if the air is discharged into the transfusion bag 12. Thus, in the co-infusion apparatus 1A, the air releasing action for the syringe 11a is carried out at the step S7013.

Specifically, in the air releasing action, the second robot arm 22 first inserts the injection needle 11c of the syringe 11a into the cap 11e held by the injection needle attaching and detaching device 43. Then, the second robot arm 22 uses the holding member 26 to pull the plunger 11b in a predetermined amount to suction the medicinal solution, which may remain in the injection needle 11c or the like, into the syringe 11a. At this time, even if a film of the medicinal solution is formed on the needle tip of injection needle 11c, this medicinal solution is suctioned into the syringe 11a. Subsequently, the second robot arm 22 uses the holding member 26 to push the plunger 11b to discharge the air in the syringe 11a. A pushing amount for the plunger 11b by the second robot arm 22 corresponds to an amount of discharged air which is a sum of the air, which has been suctioned from the vial bottle 10B2 at the first replacement process of the step S6009 and the step S7011 and remained in the syringe 11a, and the predetermined amount of the air suctioned before the plunger 11b is pushed. With this configuration, even in the case where the medicinal solution remains in the syringe 11a, the medicinal solution does not scatter outside because the medicinal solution stops short of the needle tip. In this regard, the pushed amount for the plunger 11b in the air releasing action is not limited to the afore-mentioned amount and may be any amount by which air remains in the syringe 11a without adversely affecting the transfusion obtaining process at the after-mentioned step S7014.

Further, since the air releasing action is carried out in a state that the injection needle 11c has been inserted into the cap 11e, it is possible to limit the scatter of the medicinal solution within the cap 11e even in the case where the medicinal solution scatters from the injection needle 11c. Namely, in the co-infusion apparatus 1A, the cap 11e attached to the injection needle 11c for the purpose of risk aversion at the time of handling the injection needle 11c is also used for preventing the scatter of the medicinal solution in the air releasing action for releasing unnecessary air from the syringe 11a of the injector 11. In this case, the second control section 500 at the time of carrying out the process for controlling the second robot arm 22 to insert the injection needle 11c of the injector 11 into the cap 11e held by the injection needle attaching and detaching device 43 and controlling the holding member 26 to discharge the air existing in the injector 11 is one example of a ninth control means.

Up to here, the case where the second robot arm 22 is one example of the third driving means and the second robot arm 22 transfers the injector 11 to insert the injection needle 11c into the cap 11e is described as one example. On the other hand, another configuration in which the co-infusion apparatus 1A includes an attaching and detaching device driving section being capable of transferring the injection needle attaching and detaching device 43 to an arbitrary position as one example of the third driving means may be considered. In this case, it may be considered that the second control section 500 controls one or both of the second robot arm 22 and the attaching and detaching device driving section to relatively transfer the injection needle 11c of the injector 11 and the cap 11e to attach the injection needle 11c to the cap 11e.

<Steps S7014 to S7017>

Next, the second robot arm 22 obtains the transfusion from the transfusion bag 12 with the injector 11 in the necessary amount (S7014) and again transfers the injector 11 to the needle bending detecting section 36 to detect the needle bending state of the injection needle 11c of the injector 11 (S7015) in the same manner as the steps S7007 to S7008. Further, the second robot arm 22 matches the scale of the injector 11 (S7016) and then transfers the injector 11 into the photographing range of the injector confirming camera 42 (S7017) in the same manner as the steps S7009 to S7010. At this time, the second control section 500 allows the injector confirming camera 42 to photograph the injector 11.

<Steps S6015, S7018>

After that, the first robot arm 21 and the second robot arm 22 carry out an injection process for injecting the transfusion in the injector 11 into the vial bottle 10B1 (S6015, S7018). In the injection process, the opening portion of the vial bottle 10B1 is directed toward the upper direction and the tip end of the injector 11 is directed toward the lower direction and then the suctioning of the air from the vial bottle 10B1 and the injection of the transfusion into the vial bottle 10B1 are alternately carried out in the same manner as the steps S6009, S7011.

<Steps S6016 to S6018>

Subsequently, the first robot arm 21 allows the vial bottle 10B1 to be oscillated and stirred (S6016) in the same manner as the step S6010 and then sets the vial bottle 10B1 on the weighing scale 39 (S6017). After that, the first robot arm 21 transfers the vial bottle 10B1 from the weighing scale 39 to the stirring device 32 (S6018). In this case, it may be also considered that the first robot arm 21 carries out the oscillating action at the step S6016 in parallel with one or both of the actions of the step S6017 and the step S6018 as described above.

<Steps S6019 to S6020>

Next, the first robot arm 21 takes the vial bottle 10B2 from the stirring device 32 (S6019) and then carries out a stirring confirming action for allowing an inspector to confirm a stirring status of the medicinal solution in the vial bottle 10B2 (S6020).

Specifically, the first robot arm 21 transfers the vial bottle 10B2 with keeping a predetermined posture of the vial bottle 10B2 to the vicinity of the main door 301 to carry out the action for allowing the inspector to confirm the stirring status of the medicinal solution in the vial bottle 10B2. Particularly, the first robot arm 21 stops a posture of the vial bottle 10B2 in a state that a bottle bottom of the vial bottle 10B2 is inclined at a position for allowing the inspector to visually confirm the bottle bottom of the vial bottle 10B2 from the outside of the main door 301. With this configuration, the inspector can easily confirm the stirring status of the medicinal solution in the vial bottle 10B2. For example, the posture for allowing the inspector to confirm the bottle bottom of the vial bottle 10B2 from the outside of the main door 301 is the same state as that shown in FIG. 24(A) or 24(B). Further, the posture of the vial bottle 10B2 may be a posture for allowing the inspector to confirm the status shown in FIG. 24(A) from the outside of the main door 301 by viewing from the right side in FIG. 24(A).

Further, at this time, the second control section 500 allows the touch panel monitor 14 to display a re-stirring operation key, a posture changing key, a confirming key and the like. The re-stirring operation key is an operation key for carrying out an additional stirring action for the vial bottle 10B2. In the case where the re-stirring key is operated, the second control section 500 allows the first robot arm 21 to again set the vial bottle 10B2 on the stirring device 32 to carry out the stirring action for the vial bottle 10B2 for a predetermined additional stirring time duration. After that, the second control section 500 again carries out the steps S6019 to S6020.

Further, the posture changing key is an operation key for changing the posture of the vial bottle 10B2. In the case where the posture changing key is operated, the second control section 500 allows the first robot arm 21 to change the posture of the vial bottle 10B which can be seen by the injector to one or more of predetermined postures. With this configuration, the inspector can visually confirm the stirring status of the medicinal solution in the vial bottle 10B2 from different angles. For example, it may be considered that the vial bottle 10B is oscillated by the first robot arm 21 and the vial bottle 10B2 is rotated around the predetermined rotation axis of the first robot arm 21 according to the operation with respect to the posture changing key.

The confirming key is an operation key which is operated when the inspector confirms that there is no problem in the stirring status of the medicinal solution in the vial bottle 10B2. In the case where the confirming key is operated, the second control section 500 shifts the action of the first robot arm 21 to a subsequent action.

<Step S6021>

After that, the first robot arm 21 sets the vial bottle 10B2 on the medicine reading section 34 (S6021). With this configuration, the barcode for the medicine in the vial bottle 10B2 is read by the medicine reading section 34 and the circumferential position of the vial bottle 10B2 is detected or adjusted. This relationship of the circumferential position of the vial bottle 10B2 detected or adjusted in this step is used for deciding the punctured position of the vial bottle 10B2 to be inserted by the injection needle 11c of the injector 11 or deciding the posture of the vial bottle 10B2 at the time of photographing the vial bottle 10B2 described below, for example.

<Steps S7019 to S7020>

On the other hand, the second robot arm 22 again transfers the injector 11 to the needle bending detecting section 36 to detect the needle bending state of the injection needle 11c of the injector 11 (S7019) and then carries out the air releasing action for the syringe 11a (S7020) in the same manner as the steps S7012 to S7013.

<Steps S6022, S7021>

After that, the first robot arm 21 and the second robot arm 22 carry out the partial amount obtaining for obtaining a predetermined amount of the medicinal solution from the medicinal solution in the vial bottle 10B2 as a suctioning process for suctioning the medicinal solution contained in the vial bottle 10B2 (S6022, S7022). In the suctioning process, the second control section 500 controls the first robot arm 21 and the second robot arm 22 to puncture the vial bottle 10B2 with the injection needle 11c of the injector 11 in a state that the opening portion of the vial bottle 10B2 is directed toward the upper direction and the tip end of the injector 11 is directed toward the lower direction. Next, the second control section 500 controls the first robot arm 21 and the second robot arm 22 to direct the opening portion of the vial bottle 10B2 toward the lower direction and direct the tip end of the injector 11 toward the upper direction. Then, the second control section 500 controls the holding member 26 to alternately carry out the suctioning of the medicinal solution from the vial bottle 10B2 with the injector 11 and the injection of the air from the injector 11 into the vial bottle 10B2.

<Steps S6023, S7022>

After the partial amount obtaining completes, the first robot arm 21 and the second robot arm 22 transfer the vial bottle 10B2 and the injector 11 into the photographing range R1 of the injector confirming camera 42 with keeping the state that the injection needle 11c of the injector 11 has been inserted into the vial bottle 10B2 (S6023, S7022) to photograph an image of the vial bottle 10B2 and the injector 11. After photographing the image, the first robot arm 21 and the second robot arm 22 pull off the injection needle 11c of the injector 11 from the vial bottle 10B2.

<Step S6024>

Then, the second control section 500 allows the waste cover 132a to be opened and the first robot arm 21 drops the vial bottle 10B2 into the waste containing chamber 13a to dispose of the vial bottle 10B2 (S6024).

<Steps S6025 to S6027>

Subsequently, the first robot arm 21 takes the vial bottle 10B1 from the stirring device 32 (S6025) to carry out a stirring confirming action for confirming the stirring status of the vial bottle 10B1 (S6026) and then sets the vial bottle 10B1 on the medicine reading section 34 (S6027) in the same manner as the steps S6019 to S6021.

<Steps S7023 to S7027>

On the other hand, the second robot arm 22 sets the injector 11 on the weighing scale 35 to weigh the weight of the injector 11 with the weighing scale 35 (S7023) and then transfers the injector 11 to the needle bending detecting section 36 (S7024) to detect the needle bending state of the injection needle 11c of the injector 11. Then, the second robot arm 22 carries out an injection process for injecting the medicinal solution in the injector 11 into the transfusion bag 12 (S7025). After that, the second robot arm 22 again sets the injector 11 on the weighing scale 35 to weigh the weight of the injector 11 with the weighing scale 35 (S7026) and then transfers the injector 11 to the needle bending detecting section 36 to detect the needle bending state of the injection needle 11c of the injector 11 (S7027).

<Steps S6028, S7028>

Next, the first robot arm 21 and the second robot arm 22 carry out the whole amount obtaining for obtaining the whole amount of the medicinal solution in the vial bottle 10B1 as a suctioning process for suctioning the medicinal solution contained in the vial bottle 10B1 (S6028, S7028). In the suctioning process, the first robot arm 21 and the second robot arm 22 are controlled to direct the opening portion of the vial bottle 10B1 toward the lower direction and direct the tip end of the injector 11 toward the upper direction and then the suctioning of the medicinal solution from the vial bottle 10B1 and the injection of the air into the vial bottle 10B1 are alternately carried out in the same manner as the steps S6022, S7021.

<Steps S6029, S7029>

After the whole amount obtaining completes, the first robot arm 21 and the second robot arm 22 transfer the vial bottle 10B1 and the injector 11 into the photographing range R1 of the injector confirming camera 42 with keeping the state that the injection needle 11c of the injector 11 has been inserted into the vial bottle 10B1 (S6029, S7029) to photograph an image of the vial bottle 10B1 and the injector 11. After photographing the image, the first robot arm 21 and the second robot arm 22 pull off the injection needle 11c of the injector 11 from the vial bottle 10B1.

<Steps S6030 to S6031>

Then, in order to photograph the bottle bottom of the vial bottle 10B1, the first robot arm 21 transfers the vial bottle 10B1 into the photographing range R1 of the injector confirming camera 42 to photograph an image of the bottle bottom of the vial bottle 10B1. Then, the second control section 500 allows the waste cover 132a to be opened and the first robot arm 21 drops the vial bottle 10B1 into the waste containing chamber 13a to dispose of the vial bottle 10B1 (S6031).

<Step S7030 to S7034>

On the other hand, the second robot arm 22 sets the injector 11 on the weighing scale 35 to weigh the weight of the injector 11 with the weighing scale 35 (S7030) and then transfers the injector 11 to the needle bending detecting section 36 (S7031) to detect the needle bending state of the injection needle 11c of the injector 11. Then, the second robot arm 22 carries out an injection process for injecting the medicinal solution in the injector 11 into the transfusion bag 12 (S7032). After that, the second robot arm 22 again sets the injector 11 on the weighing scale 35 to weigh the weight of the injector 11 with the weighing scale 35 (S7033) and then transfers the injector 11 to the needle bending detecting section 36 to detect the needle bending state of the injection needle 11c of the injector 11 (S7034).

<Steps S7035 to S7036>

Next, the second robot arm 22 transfers the injector 11 to the injection needle attaching and detaching device 43 to attach the cap 11e to the injection needle 11c of the injector 11 (S7035). Then, the second control section 500 allows the waste cover 132a to be opened and the second robot arm 22 drops the injector 11 into the waste containing chamber 13a to dispose of the injector 11 (S7036).

As described above, in the co-infusion apparatus 1A, a variety of actions are concurrently carried out by the first robot arm 21 and the second robot arm 22. Thus, it is possible to efficiently carry out the co-infusion action and rapidly carry out the co-infusion action.

[Eighth Embodiment]

In this embodiment, description will be given to another example of the stirring action for the vial bottle 10B in the co-infusion apparatus 1 or the co-infusion apparatus 1A. Specifically, in the previous embodiments, description has been given to the case where the medicine and the transfusion in the vial bottle 10B are stirred by the stirring device 32 in the co-infusion apparatus 1 or the co-infusion apparatus 1A. In this case, after the injection needle 11c of the injector 11 is inserted into the vial bottle 10B to carry out the injection process for injecting the transfusion into the vial bottle 10B, the medicine and the transfusion in the vial bottle 10B are stirred. Then, the injection needle 11c of the injector 11 is again inserted into the vial bottle 10B to carry out the suctioning process for suctioning the medicinal solution from the vial bottle 10B. Thus, the steps for puncturing the vial bottle 10B with the injection needle 11c are individually carried out in the injection process and the suctioning process. As a result, the required time of the co-infusion action becomes longer.

In contrast, it may be considered to use the first robot arm 21 and the second robot arm 22 to stir the medicinal solution in the vial bottle 10B. Specifically, the second control section 500 allows the first robot arm 21 and the second robot arm 22 to puncture the vial bottle 10B with the injection needle 11c of the injector 11 to carry out the injection process for injecting the transfusion into the vial bottle 10B. Then, the second control section 500 allows the first robot arm 21 and the second robot arm 22 to carry out an oscillating step for oscillating the vial bottle 10B with keeping the state that the injection needle 11c has been inserted into the vial bottle 10B. For example, in the stirring step, the vial bottle 10B is oscillated by vertical liner motions of the first robot arm 21 and the second robot arm 22, rotational motions around predetermined rotational axes of the first robot arm 21 and the second robot arm 22 and the like. After that, the second control section 500 carries out the suctioning process for suctioning the medicinal solution in the vial bottle 10B with the injector 11 without any change. With this configuration, it is possible to reduce the number of the insertions of the injection needle 11c of the injector 11 into the vial bottle 10B and omit the action for transferring the vial bottle 10B to the stirring device 32, thereby shortening the required time of the co-infusion action.

Further, it may be considered that the second control section 500 decides whether or not the stirring step using the first robot arm 21 and the second robot arm 22 should be carried out depending on the type of the medicine contained in the vial bottle 10B2. In this regard, it may be considered that a relationship between the type of the medicine and the decision for the stirring action is preliminarily registered in the medicine master or the like. Specifically, it may be considered that the second control section 500 allows the first robot arm 21 and the second robot arm 22 to carry out the stirring action in the case where the medicine contained in the vial bottle 10B2 is a medicine which is likely to dissolve. On the other hand, in the case where the medicine contained in the vial bottle 10B2 is a medicine which is not likely to dissolve, the second control section 500 allows the stirring device 32 to carry out the stirring action without allowing the first robot arm 21 and the second robot arm 22 to carry out the stirring action or after the first robot arm 21 and the second robot arm 22 carry out the stirring action.

In this regard, in the case of taking a configuration in which a injector supporting member for supporting the injector 11 is fixedly provided and only a medicine supporting member for supporting the vial bottle 10B is movable, the medicine supporting member needs to be moved around a rotational center of the injector supporting member as a basis for the rotation. As a result, a required space for this action becomes larger. In contrast, in the co-infusion apparatus 1 or the co-infusion apparatus 1A, each of the first robot arm 21 for transferring the vial bottle 10B and the second robot arm 22 for transferring the injector 11 has a multiple joint structure which can be arbitrarily moved. Thus, as shown in FIG. 57, the second control section 500 can allow the first robot arm 21 and the second robot arm 22 to transfer positions of the holding member 25 and the holding member 26 so that a center R20 of a distance H1 between both ends of the holding member 25 and the holding member 26 becomes a rotational center to rotate the vial bottle 10B.

Figure 57:
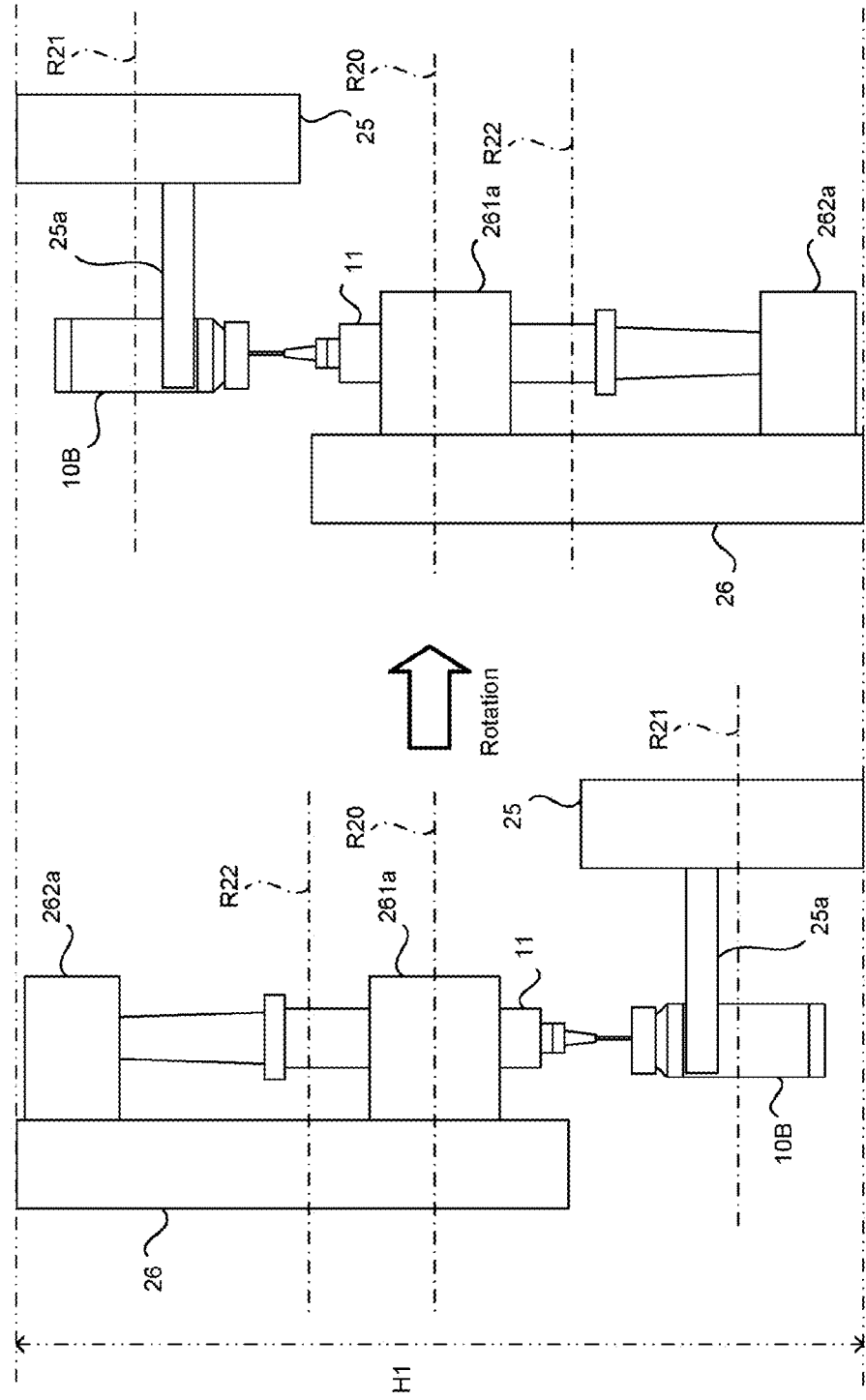
FIG. 57 is a view for explaining another example of a stirring action in the co-infusion apparatus according to the other embodiment of the present invention.

For example, when the posture is changed from the posture shown in the left-side of FIG. 57 to the posture shown in the right-side of FIG. 57, the second control section 500 allows the holding member 25 to be gradually transferred toward the upper direction and allows the holding member 26 to be gradually transferred toward the lower direction with keeping the distance H1 between the both sides of the holding member 25 and the holding member 25 constant and allows the holding member 25 and the holding member 26 to be rotated around the center R20. Further, in the case where the posture is changed from the posture shown in the right-side of FIG. 57 to the posture shown in the left-side of FIG. 57, the second control section 500 allows the holding member 25 to be gradually transferred toward the lower direction and allows the holding member 26 to be gradually transferred toward the upper direction with keeping the distance H1 between the both ends of the holding member 25 and the holding member 26 and allows the holding member 25 and the holding member 26 to be rotated around the center R20 in the same manner as the previous case. With this configuration, it is possible to make a required working space for stirring the vial bottle 10B smaller. Namely, since the rotation is carried out around the center R20 of the distance H1 between the both ends of the holding member 25 and the holding member 26 with using the center R20 as a rotational center, it is possible to make the working space smaller compared with the case where, for example, one of an original rotational center R21 of the holding member 25 and an original rotational center R22 of the holding member 26 is defined as the basic for the rotation and the other one is transferred during the rotation.

[Ninth Embodiment]

Figures 58A, 58B, 58C:
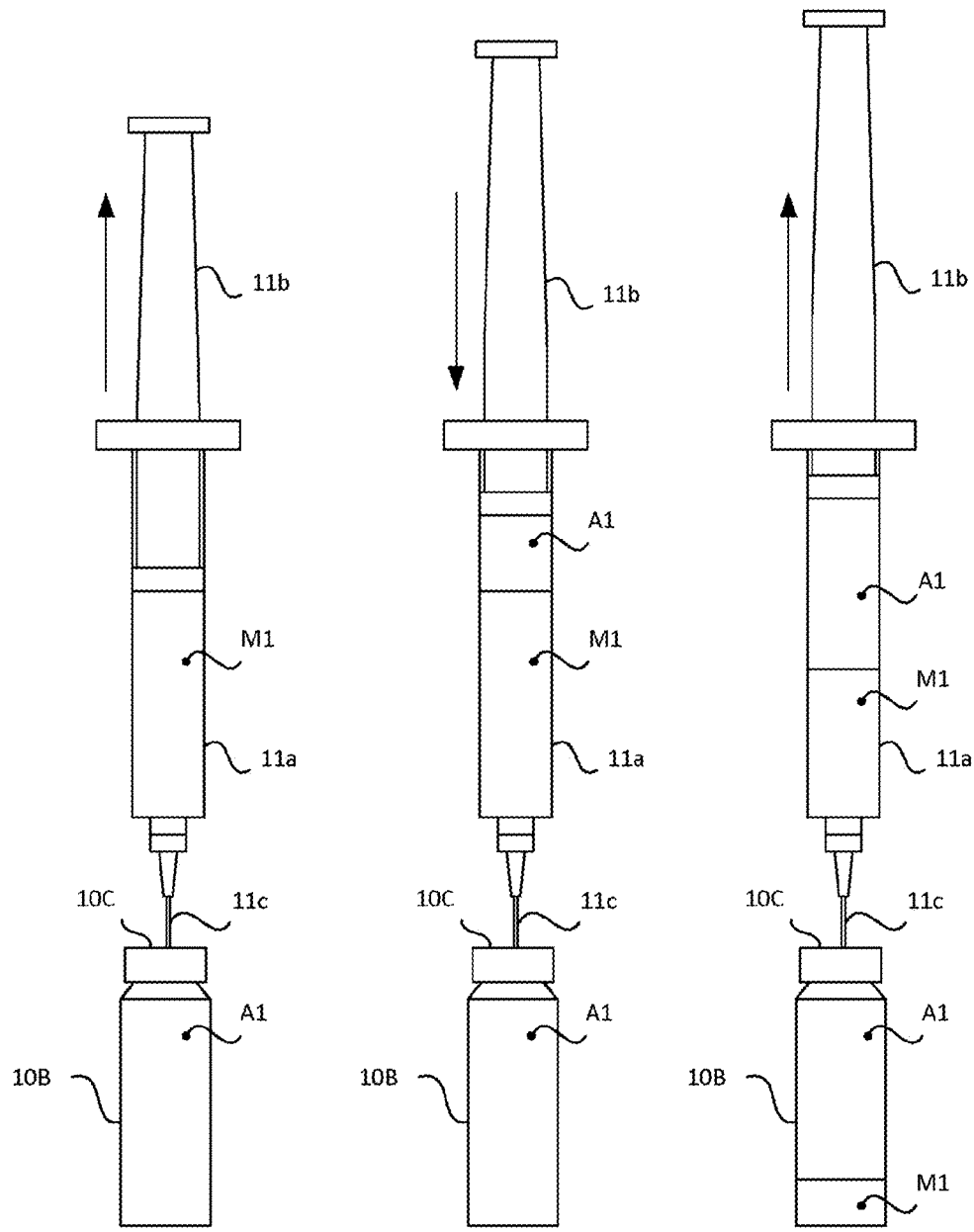
FIG. 58 is a view for explaining an injection process in the co-infusion apparatus according to the other embodiment of the present invention.

In this embodiment, description will be given to another example of the injection process for injecting the transfusion into the vial bottle 10B with the injector 11, which is carried out in the co-infusion apparatus 1 or the co-infusion apparatus 1A. Specifically, in the co-infusion apparatus 1 or the co-infusion apparatus 1A, as shown in FIG. 58(A), transfusion M1 is injected into the vial bottle 10B with the injector 11 after the injection needle 11c has been inserted into the rubber plug 10C of the vial bottle 10B in a state that the opening portion of the vial bottle 10B is directed toward the upper direction. In this case, it is assumed that initial air pressure of air A1 in the vial bottle 10B is atmospheric pressure.

In this case, when the transfusion M1 is injected from the injector 11 into the vial bottle 10B, the pressure in the vial bottle 10B becomes positive pressure and the medicinal solution is likely to leak from the vial bottle 10B. Thus, in the injection process for injecting the transfusion M1 from the injector 11 into the vial bottle 10B, there is a case where the second control section 500 controls the first robot arm 21 and the second robot arm 22 to direct the opening portion of the vial bottle 10B toward the upper direction and direct the tip end of the injector 11 toward the lower direction and then controls the first robot arm 21 and the second robot arm 22 to alternately carry out the first replacement process for suctioning the air A1 from the vial bottle 10B with the injector 11 and the second replacement process for injecting the transfusion M1 in the injector 11 into the vial bottle 10B. In this case, the second control section 500 at the time of carrying out the injection process is one example of a sixth control means.

However, the injection process carried out by replacing the air A1 in the vial bottle 10B with the transfusion M1 in the injector 11 as described above requires long time. Particularly, in the case where only the transfusion M1 exists in the syringe 11a and air does not exist between the plunger 11b and the transfusion M1 in the syringe 11a at the time of staring the injection process as shown in FIG. 58(A), required force Fs0 required for staring to pull the plunger 11b is equivalent to a product of atmospheric pressure P0 and a cross-sectional area S0 of the syringe 11a. Further, in the case where an amount of air existing in the syringe 11a is small at the time of staring the injection process, required force for pulling the plunger 11b to expand the air also becomes larger compared with the case where the amount of the air existing in the syringe 11a is large. Specifically, according to Boyle's law that a product of a volume and pressure is constant, in the case where air exists in the syringe 11a, when the air in the syringe 11a is expanded by pulling the plunger 11b and a volume of the air becomes larger, air pressure in the syringe 11a becomes smaller. Thus, a difference between the air pressure in the syringe 11a and the atmospheric pressure becomes larger. This makes the required force Fs0 for pulling the plunger 11b larger.

On the other hand, in the co-infusion apparatus 1A, the syringe 11a of the injector 11 is gripped by the gripping clicks 261a as shown in FIG. 8. In this case, a gripping direction of the syringe 11a due to the gripping clicks 261a is perpendicular to a handling direction (pushing direction and pulling direction) of the plunger 11b of the injector 11 due to the transferring member 263. Namely, since the syringe 11a is gripped by the gripping clicks 261a, the syringe 11a is in a state that change of the handling direction of the plunger 11b is restricted by static friction force between the syringe 11a and the gripping clicks 261a. In such a configuration, although it is possible to, for example, grip the syringe 11a having a variety of sizes with the gripping clicks 261a, there is a risk that the syringe 11a gripped by the gripping clicks 261a is moved toward the pulling direction of the plunger 11b in the case where pulling force for the plunger 11b becomes larger.

Thus, in the co-infusion process, it may be considered to make a pulling speed for the plunger 11b slower in the first replacement process in order to prevent the pulling force for the plunger 11b from exceeding the gripping force for the syringe 11a due to the holding member 26. This makes it possible to prevent the position of the syringe 11a from shifting. Further, it may be considered to make an acceleration at the time of starting to pull the plunger 11b smaller in the first replacement process or make a pulling amount for the plunger 11b smaller in the first replacement process. However, in the case where the working for replacing the transfusion M1 in the syringe 11a with the air A1 in the vial bottle 10B is repeatedly carried out in the injection process, in the case where the pulling speed for the plunger 11b is slow, in the case where the acceleration at the time of starting to pull the plunger 11b is small or in the case where the pulling amount for the plunger 11b is small, the required time of the injection process becomes longer.

In contrast, the required force Fs0 required for pulling the plunger 11b in the injection process changes depending on the difference between the atmospheric pressure and the air pressure in the syringe 11a. For example, in the case where only the transfusion M1 exists in the syringe 11a and air does not exist in the syringe 11a as described above, the required force Fs0 required for pulling the plunger 11b becomes a maximum value (P0×S0). When the air pressure in the syringe 11a becomes higher, the difference between the air pressure and the atmospheric pressure becomes smaller. As a result, the require force Fs0 required for pulling the plunger 11b becomes smaller. In the case where the amount of the air in the syringe 11a does not change, that is, in the case where air does not flow from the outside into the syringe 11a, when the air pressure reduces due to an increase of a volume of an air layer in the syringe 11a, the difference between the air pressure and the atmospheric pressure becomes larger. As a result, the required force Fs0 required for pulling the plunger 11b becomes larger. Regarding this point, in the co-infusion apparatus 1A, since the first replacement process and the second replacement process are repeatedly carried out, air gradually flows into the syringe 11a. Thus, in the case of assuming that air does not flow into the injection needle 11c at the time of staring to pull the plunger 11b, an expansion rate of the air at the time of pulling the plunger 11b by a predetermined amount reduces as the number of the executions of the first replacement process increases. Thus, a reducing amount of the air pressure also becomes smaller. As a result, the required force required for pulling the plunger 11b reduces.

Thus, in the injection process, it may be considered that the second control section 500 allows the transferring member 263 of the holding member 26 to change at least one of the pulling speed for the plunger 11b, the acceleration at the time of starting to pull the plunger 11b and the pulling amount for the plunger 11b in the first replacement process for suctioning the air A1 from the vial bottle 10B with the injector 11 depending on the number of the executions of the first replacement process. In this regard, it may be considered to simultaneously change a several items of the pulling speed for the plunger 11b, the acceleration at the time of starting to pull the plunger 11b and the pulling amount for the plunger 11b. In this case, the second control section 500 at the time of carrying out these processes is one example of a seventh control means.

For example, in a configuration of using a stepping motor as a driving means for the transferring member 263, it may be considered that the second control section 500 controls a driving pulse inputted into the stepping motor to change the pulling speed for the plunger 11b, the acceleration at the time of starting to pull the plunger 11b or the pulling amount for the plunger 11b in the first replacement process. Further, in a configuration of using a DC motor as a driving means for transferring the transferring member 263, it may be considered that the second control section 500 controls a driving voltage inputted into the DC motor to change the pulling speed for the plunger 11b or the acceleration at the time of starting to pull the plunger 11b in the first replacement process and controls a driving time duration of the DC motor to change the pulling amount for the plunger 11b in the first replacement process. In this regard, a control method for controlling the driving means for the transferring member 263 to change the acceleration, the speed and the transferring amount of the transferring member 263 is not limited thereto. It is possible to use a variety of technologies already known in the art as the control method.

More specifically, in the case where the first replacement process and the second replacement process are repeatedly carried out, it may be considered that the second control section 500 increases the acceleration at the time of starting to pull the plunger 11b in a step-by-step manner as the number of the executions of the first replacement process increases in order to prevent the pulling force for the plunger 11b from exceeding the gripping force for the syringe 11a due to the gripping clicks 261a and acting the syringe 11a. With this configuration, it is possible to prevent the position of the syringe 11a from shifting and shorten the required time of the injection process, thereby shortening the required time of the co-infusion action.

In the same manner, it may be considered that the second control section 500 increase the pulling amount for the plunger 11b in a step-by-step manner as the number of the executions of the first replacement process increases. With this configuration, it is possible to prevent the position of the syringe 11a from shifting and prevent the suctioning amount at one time of the first replacement process from increasing. Thus, it is possible to reduce the repeating number of the first replacement process, thereby shortening the required time of the injection process and the required time of the co-infusion action.

In the same manner, it may be considered that the second control section 500 makes the pulling speed for the plunger 11b faster in a step-by-step manner as the number of the executions of the first replacement process increases. For example, it may be considered that the second control section 500 makes a target speed at the time of pulling the plunger 11b faster in a step-by-step manner. In this case, it is also possible to prevent the position of the syringe 11a from shifting and shorten the required time of the injection process, thereby shortening the required time of the co-infusion action.

For example, in the co-infusion process, the second control section 500 controls the transferring member 263 so as to prevent force larger than the gripping force (frictional force) with respect to the syringe 11a due to the gripping clicks 261a from acting the syringe 11a when the plunger 11b is pulled at the first time to start to pull the plunger 11b with a predetermined first acceleration with utilizing a predetermined first speed as a target speed to pull the plunger 11b by a predetermined first suctioning amount as shown in FIG. 58(A). Then, as shown in FIG. 58(B), after the air A1 has flown from the vial bottle 10B into the syringe 11a, the second control section 500 allows the plunger 11b to be pushed down by a predetermined amount to inject the transfusion M1 in the syringe 11a into the vial bottle 10B. Namely, the air A1 and the transfusion M1 are replaced with each other between the syringe 11a and the vial bottle 10B.

After that, as shown in FIG. 58(C), the second control section 500 controls the transferring member 263 to pull the plunger 11b with a predetermined second acceleration larger than the first acceleration by a predetermined second suctioning amount larger than the first suctioning amount when the plunger 11b is pulled at the second time. At this time, the pulling speed for the plunger 11b may be a second speed faster than the first speed. After that, in the first replacement process at the third or later time, it may be considered that the second control section 500 allows the plunger 11b to be pulled with an acceleration equal to or larger than the second acceleration. In the same manner, in the first replacement process at the third or later time, it may be considered that the second control section 500 allows the plunger 11b to be pulled by a suctioning amount equal to or larger than the second suctioning amount. Furthermore, in the first replacement process at the third or later time, it may be considered that the second control section 500 allows the plunger 11b to be pulled with a speed equal to or larger than the second speed.

For example, the second acceleration, the second suctioning amount or the second speed is set in advance by using an arithmetic equation such as the following equation (1) for calculating the required force Fs0 required for pulling the plunger 11b so that the pulling force for the plunger 11b due to the transferring member 263 of the holding member 26 does not exceed the static frictional force with respect to the plunger 11b of the syringe 11a in the moving direction of the plunger 11b, which is caused by the gripping force for gripping the syringe 11a due to the gripping clicks 261a of the holding member 26, and the position of the syringe 11a is not shifted. In this regard, it may be considered that the second control section 500 calculates the second acceleration, the second suctioning amount or the second speed by using the following equation (2) for every time.

$$Fs0 = P0(1 - Vs0/Vs1) \times S0 \qquad (1)$$

In the case where the air pressure of the air in the syringe 11a is equal to the atmospheric pressure P0, the equation (1) represents the required force Fs0 required for pulling the plunger 11b. "Vs0" represents a volume of the air in the syringe 11a before the plunger 11b is pulled and "Vs1" represents a volume of the air in the syringe 11a after the plunger 11b has been pulled. Namely, the expansion rate of the air in the syringe 11a is "Vs1/Vs0". When the expansion rate becomes larger, the air pressure in the syringe 11a becomes smaller. "S0" represents a sectional are of the syringe 11a which can be known from the standard of the syringe 11a. For example, when the air in the syringe 11a is expanded by pulling the plunger 11b and the volume of the air in the syringe 11a doubles, the air pressure in the syringe 11a becomes "P0×1/2" and the required force Fs0 required for pulling the plunger 11b becomes "P0×1/2×S0". When the air in the syringe 11a is expanded by pulling the plunger 11b and the volume of the air in the syringe 11a triples, the air pressure in the syringe 11a becomes "P0×1/3" and the required force Fs0 required for pulling the plunger 11b becomes "P0×2/3×S0".

For the purpose of making the explanation easy, description has been given to the exemplary case of calculating the required force Fs with assuming that the air pressure of the air in the syringe 11a before the plunger 11b is pulled is equal to the atmospheric pressure P0 and air does not flow into the syringe 11a when the plunger 11b is pulled. Namely, description has been given to the exemplary case of setting the acceleration at the time of staring to pull the plunger 11b, the pulling speed for the plunger 11b, the pulling amount for the plunger 11b or the like with taking into account safeness so that a maximum value of the required force required for pulling the plunger 11b does not exceed the gripping force with respect to the syringe 11a. On the other hand, when the plunger 11b is pulled in practice, air flows into from the vial bottle 10B into the syringe 11a. Thus, it may be considered to set the acceleration at the time of staring to pull the plunger 11b, the pulling speed for the plunger 11b, the pulling amount for the plunger 11b or the like with taking into account the air pressure of the air suctioned from the vial bottle 10B into the syringe 11a so that the required force required for pulling the plunger 11b does not exceed the gripping force with respect to the syringe 11a. For example, it may be considered that the required force required for pulling the plunger 11b is calculated by multiplying a predetermined coefficient less than 1 by the required force Fs0 calculated based on the equation (1). Of course, it may be considered that the second control section 500 exactly calculates the required force required for pulling the plunger 11b with taking into account the amount of the air in the vial bottle 10B and sets the acceleration at the time of staring to pull the plunger 11b, the pulling speed for the plunger 11b, the pulling amount for the plunger 11b or the like according to the calculated required force.

In this regard, in this embodiment, description has been given to the exemplary case of changing the acceleration at the time of staring to pull the plunger 11b, the pulling speed for the plunger 11b, the pulling amount for the plunger 11b or the like depending on the number of the executions of the first replacement process with assuming that the expansion rate of the air in the syringe 11a reduces as the number of the executions of the first replacement process increases. On the other hand, it may be considered that the second control section 500 changes at least one of the pulling speed for pulling the plunger 11b by the transferring member 263 in the first replacement process, the acceleration at the time of staring to pull the plunger 11b the pulling speed for the plunger 11b and the pulling amount for the plunger 11b depending on the expansion rate of the air in the syringe 11a at the time of pulling the plunger 11b (that is, the volume "Vs1" of the air in the syringe 11a after the plunger 11b is pulled/the volume "Vs0" of the air in the syringe 11a before the plunger 11b is pulled). More specifically, it may be considered to carry out at least one of a step of making the pulling speed for pulling the plunger 11b by the transferring member 263 in the first replacement process faster in a step-by-step manner, a step of making the acceleration at the time of starting to pull the plunger 11b larger in a step-by-step manner and a step of making the pulling amount for the plunger 11b larger as the expansion rate of the air in the syringe 11a at the time of pulling the plunger 11b reduces. In this case, the second control section 500 at the time of carrying out such a process is one example of an eighth control means.

[Tenth Embodiment]

In this embodiment, description will be given to another example of the suctioning process for suctioning the medicinal solution from the vial bottle 10B with the injector 11, which is carried out in the co-infusion apparatus 1 or the co-infusion apparatus 1A, with reference to FIGS. 59(A) to 59(E). For the purpose of simplifying the drawings, only the injection needle 11c among the injector 11 is illustrated and the syringe 11a and the plunger 11b are not illustrated in FIGS. 59(A) to 59(E).

In the suctioning process in the co-infusion apparatus 1 or the co-infusion apparatus 1A, the second control section 500 controls the first robot arm 21 and the second robot arm 22 to puncture the rubber plug 10C of the vial bottle 10B with the injection needle 11c in a state that the opening portion of the vial bottle 10B is directed toward the upper direction. Then, the second control section 500 controls the first robot arm 21 and the second robot arm 22 to direct the opening portion of the vial bottle 10B toward the lower direction and direct the tip end of the injection needle 11c of the injector 11 toward the upper direction and then controls the holding member 26 to carry out a suctioning process for suctioning the medicinal solution form the vial bottle 10B with the injector 11. In this case, the second control section 500 at the time of carrying out the process for carrying out the suctioning process is one example of a tenth control means.

At this time, in the case where the whole amount obtaining for obtaining the whole amount of the medicinal solution in the vial bottle 10B is carried out with the injector 11, it is necessary to suction the medicinal solution from the vial bottle 10B without remaining the medicinal solution in the vial bottle 10B. Thus, it is necessary to control a positional relationship between the injection needle 11c and the rubber plug 10C so that the insertion amount of the injection needle 11c with respect to the rubber plug 10C becomes smaller and the tip end of the injection needle 11c is positioned as close to the rubber plug 10C as possible.

However, there is a risk that each vial bottle 10B has a different size caused by an individual difference at the time of producing or the like. Thus, even if the positional relationship between the injection needle 11c and the rubber plug 10C is set to be a predetermined positional relationship, there is a risk that the insertion amount of the injection needle 11c with respect to the rubber plug 10C changes. For example, if the depth of the insertion of the tip end of the injection needle 11c of the injector 11 with respect to the rubber plug 10C of the vial bottle 10B is deep, the tip end of the injection needle 11c gets away from the rubber plug 10C. Thus, it is impossible to suction the medicinal solution in the vial bottle 10B without remaining the medicinal solution in the vial bottle 10B. On the other hand, if the depth of the insertion of the tip end of the injection needle 11c with respect to the rubber plug 10C is shallow, there is a risk that the rubber plug 10C is not punctured by the injection needle 11c due to a deflection of the rubber plug 10C as shown in FIG. 59(A).

Thus, it may be considered that the second control section 500 reduces the insertion amount of the injection needle 11c with respect to the rubber plug 10C as the amount of the transfusion in the vial bottle 10B decreases in the suction process. In this case, the second control section 500 at the time of carrying such a process is one example of an eleventh control means. With this configuration, it becomes possible to reliably pierce the rubber plug 10C with the injection needle 11c and completely suction the medicinal solution in the vial bottle 10B.

Specifically, in the suctioning process, the second control section 500 allows the tip end of the injection needle 11c to be inserted into the rubber plug 10C until a predetermined depth P81 at the time of puncturing the rubber plug 10C of the vial bottle 10B with the injection needle 11c of the injector 11 as shown in FIG. 59(B). The depth P81 is set in advance as a depth for reliably allowing the rubber plug 10C to be punctured by the injection needle 11c with taking into account the deflection of the rubber plug 10C. Then, the second control section 500 controls the first robot arm 21 and the second robot arm 22 to invert vertical positions of the vial bottle 10B and the injector 11 and then controls the holding member 26 to suction the medicinal solution from the vial bottle 10B in a suctioning amount set in advance according to the depth P81 as shown in FIG. 59(C). In this regard, the suctioning amount may be the same as the amount of the medicinal solution to be suctioned from the vial bottle 10B. Further, it may be considered that the second control section 500 allows the medicinal solution to be suctioned until the amount of the medicine remaining in the vial bottle 10B becomes a predetermined remaining amount set in advance according to the depth P81.

Next, the second control section 500 allows the injection needle 11c of the injector 11 to be pulled off from the rubber plug 10C of the vial bottle 10B by a predetermined amount (for example, about 0.2 mm) to transfer the tip end of the injection needle 11c to a position of a predetermined depth P82 as shown in FIG. 59(D). Then, the second control section 500 controls the holding member 26 to suction the medicinal solution from the vial bottle 10B by a suctioning amount set in advance according to the depth P82. In this regard, it may be considered that the second control section 500 allows the medicinal solution to be suctioned until the amount of the medicinal solution remaining in the vial bottle 10B becomes a predetermined remaining amount set in advance according to the depth P82.

Further, the second control section 500 allows the injection needle 11c of the injector 11 to be pulled off from the rubber plug 10C of the vial bottle 10B by a predetermined amount (for example, about 0.2 mm) to transfer the tip end of the injection needle 11c to a position of a predetermined depth P83 as shown in FIG. 59(E). Then, the second control section 500 controls the holding member 26 to suction the medicinal solution from the vial bottle 10B by a suctioning amount set in advance according to the depth P83 to obtain the whole amount of the medicinal solution in the vial bottle 10B.

As described above, the second control section 500 allows the injector 11 to suction the medicinal solution in the vial bottle 10B with making the depth of the insertion of the injection needle 11c with respect to the rubber plug 10C shallower in a step-by-step manner during the suctioning process. With this configuration, it is possible to reliably pierce the rubber plug 10C with the injection needle 11c at the time of puncturing the rubber plug 10C with the injection needle 11c and suction the medicinal solution from the vial bottle 10B without remaining the medicinal solution in the vial bottle 10B. In this regard, the number of the change of the depth of the insertion of the injection needle 11c with respect to the rubber plug 10C is not limited to two described here, but may be one, three or more.

Figure 60A:
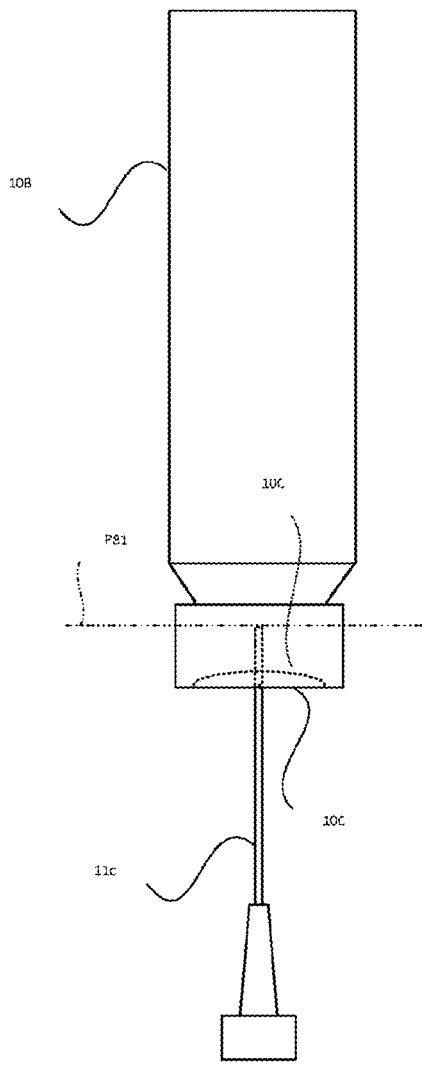
FIG. 60 is another view for explaining the suctioning process in the co-infusion apparatus according to the other embodiment of the present invention.
Figure 60B:
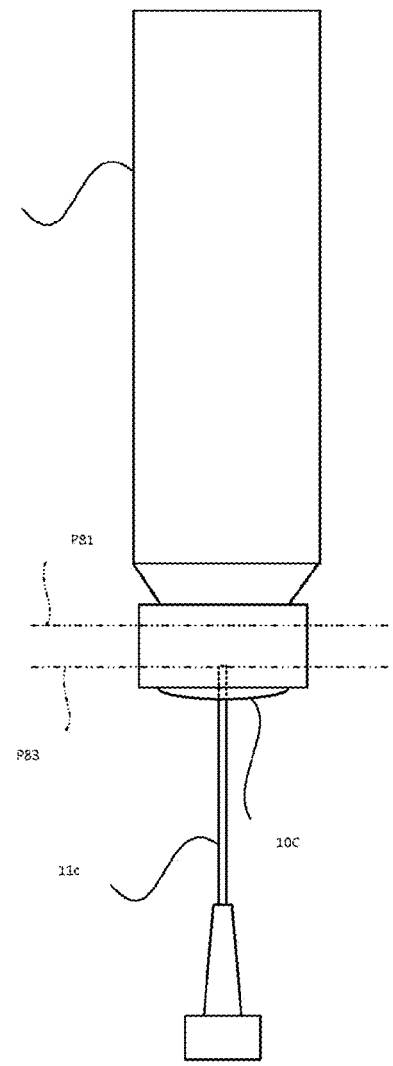

Particularly, in the suctioning process described in this embodiment, an action for pulling off the injection needle 11c from the rubber plug 10C is carried out after the injection needle 11c is sufficiently inserted into the rubber plug 10C so as to pierce the rubber plug 10C with the injection needle 11c. Thus, the rubber plug 10C is bent toward the inside of the vial bottle 10B at the time of inserting the injection needle 11c into the rubber plug 10C as shown in FIG. 60(A) and the rubber plug 10C is bend toward the outside of the vial bottle 10B at the time of gradually pulling out the injection needle 11c from the rubber plug 10C. Thus, even if the injection needle 11c is pulled off to the vicinity of the aperture of the vial bottle 10B such as the depth P83 as shown in FIG. 60(B), the injection needle 11c does not leave from the rubber plug 10C. Thus, it is possible to obtain the whole amount of the medicinal solution with the injection needle 11c.

[Eleventh Embodiment]

In this regard, in the co-infusion apparatus 1 or the co-infusion apparatus 1A, if a temperature in the co-infusion process chamber 104 is too low, there is a risk that the powdered medicine in the vial bottle 10B does not dissolve. On the other hand, if the temperature in the co-infusion process chamber 104 is too high, there is a risk that the medicinal solution vaporizes. Thus, it may be considered that a thermometer for measuring the temperature in the co-infusion process chamber 104 is provided in the co-infusion apparatus 1 or the co-infusion apparatus 1A and a measuring result from the thermometer is inputted into the second control section 500. In the co-infusion process chamber 104, it may be considered that the thermometer is provided in the vicinity of the stirring device 32 for stirring vial bottle 10B.

Then, it may be considered that the second control section 500 has a function of limiting the start of the co-infusion action based on the measuring result from the thermometer to inform whether or not the co-infusion action should be carried out. Specifically, the second control section 500 limits the start of the co-infusion action in the case where the measuring result from the thermometer is not in a predetermined temperature range and allows the touch panel monitor 14 to display a message indicating that the temperature in the co-infusion process chamber 104 is not in the temperature range. For example, it may be considered that the temperature range is 15 to 30° C. or 18 to 25° C. With this configuration, since the start of the co-infusion action is limited in the case where the temperature in the co-infusion process chamber 104 is not in the temperature range, it is possible to prevent the co-infusion action from being carried out in a state the powdered medicine is not likely to dissolve or in a state that there is a risk that the medicinal solution vaporizes, for example. Further, it may be considered that the second control section 500 stops the co-infusion action when the measuring result from the thermometer becomes out of the temperature range while the co-infusion action is carried out. Alternatively, it may be considered that the second control section 500 continues the co-infusion action and allows the data storage section 504 to store a historical data indicating that the measuring result from the thermometer becomes out of the temperature range.

DESCRIPTION OF REFERENCE SIGNS

1: Co-infusion apparatus
10: Medicine container
11: Injector
11a: Syringe

11b: Plunger
11c: Injection needle
11d: Syringe filter
12: Transfusion bag
13: Waste containing chamber door
15a: IC reader
21: First robot arm
22: Second robot arm
25: Holding member
26: Holding member
31: Ampule cutter
32: Stirring device
33: Placing shelf
33A: Placing member for rotation
34: Medicine reading section
35: Weighing scale
36: Needle bending detecting section
37: Co-infusion communication port
38: Needle insertion confirming transparent window
39: Weighing scale
41: Tray confirming camera
42: Injector confirming camera
43: Injection needle attaching and detaching device
44: Needle insertion confirming camera
45: Sterilizing lamp
100: Co-infusion control device
101: Tray
101a: Electronic paper
101b: IC tag
101c: IC reader
104: Co-infusion process chamber
110: Tray conveying section
121: Camera for transfusion
200: Medicine loading section
300: Co-infusion process section
400: First control section
401: CPU
402: ROM
403: RAM
404: Data storage section
500: Second control section
501: CPU
502: ROM
503: RAM
504: Data storage section
600: Host system

What is claimed is:

1. A co-infusion apparatus for suctioning a medicine from a medicine container with an injector based on preparation data and injecting the medicine from the injector into a transfusion container, the co-infusion apparatus comprising:
a first driving portion configured to transfer one or both of the medicine container and the injector to an arbitrary position;
a second driving portion configured to handle the injector;
a suctioning control portion configured to control the first driving portion and the second driving portion to suction the medicine from the medicine container with the injector;
a transfer control portion configured to control the first driving portion to transfer, into a photographing range, the medicine container after the medicine is suctioned by the suctioning control portion and the injector in which the medicine has been suctioned; and
a suctioning timing photographing portion configured to photograph, at one time, the medicine container and the injector transferred in the photographing range by the transfer control portion,
a container position adjusting portion configured to adjust a circumferential position of the medicine container held by the first driving portion so that characters of a medicine name on the medicine container are located in the photographing range.

2. The co-infusion apparatus according to claim 1, wherein the first driving portion includes a first robot arm and a second robot arm, each having a multiple joint structure.

3. The co-infusion apparatus according to claim 1, wherein the transfer control portion allows the medicine container and the injector to be arranged in the photographing range so that characters of a medicine name on the medicine container and characters of a scale of the injector are directed toward the same direction.

4. The co-infusion apparatus according to claim 3, wherein the transfer control portion allows the medicine container and the injector to be arranged in the photographing range so that vertical directions of the characters of the medicine name on the medicine container and the characters of the scale of the injector and a vertical direction in the photographing range are the same.

5. The co-infusion apparatus according to claim 1, wherein the transfer control portion allows the medicine container and the injector to be arranged in the photographing range so that the medicine container and the injector are aligned in a direction perpendicular to a longitudinal direction of the injector.

6. The co-infusion apparatus according to claim 1, wherein the transfer control portion allows the first driving portion to keep holding the medicine container and the injector until the medicine container and the injector are photographed by the suctioning timing photographing portion after the medicine is suctioned from the medicine container with the injector.

7. The co-infusion apparatus according to claim 1, further comprising:
an inspection image display portion configured to display an image photographed by the suctioning timing photographing portion as an inspection image.

8. The co-infusion apparatus according to claim 7, wherein the inspection image display portion allows a medicine name and a medicine volume contained in the preparation data to be displayed together with the inspection image.

9. The co-infusion apparatus according to claim 8, further comprising:
a medicine weight capturing portion configured to capture a weight of the medicine injected from the medicine container into the transfusion container with the injector, wherein
the inspection image display portion allows the weight of the medicine captured by the medicine weight capturing portion and a predetermined acceptable range for the weight of the medicine to be displayed together with the inspection image.

10. The co-infusion apparatus according to claim 9, wherein the medicine weight capturing portion calculates, as the weight of the medicine, a difference between a weight of the injector after the medicine is suctioned thereinto from the medicine container and a weight of the injector after the medicine is injected from the injector into the transfusion container.

11. The co-infusion apparatus according to claim 9 further comprising:
a weight inspecting portion configured to determine whether or not a difference between the weight of the medicine captured by the medicine weight capturing portion and a weight of the medicine corresponding to the medicine volume contained in the preparation data is in a predetermined acceptable range,
wherein
the inspection image display portion allows a determination result from the weight inspecting portion to be displayed together with the inspection image.

12. The co-infusion apparatus according to claim 11, wherein the predetermined acceptable range is a range that is set in advance for a standard volume of each injector.

13. The co-infusion apparatus according to claim 1, further comprising:
a whole amount obtaining timing photographing portion configured to photograph a bottom surface or a side surface of the medicine container in a state that an opening portion of the medicine container is directed toward a vertical upper direction or in a state that the opening portion of the medicine container is inclined at a predetermined angle with respect to the vertical upper direction when a whole amount obtaining process for suctioning a whole amount of the medicine contained in the medicine container with the injector based on the preparation data is carried out by the suctioning control portion.

14. The co-infusion apparatus according to claim 1, further comprising:
a rotation driving portion configured to rotate the medicine container in a circumferential direction and a container reading portion configured to read medicine information from the medicine container rotated by the rotation driving portion, wherein
the container position adjusting portion allows the rotation driving portion to rotate the medicine container by a rotation amount predetermined for each medicine container and then stop the rotation of the medicine container after the medicine information is read by the container reading portion.

15. The co-infusion apparatus according to claim 1, further comprising:
a tray reading portion configured to read identification information from a storage medium included in a tray on which at least one of the medicine container, a syringe of the injector, an injection needle of the injector, and the transfusion container is placed when the at least one of the medicine container, the syringe of the injector, the injection needle of the injector and the transfusion container is loaded into the co-infusion apparatus;
a collating portion configured to collate a content of the preparation data preliminarily associated with the identification information read by the tray reading portion with a content of at least one of the medicine container, the syringe of the injector, the injection needle of the injector and the transfusion container loaded in the co-infusion apparatus; and
a discharge control portion configured to allow the medicine container, the syringe of the injector, the injection needle of the injector, or the transfusion container, whose collation result by the collating portion does not indicate matching, to be removed together with the tray from a predetermined discharge port.

16. The co-infusion apparatus according to claim 15, further comprising:
an informing portion configured to, when identification information read by the tray reading portion from a subsequent tray subsequently loaded in the co-infusion apparatus after the tray is allowed to be removed by the discharge control portion is not matched with the identification information read by the tray reading portion from the tray allowed to be removed by the discharge control portion, inform thereof.

17. The co-infusion apparatus according to claim 1, further comprising:
a placing timing photographing portion configured to photograph objects including the medicine container and the injector placed on a predetermined object placing member from an upper side of the object placing member;
an interference determining portion configured to determine whether or not an object whose only one side interferes with another object exists among the objects placed on the object placing member based on a photographing result from the placing timing photographing portion; and
a separating portion configured to, when the interference determining portion determines that the object whose only one side interferes with the other object exists, insert a gripping member of the first driving portion between the two objects interfering with each other in a state that the gripping member is closed the gripping member being used for gripping the object.

18. A co-infusion apparatus for suctioning a medicine from a medicine container with an injector based on preparation data and injecting the medicine from the injector into a transfusion container, the co-infusion apparatus comprising:
a first driving portion configured to transfer one or both of the medicine container and the injector to an arbitrary position;
a second driving portion configured to handle the injector;
a suctioning control portion configured to control the first driving portion and the second driving portion to suction the medicine from the medicine container with the injector;
a transfer control portion configured to control the first driving portion to transfer, into a photographing range, the medicine container after the medicine is suctioned by the suctioning control portion and the injector in which the medicine has been suctioned; and
a suctioning timing photographing portion configured to photograph, at one time, the medicine container and the injector transferred in the photographing range by the transfer control portion,
a container position adjusting portion configured to adjust a circumferential position of the medicine container held by the first driving portion so that characters of a medicine name on the medicine container are located in the photographing range, and
an injector position adjusting portion configured to adjust a circumferential position of the injector held by the first driving portion so that characters of a scale of the injector are located in the photographing range.

19. The co-infusion apparatus according to claim 18, wherein the injector position adjusting portion includes:
a direction detecting portion configured to detect a circumferential direction of the injector placed at a predetermined placing position; and an injector rotating portion configured to allow the first driving portion to rotate the injector based on a detection result from the direction detecting portion so that the characters of the scale of the injector are located in the photographing range when the injector is transferred into the photographing range by the first driving portion.

* * * * *